United States Patent
Papa et al.

(10) Patent No.: US 9,556,126 B2
(45) Date of Patent: *Jan. 31, 2017

(54) SUBSTITUTED DIAMINOPYRIMIDYL COMPOUNDS, COMPOSITIONS THEREOF, AND METHODS OF TREATMENT THEREWITH

(71) Applicant: Signal Pharmaceuticals, LLC, San Diego, CA (US)

(72) Inventors: Patrick Papa, Carlsbad, CA (US); Brian Edwin Cathers, San Diego, CA (US); Andrew Antony Calabrese, San Diego, CA (US); Brandon Wade Whitefield, San Diego, CA (US); Brydon Bennett, San Diego, CA (US); Daniel Cashion, San Diego, CA (US); Deborah Mortensen, San Diego, CA (US); Dehua Huang, San Diego, CA (US); Eduardo Torres, San Diego, CA (US); Jason Parnes, San Diego, CA (US); John Sapienza, Chula Vista, CA (US); Joshua Hansen, La Jolla, CA (US); Katerina Leftheris, San Diego, CA (US); Matthew Correa, San Diego, CA (US); Maria Mercedes Delgado, San Diego, CA (US); Raj K. Raheja, Poway, CA (US); Sogole Bahmanyar, San Diego, CA (US); Sayee Hegde, San Diego, CA (US); Stephen Norris, San Diego, CA (US); Veronique Plantevin-Krenitsky, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/576,197

(22) Filed: Dec. 19, 2014

(65) Prior Publication Data
US 2015/0175557 A1    Jun. 25, 2015

Related U.S. Application Data

(60) Provisional application No. 61/919,216, filed on Dec. 20, 2013.

(51) Int. Cl.
| | | |
|---|---|---|
| *C07D 403/12* | (2006.01) | |
| *A61K 31/505* | (2006.01) | |
| *C07D 239/48* | (2006.01) | |
| *C07D 401/12* | (2006.01) | |
| *C07D 409/12* | (2006.01) | |
| *C07D 413/12* | (2006.01) | |
| *C07D 405/12* | (2006.01) | |
| *C07D 471/04* | (2006.01) | |
| *C07D 405/14* | (2006.01) | |
| *A61K 31/506* | (2006.01) | |
| *C07D 417/12* | (2006.01) | |

(52) U.S. Cl.
CPC .......... *C07D 239/48* (2013.01); *A61K 31/505* (2013.01); *A61K 31/506* (2013.01); *C07D 401/12* (2013.01); *C07D 403/12* (2013.01); *C07D 405/12* (2013.01); *C07D 405/14* (2013.01); *C07D 409/12* (2013.01); *C07D 413/12* (2013.01); *C07D 417/12* (2013.01); *C07D 471/04* (2013.01)

(58) Field of Classification Search
CPC ... C07D 403/12; C07D 239/48; A61K 31/505; A61K 31/506
USPC ................. 544/296, 324; 514/275
See application file for complete search history.

(56) References Cited

U.S. PATENT DOCUMENTS

| | | | |
|---|---|---|---|
| 7,468,382 B2 | 12/2008 | Brunette et al. | |
| 8,173,635 B2* | 5/2012 | Jimenez et al. | 514/210.21 |
| 8,268,840 B2 | 9/2012 | Brookfield et al. | |
| 8,785,470 B2 | 7/2014 | Castro et al. | |

(Continued)

FOREIGN PATENT DOCUMENTS

| | | |
|---|---|---|
| JP | 2011173854 | 9/2011 |
| JP | 2011173853 | 2/2013 |
| WO | WO9961444 | 12/1999 |
| WO | WO 0076980 | 12/2000 |
| WO | WO 02/04429 A1 | 1/2002 |
| WO | WO 03002544 | 1/2003 |

(Continued)

OTHER PUBLICATIONS

Simone, Oncology: Introduction, Cecil Textbook of Medicine, 20th Edition, vol. 1, pp. 1004-1010, 1996.*

(Continued)

*Primary Examiner* — Deepak Rao
(74) *Attorney, Agent, or Firm* — Jones Day

(57) ABSTRACT

Provided herein are diaminopyrimidyl Compounds having the following structures:

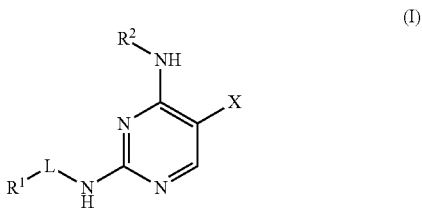

(I)

wherein X, L, $R^1$, and $R^2$ are as defined herein, compositions comprising an effective amount of a Diaminopyrimidyl Compound, and methods for treating or (Continued)

preventing PKC-theta-mediated disorders, or a condition treatable or preventable by inhibition of a kinase, for example, PKC-theta.

32 Claims, No Drawings

(56) References Cited

U.S. PATENT DOCUMENTS

| | | | |
|---|---|---|---|
| 9,156,798 B2* | 10/2015 | Bahmanyar | ......... C07D 239/48 |
| 2006/0025433 A1 | 2/2006 | Barbosa et al. | |
| 2013/0029987 A1 | 1/2013 | Bennett et al. | |
| 2015/0087673 A1 | 3/2015 | Hitoshi et al. | |

FOREIGN PATENT DOCUMENTS

| | | |
|---|---|---|
| WO | WO 03082855 | 10/2003 |
| WO | WO2004065378 | 8/2004 |
| WO | WO 2004067516 | 8/2004 |
| WO | WO 2005/092899 | 10/2005 |
| WO | WO 2006014482 | 2/2006 |
| WO | WO2006034872 | 4/2006 |
| WO | WO2007003596 | 1/2007 |
| WO | WO 2007076247 | 7/2007 |
| WO | WO2008107096 | 9/2008 |
| WO | WO 2009/071535 | 6/2009 |
| WO | WO2009115267 | 9/2009 |
| WO | WO2009150240 | 12/2009 |
| WO | WO 2010024430 | 3/2010 |
| WO | WO2010025831 | 3/2010 |
| WO | WO2010025833 | 3/2010 |
| WO | WO2010025850 | 3/2010 |
| WO | WO2010025851 | 3/2010 |
| WO | WO 2010090875 | 8/2010 |
| WO | WO 2010134533 | 11/2010 |
| WO | WO 2010141406 | 12/2010 |
| WO | WO2012062783 | 5/2012 |
| WO | WO2012145569 | 10/2012 |
| WO | WO 2012156467 | 11/2012 |
| WO | WO2013078468 | 5/2013 |
| WO | WO2013/092854 A1 | 6/2013 |
| WO | WO2013079494 | 6/2013 |
| WO | WO2013164321 | 11/2013 |
| WO | WO2013164323 | 11/2013 |
| WO | WO2012083122 | 12/2013 |
| WO | WO 2014044025 | 3/2014 |
| WO | WO 2014124230 | 8/2014 |

OTHER PUBLICATIONS

Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Hayashi et al., Protein Kinase C theta (PKCe): A key role in T cell life and death, Pharmacological Research 55 (2007), pp. 537-544.*
Pimlott, PubMed Abstract (Nucl Med Commun., 26(3):183-8), 2005.*
Hulikal, Deuterium Labeled Compounds in Drug Discovery Process, Abstract, 2010.*
Hoyer et al., Interleukin-2 in the development and control of inflammatory disease, Immunological Reviews, vol. 226, Issue 1, pp. 19-28 (2008).*
Modiano et al., Protein Kinase C Regulates Both Production and Secretion of Interleukin 2, The Journal of Biological Chemistry, vol. 266, No. 16, pp. 10552-10561 (1991).*

Abboushi et al., Ceramide Inhibits IL-2 Production by Preventing Protein Kinase C-Dependent NFkB Activation: Possible Role in Protein Kinase C theta Regulation, The Journal of Immunology, vol. 173, pp. 3193-3200 (2004).*
Belot et al., "Protein kinase cδ deficiency causes mendelian systemic lupus erythematosus with B cell-defective apoptosis and hyperproliferation," *Arthritis&Rheumatism*, 65:2161-2165 (2013).
Chand et al., "Protein kinase C-theta inhibitors: a novel therapy for inflammatory disorders," *Curr Pharmaceut Design*, 18(30):4725-4746 (2012).
Chaudhary et al., "PKCtheta: A potential therapeutic target for T-cell-mediated diseases," *Curr Opin Investig Drugs* 7(5):432-437 (2006).
Cohen, "Protein kinases—the major drug targets of the twenty-first century?" *Nature*, 1:309-315 (2002).
Cohen, "The role of protein phosphorylation in human health and disease. The Sir Hans Krebs Medal Lecture," *Eur. J. Biochem.*, 268:5001-5010 (2001).
Cywin et al., "Discovery of potent and selective PKC-theta inhibitors," *Bioorganic Medicinal Chemistry Letters*, 17:225-230 (2007).
Gaestel et al. "Protein kinases as small molecule inhibitor targets in inflammation," *Curr.Med.Chem.*14: 2214-223 (2007).
Grimminger et al., "Targeting non-malignant disorders with tyrosine kinase inhibitors," *Nat. Rev. Drug Disc.* 9(12):956-970 (2010).
Healy et al., "PKC-theta-deficient mice are protected from Th1-dependent antigen-induced arthritis," *J Immunol.* 177(3):1886-1893 (2006).
Isakov et al., "Protein kinase C(theta) in T cell activation," *Annu. Rev. Immunol.*, 20:761-94 (2002).
Kim et al., "PKC-theta knockout mice are protected from fat-induced insulin resistance," *J Clin Invest.*, 114(6):823-7 (2004).
Madaro et al., "PKC theta ablation improves healing in a mouse model of muscular dystrophy," *PLoS One*, 7(2):e31515 (2012).
Mecklenbrauker et al., "Protein kinase Cdelta controls self-antigen-induced B-cell tolerance," *Nature*, 416(6883):860-865 (2002).
Miles et al., "Overexpression of nPKC theta is inhibitory for agrin-induced nicotinic acetylcholine receptor clustering in C2C12 myotubes," *J Neurosci Res.* 71(2):188-195 (2003).
Miyamoto et al., "Increased proliferation of B cells and auto-immunity in mice lacking protein kinase Cdelta," *Nature*, 416(6883):865-9 (2002).
Powrie et al., "Cytokine regulation of T-cell function: potential for therapeutic intervention," *Immunology Today*, 14: 270 (1993).
Salek-Ardakani et al., "Protein kinase Ctheta controls Th1 cells in experimental autoimmune encephalomyelitis," *J Immunol.*, 175(11):7635-41(2005).
Skvara et al., "The PKC inhibitor AEB071 may be a therapeutic option for psoriasis *J Clin Invest*," *J. Clin. Invest.*, 118(9):3151-3159 (2008).
Villalba et al., "Protein kinase C-theta (PKCtheta), a potential drug target for therapeutic intervention with human T cell leukemias," *Current Cancer Targets*, 2(2):125-37 (2002).
Waldmann, "The IL-2/IL-2 receptor system: a target for rational immune intervention," *Immunol Today*, 14(6):264-70 (1993).
Wilen, S. H., et al., *Tetrahedron* 33:2725 (1977).
Zanin-Zhorov et al., "Protein kinase C-theta mediates negative feedback on regulatory T cell function," *Science*, 328(5976):372-726 (2010).
Zhang et al., "The yin and yang of protein kinase C-theta (PKCθ): a novel drug target for selective immunosuppression," *Adv. Pharmacol.*, 66:267-312 (2013).
Estrada et al., (2012), "Discovery of Highly Potent, Selective, and Brain-Penetrable Leucine-Rich Repeat Kinase 2 (LRRK2) Small Molecule Inhibitors," J. Med. Chem., 55 (22), pp. 9416-9433. DOI: 10.1021/jm301020q.

* cited by examiner

SUBSTITUTED DIAMINOPYRIMIDYL COMPOUNDS, COMPOSITIONS THEREOF, AND METHODS OF TREATMENT THEREWITH

This application claims the benefit of U.S. Provisional Application No. 61/919,216, filed Dec. 20, 2013, the entire contents of which are incorporated herein by reference.

FIELD

Provided herein are certain alkylheteroaryl-diaminopyrimidyl compounds, compositions comprising an effective amount of such compounds, and methods for treating or preventing PKC-theta mediated disorders, comprising administering an effective amount of such alkylheteroaryl-diaminopyrimidyl compounds to a subject in need thereof.

BACKGROUND

The connection between abnormal protein phosphorylation and the cause or consequence of diseases has been known for over 20 years. Accordingly, protein kinases have become a very important group of drug targets. [See Cohen, *Nature*, 1:309-315 (2002); Gaestel et al. *Curr. Med. Chem.* 14: 2214-223 (2007); Grimminger et al. *Nat. Rev. Drug Disc.* 9(12):956-970 (2010)]. Various protein kinase inhibitors have been used clinically in the treatment of a wide variety of diseases, such as cancer and chronic inflammatory diseases, including rheumatoid arthritis and psoriasis. [See Cohen, *Eur. J. Biochem.*, 268:5001-5010 (2001); Protein Kinase Inhibitors for the Treatment of Disease: The Promise and the Problems, *Handbook of Experimental Pharmacology*, Springer Berlin Heidelberg, 167 (2005)].

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein kinase C (PKC) family is a group of serine/threonine kinases that is encompasses twelve related isoenzymes. The PKCs are expressed in a wide range of tissues and cell types. The PKC isozymes can be classified into three groups. Group I (classical PKCs) includes the $Ca^{2+}$ and DAG (diacylglycerol) dependent isozymes: PKC-α, PKC-βI, PKC-βII and PKC-γ. Group II (novel PKCs) includes the $Ca^{2+}$ independent isozymes: PKC-δ (or PKC-delta), PKC-ε, PKC-η (or PKC-eta) and PKC-θ (or PKC-theta). Group III (atypical PKCs) includes the $Ca^{2+}$ and DAG independent isozymes: PKC-τ, PKC-ζ and PKC-μ (protein kinase D). The PKC-theta isoform of protein kinase C is selectively expressed in T lymphocytes and plays an important role in the T cell antigen receptor (TCR)-triggered activation of mature T cells, and the subsequent release of cytokines such as IL-2 and T cell proliferation (Isakov and Altman, Annu. Rev. Immunol., 2002, 20, 761-94). It has been well established that T cells play an important role in regulating the immune response (Powrie and Coffman, Immunology Today, 1993, 14, 270) and the activation of T cells is often the initiating event in a variety of immunological disorders. Upon activation via the TCR, T cells produce cytokines, including IL-2, leading to cell proliferation, differentiation, and effector function. Clinical studies with inhibitors of IL-2 have shown that interference with T cell activation and proliferation effectively suppresses immune response in vivo (Waldmann, Immunology Today, 1993, 14, 264). Accordingly, agents that inhibit T lymphocyte activation and subsequent cytokine production are therapeutically useful for selectively suppressing the immune response in a patient in need of such immunosuppression and therefore are useful in treating immunological disorders such as autoimmune and inflammatory diseases. PKC-theta activation has also been implicated in leukemia and thus inhibitors of PKC-theta may be useful for the treatment of leukemia (Villalba and Altman, Current Cancer Targets, 2002, 2, 125).

PKC-delta is closely related to PKC-theta, however, they exhibit different tissue expression patterns and serve unique cell functions. While PKC-theta is highly expressed in T-lymphocytes, NK cells and to a lesser extent in skeletal muscle, PKC-delta is highly expressed in myeloid cells and B-lymphocytes (ExPasy database; PRKCT and PRKCD). PKC-delta is important for the regulation of B-cell tolerance so that mice lacking PKC-delta exhibit increased numbers of self-reactive B-cells, elevated IL-6, express auto-antibodies to nuclear antigens, and exhibit a lupus-like pathology (Mecklenbrauker et al., Nature, 2002, 416, 860-865; Miyamoto et al., Nature, 2002, 416, 865-869). Furthermore, genetic examination of siblings with juvenile onset lupus identified a mutation in the PKC-delta (PRCKD) gene (Belot et al., Arthritis&Rheumatism, 2013, 65, 2161-2165). For this reason, inhibition of PKC-delta may be detrimental in the treatment of autoimmune disease and there is rationale for avoiding chronic inhibition of this enzyme. Selective inhibition of PKC-delta for therapy has previously been clinically evaluated (delcasertib; Kai Pharmaceuticals) in the context of acute treatment of ischemia-reperfusion injury.

There remains a need to develop effective therapeutic agents for the majority of the diseases and disorders associated with activation of PKC-theta (Chaudhary and Kasaian, Curr Opin Investig Drugs 2006 7(5):432-437; Zhang, E. Y, Kong, K., and Altman, A., Adv Pharmacol 2013, Vol 66, 267-312; Chand, S., et. Al. Curr Pharmaceut Design 212, Vol 18(30):4725-4746). Accordingly, it would be beneficial to provide safe and effective compounds that are useful as selective inhibitors of PKC-theta and thus in the treatment of disorders and diseases associated with activation of PKC-theta. In particular there remains a need for effective therapeutic agents that are selective inhibitors of PKC-theta, without affecting other members of the PKC family, such as PKC-delta and/or PKC-eta.

Citation or identification of any reference in Section 2 of this application is not to be construed as an admission that the reference is prior art to the present application.

SUMMARY

Provided herein are compounds having the following formula (I):

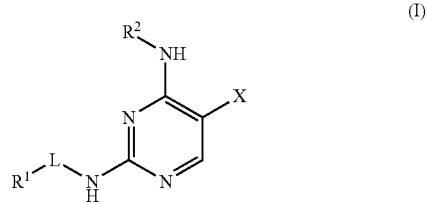

or a pharmaceutically acceptable salt, tautomer, isotopologue, or stereoisomer thereof, wherein L, X, $R^1$, and $R^2$ are as defined herein.

In one aspect, provided herein are Diaminopyrimidyl Compounds as described in the instant disclosure, such as, for example, a compound of formula (I), or a compound from Table 1 or Table 2, or a pharmaceutically acceptable salt, tautomer, isotopologue, or stereoisomer thereof.

In one aspect, provided herein are pharmaceutical compositions comprising an effective amount of a Diaminopyrimidyl Compound, as described herein, and a pharmaceutically acceptable carrier, excipient or vehicle. In some embodiments the pharmaceutical composition is suitable for oral, parenteral, mucosal, transdermal or topical administration.

In one aspect, provided herein are methods or compounds for use in methods for treating or preventing PKC-theta mediated disorders, such as graft-versus-host disease, organ transplant rejection, psoriasis, Duchenne muscular dystrophy, rheumatoid arthritis, diabetes, insulin resistance, myasthenia gravis, multiple sclerosis, colitis, psoriatic arthritis, ankylosing spondylitis, atopic dermatitis, Sjogren syndrome, asthma, or lupus, wherein the methods comprise administering to a subject in need thereof an effective amount of a Diaminopyrimidyl Compound as described herein.

In one aspect, provided herein are methods for inhibiting a kinase, for example PKC-theta, in a cell expressing said kinase, comprising contacting said cell with an effective amount of a Diaminopyrimidyl Compound, as described herein. In some embodiments, the Diaminopyrimidyl Compounds inhibit PKC-theta selectively over PKC-delta. In other such embodiments, the Diaminopyrimidyl Compounds inhibit PKC-theta selectively over PKC-delta and/or PKC-eta.

In another aspect provided herein are methods for preparing Diaminopyrimidyl Compounds as described herein.

The present embodiments can be understood more fully by reference to the detailed description and examples, which are intended to exemplify non-limiting embodiments.

DETAILED DESCRIPTION

Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. Examples of unsaturated alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are as defined above. Substituted cycloalkylalkyl groups may be substituted at the alkyl, the cycloalkyl, or both the alkyl and the cycloalkyl portions of the group. Representative cycloalkylalkyl groups include but are not limited to methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopentyl, propylcyclohexyl and the like.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocyclylalkyl groups include but are not limited to 4-ethyl-morpholinyl, 4-propylmorpholinyl, furan-2-yl methyl, furan-3-yl methyl, pyridin-3-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: —NH$_2$.

An "alkylamino" group is a radical of the formula: —NH-alkyl or —N(alkyl)$_2$, wherein each alkyl is independently as defined above.

A "carboxy" group is a radical of the formula: —C(O)OH.

An "aminocarbonyl" group is a radical of the formula: —C(O)N(R$^\#$)$_2$, —C(O)NH(R$^\#$) or —C(O)NH$_2$, wherein each R$^\#$ is independently a substituted or unsubstituted alkyl, cycloalkyl, aryl, aralkyl, heterocyclyl or heterocyclyl group as defined herein.

An "acylamino" group is a radical of the formula: —NHC(O)(R$^\#$) or —N(alkyl)C(O)(R$^\#$), wherein each alkyl and R$^\#$ are independently as defined above.

A "sulfonylamino" group is a radical of the formula: —NHSO$_2$(R$^\#$) or —N(alkyl)SO$_2$(R$^\#$), wherein each alkyl and R$^\#$ are defined above.

A "urea" group is a radical of the formula: —N(alkyl)C(O)N(R$^\#$)$_2$, —N(alkyl)C(O)NH(R$^\#$), —N(alkyl)C(O)NH$_2$, —NHC(O)N(R$^\#$)$_2$, —NHC(O)NH(R$^\#$), or —NH(CO)NHR$^\#$, wherein each alkyl and R$^\#$ are independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

As used herein, the term "Diaminopyrimidyl Compound" refers to compounds of formula (I) as well as to further embodiments provided herein. In one embodiment, a "Diaminopyrimidyl Compound" is a compound set forth in Tables 1, or 2. The term "Diaminopyrimidyl Compound" includes pharmaceutically acceptable salts, tautomers, isotopologues, and stereoisomers of the compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "stereoisomer" or "stereomerically pure" means one stereoisomer of a Diaminopyrimidyl Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Diaminopyrimidyl Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Diaminopyrimidyl Compounds, as well as the use of mixtures of those forms, are encompassed by the embodiments disclosed herein. For example, mixtures comprising equal or unequal amounts of the enantiomers of a particular Diaminopyrimidyl Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Diaminopyrimidyl Compounds can include E and Z isomers, or a mixture thereof, and cis and trans isomers or a mixture thereof. In certain embodiments, the Diaminopyrimidyl Compounds are isolated as either the E or Z isomer. In other embodiments, the Diaminopyrimidyl Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

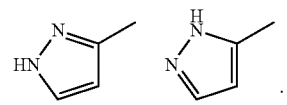

As readily understood by one skilled in the art, a wide variety of functional groups and other structures may exhibit tautomerism and all tautomers of compounds of formula (I) are within the scope of the present invention.

It should also be noted the Diaminopyrimidyl Compounds can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom.

Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Diaminopyrimidyl Compounds as described herein, whether radioactive or not, are intended to be encompassed within the scope of the embodiments provided herein. In some embodiments, there are provided isotopologues of the Diaminopyrimidyl Compounds, for example, the isotopologues are deuterium, carbon-13, or nitrogen-15 enriched Diaminopyrimidyl Compounds.

It is understood that, independently from the selection of substituents for each of L, X, $R^1$ or $R^2$, stereomerical or isotopic composition, each Diaminopyrimidyl Compound referred to herein can be provided in the form of any of the pharmaceutically acceptable salts discussed herein. Equally, it is understood that the isotopic composition may vary independently from the stereomerical composition of each Diaminopyrimidyl Compound referred to herein. Further, the isotopic composition, while being restricted to those elements present in the respective Diaminopyrimidyl Compound or salt thereof, may otherwise vary independently from the selection of substituents for each of L, X, $R^1$ or $R^2$ or from the selection of the pharmaceutically acceptable salt of the respective Diaminopyrimidyl Compound.

It should be noted that if there is a discrepancy between a depicted structure and a name for that structure, the depicted structure is to be accorded more weight.

As used herein, "inhibit" and "inhibition" mean that a specified response of a designated activity (e.g., kinase or phosphorylation activity) is comparatively decreased in the presence of a Diaminopyrimidyl Compound. Inhibition of kinase activity, for example PKC-theta activity, can be determined by the biochemical assays described herein.

As used herein, "selective" or "selectively", means having an activity preference for a specific target, for example a kinase such as PKC-theta, over other targets, for example, a kinase such as PKC-delta and/or PKC-eta, which can be quantified based upon assays which demonstrate kinase activity, such biochemical assays disclosed herein. A Diaminopyrimidyl Compound's selectivity is determined from a comparison of its $IC_{50}$ (or $EC_{50}$ or $ED_{50}$ if using an organism assay) at the relevant targets. For example, a Diaminopyrimidyl Compound having an $IC_{50}$ of 50 nM for PKC-delta and an $IC_{50}$ of 10 nM for PKC-theta has a selectivity ratio for PKC-delta over PKC-theta of 5:1, or is 5-fold selective for PKC-theta over PKC-delta. In some embodiments, Diaminopyrimidyl Compounds are about 5-fold, about 10-fold, about 15-fold, about 20-fold, about 50-fold, about 100-fold, about 150-fold, about 200-fold, about 250-fold, about 300-fold, or about 500-fold selective for PKC-theta over PKC-delta. In others, Diaminopyrimidyl Compounds are about 5-fold, about 10-fold, about 15-fold, about 20-fold, about 50-fold, about 100-fold, about 150-fold, about 200-fold, about 250-fold, about 300-fold, or about 500-fold selective for PKC-theta over PKC-delta and PKC-eta.

The role of PKC-theta in disorders have been reported. For example, PKC-theta mediated disorders include psoriasis (Skvara et al., J Clin Invest. 2008; 118(9):3151-3159), Duchenne muscular dystrophy (Madaro et al, PLoS One 2012; 7(2):e31515), rheumatoid arthritis (Healy et al., J Immunol. 2006; 177(3):1886-1893; Zanin-Zhorov et al., Science 2010; 328(5976):372-726), Type 2 diabetes and insulin resistance (Kim et al., J Clin Invest. 2004; 114(6): 823-7), myasthenia gravis (Miles and Wagner, J Neurosci Res. 2003; 71(2):188-195), multiple sclerosis (Salek-Ardakani et al., J Immunol. 2005; 175(11):7635-41), and colitis ((Zanin-Zhorov et al., Science 2010; 328(5976):372-726).

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a PKC-theta mediated disorder, such as, for example, graft-versus-host disease, organ transplant rejection, psoriasis, Duchenne muscular dystrophy, rheumatoid arthritis, diabetes, insulin resistance, myasthenia gravis, multiple sclerosis, colitis, psoriatic arthritis, ankylosing spondylitis, atopic dermatitis, Sjogren syndrome, asthma, or lupus. In some embodiments, "treating" means an alleviation, in whole or in part, of a disorder, disease or condition, or symptoms associated with a disorder, disease or condition, for example, a PKC-theta mediated disorder, such as, for example, graft-versus-host disease, organ transplant rejection, psoriasis, Duchenne muscular dystrophy, rheumatoid arthritis, diabetes, insulin resistance, myasthenia gravis, multiple sclerosis, colitis, psoriatic arthritis, ankylosing spondylitis, atopic dermatitis, Sjogren syndrome, asthma, or lupus, or a slowing, or halting of further progression or worsening of those symptoms. In another embodiment, "treating" means and alleviation, in whole or in part, of a disorder, disease or condition, or symptoms associated with a condition, treatable or preventable by inhibition of PKC-theta. In another embodiment, "treating" means and alleviation, in whole or in part, of a disorder, disease or condition, or symptoms associated with a condition, treatable or preventable by inhibition of PKC-theta selectively over PKC-delta. In yet another embodiment, "treating" means and alleviation, in whole or in part, of a disorder, disease or condition, or symptoms associated with a condition, treatable or preventable by inhibition of PKC-theta selectively over PKC-delta and/or PKC-eta.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a PKC-theta mediated disorder, such as, for example, graft-versus-host disease, organ transplant rejection, psoriasis, Duchenne muscular dystrophy, rheumatoid arthritis, diabetes, insulin resistance, myasthenia gravis, multiple sclerosis, colitis, psoriatic arthritis, ankylosing spondylitis, atopic dermatitis, Sjogren syndrome, asthma, or lupus, as described herein, or symptoms thereof.

The term "effective amount" in connection with a Diaminopyrimidyl Compound means an amount capable of treating or preventing a disorder, disease or condition, or symptoms thereof, disclosed herein.

The term "subject" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human, in another embodiment a cell from any one of the foregoing animals. In one embodiment, a subject is a non-human animal, in another embodiment a non-human mammal. In one embodiment, a subject is a human having or at risk for having a condition, treatable or preventable by inhibition of a kinase, for example PKC-theta, or a symptom thereof.

Diaminopyrimidyl Compounds

Provided herein are compounds having the following formula (I):

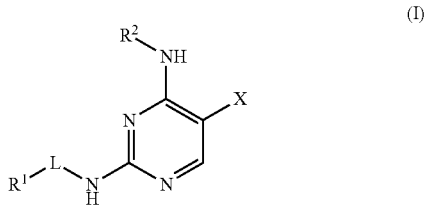

a pharmaceutically acceptable salt, tautomer, isotopologue, or stereoisomer thereof,
wherein:
X is CN or $CF_3$;
L is ($C_{1-4}$ alkyl);
$R^1$ is substituted or unsubstituted heteroaryl; and
$R^2$ is substituted or unsubstituted cycloalkyl.

In some embodiments of compounds of formula (I), X is CN. In others, X is $CF_3$.

In some embodiments of compounds of formula (I), L is $CH_2$. In another, L is $CH_2CH_2$ or $CH_2CH_2CH_2$. In still another, L is $CH_2$, $CH_2CH_2$ or $CH_2CH_2CH_2$.

In some embodiments of compounds of formula (I), X is CN and L is $CH_2$ ($C_1$ alkyl). In others, X is $CF_3$ and L is $CH_2$ ($C_1$ alkyl). In some embodiments of compounds of formula (I), X is CN and L is $CH_2CH_2$ ($C_2$ alkyl). In others, X is $CF_3$ and L is $CH_2CH_2$ ($C_2$ alkyl). In some embodiments of compounds of formula (I), X is CN and L is $CH_2CH_2CH_2$ ($C_3$ alkyl). In others, X is $CF_3$ and L is $CH_2CH_2CH_2$ ($C_3$ alkyl). In some embodiments of compounds of formula (I), X is CN and L is $CH_2CH_2CH_2CH_2$ ($C_4$ alkyl). In others, X is $CF_3$ and L is $CH_2CH_2CH_2CH_2$ ($C_4$ alkyl).

In some embodiments of compounds of formula (I), X is CN, L is $CH_2$ ($C_1$ alkyl) and $R^1$ is substituted heteroaryl. In others, X is $CF_3$, L is $CH_2$ ($C_1$ alkyl) and $R^1$ is substituted heteroaryl. In some embodiments of compounds of formula (I), X is CN, L is $CH_2CH_2$ ($C_2$ alkyl) and $R^1$ is substituted heteroaryl. In others, X is $CF_3$, L is $CH_2CH_2$ ($C_2$ alkyl) and $R^1$ is substituted heteroaryl. In some embodiments of compounds of formula (I), X is CN, L is $CH_2CH_2CH_2$ ($C_3$ alkyl) and $R^1$ is substituted heteroaryl. In others, X is $CF_3$, L is $CH_2CH_2CH_2$ ($C_3$ alkyl) and $R^1$ is substituted heteroaryl. In some embodiments of compounds of formula (I), X is CN, L is $CH_2CH_2CH_2CH_2$ ($C_4$ alkyl) and $R^1$ is substituted heteroaryl. In others, X is $CF_3$, L is $CH_2CH_2CH_2CH_2$ ($C_4$ alkyl) and $R^1$ is substituted heteroaryl. In some embodiments of compounds of formula (I), X is CN, L is $CH_2$ ($C_1$ alkyl) and $R^1$ is unsubstituted heteroaryl. In others, X is $CF_3$, L is $CH_2$ ($C_1$ alkyl) and $R^1$ is unsubstituted heteroaryl. In some embodiments of compounds of formula (I), X is CN, L is $CH_2CH_2$ ($C_2$ alkyl) and $R^1$ is unsubstituted heteroaryl. In others, X is $CF_3$, L is $CH_2CH_2$ ($C_2$ alkyl) and $R^1$ is unsubstituted heteroaryl. In some embodiments of compounds of formula (I), X is CN, L is $CH_2CH_2CH_2$ ($C_3$ alkyl) and $R^1$ is unsubstituted heteroaryl. In others, X is $CF_3$, L is $CH_2CH_2CH_2$ ($C_3$ alkyl) and $R^1$ is unsubstituted heteroaryl. In some embodiments of compounds of formula (I), X is CN, L is $CH_2CH_2CH_2CH_2$ ($C_4$ alkyl) and $R^1$ is unsubstituted heteroaryl. In others, X is $CF_3$, L is $CH_2CH_2CH_2CH_2$ ($C_4$ alkyl) and $R^1$ is unsubstituted heteroaryl.

In some embodiments of compounds of formula (I), X is CN, L is $CH_2$ ($C_1$ alkyl), $R^1$ is substituted heteroaryl and $R^2$ is substituted cycloalkyl. In others, X is $CF_3$, L is $CH_2$ ($C_1$ alkyl), $R^1$ is substituted heteroaryl and $R^2$ is substituted cycloalkyl. In some embodiments of compounds of formula (I), X is CN, L is $CH_2CH_2$ ($C_2$ alkyl), $R^1$ is substituted heteroaryl and $R^2$ is substituted cycloalkyl. In others, X is $CF_3$, L is $CH_2CH_2$ ($C_2$ alkyl), $R^1$ is substituted heteroaryl and $R^2$ is substituted cycloalkyl. In some embodiments of compounds of formula (I), X is CN, L is $CH_2CH_2CH_2$ ($C_3$ alkyl), $R^1$ is substituted heteroaryl and $R^2$ is substituted cycloalkyl. In others, X is $CF_3$, L is $CH_2CH_2CH_2$ ($C_3$ alkyl), $R^1$ is substituted heteroaryl and $R^2$ is substituted cycloalkyl. In some embodiments of compounds of formula (I), X is CN, L is $CH_2CH_2CH_2CH_2$ ($C_4$ alkyl), $R^1$ is substituted heteroaryl and $R^2$ is substituted cycloalkyl. In others, X is $CF_3$, L is $CH_2CH_2CH_2CH_2$ ($C_4$ alkyl), $R^1$ is substituted heteroaryl and $R^2$ is substituted cycloalkyl. In some embodiments of compounds of formula (I), X is CN, L is $CH_2$ ($C_1$ alkyl), $R^1$ is unsubstituted heteroaryl and $R^2$ is substituted cycloalkyl. In others, X is $CF_3$, L is $CH_2$ ($C_1$ alkyl), $R^1$ is unsubstituted heteroaryl and $R^2$ is substituted cycloalkyl. In some embodiments of compounds of formula (I), X is CN, L is $CH_2CH_2$ ($C_2$ alkyl), $R^1$ is unsubstituted heteroaryl and $R^2$ is substituted cycloalkyl. In others, X is $CF_3$, L is $CH_2CH_2$ ($C_2$ alkyl), $R^1$ is unsubstituted heteroaryl and $R^2$ is substituted cycloalkyl. In some embodiments of compounds of formula (I), X is CN, L is $CH_2CH_2CH_2$ ($C_3$ alkyl), $R^1$ is unsubstituted heteroaryl and $R^2$ is substituted cycloalkyl. In others, X is $CF_3$, L is $CH_2CH_2CH_2$ ($C_3$ alkyl), $R^1$ is unsubstituted heteroaryl and $R^2$ is substituted cycloalkyl. In some embodiments of compounds of formula (I), X is CN, L is $CH_2CH_2CH_2CH_2$ ($C_4$ alkyl), $R^1$ is unsubstituted heteroaryl and $R^2$ is substituted cycloalkyl. In others, X is $CF_3$, L is $CH_2CH_2CH_2CH_2$ ($C_4$ alkyl), $R^1$ is unsubstituted heteroaryl and $R^2$ is substituted cycloalkyl.

In some embodiments of compounds of formula (I), X is CN, L is $CH_2$ ($C_1$ alkyl), $R^1$ is substituted heteroaryl and $R^2$ is unsubstituted cycloalkyl. In others, X is $CF_3$, L is $CH_2$ ($C_1$ alkyl), $R^1$ is substituted heteroaryl and $R^2$ is unsubstituted cycloalkyl. In some embodiments of compounds of formula (I), X is CN, L is $CH_2CH_2$ ($C_2$ alkyl), $R^1$ is substituted heteroaryl and $R^2$ is unsubstituted cycloalkyl. In others, X is $CF_3$, L is $CH_2CH_2$ ($C_2$ alkyl), $R^1$ is substituted heteroaryl and $R^2$ is unsubstituted cycloalkyl. In some embodiments of compounds of formula (I), X is CN, L is $CH_2CH_2CH_2$ ($C_3$ alkyl), $R^1$ is substituted heteroaryl and $R^2$ is unsubstituted cycloalkyl. In others, X is $CF_3$, L is $CH_2CH_2CH_2$ ($C_3$ alkyl), $R^1$ is substituted heteroaryl and $R^2$ is unsubstituted cycloalkyl. In some embodiments of compounds of formula (I), X is CN, L is $CH_2CH_2CH_2CH_2$ ($C_4$ alkyl), $R^1$ is substituted heteroaryl and $R^2$ is unsubstituted cycloalkyl. In others, X is $CF_3$, L is $CH_2CH_2CH_2CH_2$ ($C_4$ alkyl), $R^1$ is substituted heteroaryl and $R^2$ is unsubstituted cycloalkyl. In some embodiments of compounds of formula (I), X is CN, L is $CH_2$ ($C_1$ alkyl), $R^1$ is unsubstituted heteroaryl and $R^2$ is unsubstituted cycloalkyl. In others, X is $CF_3$, L is $CH_2$ ($C_1$ alkyl), $R^1$ is unsubstituted heteroaryl and $R^2$ is unsubstituted cycloalkyl. In some embodiments of compounds of formula (I), X is CN, L is $CH_2CH_2$ ($C_2$ alkyl), $R^1$ is unsubstituted heteroaryl and $R^2$ is unsubstituted cycloalkyl. In others, X is $CF_3$, L is $CH_2CH_2$ ($C_2$ alkyl), $R^1$ is unsubstituted heteroaryl and $R^2$ is unsubstituted cycloalkyl. In some embodiments of compounds of formula (I), X is CN, L is $CH_2CH_2CH_2$ ($C_3$ alkyl), $R^1$ is unsubstituted heteroaryl and $R^2$ is unsubstituted cycloalkyl. In others, X is $CF_3$, L is $CH_2CH_2CH_2$ ($C_3$ alkyl), $R^1$ is unsubstituted heteroaryl and $R^2$ is unsubstituted cycloalkyl. In some embodiments of compounds of formula (I), X is CN, L is CH$_2$CH$_2$CH$_2$CH$_2$ (C$_4$ alkyl), R$^1$ is unsubstituted heteroaryl and R$^2$ is unsubstituted cycloalkyl. In others, X is CF$_3$, L is CH$_2$CH$_2$CH$_2$CH$_2$ (C$_4$ alkyl), R$^1$ is unsubstituted heteroaryl and R$^2$ is unsubstituted cycloalkyl.

In some embodiments of compounds of formula (I), R$^1$ is a substituted or unsubstituted pyridyl, pyridyl-1-oxide, or pyrimidyl. In some such embodiments, R$^1$ is substituted with one or more halogen, —OR$^3$, substituted or unsubstituted C$_{1-4}$ alkyl, or substituted or unsubstituted aryl, wherein R$^3$ is H, substituted or unsubstituted C$_{1-6}$ alkyl, or substituted or unsubstituted aryl. In some such embodiments, R$^1$ is substituted with one or more halogen, —OR$^3$, substituted or unsubstituted C$_{1-4}$ alkyl, or substituted or unsubstituted aryl, wherein each R$^3$ is independently H, substituted or unsubstituted C$_{1-6}$ alkyl, or substituted or unsubstituted aryl. In some embodiments, R$^1$ is substituted with one or more F, Cl, Br, I, methyl, ethyl, propyl, isopropyl, butyl, isobutyl, t-butyl, phenyl, naphthyl, —CH$_2$F, —CHF$_2$, —CF$_3$, —CHFCH$_3$, —CF$_2$CH$_3$, —C(CH$_3$)$_2$F, —OCH$_3$, —OCH$_2$F, —OCHF$_2$, —OCF$_3$, —OCH$_2$CH$_3$, —OCH$_2$CH$_2$F, —OCH$_2$CHF$_2$, —OCH$_2$CF$_3$, —OCH$_2$CH(CH$_3$)F, —OCH$_2$C(CH$_3$)$_2$F, —OCH$_2$C(CH$_3$)F$_2$, —OCH$_2$CH$_2$CF$_3$, or —O-phenyl, wherein each phenyl is optionally substituted with halogen or substituted or unsubstituted C$_{1-4}$ alkyl. For example, R$^1$ is substituted with one or more F, methyl, ethyl, isopropyl, phenyl, —CF$_3$, —CF$_2$CH$_3$, —C(CH$_3$)$_2$F, —OCH$_3$, —OCH$_2$CH$_3$, —OCH$_2$CH$_2$F, —OCH$_2$CHF$_2$, —OCH$_2$C(CH$_3$)F$_2$, —OCH$_2$CH$_2$CF$_3$, or —O-phenyl, wherein each phenyl is optionally substituted with F or methyl.

In other embodiments, R$^1$ is a substituted or unsubstituted pyrazinyl. In some embodiments, R$^1$ is a substituted or unsubstituted pyridyl, pyridyl-1-oxide, pyrimidyl or pyrazinyl. In some such embodiments, R$^1$ is substituted with one or more Cl, or —OCH$_2$CF$_3$. In other such embodiments, R$^1$ is substituted with one or more F, Cl, methyl, ethyl, isopropyl, phenyl, —CF$_3$, —CF$_2$CH$_3$, —C(CH$_3$)$_2$F, —OCH$_3$, —OCH$_2$CH$_3$, —OCH$_2$CF$_3$, —OCH$_2$CH$_2$F, —OCH$_2$CHF$_2$, —OCH$_2$C(CH$_3$)F$_2$, —OCH$_2$CH$_2$CF$_3$, or —O-phenyl, wherein each phenyl is optionally substituted with F or methyl.

In some embodiments of compounds of formula (I), R$^1$ is selected from

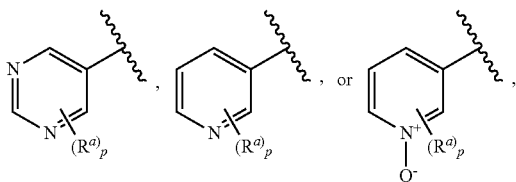

wherein R$^a$ is selected from halogen, —OR$^3$, substituted or unsubstituted C$_{1-4}$ alkyl, or substituted or unsubstituted aryl, wherein R$^3$ is H, substituted or unsubstituted C$_{1-6}$ alkyl, or substituted or unsubstituted aryl; and p is 0-3. In other embodiments, R$^a$ is selected from halogen, —OR$^3$, substituted or unsubstituted C$_{1-4}$ alkyl, substituted or unsubstituted aryl, wherein each R$^3$ is independently H, substituted or unsubstituted C$_{1-6}$ alkyl, or substituted or unsubstituted aryl; and p is 0-3.

In some such embodiments, R$^a$ is selected from F, Cl, Br, I, methyl, ethyl, propyl, isopropyl, butyl, isobutyl, t-butyl, phenyl, naphthyl, —CH$_2$F, —CHF$_2$, —CF$_3$, —CHFCH$_3$, —CF$_2$CH$_3$, —C(CH$_3$)$_2$F, —OCH$_3$, —OCH$_2$F, —OCHF$_2$, —OCF$_3$, —OCH$_2$CH$_3$, —OCH$_2$CH$_2$F, —OCH$_2$CHF$_2$, —OCH$_2$CF$_3$, —OCH$_2$CH(CH$_3$)F, —OCH$_2$C(CH$_3$)$_2$F, —OCH$_2$C(CH$_3$)F$_2$, —OCH$_2$CH$_2$CF$_3$, or —O-phenyl, wherein each phenyl is optionally substituted with halogen or substituted or unsubstituted C$_{1-4}$ alkyl; and p is 1-2. For example, R$^a$ is selected from F, methyl, ethyl, isopropyl, phenyl, —CF$_3$, —CF$_2$CH$_3$, —C(CH$_3$)$_2$F, —OCH$_3$, —OCH$_2$CH$_3$, —OCH$_2$CH$_2$F, —OCH$_2$CHF$_2$, —OCH$_2$C(CH$_3$)F$_2$, —OCH$_2$CH$_2$CF$_3$, or —O-phenyl, wherein each phenyl is optionally substituted with F or methyl and p is 1 or 2.

In some other embodiments of compounds of formula (I), R$^a$ is selected from Cl, or —OCH$_2$CF$_3$. In some embodiments of compounds of formula (I), R$^a$ is selected from F, Cl, methyl, ethyl, isopropyl, phenyl, —CF$_3$, —CF$_2$CH$_3$, —C(CH$_3$)$_2$F, —OCH$_3$, —OCH$_2$CH$_3$, OCH$_2$CF$_3$, —OCH$_2$CH$_2$F, —OCH$_2$CHF$_2$, —OCH$_2$C(CH$_3$)F$_2$, —OCH$_2$CH$_2$CF$_3$, or —O-phenyl, wherein each phenyl is optionally substituted with F or methyl and p is 1 or 2.

In some embodiments of compounds of formula (I), R$^1$ is selected from

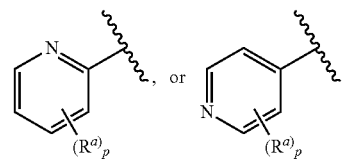

wherein R$^a$ is selected from halogen, —OR$^3$, substituted or unsubstituted C$_{1-4}$ alkyl, or substituted or unsubstituted aryl, wherein each R$^3$ is independently H, substituted or unsubstituted C$_{1-6}$ alkyl, or substituted or unsubstituted aryl; and p is 0-3. For example, R$^a$ is selected from F, methyl, ethyl, isopropyl, phenyl, —CF$_3$, —CF$_2$CH$_3$, —C(CH$_3$)$_2$F, —OCH$_3$, —OCH$_2$CH$_3$, —OCH$_2$CH$_2$F, —OCH$_2$CHF$_2$, —OCH$_2$C(CH$_3$)F$_2$, —OCH$_2$CH$_2$CF$_3$, or —O-phenyl, wherein each phenyl is optionally substituted with F or methyl and p is 1 or 2. For example, R$^a$ is selected from methyl, —CF$_3$, or —OCH$_2$CH$_3$.

In some embodiments of compounds of formula (I), R$^1$ is a substituted or unsubstituted indolyl, indolinonyl, benzoxazolyl, pyrrolopyridyl, indazolyl, benzimidazolyl, dihydrobenzimidazolonyl, or quinolyl. In some such embodiments, R$^1$ is substituted with one or more halogen, CN, —OR$^3$, substituted or unsubstituted C$_{1-4}$ alkyl, or substituted or unsubstituted aryl, wherein each R$^3$ is independently H, substituted or unsubstituted C$_{1-6}$ alkyl, or substituted or unsubstituted aryl. In some such embodiments, R$^1$ is substituted with one or more F, Cl, CN, methyl, ethyl, —CH$_2$SO$_2$NHCH$_3$, —OH, —OCH$_3$, or OCF$_3$.

In some embodiments of compounds of formula (I), R$^1$ is selected from

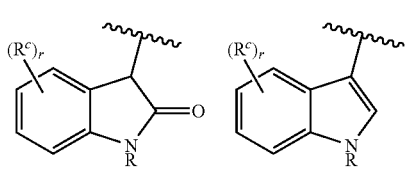

-continued

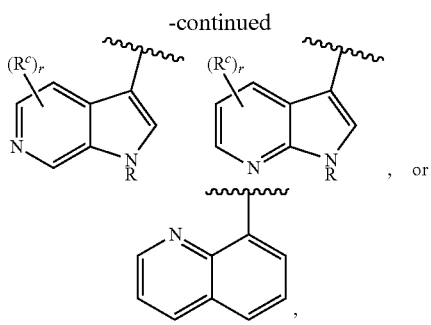

wherein $R^c$ is selected from halogen, CN, —$OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl; R is H or $C_{1-4}$ alkyl; and r is 0-3. For example, $R^c$ is selected from F, Cl, CN, methyl, ethyl, —$CH_2SO_2NHCH_3$, —OH, —$OCH_3$, or —$OCF_3$.

In some embodiments of compounds of formula (I), $R^1$ is a substituted or unsubstituted furanyl, pyrrolyl, thiophenyl, oxazolyl, pyrazolyl, imidazolyl, oxadiazolyl, or triazolyl. In some such embodiments, $R^1$ is substituted with one or more halogen, CN, —$OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl. In some such embodiments, $R^1$ is substituted with one or more CN, methyl, ethyl, —$CF_3$, or —$CH_2OCH_3$.

In some embodiments of compounds of formula (I), $R^1$ is selected from

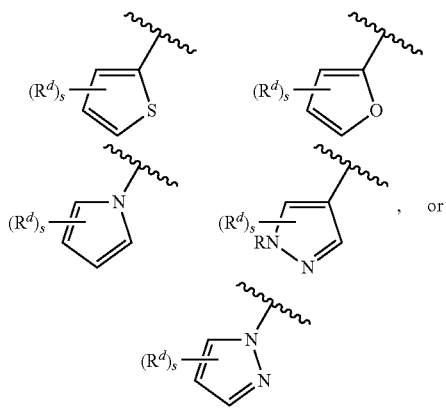

wherein $R^d$ is selected from halogen, CN, —$OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl; R is independently H or $C_{1-4}$ alkyl; and s is 0-3. For example, $R^d$ is selected from CN, methyl, ethyl, —$CF_3$, or —$CH_2OCH_3$.

In some embodiments, $R^1$ is a substituted or unsubstituted pyridyl, pyridyl-1-oxide, pyrimidyl, pyridazinyl, indolyl, indolinonyl, benzoxazolyl, pyrrolopyridyl, indazolyl, benzimidazolyl, dihydrobenzimidazolonyl, quinolyl, furanyl, pyrrolyl, thiophenyl, oxazolyl, pyrazolyl, imidazolyl, oxadiazolyl, or triazolyl. In some such embodiments, $R^1$ is substituted with one or more halogen, CN, —$OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl. In some such embodiments, $R^1$ is substituted with one or more F, Cl, CN, methyl, ethyl, isopropyl, phenyl, —$CF_3$, —$CF_2CH_3$, —$C(CH_3)_2F$, —$CH_2OCH_3$, —$CH_2SO_2NHCH_3$, —OH, —$OCH_3$, —$OCF_3$, —$OCH_2CH_3$, —$OCH(CH_3)_2$, —$OCH_2CF_3$, —$OCH_2CH_2F$, —$OCH_2CHF_2$, —$OCH_2C(CH_3)F_2$, —$OCH_2CH_2CF_3$, or —O-phenyl, wherein each phenyl is optionally substituted with F or methyl.

In some embodiments of compounds of formula (I), $R^2$ is substituted or unsubstituted $C_{3-12}$ cycloalkyl. For example, $R^2$ is substituted or unsubstituted cyclopropyl, cyclobutyl, cyclopentyl, cyclohexyl, cycloheptyl, or adamantyl. In some such embodiments, $R^2$ is substituted with one or more $C_{1-4}$ alkyl, —$OR^4$, or —$C(=O)NR_2$, wherein $R^4$ is H or $C_{1-6}$ alkyl, and each R is independently H or $C_{1-4}$ alkyl. In other such embodiments, $R^2$ is substituted with one or more $C_{1-4}$ alkyl, —$OR^4$, or —$C(=O)NR_2$, wherein each $R^4$ is independently H or $C_{1-6}$ alkyl, and each R is independently H or $C_{1-4}$ alkyl. In others, $R^2$ is substituted with one or more methyl, ethyl, propyl, isopropyl, —$CH_2OH$, —$CH(CH_3)OH$, —$C(CH_3)_2OH$, —OH, —$OCH_3$, —$OCH_2CH_3$, —$C(=O)NH_2$, —$C(=O)NHCH_3$, or —$C(=O)N(CH_3)_2$. For example, $R^2$ is substituted with one or more methyl, —$CH_2OH$, —$C(CH_3)_2OH$, —OH, —$OCH_3$, or —$C(=O)NHCH_3$.

In some embodiments of compounds of formula (I), $R^2$ is selected from

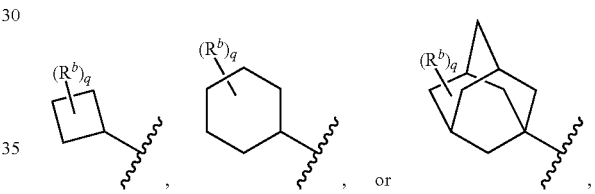

wherein $R^b$ is selected from $C_{1-4}$ alkyl, —$OR^4$, or —$C(=O)NR_2$, wherein $R^4$ is H or $C_{1-6}$ alkyl, each R is independently H or $C_{1-4}$ alkyl, and q is 0-6. In other embodiments, $R^b$ is selected from $C_{1-4}$ alkyl, —$OR^4$, or —$C(=O)NR_2$, wherein each $R^4$ is independently H or $C_{1-6}$ alkyl, each R is independently H or $C_{1-4}$ alkyl, and q is 0-6.

In some such embodiments, $R^b$ is selected from methyl, ethyl, propyl, isopropyl, —$CH_2OH$, —$CH(CH_3)OH$, —$C(CH_3)_2OH$, —OH, —$OCH_3$, —$OCH_2CH_3$, —$C(=O)NH_2$, —$C(=O)NHCH_3$, or —$C(=O)N(CH_3)_2$, and q is 1-5. In others, $R^b$ is selected from methyl, —$CH_2OH$, —$C(CH_3)_2OH$, —OH, —$OCH_3$, or —$C(=O)NHCH_3$, and q is 1-5. In some such embodiments, $R^b$ is selected from triazolyl, —$C(=O)NH_2$, or —$C(=O)N(CH_3)_2$. In others, $R^b$ is selected from methyl, triazolyl, —$CH_2OH$, —$C(CH_3)_2OH$, —OH, —$OCH_3$, —$C(=O)NH_2$, —$C(=O)NHCH_3$, or —$C(=O)N(CH_3)_2$.

In some embodiments of compounds of formula (I), $R^2$ is selected from

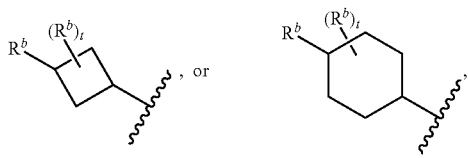

wherein $R^b$ is selected from $C_{1-4}$ alkyl, —$OR^4$, or —C(=O)$NR_2$, wherein $R^4$ is H or $C_{1-6}$ alkyl, each R is independently H or $C_{1-4}$ alkyl, and t is 0-5. In other embodiments, wherein $R^b$ is selected from $C_{1-4}$ alkyl, —$OR^4$, or —C(=O)$NR_2$, wherein each $R^4$ is independently H or $C_{1-6}$ alkyl, each R is independently H or $C_{1-4}$ alkyl, and t is 0-5.

In some such embodiments, $R^b$ is selected from methyl, ethyl, propyl, isopropyl, —$CH_2OH$, —CH($CH_3$)OH, —C($CH_3$)$_2$OH, —OH, —$OCH_3$, —$OCH_2CH_3$, —C(=O)$NH_2$, —C(=O)$NHCH_3$, or —C(=O)N($CH_3$)$_2$, and t is 0-4. In others, $R^b$ is selected from methyl, —$CH_2OH$, —C($CH_3$)$_2$OH, —OH, —$OCH_3$, or —C(=O)$NHCH_3$, and t is 0-4.

In some other embodiments of compounds of formula (I), $R^2$ is selected from

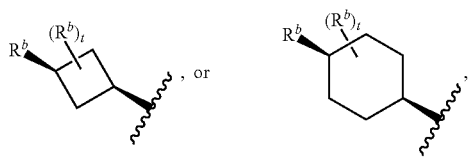, or wherein $R^b$ is selected from $C_{1-4}$ alkyl, —$OR^4$, or —C(=O)$NR_2$, wherein $R^4$ is H or $C_{1-6}$ alkyl, each R is independently H or $C_{1-4}$ alkyl, and t is 0-5. In other embodiments, $R^b$ is selected from $C_{1-4}$ alkyl, —$OR^4$, or —C(=O)$NR_2$, wherein each $R^4$ is independently H or $C_{1-6}$ alkyl, each R is independently H or $C_{1-4}$ alkyl, and t is 0-5.

In some such embodiments, $R^b$ is selected from methyl, ethyl, propyl, isopropyl, —$CH_2OH$, —CH($CH_3$)OH, —C($CH_3$)$_2$OH, —OH, —$OCH_3$, —$OCH_2CH_3$, —C(=O)$NH_2$, —C(=O)$NHCH_3$, or —C(=O)N($CH_3$)$_2$, and t is 0-4. In others, $R^b$ is selected from methyl, —$CH_2OH$, —C($CH_3$)$_2$OH, —OH, —$OCH_3$, or —C(=O)$NHCH_3$, and t is 0-4.

In other embodiments, $R^b$ is selected from triazolyl, $C_{1-4}$ alkyl, —$OR^4$, —C(=O)$NR_2$, wherein each $R^4$ is independently H or $C_{1-6}$ alkyl, and each R is independently H or $C_{1-4}$ alkyl, and t is 0-5. For example, $R^b$ is selected from triazolyl, —C(=O)$NH_2$, or —C(=O)N($CH_3$)$_2$. In others, $R^b$ is selected from methyl, triazolyl, —$CH_2OH$, —C($CH_3$)$_2$OH, —OH, —$OCH_3$, —C(=O)$NH_2$, —C(=O)$NHCH_3$, or —C(=O)N($CH_3$)$_2$.

In some embodiments of compounds of formula (I), $R^2$ is selected from

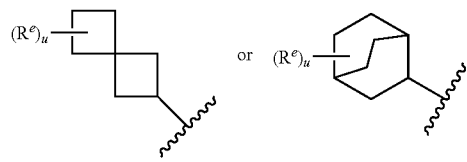

wherein $R^e$ is selected from $C_{1-4}$ alkyl, —$OR^4$, or —C(=O)$NR_2$, wherein each $R^4$ is independently H or $C_{1-6}$ alkyl, each R is independently H or $C_{1-4}$ alkyl, and u is 0-4. For example, $R^e$ is selected from methyl or —OH.

In some such embodiments of $R^2$, $R^1$ is selected from

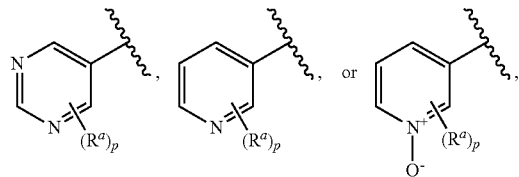

wherein $R^a$ is selected from halogen, —$OR^3$, substituted or unsubstituted $C_{1-4}$ alkyl, or substituted or unsubstituted aryl, wherein $R^3$ is H, substituted or unsubstituted $C_{1-6}$ alkyl, or substituted or unsubstituted aryl; and p is 0-3. In other embodiments, $R^a$ is selected from halogen, —$OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl; and p is 0-3.

In other such embodiments of $R^2$, $R^1$ is selected from

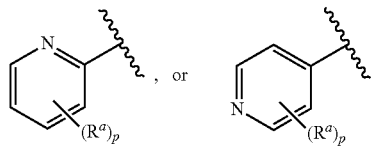

wherein $R^a$ is selected from halogen, —$OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl; and p is 0-3.

In still other such embodiments of $R^2$, $R^1$ is selected from

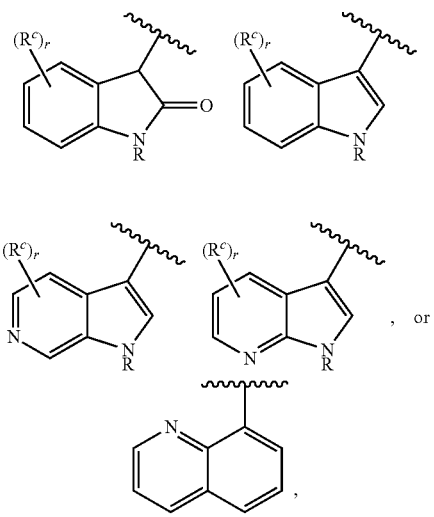

wherein $R^c$ is selected from halogen, CN, —$OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl; R is independently H or $C_{1-4}$ alkyl; and r is 0-3.

In yet other such embodiments of $R^2$, $R^1$ is selected from

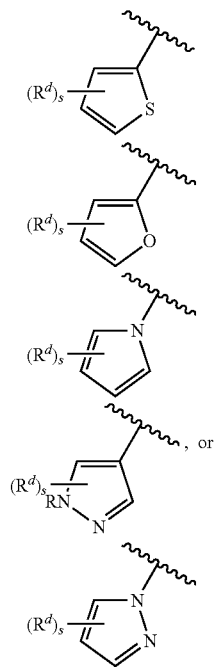

wherein $R^d$ is selected from halogen, CN, —$OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl; R is independently H or $C_{1-4}$ alkyl; and s is 0-3.

Further embodiments provided herein include combinations of one or more of the particular embodiments set forth above.

Representative compounds of formula (I) are set forth in Table 1.

In other embodiments, the Diaminopyrimidyl Compound is selected from Table 2.

Diaminopyrimidyl Compounds set forth in Table 1 and Table 2 were tested in the PKC assays described herein and were found to have activity as PKC-theta inhibitors. In one embodiment, the Diaminopyrimidyl Compound is a compound as described herein, wherein the compound at a concentration of 10 μM inhibits PKC-theta by at least about 50% or more. In embodiment, the Diaminopyrimidyl Compound is a compound as described herein, wherein the compound at a concentration of 100 nM inhibits PKC-theta by at least about 50% or more. In some such embodiments, the Diaminopyrimidyl Compound is at least 5-fold selective for PKC-theta over PKC-delta. In some such embodiments, the Diaminopyrimidyl Compound is at least 20-fold selective for PKC-theta over PKC-delta. In some such embodiments, the Diaminopyrimidyl Compound is at least 100-fold selective for PKC-theta over PKC-delta. In some such embodiments, the Diaminopyrimidyl Compound is more than 100-fold selective for PKC-theta over PKC-delta. In others, the Diaminopyrimidyl Compound is at least 20-fold selective for PKC-theta over PKC-delta and PKC-eta. In others, the Diaminopyrimidyl Compound is at least 100-fold selective for PKC-theta over PKC-delta and PKC-eta.

Methods for Making Diaminopyrimidyl Compounds

The Diaminopyrimidyl Compounds can be made using conventional organic syntheses and commercially available starting materials. By way of example and not limitation, Diaminopyrimidyl Compounds of formula (I) can be prepared as outlined in Schemes 1 and 2, shown below, as well as in the examples set forth herein. It should be noted that one skilled in the art would know how to modify the procedures set forth in the illustrative schemes and examples to arrive at the desired products.

Scheme 1

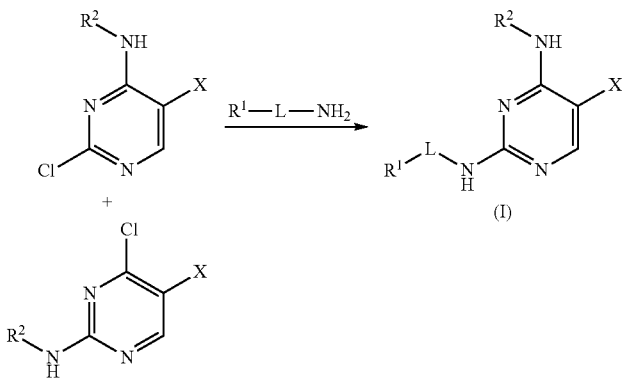

Synthesis of compounds of formula (I), wherein X, L, $R^1$ and $R^2$ are as defined herein, is shown in Scheme 1. Treatment of the 2,4-dichloropyrimidine containing starting material with $R^2NH_2$ in an organic solvent (for example, DMF, THF, ethanol, methanol, or isopropanol) in the presence of a base (for example, DIEA, TEA, 1,8-diazabicyclo[5.4.0]undec-7-ene, N-methylmorpholine, sodium carbonate, sodium bicarbonate, cesium carbonate, or potassium phosphate) provides introduction of the $R^2$ sidechain. Subsequent treatment with $R^1$-L-$NH_2$ in an organic solvent (for example, THF, ethanol, NMP, DMF, DMSO, dioxane, 1-butanol, methanol, or isopropanol) in the presence of a base (for example, DIEA, 1,8-diazabicyclo[5.4.0]undec-7-ene, N-methylmorpholine, TEA, cesium carbonate, potassium carbonate, sodium carbonate, sodium bicarbonate, or potassium phosphate) at elevated temperature (for example, 60° C. to 80° C.) provides compounds of formula (I).

Scheme 2

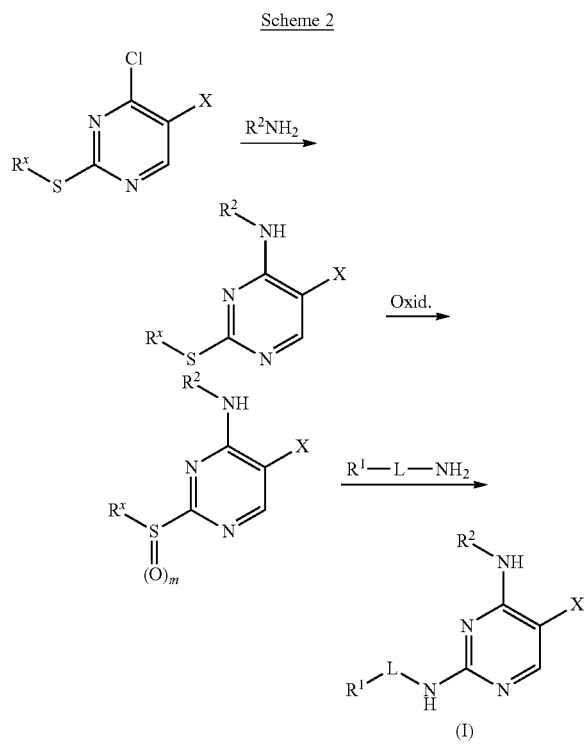

Alternatively, compounds of formula (I) can be prepared starting from 4-chloro-2-alkylthiopyrimidine-carbonitrile (wherein $R^x$ is a $C_{1-2}$ alkyl), by treatment with $R^2NH_2$ at room temperature or at elevated temperature (for example, 25° C. to 70° C.) in an organic solvent (for example, ethanol, n-butanol, NMP, DMF, DMSO, or dioxane), in the presence of a base (for example, DIEA, TEA, N-methylmorpholine, 1,8-diazabicyclo[5.4.0]undec-7-ene, potassium carbonate, sodium carbonate, sodium bicarbonate, cesium carbonate or potassium phosphate). Oxidation of the alkylthiol moiety is achieved by treatment in an organic solvent (such as, for example, THF, DCM, NMP, DMF, or DMA) with an oxidant (such as mCPBA, oxone, hydrogen peroxide, or 3-phenyl-2-(phenylsulfonyl)-1,2-oxaziridine). The resulting mixture of sulfone (m=1) and sulfoxide (m=2) is treated at room temperature or elevated temperature (for example, 25° C.-110° C.) with $R^1$-L-$NH_2$ in a solvent (such as, for example, dioxane, DMSO, NMP, DMF, THF, or n-butanol) in the presence of an organic base (such as DIEA, TEA, 1,8-diazabicyclo[5.4.0]undec-7-ene, or N-methylmorpholine), to afford the compounds of formula (I), wherein X is CN.

In one aspect, provided herein are methods for preparing a compound of formula (I):

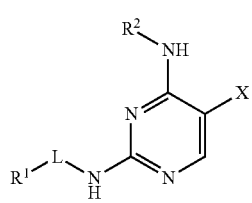

the methods comprising contacting a compound of formula (Ia)

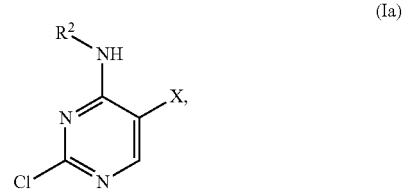

With $R^1$-L-$NH_2$, in an organic solvent, in the presence of a base, under conditions suitable to provide a compound of formula (I), wherein:

X is CN or $CF_3$;

L is ($C_{1-4}$ alkyl);

$R^1$ is substituted or unsubstituted heteroaryl; and $R^2$ is substituted or unsubstituted cycloalkyl.

In one embodiment, the solvent is THF, ethanol, NMP, DMF, DMSO, dioxane, 1-butanol, methanol, or isopropanol. In another, the base is DIEA, 1,8-diazabicyclo[5.4.0]undec-7-ene, N-methylmorpholine, TEA, cesium carbonate, potassium carbonate, sodium carbonate, sodium bicarbonate, or potassium phosphate. In some embodiments, the contacting is performed at elevated temperature, for example, from about 60° C. to about 80° C.

In some embodiments, the methods further comprise preparing a compound of formula (Ia):

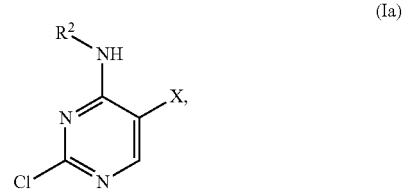

the methods comprising contacting a compound of formula (Ib)

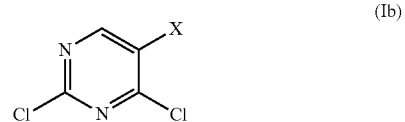

With $R^2NH_2$, in an organic solvent, in the presence of a base, under conditions suitable to provide a compound of formula (Ia).

In one embodiment, the solvent is DMF, THF, ethanol, methanol, or isopropanol. In another, the base is DIEA, TEA, 1,8-diazabicyclo[5.4.0]undec-7-ene, N-methylmorpholine, sodium carbonate, sodium bicarbonate, cesium carbonate, or potassium phosphate.

In one aspect, provided herein are methods for preparing a compound of formula (I):

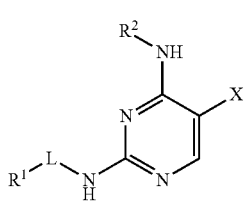
(I)

the methods comprising contacting a compound of formula (Ic)

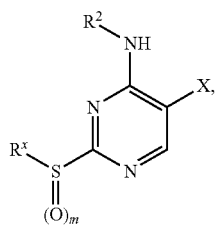
(Ic)

With $R^1$-L-$NH_2$, in an organic solvent, in the presence of a base, under conditions suitable to provide a compound of formula (I), wherein:
X is CN or $CF_3$;
L is ($C_{1-4}$ alkyl);
$R^1$ is substituted or unsubstituted heteroaryl; and
$R^2$ is substituted or unsubstituted cycloalkyl;
$R^x$ is a $C_{1-2}$ alkyl; and
m is 1 or 2.

In one embodiment, the solvent is dioxane, DMSO, NMP, DMF, THF, or n-butanol. In another, the base is DIEA, TEA, 1,8-diazabicyclo[5.4.0]undec-7-ene, or N-methylmorpholine. In some embodiments, the contacting is performed at room temperature or elevated temperature, for example, from about 25° C. to about 110° C.

In some embodiments, the methods further comprise preparing a compound of formula (Ic):

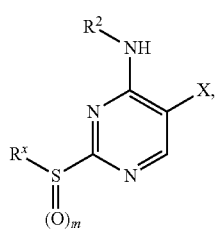
(Ic)

the methods comprising oxidizing a compound of formula (Id)

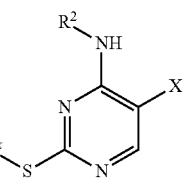
(Id)

In a solvent, with an oxidant, under conditions suitable to provide a compound of formula (Ic).

In one embodiment, the solvent is THF, DCM, NMP, DMF, or DMA. In another, the oxidant is mCPBA, oxone, hydrogen peroxide, or 3-phenyl-2-(phenylsulfonyl)-1,2-oxaziridine.

In some embodiments, the methods further comprise preparing a compound of formula (Id):

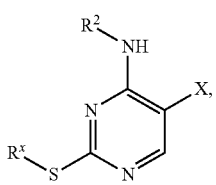
(Id)

the methods comprising contacting a compound of formula (Ie)

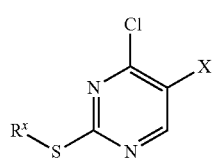
(Ie)

With $R^2NH_2$, in an organic solvent, in the presence of a base, under conditions suitable to provide a compound of formula (Id).

In one embodiment, the solvent is ethanol, n-butanol, NMP, DMF, DMSO, or dioxane. In another, the base is DIEA, TEA, N-methylmorpholine, 1,8-diazabicyclo[5.4.0]undec-7-ene, potassium carbonate, sodium carbonate, sodium bicarbonate, cesium carbonate or potassium phosphate. In some embodiments, the contacting is performed at room temperature or elevated temperature, for example, from about 25° C. to about 70° C.

Methods of Use

The Diaminopyrimidyl Compounds have utility as pharmaceuticals to treat, prevent or improve conditions in animals or humans. Further, the Diaminopyrimidyl Compounds are active against protein kinases, particularly PKC-theta. Accordingly, provided herein are many uses of the Diaminopyrimidyl Compounds, including the treatment or prevention of those diseases set forth below. The methods provided herein comprise the administration of an effective amount of one or more Diaminopyrimidyl Compound(s) to a subject in need thereof.

In one aspect provided herein are compounds for use in methods for treating or preventing a PKC-theta mediated disorder, such as, for example, graft-versus-host disease, organ transplant rejection, psoriasis, Duchenne muscular dystrophy, rheumatoid arthritis, diabetes, insulin resistance, myasthenia gravis, multiple sclerosis, colitis, psoriatic arthritis, ankylosing spondylitis, atopic dermatitis, Sjogren syndrome, asthma, or lupus, comprising administering to a subject in need thereof an effective amount of a Diaminopyrimidyl Compound.

In another aspect provided herein are methods and compounds for use in methods for treating or preventing a PKC-theta mediated disorder, such as, for example, graft-versus-host disease, organ transplant rejection, psoriasis, Duchenne muscular dystrophy, rheumatoid arthritis, diabetes, insulin resistance, myasthenia gravis, multiple sclerosis, colitis, psoriatic arthritis, ankylosing spondylitis, atopic dermatitis, Sjogren syndrome, asthma, or lupus.

In one aspect provided herein are methods and compounds for use in methods of inhibiting a kinase in a cell expressing said kinase in vivo, ex vivo or in vitro, comprising contacting said cell with an effective amount of a Diaminopyrimidyl Compound. In one embodiment, the kinase is PKC-theta. In some embodiments, the Diaminopyrimidyl Compound is selective for PKC-theta over PKC-delta. In others, the Diaminopyrimidyl Compound is selective for PKC-theta over PKC-delta and PKC-eta.

In some such embodiments, the Diaminopyrimidyl Compound is at least 5-fold selective for PKC-theta over PKC-delta. In some such embodiments, the Diaminopyrimidyl Compound is at least 20-fold selective for PKC-theta over PKC-delta. In some such embodiments, the Diaminopyrimidyl Compound is at least 100-fold selective for PKC-theta over PKC-delta. In some such embodiments, the Diaminopyrimidyl Compound is more than 100-fold selective for PKC-theta over PKC-delta. In others, the Diaminopyrimidyl Compound is at least 20-fold selective for PKC-theta over PKC-delta and PKC-eta. In others, the Diaminopyrimidyl Compound is at least 100-fold selective for PKC-theta over PKC-delta and PKC-eta.

For example, the Diaminopyrimidyl Compound is a compound from Table 1, or Table 2.

Pharmaceutical Compositions and Routes of Administration

The Diaminopyrimidyl Compounds can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrrolicione or aluminum stearate), a dispersing agent (e.g., hydroxypropylmethylcellulose), a diluent (e.g., water), and base wax (e.g., cocoa butter, white petrolatum or polyethylene glycol). The effective amount of the Diaminopyrimidyl Compounds in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a Diaminopyrimidyl Compound to be administered to a subject is rather widely variable and can be subject to the judgment of a health-care practitioner. In general, the Diaminopyrimidyl Compounds can be administered one to four times a day in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the Diaminopyrimidyl Compound administered will depend on such factors as the solubility of the active component, the formulation used and the route of administration. In one embodiment, application of a topical concentration provides intracellular exposures or concentrations of about 0.01-10 µM.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a Diaminopyrimidyl Compound to a subject in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Diaminopyrimidyl Compound to a subject in need thereof. In a particular embodiment, the methods disclosed herein comprise the administration of 400 mg/day, 600 mg/day or 800 mg/day of a Diaminopyrimidyl Compound to a subject in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a Diaminopyrimidyl Compound.

In a particular embodiment, provided herein are unit dosage formulations comprising about 100 mg or 400 mg of a Diaminopyrimidyl Compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Diaminopyrimidyl Compound.

A Diaminopyrimidyl Compound can be administered once, twice, three, four or more times daily. In a particular embodiment, doses of 600 mg or less are administered as a once daily dose and doses of more than 600 mg are administered twice daily in an amount equal to one half of the total daily dose.

A Diaminopyrimidyl Compound can be administered orally for reasons of convenience. In one embodiment, when administered orally, a Diaminopyrimidyl Compound is administered with a meal and water. In another embodiment, the Diaminopyrimidyl Compound is dispersed in water or juice (e.g., apple juice or orange juice) and administered orally as a suspension.

The Diaminopyrimidyl Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Diaminopyrimidyl Compound without an additional carrier, excipient or vehicle.

In another embodiment, provided herein are compositions comprising an effective amount of a Diaminopyrimidyl Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Diaminopyrimidyl Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Diaminopyrimidyl Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Diaminopyrimidyl Compound can be delayed or prolonged by proper formulation. For example, a slowly soluble pellet of the Diaminopyrimidyl Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Diaminopyrimidyl Compound in oily or emulsified vehicles that allow it to disperse slowly in the serum.

EXAMPLES

The following Examples are presented by way of illustration, not limitation. Compounds are named using the automatic name generating tool provided in Chemdraw Ultra 9.0 (Cambridgesoft), which generates systematic names for chemical structures, with support for the Cahn-Ingold-Prelog rules for stereochemistry. One skilled in the art can modify the procedures set forth in the illustrative examples to arrive at the desired products, for example, the compounds listed in Tables 1 and 2.

Abbreviations used:

| | |
|---|---|
| BOC$_2$O | Di-tert-butyl dicarbonate |
| DCM | Dichloromethane |
| DEA | Diethylamine |
| DIEA | N,N-Diisopropylethylamine |
| DMA | N,N-Dimethylacetamide |
| DMF | N,N-Dimethylformamide |
| DMSO | Dimethylsulfoxide |
| EDC | Ethyl-(N',N'-dimethylamino)propylcarbodiimide hydrochloride |
| ESI | Electrospray ionization |
| HATU | O-(7-azabenzotriazol-1-yl)-N,N,N',N'-tetramethyluronium hexafluorophosphate |
| HOBt | 1-Hydroxybenzotriazole |
| HPLC | High performance liquid chromatography |
| HTRF | Homogeneous time resolved fluorescence |
| LCMS | Liquid chromatography mass spectrometry |
| mCPBA | Meta-chloroperoxybenzoic acid |
| MeOH | Methanol |
| MS | Mass spectrometry |
| NMP | N-methylpyrrolidone |
| NMR | Nuclear magnetic resonance |
| SFC | Supercritical fluid chromatography |
| TBTU | O-benzotriazol-1-yl-N,N,N',N'-tetramethyluronium tetrafluoroborate |

| | |
|---|---|
| TEA | Triethylamine |
| TFA | Trifluoroacetic acid |
| THF | Tetrahydrofuran |
| TLC | Thin layer chromatography |

Compound Synthesis

Example 1

2-(((4-(2,2-Difluoropropoxy)pyrimidin-5-yl)methyl)amino)-4-(((1R,4S)-4-hydroxy-3,3-dimethylcyclohexyl)amino)pyrimidine-5-carbonitrile

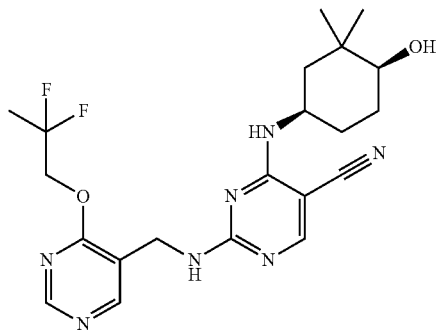 [SMILES: CC(F)(F)COc1ncncc1CNc1ncc(C#N)c(N[C@@H]2CC[C@H](O)C(C)(C)C2)n1]

A. 7,7-Dimethyl-1,4-dioxaspiro[4.5]decan-8-one

To a solution of 1,4-dioxaspiro[4.5]decan-8-one (1.0 equiv.) in anhydrous THF (0.6 M) was added sodium hydride (2.0 equiv, 60% in mineral oil) at 0° C. under nitrogen. After the resulting reaction mixture was stirred at room temperature for 60 min, iodomethane (2.5 equiv.) was added. The reaction was stirred at 10° C. overnight. TLC (petroleum ether: ethyl acetate=10:1) showed that the reaction was completed. The reaction was quenched with saturated aqueous ammonium chloride solution and the aqueous layer was extracted with ethyl acetate. The combined organic layers were washed with brine, dried over anhydrous sodium sulfate and filtered. The filtrate was concentrated under vacuum, and the residue was purified by silica gel column chromatography (10% ethyl acetate in petroleum ether) to afford the 7,7-dimethyl-1,4-dioxaspiro[4.5]decan-8-one (40% yield) as colorless oil. $^1$H NMR (400 MHz, CDCl$_3$) δ (ppm) 3.99 (s, 4H), 2.55-2.58 (m, 2H), 1.97-2.00 (m, 2H), 1.87 (s, 2H), 1.16 (s, 6H).

B. 7,7-Dimethyl-1,4-dioxaspiro[4.5]decan-8-ol

To a solution of 7,7-dimethyl-1,4-dioxaspiro[4.5]decan-8-one (1.0 equiv.) in MeOH (0.5 M) was added sodium borohydride (1.0 equiv.) slowly at 0° C. under nitrogen, and the resulting reaction mixture was stirred at room temperature for 60 min. TLC (petroleum ether: ethyl acetate=10:1) showed that the reaction was completed. Water was added, and the solvent was removed under reduced pressure. The aqueous layer was extracted with DCM. The combined organic layers were washed with brine, dried over anhydrous sodium sulfate and filtered. The filtrate was concentrated under vacuum to give 7,7-dimethyl-1,4-dioxaspiro[4.5]decan-8-ol (99% yield), which was used in the next step without further purification. $^1$H NMR (400 MHz, CDCl$_3$) δ (ppm) 3.85-3.94 (m, 4H), 3.37-3.40 (m, 1H), 1.41-1.81 (m, 7H), 0.97 (s, 6H).

C. 4-Hydroxy-3,3-dimethylcyclohexanone

A solution of 7,7-dimethyl-1,4-dioxaspiro[4.5]decan-8-ol (1.0 equiv.) in 2.0 N hydrochloric acid aqueous solution (3.7 equiv.) and MeOH (0.9 M) was stirred at room temperature overnight. TLC (petroleum ether: ethyl acetate=3:1) showed that the reaction was completed. The solvent was removed under reduced pressure, the resulting residue was basified with saturated aqueous sodium bicarbonate solution and the aqueous layer was extracted with ethyl acetate. The combined organic layers were washed with brine, dried over anhydrous sodium sulfate and filtered. The filtrate was concentrated under vacuum to give 4-hydroxy-3,3-dimethylcyclohexanone (88% yield), which was used in the next step without further purification. $^1$H NMR (400 MHz, CDCl$_3$) δ (ppm) 3.69-3.71 (m, 1H), 2.42-2.45 (m, 2H), 2.09-2.25 (m, 1H), 2.04-2.08 (m, 4H), 1.91-1.95 (m, 1H), 0.98 (s, 6H)

D. (E)-4-Hydroxy-3,3-dimethylcyclohexanone oxime

The mixture of 4-hydroxy-3,3-dimethylcyclohexanone (1.0 equiv.), hydroxylamine hydrochloride (2.0 equiv.) and sodium bicarbonate (2.5 equiv.) in MeOH (0.7 M) was stirred at room temperature overnight. The solvent were removed and the residue was passed through a short silica gel column (50% ethyl acetate in petroleum ether) to afford the crude (E)-4-hydroxy-3,3-dimethylcyclohexanone oxime (96% yield) as a colorless oil.

E. 4-Amino-2,2-dimethylcyclohexanol

To a solution of (E)-4-hydroxy-3,3-dimethylcyclohexanone oxime (1.0 equiv.) in MeOH (0.8 M) was added Raney-Ni (10 equiv.). The reaction mixture was stirred at room temperature under hydrogen atmosphere overnight. TLC (DCM: MeOH=10:1) showed that the reaction was completed. The mixture was filtered and the filtrate was concentrated in vacuo to give 4-amino-2,2-dimethylcyclohexanol (92% yield), which was used in the next step without further purification.

F. Benzyl (4-hydroxy-3,3-dimethylcyclohexyl)carbamate

To a mixture of 4-amino-2,2-dimethylcyclohexanol (1.0 equiv.) in 1.7 M sodium carbonate solution (1.3 equiv.) and THF (1.3 M) was added benzyl chloroformate (1.5 equiv.) slowly at 0° C. After addition, the mixture was stirred at room temperature overnight. TLC (dichloromethane: MeOH=10:1) showed that the reaction was completed. The mixture was filtered and the aqueous layer was extracted with ethyl acetate. The combined organic layers were washed with brine, dried over anhydrous sodium sulfate and filtered. The filtrate was concentrated under vacuum to give crude racemic product, which was purified by silica gel column chromatography (DCM: MeOH=20:1) to afford benzyl (4-hydroxy-3,3-dimethylcyclohexyl)carbamate (110 g, 49.4%) as colorless oil.

G. Benzyl 4-hydroxy-3,3-dimethylcyclohexyl)carbamate

The racemic mixture (1.0 equiv.) was separated by chiral supercritical fluid chromatography (Instrument: Thar200 preparative SFC, column: ChiralPak AD-10 μm, 300×50 mm I.D, mobile phase: A: $CO_2$ and 40% B: ethanol (0.1% $NH_3.H_2O$), flow rate: 240 mL/min, back pressure: 100 bar, column temperature: 38° C., wavelength: 210 nm, cycle time: ~4.0 min) peak one was isolated to afford 1 isomer of benzyl 4-hydroxy-3,3-dimethylcyclohexyl)carbamate (22% yield)

H. (1S,4R)-4-Amino-2,2-dimethylcyclohexanol

Benzyl-4-hydroxy-3,3-dimethylcyclohexylcarbamate (peak 1) (1.0 equiv.) and palladium on carbon (10%) in MeOH (0.37 M) was stirred at room temperature under hydrogen balloon overnight. TLC (DCM: MeOH=10:1) showed that the reaction was completed. The mixture was filtered through a celite pad and evaporation of the solvents under reduced pressure provided 4-amino-2,2-dimethylcyclohexanol (95% yield) as a white solid. $^1$H NMR (400 MHz, DMSO-$d_6$) δ (ppm) 3.70 (s, 2H), 3.16 (s, 1H), 2.65-2.71 (m, 1H), 1.18-1.65 (m, 6H), 0.83 (m, 6H).

I. 4-(((1S,4R)-4-Hydroxy-3,3-dimethylcyclohexyl)amino)-2-(methylthio)pyrimidine-5-carbonitrile To a mixture of 4-chloro-2-(methylthio)pyrimidine-5-carbonitrile (1.0 equiv.) and DIEA (3.0 equiv) in THF (0.05 M) was added 4-amino-2,2-dimethylcyclohexanol (peak 1, obtained above) (1.2 equiv.). The mixture was stirred at 50° C. overnight. After reaction completion, the solvent was removed under reduced pressure, and the residue was purified by silica gel column chromatography (20% ethyl acetate in petroleum ether) to afford the title compound (82% yield) as a white solid. MS (ESI) m/z 293.1 [M+H]$^+$. The single crystal X-ray diffraction studies were carried out on a Bruker Kappa APEX-II CCD diffractometer equipped with Mo $K_\alpha$ radiation (λ=0.71073 Å). Crystals of the subject compound were grown by vapor diffusion of pentane into an isopropanol solution. A 0.215×0.183×0.055 mm colorless plate was mounted on a cryoloop with paratone oil. Data were collected in a nitrogen gas stream at 90 (2) K using φ and ω scans. Crystal-to-detector distance was 60 mm and exposure time was 5 seconds per frame using a scan width of 0.5°. Data collection was 99.9% complete to 25.00° in θ. A total of 45590 reflections were collected covering the indices, −53<=h<=56, −14<=k<=13, −23<=l<=27. 21888 reflections were found to be symmetry independent, with a $R_{int}$ of 0.0549. Indexing and unit cell refinement indicated a C-centered, monoclinic lattice. The space group was found to be C2. The data were integrated using the Bruker SAINT software program and scaled using the SADABS software program. Solution by direct methods (SHELXS) produced a complete phasing model consistent with the proposed structure.

All non-hydrogen atoms were refined anisotropically by full-matrix least-squares (SHELXL-2013). All hydrogen atoms were placed using a riding model. Their positions were constrained relative to their parent atom using the appropriate HFIX command in SHELXL-2013. The absolute stereochemistry was shown to be 4-(((1S,4R)-4-hydroxy-3,3-dimethylcyclohexyl)amino)-2-(methylthio)pyrimidine-5-carbonitrile.

J. 4-(((1S,4R)-4-Hydroxy-3,3-dimethylcyclohexyl)amino)-2-(methylsulfinyl)pyrimidine-5-carbonitrile and 4-(((1S,4R)-4-hydroxy-3,3-dimethylcyclohexyl)amino)-2-(methylsulfonyl)pyrimidine-5-carbonitrile To a solution of 4-(((1S,4R)-4-hydroxy-3,3-dimethylcyclohexyl)amino)-2-(methylthio)pyrimidine-5-carbonitrile (1.0 equiv.) in THF (0.1 M) was added 3-chloroperbenzoic acid (85%, 2.0 equiv.) at 0° C. Then the mixture was stirred at room temperature for 2 h. After reaction completion, the solvent was removed under reduced pressure and the residue was purified by silica gel chromatography (50% ethyl acetate in petroleum ether) to afford the title compounds as a yellow solid, MS (ESI) m/z 309.1, 325.1 [M+H]$^+$, which were used in the next step without further purification.

K. 4-(2,2-Difluoropropoxy)pyrimidine-5-carbonitrile

A solution of 2,2-difluoropropan-1-ol (1.2 equiv.) in anhydrous DMSO (1.0 M) was treated with 60% NaH (1.1 equiv.). The resulting mixture was stirred at room temperature for 5 min, followed by the addition of 4-chloropyrimidine-5-carbonitrile (1.0 equiv.) in one portion. The reaction mixture was stirred at room temperature for 1 h. Ethyl acetate was added and the reaction partitioned with water and brine. The organic layer was concentrated to give a yellow oil (4.19 g), which was purified by silica gel column chromatography (0-75% ethyl acetate in hexane, 100 g column). The desired fractions were combined and volatile solvents were removed under reduced pressure. The residue was triturated with hexanes and volatile solvents were removed under reduced pressure to afford 4-(2,2-difluoropropoxy)pyrimidine-5-carbonitrile (72.4% yield) as a yellow oil. MS(ESI) m/z 199.8 [M+1]$^+$.

L. (4-(2,2-Difluoropropoxy)pyrimidin-5-yl)methanamine 4-(2,2-difluoropropoxy)pyrimidine-5-carbonitrile (1.0 equiv.) was dissolved in a 1:1 mixture of ethanol and ethyl acetate (0.2 M). Sponge nickel catalyst (50% aqueous slurry) (19 equiv.) and ammonium hydroxide (12 equiv.) were added to the reaction vessel, which was purged thoroughly with hydrogen gas and allowed to stir at room temperature for 16 h. The reaction mixture was filtered through a microfiber filter containing celite, washed with ethanol, and volatile solvents were removed under reduced pressure. The residue was purified using silica gel chromatography (60-100% ethyl acetate in hexanes followed by 1-20% MeOH in ethyl acetate). The desired fractions were combined and volatile solvents were removed under reduced pressure to afford (4-(2,2-difluoropropoxy)pyrimidin-5-yl)methanamine (82% yield). MS(ESI) m/z 204.1 [M+1]$^+$.

M. 2-(((4-(2,2-Difluoropropoxy)pyrimidin-5-yl)methyl)amino)-4-(((1R,4S)-4-hydroxy-3,3-dimethylcyclohexyl)amino)pyrimidine-5-carbonitrile A solution of 4-(((1S,4R)-4-hydroxy-3,3-dimethylcyclohexyl)amino)-2-(methylsulfinyl)pyrimidine-5-carbonitrile (1.0 equiv) and (4-(2,2-difluoropropoxy)pyrimidin-5-yl)methanamine (1.5 equiv) in dioxane (0.15 M) was heated at 110° C. for 1 h. Standard work-up provided 2-(((4-(2,2-difluoropropoxy)pyrimidin-5-yl)methyl)amino)-4-(((1R,4S)-4-hydroxy-3,3-dimethylcyclohexyl)amino)pyrimidine-5-carbonitrile (69.6% yield). $^1$H NMR (400 MHz, DMSO-$d_6$): δ (ppm) 8.72 (s, 1H), 8.26 (s, 1H), 8.18 (s, 1H), 7.99 (t, J=5.66 Hz, 1H), 7.17 (d, J=7.81 Hz, 1H), 4.64 (t, J=12.89 Hz, 2H), 4.39-4.49 (m, 2H), 4.29 (d, J=3.51 Hz, 1H), 3.85-4.00 (m, 1H), 3.12 (br. s., 1H), 1.73 (t, J=19.14 Hz, 4H), 1.42-1.55 (m, 3H), 1.21-1.33 (m, 3H), 1.10 (br. s., 1H), 0.59-0.78 (m, 5H). MS (ESI) m/z 448.2 [M+1]$^+$.

Example 2

4-(((1S,4R)-4-Hydroxy-3,3-dimethylcyclohexyl) amino)-2-((2-(5-methyl-1H-tetrazol-1-yl)benzyl) amino)pyrimidine-5-carbonitrile

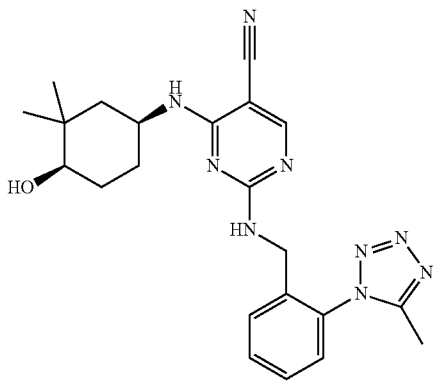 [SMILES: Cc1nnnn1-c1ccccc1CNc1ncc(C#N)c(N[C@H]2CC[C@@H](O)C(C)(C)C2)n1]

A. 4-(((1S,4R)-4-Hydroxy-3,3-dimethylcyclohexyl) amino)-2-(methylthio)pyrimidine-5-carbonitrile To a mixture of 4-chloro-2-(methylthio)pyrimidine-5-carbonitrile (1.0 equiv.) and DIEA (3.0 equiv) in THF (0.05 M) was added (1R,4S)-4-amino-2,2-dimethylcyclohexanol (stereochemistry determined as described herein) (1.2 equiv.). The mixture was stirred at 50° C. overnight. After reaction completion, the solvent was removed under reduced pressure, and the residue was purified by silica gel column chromatography (20% ethyl acetate in petroleum ether) to afford the title compound (82% yield) as a white solid. MS (ESI) m/z 293.1 [M+H]$^+$.

B. Mixture of 4-(((1S,4R)-4-hydroxy-3,3-dimethyl-cyclohexyl)amino)-2-(methylsulfinyl)pyrimidine-5-carbonitrile and 4-(((1S,4R)-4-hydroxy-3,3-dimethylcyclohexyl)amino)-2-(methylsulfonyl)pyrimidine-5-carbonitrile To a solution of 4-(((1S,4R)-4-hydroxy-3,3-dimethylcyclohexyl)amino)-2-(methylthio)pyrimidine-5-carbonitrile (1.0 equiv.) in THF (0.1 M) was added 3-chloroperbenzoic acid (85%, 2.0 equivat 0° C. Then the mixture was stirred at room temperature for 2 h. After reaction completion, the solvent was removed under vacuum and the residue was purified by silica gel chromatography (50% ethyl acetate in petroleum ether) to afford the title mixed compound as a yellow solid, MS (ESI) m/z 309.1, 325.1 [M+H]$^+$, which was used in the next step without further purification.

C. N-(2-Bromophenyl)acetamide

To a solution of 2-bromophenylamine (1.0 equiv.) in DCM (0.2 M) was added acetyl chloride (1.5 M) at 0° C. The resulting mixture was stirred at this temperature overnight. 1 N hydrochloric acid (0.4 equiv.) was added to quench the reaction. The mixture was extracted with DCM and sodium bicarbonate and the combined organic layers were washed with brine, dried over sodium sulfate, concentrated and triturated from 16% ethyl acetate in petroleum ether to give the desired product (73% yield) as a white power. $^1$H-NMR (400 MHz, DMSO-d$_6$) δ (ppm) 8.33-8.31 (m, 1H), 7.61 (br, 1H), 7.54-7.52 (m, 1H), 7.33-7.26 (m, 1H), 6.99-6.95 (m, 1H), 2.24 (s, 3H); MS (ESI) m/z 203.2 [M+H]$^+$.

D. 1-(2-bromophenyl)-5-methyl-1H-tetrazole

To a solution of N-(2-bromophenyl)acetamide (1.0 equiv.) in acetonitrile (0.4 M) at −5° C., was added trifluoromethanesulfonic anhydride (2.0 equiv.) dropwise and the mixture was stirred for 5 min. Trimethylsilyl azide (4.0 equiv.) was added slowly while maintaining the temperature at −5° C., then the mixture was stirred at 0° C. for 80 mins. The mixture was poured into ice-cold sodium bicarbonate solution, extracted with ethyl acetate, and the combined organic layers were washed with brine, dried over anhydrous sodium sulfate, filtered, and concentrated to afford the crude residue. The residue was purified by silica gel column chromatography (16% ethyl acetate in petroleum ether) to give the desired product (44% yield) as a yellow solid. MS (ESI) m/z 239.1 [M+H]$^+$.

E. 2-(5-Methyl-1H-tetrazol-1-yl)benzonitrile

A mixture of 1-(2-bromophenyl)-5-methyl-1H-tetrazole (1.0 equiv.), zinc dust (0.25 M), zinc cyanide (0.65 equiv.), tris(dibenzylideneacetone)dipalladium (0.1 equiv.), and 1,1'-ferrocenediyl-bis(diphenylphosphine) (0.08 equiv.) in ethylene glycol dimethyl ether (0.2 M) was stirred at 90° C. overnight. After reaction completion, the solvent was removed under reduced pressure, and the residue was purified by silica gel chromatography (50% ethyl acetate in petroleum ether) to afford the title compound (65% yield) as a yellow solid. $^1$H-NMR (400 MHz, CDCl$_3$) δ (ppm) 7.958-7.956 (m, 1H), 7.94-7.87 (m, 1H), 7.80-7.76 (m, 1H), 7.59-7.57 (m, 1H), 2.63 (s, 3H); MS (ESI) m/z 186.1 [M+H]$^+$.

F. (2-(5-Methyl-1H-tetrazol-1-yl)phenyl)methanamine hydrochloride

To a solution of 2-(5-methyl-1H-tetrazol-1-yl)benzonitrile (1.0 equiv.) in MeOH (0.4 M) was added palladium on charcoal and concentrated hydrochloric acid (1.0 equiv.). The reaction mixture was stirred at room temperature under hydrogen atmosphere (50 psi) overnight. After reaction completion, the mixture was filtered through celite. The filtrate was concentrated in vacuo to give the crude product (81% yield), which was used in the next step without further purification. 1H-NMR (400 MHz, CDCl$_3$) δ (ppm) 7.85-7.75 (m, 3H), 7.66-7.64 (m, 1H), 3.96 (s, 2H), 2.60 (s, 3H); MS (ESI) m/z 190.1 [M+H]$^+$.

G. 4-(((1S,4R)-4-Hydroxy-3,3-dimethylcyclohexyl) amino)-2-((2-(5-methyl-1H-tetrazol-1-yl)benzyl) amino)pyrimidine-5-carbonitrile To a mixture of 4-(((1S,4R)-4-hydroxy-3,3-dimethylcyclohexyl)amino)-2-(methylsulfinyl)pyrimidine-5-carbonitrile and 4-(((1S,4R)-4-hydroxy-3,3-dimethylcyclohexyl) amino)-2-(methylsulfonyl)pyrimidine-5-carbonitrile (1.0 equiv) in dioxane (0.4M) was added (2-(5-methyl-1H-tetrazol-1-yl)phenyl)methanamine hydrochloride (1.0 equiv.) and DIEA (2.0 equiv.). The mixture was stirred at 120° C. in microwave for 2 h. After completion of the reaction and standard work-up, the desired product was obtained (37% yield). $^1$H-NMR (400 MHz, DMSO-d$_6$) δ (ppm) 8.12 (s, 1H), 7.82-7.78 (m, 1H), 7.63-7.61 (m, 1H), 7.58-7.51 (m, 3H), 7.02-6.92 (m, 1H), 4.32-4.17 (m, 3H), 4.01-3.99 (m, 1H), 3.21-3.14 (m, 1H), 2.41-2.36 (m, 3H), 1.65-1.47 (m, 1H), 1.36 (br, 1H), 1.23-1.17 (m, 2H), 0.81 (s, 3H), 0.73 (s, 3H); MS (ESI) m/z 434.2 [M+H]$^+$.

Example 3

2-(((4-(4-Fluorophenyl)pyrimidin-5-yl)methyl)amino)-4-(((1s,4s)-4-hydroxycyclohexyl)amino)pyrimidine-5-carbonitrile

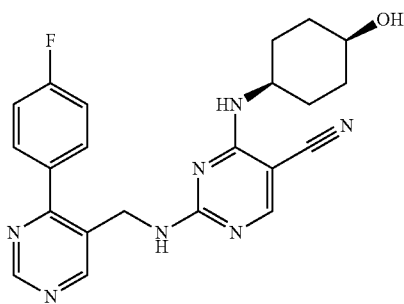 [SMILES: N#Cc1cnc(NCc2cncnc2-c2ccc(F)cc2)nc1N[C@H]1CC[C@@H](O)CC1]

A. 4-(4-Fluorophenyl)pyrimidine-5-carbonitrile

A mixture of 4-chloropyrimidine-5-carbonitrile (1.0 equiv.), (4-fluorophenyl)boronic acid (1.2 equiv.), 1,1'-bis(diphenylphosphino ferrocene-palladium(ii)dichloride dichloromethane complex (10 mol %) and potassium carbonate (3.0 equiv.) in dioxane/water 3:1 (0.5 M) was purged with nitrogen for 3 min. The pressure reaction vessel was tightly capped and heated at 100° C. for 5 h. Ethyl acetate and water were added and layers were separated. The organic layer was washed with brine, dried over sodium sulfate and concentrated to give a brown, sticky oil, which was purified by silica gel column chromatography (0-30% ethyl acetate in hexane, 100 g column) to give the title compound (58% yield) as a white solid. $^1$H NMR (500 MHz, CDCl$_3$) δ (ppm) 9.39 (s, 1H), 9.06 (s, 1H), 8.23-8.17 (m, 2H), 7.31-7.27 (m, 2H). MS (ESI) m/z 200.2 [M+1]$^+$.

B. (4-(4-fluorophenyl)pyrimidin-5-yl)methanamine

A mixture of 4-(4-fluorophenyl)pyrimidine-5-carbonitrile (1.0 equiv.) and Raney-nickel (20 mol %) in MeOH (0.1 M) was degassed under vacuum and followed by the addition of 30% ammonium hydroxide (10 equiv.). The resulting mixture was hydrogenated with hydrogen gas at room temperature overnight. The mixture was filtered through a pad of celite and the cake was rinsed with MeOH. The filtrate was concentrated and further dried to give a brown oil, which was purified by silica gel column chromatography (0-10% MeOH in DCM, 25 g column) to give the title compound (32% yield) as a yellow solid. $^1$H NMR (400 MHz, CDCl$_3$) δ (ppm) 9.19 (s, 1H), 8.88 (s, 1H), 7.71-7.78 (m, 2H), 7.17-7.24 (m, 2H), 3.99 (s, 2H), 1.41 (br. s., 2H). MS (ESI) m/z 204.1 [M+1]$^+$.

2-(((4-(4-Fluorophenyl)pyrimidin-5-yl)methyl)amino)-4-(((1s,4s)-4-hydroxycyclohexyl)amino)pyrimidine-5-carbonitrile A suspension of a mixture of 4-(((1s,4s)-4-hydroxycyclohexyl)amino)-2-(methylsulfonyl)pyrimidine-5-carbonitrile and 4-(((1s,4s)-4-hydroxycyclohexyl)amino)-2-(methylsulfinyl)pyrimidine-5-carbonitrile (1.0 equiv.) and crude (4-(4-fluorophenyl)pyrimidin-5-yl)methanamine (2.0 equiv.) in dioxane (0.2 M) was heated at 120° C. by microwave for 1 h. Water and ethyl acetate were added. Standard work-up methods afforded the title compound (10% yield) as a white solid. $^1$H NMR (400 MHz, DMSO-d$_6$) δ (ppm) 9.12 (s, 1H), 8.75 (s, 1H), 8.24 (t, J=5.7 Hz, 1H), 8.15 (s, 1H), 7.76 (dd, J=5.5, 8.6 Hz, 2H), 7.37 (t, J=8.8 Hz, 2H), 7.08 (d, J=7.4 Hz, 1H), 4.64-4.54 (m, 2H), 4.37-4.27 (m, 1H), 3.66 (br. s., 1H), 3.46 (d, J=7.0 Hz, 1H), 1.72-1.52 (m, 2H), 1.52-1.37 (m, 3H), 1.24-1.08 (m, 3H). MS (ESI) m/z 420.1 [M+1]$^+$.

Example 4

Cis-1-methyl-4-((2-(((4-(p-tolyloxy)pyrimidin-5-yl)methyl)amino)-5-(trifluoromethyl)pyrimidin-4-yl)amino)cyclohexanol

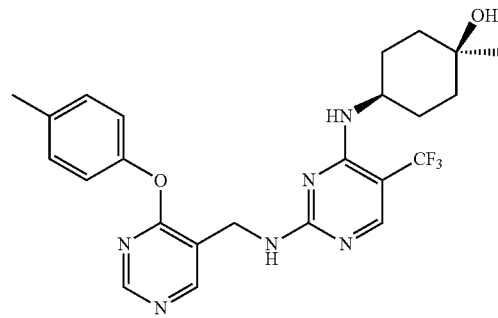

A. 4-(p-Tolyloxy)pyrimidine-5-carbonitrile p-Cresol (1.0 equiv.) was placed in a round bottom flask with DMSO (1.0 M) and sodium hydride (0.9 equiv). The reaction mixture was stirred at ambient temperature for 5 min. To the mixture was added 4-chloropyrimidine-5-carbonitrile (1.0 equiv.). The reaction was stirred at 25° C. for 2 h. The reaction mixture was partitioned between ethyl acetate and water. The organic layer was washed with brine (3×) and dried over sodium sulfate. Volatile organic solvents were removed under reduced pressure to give 4-(p-tolyloxy)pyrimidine-5-carbonitrile (41.6% yield) as a light brown solid which was used in the next step without further purification. $^1$H NMR (400 MHz, DMSO-d$_6$) δ (ppm) 9.24 (s, 1H), 8.94 (s, 1H), 7.29 (dd, J=0.8, 8.6 Hz, 2H), 7.21-7.16 (m, 2H), 2.34 (s, 3H). MS (ESI) m/z 211.7 [M+1]$^+$

B. (4-(4-(Trifluoromethyl)phenoxy)pyrimidin-5-yl) methanamine

To 4-(p-tolyloxy)pyrimidine-5-carbonitrile (1.0 equiv.) in 2-propanol (0.3 M) was added ammonium hydroxide (1.2 equiv) and Raney Nickel. The reaction vessel was purged thoroughly with hydrogen gas and allowed to stir at room temperature for 16 h. The reaction mixture was filtered through a microfiber filter with celite and washed with MeOH. Volatile organic solvents were removed under reduced pressure. The residue was loaded onto a silica gel column and purified using 0-15% MeOH in DCM. The desired fractions were combined and the solvent was removed under reduced pressure to afford (4-(4-(trifluoromethyl)phenoxy)pyrimidin-5-yl)methanamine as an amber colored oil which after 16 h turned into a yellow solid.

C. 4-Chloro-N-((4-(p-tolyloxy)pyrimidin-5-yl) methyl)-5-(trifluoromethyl)pyrimidin-2-amine (4-(p-Tolyloxy)pyrimidin-5-yl)methanamine (1.0 equiv.) was placed in a round bottom flask with DIEA (1.0 equiv.), and DMF (0.4 M). The flask was placed in a cooling bath and cooled to −10° C. To the flask was added 2,4-dichloro-5-(trifluoromethyl)pyrimidine (1.0 equiv.) and stirring continued at −10° C. The reaction mixture was allowed to warm to room temperature over 3 h. The reaction mixture was loaded directly onto a silica gel column (100 g) and purified using 5-27% ethyl acetate in hexanes, followed by 27% ethyl acetate in hexanes. Fractions containing desired product (lower $R_f$ spot by thin layer chromatography) were combined and the solvent was were removed under reduced pressure to give 4-chloro-N-((4-(p-tolyloxy)pyrimidin-5-yl)methyl)-5-(trifluoromethyl)pyrimidin-2-amine (27.0% yield) as a light yellow solid. MS (ESI) m/z 396.2 [M+1]$^+$

D. (1s,4s)-1-Methyl-4-((2-(((4-(p-tolyloxy)pyrimidin-5-yl)methyl)amino)-5-(trifluoromethyl)pyrimidin-4-yl)amino)cyclohexanol 4-Chloro-N-((4-(p-tolyloxy)pyrimidin-5-yl)methyl)-5-(trifluoromethyl)pyrimidin-2-amine (1.0 equiv.) was placed in a sealable flask with (1s,4s)-4-amino-1-methylcyclohexanol (1.0 equiv.), DIEA (1.2 equiv.) and THF (0.1 M). The flask was purged with nitrogen and sealed. The reaction mixture was heated to 60° C. for 18 h. The reaction mixture was loaded directly onto a silica gel column and purified using 0-10% MeOH in DCM. Fractions containing desired product were combined and volatile organic solvents were removed under reduced pressure to give an off-white foam. The foam was purified using standard methods to give cis-1-methyl-4-((2-(((4-(p-tolyloxy)pyrimidin-5-yl)methyl)amino)-5-(trifluoromethyl)pyrimidin-4-yl)amino)cyclohexanol (40.0% yield) as a white solid. $^1$H NMR (400 MHz, CD$_3$OD) δ (ppm) 8.51 (s, 1H), 8.44 (s, 1H), 7.99 (s, 1H), 7.24 (d, J=8.59 Hz, 2H), 7.02-7.09 (m, 2H), 4.67 (s, 2H), 3.87 (br. s., 1H), 2.36 (s, 3H), 1.56 (br. s., 6H), 1.27 (br. s., 2H), 1.12 (br. s., 3H). MS (ESI) m/z 489.3 [M+1]$^+$

Example 5

5-((4-(((1R,4S)-4-Hydroxy-3,3-dimethylcyclohexylamino)-5-(trifluoromethyl)pyrimidin-2-ylamino) methyl)-2-methyl-4-(trifluoromethyl)pyridine 1-oxide

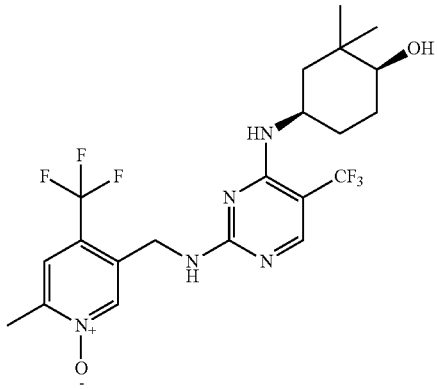 [SMILES: Cc1cc(C(F)(F)F)c(CNc2ncc(C(F)(F)F)c(N[C@@H]3CC[C@H](O)C(C)(C)C3)n2)c[n+]1O]

A. tert-Butyl ((6-Methyl-4-(trifluoromethyl)pyridin-3-yl)methyl)carbamate

6-Methyl-4-(trifluoromethyl)nicotinonitrile (1.0 equiv.) was dissolved in MeOH (0.1 M), wet Raney nickel was added, followed by ammonium hydroxide (32 equiv.). The reaction vessel was evacuated three times, refilled with hydrogen and then equipped with a hydrogen balloon and stirred at room temperature for 48 h. The mixture was filtered through a short pad of celite which was washed with MeOH. Ethanol was added to remove excess water upon concentration. The volatile solvents were removed to afford crude product which was dissolved in DCM. DIEA (1.8 equiv.) was added followed by BOC$_2$O (0.95 equiv.). The reaction was stirred at room temperature for 1 h. The volatile solvent was removed and the residue was purified via Biotage chromatography (10-100% ethyl acetate in hexanes) to afford tert-butyl ((6-methyl-4-(trifluoromethyl)pyridin-3-yl)methyl)carbamate (90% yield); MS(ESI) m/z 290.3 [M+1]$^+$.

B. 5-(Aminomethyl)-2-methyl-4-(trifluoromethyl) pyridine 1-oxide

To a round-bottomed flask was added tert-butyl ((6-methyl-4-(trifluoromethyl)pyridin-3-yl)methyl)carbamate (1.0 equiv.) which was dissolved in DCM (0.7 M). To this solution was added m-chloroperoxybenzoic acid (1.3 equiv.) and the mixture was stirred at room temperature for 12 h. The solvent was removed to afford a crude solid which was dissolved in MeOH and 4 N HCl in dioxane (4.2 equiv.) was added at room temperature. The mixture was stirred for 24 h and some precipitate begun to form. The volatile solvents were removed under reduced pressure to afford a crude residue. The residue was dissolved in methanol and the resulting mixture was loaded on a Strata ion-exchange column. The column was washed successively with water, acetonitrile, MeOH and 7 N ammonia in MeOH. The product eluted with the 7 N ammonia in MeOH eluent and product containing eluent was concentrated under reduced pressure to afford 5-(aminomethyl)-2-methyl-4-(trifluoromethyl)pyridine 1-oxide (90% yield) as the free base; MS(ESI) m/z 207.0 [M+1]+.

C. 5-((4-((1R,4S)-4-Hydroxy-3,3-dimethylcyclohexylamino)-5-(trifluoromethyl)pyrimidin-2-ylamino)methyl)-2-methyl-4-(trifluoromethyl)pyridine 1-oxide A solution of (1S,4R)-2,2-dimethyl-4-((2-(methylsulfinyl)-5-(trifluoromethyl)pyrimidin-4-yl)amino)cyclohexanol (1.0 equiv.) and 5-(aminomethyl)-2-methyl-4-(trifluoromethyl)pyridine 1-oxide (1.0 equiv.) in dioxane (0.15 M) was heated at 110° C. for 14 h. Standard work-up afforded 5-(((4-(((1R,4S)-4-hydroxy-3,3-dimethylcyclohexyl)amino)-5-(trifluoromethyl)pyrimidin-2-yl)amino)methyl)-2-methyl-4-(trifluoromethyl)pyridine 1-oxide (30% yield). $^1$H NMR (400 MHz, DMSO-$d_6$) δ (ppm) 8.06 (s, 1H) 7.81-7.99 (m, 3H) 5.94-6.14 (m, 1H) 4.53 (m, 2H) 4.24-4.42 (m, 1H) 3.91 (m, 1H) 2.98-3.24 (m, 1H) 2.23-2.39 (m, 3H) 1.28-1.75 (m, 4H) 0.83-1.24 (m, 3H) 0.74 (s, 3H) 0.57 (s, 3H); MS(ESI) m/z 494.3 [M+1]+.

Example 6

(1S,3R)-3-(2-((4-Isopropylpyrimidin-5-yl)methylamino)-5-(trifluoromethyl)pyrimidin-4-ylamino)-2,2-dimethylcyclobutanol

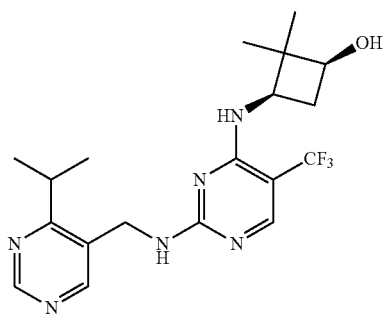 [SMILES: CC(C)c1ncncc1CNc1ncc(C(F)(F)F)c(N[C@@H]2C[C@H](O)C2(C)C)n1]

A. tert-Butyl ((4-isopropylpyrimidin-5-yl)methyl)carbamate (4-isopropylpyrimidin-5-yl)methanamine (1.0 equiv.), di-tert-butyl dicarbonate (1.0 equiv.) and triethylamine (2.5 equiv.) were combined in THF (0.25 M). The solution was stirred at ambient temperature. After 90 min, LCMS showed the desired mixture of products. The solution was decanted directly onto a 100 gram biotage column (0-20% ethyl acetate in hexanes, then 20% ethyl acetate in hexanes, then 30% ethyl acetate in hexanes) to afford tert-butyl ((4-isopropylpyrimidin-5-yl)methyl)carbamate (33.5% yield). MS(ESI) m/z 252.0 [M+1]+.

B. (4-Isopropylpyrimidin-5-yl)methanamine dihydrochloride tert-Butyl ((4-isopropylpyrimidin-5-yl)methyl)carbamate (1.0 equiv.) was combined in DCM (3.8 M) and cooled to 0° C. Hydrogen chloride (4 M) in dioxanes (3.1 equiv.) was then added via syringe. The solution was allowed to stir at ambient temperature. After 5 h, additional solution of hydrogen chloride (4 M) in dioxanes was added and stirring continued. After another 2 h, the volatile organic solvents were removed under reduced pressure to afford (4-isopropylpyrimidin-5-yl)methanamine dihydrochloride (95% yield) as a bis hydrochloride salt. MS (ESI) m/z 151.3 [M+1]+.

C. Methyl 2,2-dimethyl-3-oxocyclobutanecarboxylate

To a stirred mixture of 1-chloro-N,N,2-trimethylprop-1-en-1-amine (1.0 equiv.) and zinc trifluoromethanesulfonate (1.3 equiv.) was added methyl acrylate (1.2 equiv.) under nitrogen. Then the resulting mixture was sonicated for 12 h. After reaction completion, aqueous solution of sodium bicarbonate was added and the mixture was extracted with ethyl acetate, washed with brine, dried over anhydrous sodium sulfate and filtered. The filtrate was concentrated under vacuum, the residue was purified by silica gel column chromatography (20% ethyl acetate in petroleum ether) to afford the title product as a yellow oil (37% yield). $^1$H NMR (400 MHz, CDCl$_3$) δ (ppm) 3.76 (s, 3H), 3.59-3.51 (m, 1H), 3.15-3.06 (m, 1H), 2.99-2.94 (m, 1H), 1.32 (s, 3H), 1.12 (s, 3H).

D. 2,2-Dimethyl-3-oxocyclobutanecarboxylic acid

To a solution of methyl 2,2-dimethyl-3-oxocyclobutanecarboxylate (1.0 equiv.) in MeOH (1.1 M) was added aqueous solution of sodium hydroxide (4.48 N, 2.0 equiv.), and the resulting mixture was stirred at 50° C. for 2 h. The starting material was consumed as monitored by thin layer chromatography, eluting with 20% ethyl acetate in petroleum ether. After removal of the volatile solvent, aqueous solution of hydrochloride (2 N, 1.4 equiv.) was added to the reaction mixture, and the mixture was extracted with ethyl acetate. The combined organic layers were washed with brine, dried over anhydrous sodium sulfate and filtered. The filtrate was concentrated under vacuum to afford the product (88% yield) as a white solid, which was used for the next step without further purification. $^1$H NMR (300 MHz, DMSO-$d_6$) δ (ppm) 12.4 (br, 1H), 3.31-3.23 (m, 1H), 3.17-3.08 (m, 1H), 2.97-2.91 (m, 1H), 1.22 (s, 3H), 1.04 (s, 3H).

E. tert-Butyl (2,2-dimethyl-3-oxocyclobutyl)carbamate

To a solution of 2,2-dimethyl-3-oxocyclobutanecarboxylic acid (1.0 equiv.) and triethylamine (1.5 equiv.) in toluene (0.2 M) was added diphenylphosphoryl azide (1.5 equiv.) slowly at 0° C. The mixture was then stirred at 100° C. for 4 h. The reaction mixture was cooled to room temperature, and tert-butanol (2.5 equiv.) was added. The resulting mixture was then refluxed for 15 h. After reaction completion, aqueous solution of sodium bicarbonate was added, and the mixture was extracted with ethyl acetate, the organic layer was washed with aqueous solution of sodium bicarbonate and brine, dried over anhydrous sodium sulfate and filtered. The filtrate was concentrated under vacuum, the residue was purified by silica gel column chromatography (7% ethyl acetate in petroleum ether) to afford the title product (16% yield). $^1$H NMR (300 MHz, CDCl$_3$) δ (ppm) 4.79 (br, 1H), 4.03-4.01 (m, 1H), 3.43 (dd, $J_1$=18.0 Hz, $J_2$=9.0 Hz, 1H), 2.94 (dd, $J_1$=18.0 Hz, $J_2$=6.9 Hz, 1H), 1.48 (s, 9H), 1.28 (s, 3H), 1.13 (s, 3H).

F. tert-Butyl (3-hydroxy-2,2-dimethylcyclobutyl)carbamate

To a solution of tert-butyl (2,2-dimethyl-3-oxocyclobutyl) carbamate (1.0 equiv.) in MeOH (0.1 M) was added sodium borohydride (1.0 equiv.) in small portions at 0° C. After addition, the mixture was stirred at room temperature for 2 h, then the mixture was quenched with acetone. The solvent was removed under vacuum, the residue was passed through a short silica gel column chromatography (40% ethyl acetate in petroleum ether) to afford the crude title product (85% yield), which was used for the next step without further purification. MS (ESI) m/z 216.2 [M+H]$^+$.

G. 3-Amino-2,2-dimethylcyclobutanol

To a solution of tert-butyl (3-hydroxy-2,2-dimethylcyclobutyl)carbamate (1.0 equiv.) in anhydrous DCM (0.5 M) was added TFA (1.4 equiv.) at 0° C. and the mixture was stirred at room temperature for 30 min. After removal of the volatile solvents, the residue was neutralized with a MeOH solution of ammonia and the final resulting mixture was concentrated to give the crude title product, which was used in the next step without further purification. MS (ESI) m/z 116.2 [M+H]$^+$.

H. 3-Amino-2,2-dimethylcyclobutanol hydrochloride

3-Amino-2,2-dimethylcyclobutanol was separated by chiral SFC (Instrument: Thar200 preparative SFC, column: ChiralPak IC-10 µm, 250×30 mm I.D, mobile phase: A: CO$_2$ and 25% B: isopropanol, flow rate: 200 mL/min, back pressure: 100 bar, column temperature: 38° C., wavelength: 210 nm, cycle time: ~4.5 min). Peak one was isolated to afford one isomer of 3-hydroxy-2,2-dimethylcyclobutylcarbamate. To the isolated compound was added the HCl(g)/MeOH (4.0 equiv.) at 0° C., then stirred at room temperature for 20 min. The mixture was concentrated under reduced pressure to give 3-amino-2,2-dimethylcyclobutanol hydrochloride (22% yield) as a white solid. $^1$H NMR (DMSO-d$_6$ 400 MHz) δ (ppm) 8.26 (s, 3H), 3.53-3.57 (m, 1H), 2.84-2.85 (m, 1H), 2.35-2.40 (m, 1H), 1.85-1.88 (m, 1H), 1.06 (s, 3H), 0.99 (s, 3H).

I. (1S,3R)-2,2-Dimethyl-3-((2-(methylthio)-5-(trifluoromethyl)pyrimidin-4-yl)amino)cyclobutanol In a round-bottomed flask, 3-amino-2,2-dimethylcyclobutanol hydrochloride (peak 1, obtained above) (1.0 equiv.) and DIEA (1.3 equiv.) were combined in THF (1.0 M) and DMF (1.0 M). To this solution was added 4-chloro-2-(methylthio)-5-(trifluoromethyl)pyrimidine (1.0 equiv.) at 0° C. The mixture was allowed to warm to room temperature over 2 h; LCMS showed the desired product. Ethyl acetate was added and the organic phase was separated and dried over sodium sulfate. The organic phase was filtered and concentrated to a residue. The dried residue was purified by silica gel chromatography (Biotage column, 0-50% hexane in ethyl acetate; 340 g SNAP column). Concentration of the desired fractions afforded the title compound. The stereochemistry was determined as described for other intermediates described herein, by X-ray crystallography. $^1$H NMR (500 MHz, CDCl$_3$) δ (ppm) 8.22 (d, J=0.63 Hz, 1H) 5.21 (br. s., 1H) 4.08-4.23 (m, 1H) 3.78-3.91 (m, 1H) 2.80 (dt, J=11.66, 7.41 Hz, 1H) 2.52-2.57 (m, 3H) 1.79 (ddd, J=11.66, 9.46, 7.88 Hz, 1H) 1.67 (d, J=6.31 Hz, 1H) 1.24-1.32 (m, 3H) 0.97-1.06 (m, 3H).

J. (1S,3R)-3-(2-((4-Isopropylpyrimidin-5-yl)methylamino)-5-(trifluoromethyl)pyrimidin-4-ylamino)-2,2-dimethylcyclobutanol In a round-bottomed flask, (1S,3R)-2,2-dimethyl-3-((2-(methylthio)-5-(trifluoromethyl)pyrimidin-4-yl)amino)cyclobutanol (1.0 equiv.) and 3-chlorobenzoperoxoic acid (2.0 equiv.) were combined in THF (0.5 M). The reaction was stirred at 25° C. for 45 min. The mixture was diluted with ethyl acetate. To this solution was added potassium carbonate (4.0 equiv.). The mixture was stirred at room temperature for 30 min and then filtered. The filtrate was concentrated to afford the crude product. A solution of (1S,3R)-2,2-dimethyl-3-((2-(methylsulfonyl)-5-(trifluoromethyl)pyrimidin-4-yl)amino)cyclobutanol (1.0 equiv.), DIEA (3.0 equiv.) and (4-isopropylpyrimidin-5-yl)methanamine dihydrochloride (1.5 equiv.) were combined in dioxane (0.4 M) and stirred at ambient temperature. Additional dioxane was added to ensure solubility. After 1 h at room temperature, LCMS indicated the presence of some product. After 12 h, the reaction was heated to 75° C. for 6 h. Standard work-up afforded the title compound (39% yield). $^1$H NMR (400 MHz, DMSO-d$_6$) δ (ppm) 8.97 (s, 1H) 8.32-8.68 (m, 1H) 8.03 (s, 1H) 7.26-7.93 (m, 1H) 6.07 (d, J=7.03 Hz, 1H) 4.79 (m, 1H) 4.54 (br. s., 2H) 3.80-3.96 (m, 1H) 3.37-3.59 (m, 1H) 2.15-2.41 (m, 1H) 2.05 (m, 1H) 1.06-1.24 (m, 6H) 0.67-0.92 (m, 6H); MS(ESI) m/z 411.3 [M+1]$^+$.

Example 7

4-((1R,3S)-3-Hydroxy-2,2-dimethylcyclobutylamino)-2-((4-isopropylpyrimidin-5-yl)methylamino)pyrimidine-5-carbonitrile; 4-((1S,3R)-3-Hydroxy-2,2-dimethylcyclobutylamino)-2-((4-isopropylpyrimidin-5-yl)methylamino)pyrimidine-5-carbonitrile

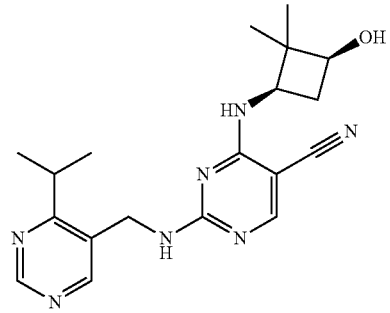

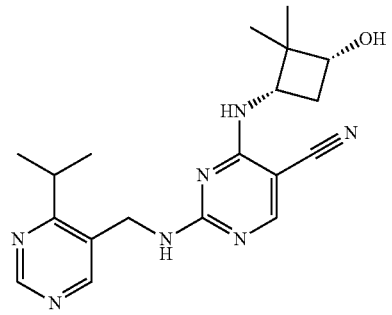

A. 4-(3-Ethoxy-2,2-dimethylcyclobutylamino)-2-(methylthio)pyrimidine-5-carbonitrile A solution of 3-ethoxy-2,2-dimethylcyclobutanamine (1.0 equiv.) and 4-chloro-2-(methylthio)pyrimidine-5-carbonitrile (1.1 equiv.) in tert-butanol/1,2-dichloroethane (0.5 M) was treated with potassium carbonate powder (3.0 equiv.). The resulting reaction mixture was then heated at 70° C. under nitrogen for 3 h. After cooling, ethyl acetate was added and the mixture was vigorously stirred. The solid was removed by vacuum-filtration. The filtrate was concentrated and further dried to give (100% yield) of waxy, yellow solid, which was used in the next step without further purification. MS (ESI) m/z 293.0 [M+1]$^+$.

B. 4-(3-Hydroxy-2,2-dimethylcyclobutylamino)-2-(methylthio)pyrimidine-5-carbonitrile A cooled (0° C.), stirred solution of 4-((3-ethoxy-2,2-dimethylcyclobutyl)amino)-2-(methylthio)pyrimidine-5-carbonitrile (1.0 equiv.) in DCM (0.7 M) was treated with 1.0 M tribromoborane in DCM (3.0 equiv.). The cooling bath was removed and the reaction mixture was stirred at room temperature for 1 h. The reaction was quenched with MeOH. DCM and saturated sodium bicarbonate were added. The separated aqueous layer was extracted with DCM. The organic extract was dried over sodium sulfate, filtered and concentrated to give a brown oil, which was purified by silica gel column chromatography (0-45% ethyl acetate in hexane, 25 g column) to give (37% yield) of yellow solid. $^1$H NMR (400 MHz, CDCl$_3$) δ (ppm) 8.24 (s, 1H), 5.42 (d, J=7.03 Hz, 1H), 4.09 (dt, J=7.62, 9.37 Hz, 1H), 3.80-3.89 (m, 1H), 2.77 (dt, J=7.42, 11.72 Hz, 1H), 2.48-2.54 (m, 3H), 1.84 (ddd, J=8.20, 9.47, 11.62 Hz, 1H), 1.74 (d, J=6.25 Hz, 1H), 1.23-1.28 (m, 3H), 0.99-1.03 (m, 3H). MS (ESI) m/z 264.8 [M+1]$^+$.

C. 4-(3-Hydroxy-2,2-dimethylcyclobutylamino)-2-(methylsulfonyl)pyrimidine-5-carbonitrile A solution of 4-((3-hydroxy-2,2-dimethylcyclobutyl) amino)-2-(methylthio)pyrimidine-5-carbonitrile (1.0 equiv.) in THF (0.25 M) was treated with 77% 3-chloroperoxybenzoic acid (2.0 equiv.) at room temperature portion-wise and slowly to keep the temperature low. The reaction solution was stirred at room temperature for 1 h and LCMS showed complete reaction with the formation of the above two products. The reaction was diluted with ethyl acetate and treated with potassium carbonate powder (4.0 equiv.). The mixture was stirred vigorously for 2 h and filtered. The cake was rinsed with ethyl acetate thoroughly. The filtrate was concentrated to give 0.76 g (crude 100%) of yellow foam, which was used in the next step without further purification. MS (ESI) m/z 297.1 [M+1]$^+$. MS (ESI) m/z 281.1 [M+1]$^+$

D. (4-Isopropylpyrimidin-5-yl)methanamine

A mixture of 4-(2-fluoropropan-2-yl)pyrimidine-5-carbonitrile (1.0 equiv.) and Raney-nickel in THF (0.5 M) was degassed under vacuum. The resulting mixture was hydrogenated under a fully-inflated balloon at room temperature overnight. The mixture was filtered through a pad of celite and the cake was rinsed with MeOH. The filtrate was concentrated and further dried to give a brown oil, which was purified by silica gel column chromatography (0-20% MeOH in ethyl acetate, 50 g column) to give (30% yield) of pale yellow oil as a 3:2 mixture of the above two products. MS (ESI) m/z 152.0 [M+1]$^+$. MS (ESI) m/z 170.0 [M+1]$^+$.

E. 4-((1R,3S)-3-Hydroxy-2,2-dimethylcyclobutylamino)-2-((4-isopropylpyrimidin-5-yl)methylamino)pyrimidine-5-carbonitrile and 4-((1S,3R)-3-hydroxy-2,2-dimethylcyclobutylamino)-2-((4-isopropylpyrimidin-5-yl)methylamino)pyrimidine-5-carbonitrile A solution of crude (4-isopropylpyrimidin-5-yl)methanamine (2.0 equiv.) and 4-((3-hydroxy-2,2-dimethylcyclobutyl)amino)-2-(methylsulfonyl)pyrimidine-5-carbonitrile (1.0 equiv.) in dioxane (0.2 M) was heated at 110° C. by microwave for 1 h. The reaction was concentrated to give a solid residue, which was purified by standard chiral separation methods, to yield the following two compounds.

4-((1R,3S)-3-Hydroxy-2,2-dimethylcyclobutylamino)-2-((4-isopropylpyrimidin-5-yl)methylamino)pyrimidine-5-carbonitrile The absolute stereochemistry was determined as described herein for other compounds. 99.5% ee. $^1$H NMR (400 MHz, DMSO-d$_6$) δ (ppm) 8.96-9.03 (m, 1H), 8.43-8.54 (m, 1H), 8.17-8.24 (m, 1H), 8.11 (t, J=5.66 Hz, 1H), 7.29 (d, J=7.42 Hz, 1H), 4.81 (d, J=5.47 Hz, 1H), 4.50-4.62 (m, 2H), 3.74-3.85 (m, 1H), 3.39-3.54 (m, 1H), 3.28 (dt, J=6.69, 13.57 Hz, 1H), 2.19-2.36 (m, 1H), 2.08-2.19 (m, 1H), 1.18 (d, J=5.47 Hz, 3H), 1.20 (d, J=5.47 Hz, 3H), 1.14 (s, 1H), 0.87 (s, 2H), 0.78 (s, 3H); MS (ESI) m/z 368.1 [M+1]$^+$.

4-((1S,3R)-3-Hydroxy-2,2-dimethylcyclobutylamino)-2-((4-isopropylpyrimidin-5-yl)methylamino)pyrimidine-5-carbonitrile 100% ee. $^1$H NMR (400 MHz, DMSO-d$_6$) δ (ppm) 8.98-9.03 (m, 1H), 8.44-8.53 (m, 1H), 8.17-8.24 (m, 1H), 8.11 (t, J=5.86 Hz, 1H), 7.29 (d, J=7.42 Hz, 1H), 4.81 (d, J=5.08 Hz, 1H), 4.49-4.62 (m, 2H), 3.74-3.85 (m, 1H), 3.41-3.55 (m, 1H), 3.28 (dt, J=6.54, 13.47 Hz, 1H), 2.19-2.35 (m, 1H), 2.09-2.19 (m, 1H), 1.19 (d, J=0.78 Hz, 3H), 1.19 (d, J=11.72 Hz, 3H), 1.14 (s, 1H), 0.87 (s, 2H), 0.78 (s, 3H); MS (ESI) m/z 368.1 [M+1]$^+$.

Example 8

(1S,3R)-3-((2-(((4-(2-Fluoropropan-2-yl)pyrimidin-5-yl)methyl)amino)-5-(trifluoromethyl)pyrimidin-4-yl)amino)-2,2-dimethylcyclobutanol

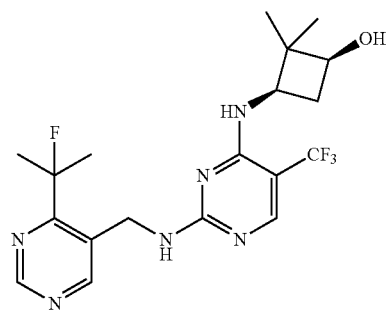 [SMILES: CC(C)(F)c1ncncc1CNc1ncc(C(F)(F)F)c(N[C@@H]2C[C@H](O)C2(C)C)n1]

A. tert-Butyl ((4-(2-fluoropropan-2-yl)pyrimidin-5-yl)methyl)carbamate

A mixture of (4-(2-fluoropropan-2-yl)pyrimidin-5-yl)methanamine and (4-isopropylpyrimidin-5-yl)methanamine (1.0 equiv.), di-tert-butyl dicarbonate (1.0 equiv.) and triethylamine (2.5 equiv.) were combined in THF (0.25 M). The solution was stirred at ambient temperature. After 90 min, the solution was decanted directly onto a 100 gram biotage column (0-20% ethyl acetate in hexanes (2.5 L), then 20% ethyl acetate in hexanes, then 30% ethyl acetate in hexanes) to afford the fluoro desired (39% yield). MS(ESI) m/z 270.0 [M+1]$^+$.

B. (4-(2-Fluoropropan-2-yl)pyrimidin-5-yl)methanamine dihydrochloride tert-Butyl ((4-(2-fluoropropan-2-yl)pyrimidin-5-yl)methyl)carbamate (1.0 equiv.) was combined in DCM (1.5 M) at ambient temperature, and 4.0 M hydrogen chloride in dioxanes was added via syringe. The solution was allowed to stir at ambient temperature. After 16 h, the solution was condensed under reduced pressure to afford the title compound as a white solid (100% yield). $^1$H NMR (400 MHz, DMSO-d$_6$) δ ppm 9.17 (d, J=1.56 Hz, 1H), 8.89 (s, 1H), 8.32 (br. s., 2H), 4.22 (dd, J=5.66, 3.32 Hz, 2H), 1.59-1.84 (m, 6H); MS(ESI) m/z [M+1]$^+$.

C. (1S,3R)-2,2-Dimethyl-3-((2-(methylsulfonyl)-5-(trifluoromethyl)-pyrimidin-4-yl)amino)cyclobutanol and (1S,3R)-2,2-dimethyl-3-((2-(methylsulfinyl)-5-(trifluoromethyl)pyrimidin-4-yl)amino)cyclobutanol A solution of (1S,3R)-2,2-dimethyl-3-((2-(methylthio)-5-(trifluoromethyl)pyrimidin-4-yl)amino)cyclobutanol (1.0 equiv.) in THF (0.5M) was treated with 3-chloroperoxybenzoic acid (2.0 equiv.) portionwise over 30 seconds. The reaction solution was stirred at ambient temperature. After 45 min the solution was diluted with ethyl acetate followed by the addition of granular potassium carbonate (4.0 equiv.). The mixture was allowed to stir at ambient temperature for 30 min. The solution was then filtered through a paper frit and the filtrate condensed under reduced pressure to afford an 80% sulfone and 20% sulfoxide white foam (96% yield). MS(ESI) m/z 324.0 [M+1]$^+$ and MS(ESI) m/z 340.4 [M+1]$^+$.

D. (1S,3R)-3-((2-(((4-(2-Fluoropropan-2-yl)pyrimidin-5-yl)methyl)amino)-5-(trifluoromethyl)pyrimidin-4-yl)amino)-2,2-dimethylcyclobutanol A solution of (1S,3R)-2,2-Dimethyl-3-((2-(methylsulfonyl)-5-(trifluoromethyl)pyrimidin-4-yl)amino)cyclobutanol (1.0 equiv.) and (4-(2-fluoropropan-2-yl)pyrimidin-5-yl)methanamine dihydrochloride (1.3 equiv.) were combined in dioxane (0.4 M) and stirred at ambient temperature. After 1 h, the solution was heated to 75° C. After 16 h, the solution was concentrated under reduced pressure and after standard work-up the title compound (50.9% yield) was obtained. The absolute stereochemistry was determined, using the chiral intermediate, as described herein for other compounds. $^1$H NMR (400 MHz, DMSO-d$_6$) δ (ppm) 9.01 (s, 1H), 8.47-8.67 (m, 1H), 7.94-8.14 (m, 1H), 7.78 (br. s., 1H), 6.07 (d, J=7.81 Hz, 1H), 4.66-4.91 (m, 2H), 3.35 (br. s., 1H), 1.96-2.22 (m, 1H), 1.62-1.82 (m, 6H), 0.54-1.23 (m, 6H); MS(ESI) m/z 429.3 [M+1]$^+$.

Example 9

3-(((5-Cyano-4-(((1s,4s)-4-hydroxy-4-methylcyclohexyl)amino)pyrimidin-2-yl)amino)methyl)-4-(trifluoromethyl)pyridine 1-oxide

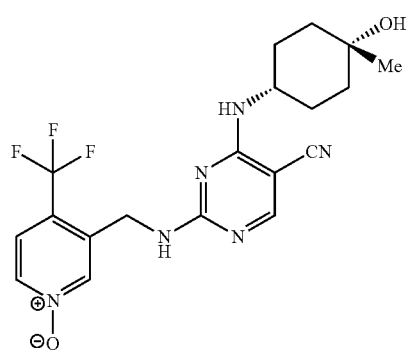 [SMILES: C[C@]1(O)CC[C@@H](Nc2nc(NCc3c[n+]([O-])ccc3C(F)(F)F)ncc2C#N)CC1]

A. 3-(((5-Cyano-4-(((1s,4s)-4-hydroxy-4-methylcyclohexyl)amino)pyrimidin-2-yl)amino)methyl)-4-(trifluoromethyl)pyridine 1-oxide 3-(((4-Chloro-5-cyanopyrimidin-2-yl)amino)methyl)-4-(trifluoromethyl)pyridine 1-oxide (1.0 equiv.) was placed in a sealable flask with (1s,4s)-4-amino-1-methylcyclohexanol (1.1 equiv.), DIEA (1.1 equiv.), and THF (0.3 M). The flask was purged with nitrogen and sealed. The reaction mixture was heated to 60° C. for 18 h. After standard work-up, 3-(((5-cyano-4-(((1s,4s)-4-hydroxy-4-methylcyclohexyl)amino)pyrimidin-2-yl)amino)methyl)-4-(trifluoromethyl)pyridine 1-oxide was obtained (57% yield). $^1$H NMR (400 MHz, DMSO-d$_6$) δ (ppm) 8.26-8.35 (m, 1H) 8.15-8.25 (m, 2H) 7.94-8.09 (m, 1H) 7.70-7.81 (m, 1H) 7.31 (d, J=7.42 Hz, 1H) 4.44-4.66 (m, 2H) 3.85-4.10 (m, 1H) 1.54-1.71 (m, 1H) 1.43 (m, 1H) 1.22 (m, 1H) 0.92-1.14 (m, 4H); MS(ESI) m/z 423.4 [M+1]$^+$.

Example 10

2-(((2-Fluoro-4-phenylpyrimidin-5-yl)methyl)amino)-4-(((1s,4s)-4-hydroxy-4-methylcyclohexyl)amino)pyrimidine-5-carbonitrile

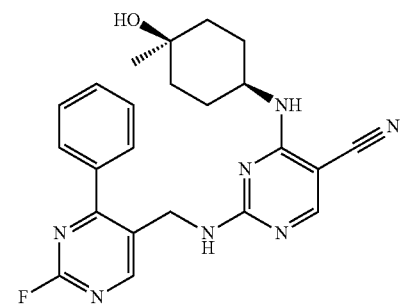 [SMILES: C[C@]1(O)CC[C@@H](Nc2nc(NCc3cnc(F)nc3-c3ccccc3)ncc2C#N)CC1]

A. 4-(((1s,4s)-4-Hydroxy-4-methylcyclohexyl)amino)-2-(methylthio)pyrimidine-5-carbonitrile A mixture of 4-chloro-2-(methylthio)pyrimidine-5-carbonitrile (1.0 equiv.), (1s,4s)-4-amino-1-methylcyclohexanol (1.2 equiv.) and DIEA (2.4 equiv.) in THF (0.2 M) was stirred at 50° C. for 2 h. After reaction completion, the solvent was removed reduced pressure, the residue was purified by purified by silica gel chromatography (20% ethyl acetate in petroleum ether) to afford the title compound (83% yield) as a white solid. MS (ESI) m/z 279.1 [M+H]$^+$.

B. Mixture of 4-(((1s,4s)-4-hydroxy-4-methylcyclohexyl)amino)-2-(methylsulfinyl)pyrimidine-5-carbonitrile and 4-(((1s,4s)-4-hydroxy-4-methylcyclohexyl)amino)-2-(methylsulfonyl)pyrimidine-5-carbonitrile To a cooled solution (0° C.) of 4-(((1s,4s)-4-hydroxy-4-methylcyclohexyl)amino)-2-(methylthio)pyrimidine-5-carbonitrile (1.0 equiv.) in DCM (0.5 M) was added 3-chloroperbenzoic acid (1.1 equiv.) in small portions at 0° C. Then the mixture was stirred at room temperature for 1 h. After reaction completion, the reaction mixture was concentrated. The residue was purified by silica gel column chromatography (10% MeOH in DCM) to afford the desired product as a white solid, which was used in the next step without further purification. MS (ESI) m/z=295.2 [M+1]$^+$/311.2 [M+1]$^+$.

C. 3-Oxo-3-phenylpropanenitrile

To a solution of benzoic acid methyl ester (1.0 equiv.) and methyl cyanide (2.0 equiv.) in anhydrous THF (1.0 M) was added sodium hydride (60% in mineral oil, 2 equiv.) under nitrogen. After the resulting reaction mixture was stirred at 70° C. overnight, the reaction mixture was quenched with ice-water and extracted with ethyl acetate. The combined organic layers were washed with brine, dried over anhydrous sodium sulfate and filtered. Concentration under vacuum afforded the crude product as a brown solid. $^1$H-NMR (400 MHz, CDCl$_3$) δ (ppm) 7.94-7.92 (m, 2H), 7.69-7.65 (m, 1H), 7.55-7.54 (m, 2H), 4.08 (s, 2H).

D. 2-Amino-4-phenylpyrimidine-5-carbonitrile

A solution of 3-oxo-3-phenylpropanenitrile (1.0 equiv.) in 1,1-dimethoxy-N,N-dimethylmethanamine (2.2 M) was stirred at 50° C. under nitrogen overnight. After reaction completion, the reaction mixture was concentrated. The residue was purified by silica gel column chromatography (30% ethyl acetate in petroleum ether) to afford 2-benzoyl-3-(dimethylamino)acrylonitrile (8% yield) as a yellow oil. $^1$H-NMR (400 MHz, DMSO-d$_6$) δ (ppm) 7.83 (s, 1H), 7.61-7.60 (m, 2H), 7.52-7.50 (m, 1H), 7.47-7.45 (m, 2H), 3.37 (s, 3H), 3.28 (s, 3H); MS (ESI) m/z=201.2 [M+1]$^+$.
A solution of 2-benzoyl-3-(dimethylamino)acrylonitrile (1.0 equiv.), potassium carbonate (2.0 equiv.) and guanidine nitrate (1.3 equiv.) in ethanol (0.2 M) was stirred at 80° C. under nitrogen overnight. After reaction completion, the reaction mixture was concentrated. The residue was purified by silica gel column chromatography (30% ethyl acetate in petroleum ether) to afford the desired mixture product (48% yield) as a yellow solid, which were used for the next step without further purification. $^1$H-NMR (400 MHz, DMSO-d$_6$) δ (ppm) 8.73 (s, 1H), 7.87-7.83 (m, 4H), 7.58-7.56 (m, 3H); MS (ESI) m/z=197.2 [M+1]$^+$.

E. 5-(Aminomethyl)-4-phenylpyrimidin-2-amine

To a solution of 2-amino-4-phenylpyrimidine-5-carbonitrile (1.0 equiv.) in THF (0.15 M) was added ammonium hydroxide and Raney nickel. The mixture was stirred at room temperature under hydrogen atmosphere overnight and then the reaction mixture was filtered through celite. The filtrate was concentrated in vacuo to give the crude title compound (56% yield) as a yellow solid. The product was used without further purification. $^1$H-NMR (300 MHz, DMSO-d$_6$) δ (ppm) 8.34 (s, 1H), 7.69-7.65 (m, 2H), 7.46-7.44 (m, 3H), 6.50 (br, 2H), 3.54 (s, 2H), 1.70 (br, 2H); MS (ESI) m/z=201.2 [M+1]$^+$.

F. 2-(((2-Amino-4-phenylpyrimidin-5-yl)methyl)amino)-4-(((1s,4s)-4-hydroxy-4-methylcyclohexyl)amino)pyrimidine-5-carbonitrile A mixture of 4-(((1s,4s)-4-hydroxy-4-methylcyclohexyl)amino)-2-(methylsulfinyl)pyrimidine-5-carbonitrile and 4-(((1s,4s)-4-hydroxy-4-methylcyclohexyl)amino)-2-(methylsulfonyl)pyrimidine-5-carbonitrile (1.0 equiv.), 5-(aminomethyl)-4-phenylpyrimidin-2-amine (1.0 equiv.) and DIEA (1.7 equiv.) in THF (0.2 M) was stirred at 120° C. in a micro-wave reactor for 2 h. After reaction completion, the solvent was removed under reduced pressure, the residue was purified by silica gel chromatography (5% MeOH in DCM) to give the desired product (74% yield) as a yellow solid. MS (ESI) m/z 431.2 [M+H]$^+$.

G. 2-(((2-Fluoro-4-phenylpyrimidin-5-yl)methyl)amino)-4-(((1s,4s)-4-hydroxy-4-methylcyclohexyl)amino)pyrimidine-5-carbonitrile To a suspension of 2-(((2-amino-4-phenylpyrimidin-5-yl)methyl)amino)-4-(((1s,4s)-4-hydroxy-4-methylcyclohexyl)amino)pyrimidine-5-carbonitrile (1.0 equiv.) in tetrafluoroborate acid and acetone was added aqueous solution of sodium nitrite (1.7 equiv.) drop-wise at 0° C. over 30 min, and then the reaction mixture was stirred at room temperature for 2 h. The reaction was quenched with sodium bicarbonate power and standard work up afforded the title compound (6% yield) as a white solid. $^1$H-NMR (400 MHz, CD$_3$OD) δ (ppm) 8.59 (s, 1H), 7.97 (s, 1H), 7.61-7.60 (m, 2H), 7.47-7.46 (m, 3H), 4.60 (s, 2H), 3.55-3.53 (m, 1H), 1.65-1.49 (m, 6H), 1.40-1.35 (m, 2H), 1.10 (s, 3H); MS (ESI) m/z 433.2 [M+H]$^+$.

Example 11

3-(((4-(((1R,3S)-3-(Hydroxymethyl)-2,2-dimethylcyclobutyl)amino)-5-(trifluoromethyl)pyrimidin-2-yl)amino)methyl)-4-(trifluoromethyl)pyridine 1-oxide

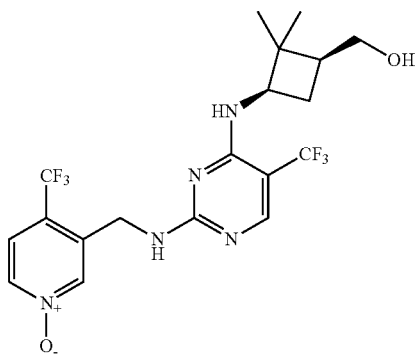

A. 3-(((4-Chloro-5-(trifluoromethyl)pyrimidin-2-yl) amino)methyl)-4-(trifluoromethyl)pyridine 1-oxide 3-(Aminomethyl)-4-(trifluoromethyl)pyridine 1-oxide hydrochloride (1.0 equiv.) was dissolved in DIEA (2.5 equiv.) and DMF (0.4 M). The homogeneous solution was cooled to −20° C. using an ice and brine bath. To the solution was added 2,4-dichloro-5-(trifluoromethyl)pyrimidine (1.0 equiv.). The solution was stirred for 10 min at −20° C. and then warmed to ambient temperature for 30 min. After 30 min, the solution was diluted with ethyl acetate and water. The aqueous layer was separated and extracted with ethyl acetate (3×). The organic layers were combined and dried over magnesium sulfate, filtered and the solvent was removed under reduced pressure to afford a white solid. The solid was purified via biotage chromatography (0-60% ethyl acetate in hexanes, then 60% ethyl acetate) to afford the title compound as a white solid (47% yield). MS(ESI) m/z 372.8[M]$^+$.

B. 3-(((4-(((1R,3S)-3-(Hydroxymethyl)-2,2-dimethylcyclobutyl)amino)-5-(trifluoromethyl)pyrimidin-2-yl)amino)methyl)-4-(trifluoromethyl)pyridine 1-oxide 3-(((4-Chloro-5-(trifluoromethyl)pyrimidin-2-yl)amino) methyl)-4-(trifluoromethyl)pyridine 1-oxide (1.0 equiv.), ((1S,3R)-3-amino-2,2-dimethylcyclobutyl) MeOH and DIEA (1.2 equiv.) were combined in ethanol (0.1 M). The solution was stirred at 85° C. in a screw capped scintillation vial. After 16 h, the solution was condensed under reduced pressure and the residue was purified by standard chiral separation methods to afford the title compound (54% yield). $^1$H NMR (400 MHz, DMSO-d$_6$) δ (ppm) 8.26 (d, J=6.64 Hz, 1H), 8.07 (s, 1H), 7.96-8.03 (m, 1H), 7.89-7.96 (m, 1H), 7.75 (d, J=6.64 Hz, 1H), 6.30 (d, J=7.81 Hz, 1H), 4.61 (br. s., 2H), 4.25-4.41 (m, 1H), 4.04-4.18 (m, 1H), 1.90-2.02 (m, 1H), 1.73-1.89 (m, 1H), 1.54-1.69 (m, 1H), 1.21 (br. s., 1H), 0.68-0.92 (m, 6H); MS(ESI) m/z 466.2 [M+1]

Example 12

(1R,2R,5S)-2-methyl-5-(5-(trifluoromethyl)-2-((4-(trifluoromethyl)pyridin-3-yl)methylamino)pyrimidin-4-ylamino)cyclohexanol

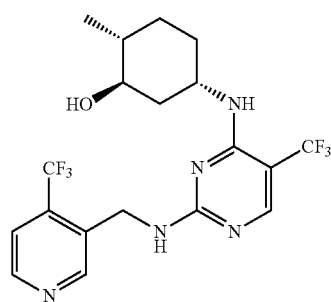 [SMILES: C[C@@H]1CC[C@H](Nc2nc(NCc3cnccc3C(F)(F)F)ncc2C(F)(F)F)C[C@H]1O]

A. 4-Chloro-5-(trifluoromethyl)-N-((4-(trifluoromethyl)pyridin-3-yl)methyl)pyrimidin-2-amine (4-(Trifluoromethyl)pyridin-3-yl)methanamine, HCl (1.0 equiv.) was placed in a round bottom flask with DIEA (2.5 M) and DMF (0.6 M). The flask was cooled to 0° C. and 2,4-dichloro-5-(trifluoromethyl)pyrimidine (1.0 equiv.) was slowly added portion-wise. The reaction mixture was stirred overnight and allowed to warm to room temperature. The reaction mixture was loaded directly onto a silica gel column and purified using 0-20% ethyl acetate in hexanes followed by 20% ethyl acetate in hexanes. Fractions containing the desired isomer (lower Rf spot by thin layer chromatography) were combined and volatile organic solvents were removed under reduced pressure to give 4-chloro-5-(trifluoromethyl)-N-((4-(trifluoromethyl)pyridin-3-yl)methyl)pyrimidin-2-amine (17.2% yield) as a white solid. MS (ESI) m/z 357.2 [M+1]$^+$

B. (1R,2R,5S)-2-Methyl-5-(5-(trifluoromethyl)-2-((4-(trifluoromethyl)-pyridin-3-yl)methylamino)pyrimidin-4-ylamino)cyclohexanol 4-Chloro-5-(trifluoromethyl)-N-((4-(trifluoromethyl) pyridin-3-yl)methyl)pyrimidin-2-amine (1.0 equiv.) was placed in a sealable flask with (1R,2R,5S)-5-amino-2-methylcyclohexanol (1.1 equiv.), DIEA (2.0 equiv.), and THF (0.1 M). The flask was purged with nitrogen and sealed. The reaction mixture was heated to 60° C. for 18 h. Standard work-up, afforded (1R,2R,5S)-2-methyl-5-(5-(trifluoromethyl)-2-((4-(trifluoromethyl)pyridin-3-yl)methylamino)pyrimidin-4-ylamino)cyclohexanol (47.3% yield) as a white solid. $^1$H NMR (400 MHz, DMSO-d$_6$) δ (ppm) 8.65-8.76 (m, 2H) 8.01-8.14 (m, 1H) 7.71 (d, J=5.08 Hz, 1H) 5.74 (br. s., 1H) 4.67-4.80 (m, 1H) 4.57-4.67 (m, 1H) 4.54 (br. s., 1H) 4.39 (d, J=4.30 Hz, 1H) 4.14 (br. s., 1H) 3.21-3.31 (m, 1H) 1.78 (br. s., 1H) 1.54 (br. s., 1H) 1.41 (br. s., 1H) 1.33 (br. s., 1H) 1.10-1.24 (m, 1H) 0.96 (br. s., 1H) 0.81-0.89 (m, 2H). MS (ESI) m/z 450.2 [M+1]$^+$

Example 13 cis-4-((5-Cyano-2-(((4-(trifluoromethyl)pyridin-3-yl)methyl)amino)pyrimidin-4-yl)amino)-N-methylcyclohexanecarboxamide

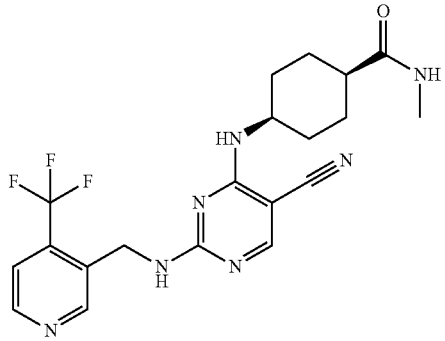 [SMILES: CNC(=O)[C@H]1CC[C@@H](Nc2nc(NCc3cnccc3C(F)(F)F)ncc2C#N)CC1]

A. 4-Chloro-2-((4-(trifluoromethyl)pyridin-3-yl) methylamino)pyrimidine-5-carbonitrile To (4-(trifluoromethyl)pyridin-3-yl)methanamine hydrochloride (1.0 equiv.) in DMF (1.0 M) was added DIEA (2.5 equiv.). The reaction was cooled to −20° C. (ice/brine bath) then added 2,4-dichloropyrimidine-5-carbonitrile (1.0 equiv.). The reaction mixture was stirred for 10 min, then removed from the ice bath and allowed to stir for 30 min.

The reaction mixture was diluted with ethyl acetate and partitioned with water. The organic layer was separated and volatile solvents were removed under reduced pressure. The residue was purified using silica gel chromatography (5-50% ethyl acetate in hexanes). The desired fractions were combined and volatile solvents were removed under reduced pressure. The residue was triturated in 10% ethyl acetate in hexanes, filtered, washed with hexanes, and dried in vacuo to afford 4-chloro-2-(((4-(trifluoromethyl)pyridin-3-yl)methyl)amino)pyrimidine-5-carbonitrile (43.0% yield) as a pale tan solid; MS (ESI) m/z 314.0 [M+1]$^+$ B. cis-4-((5-Cyano-2-(((4-(trifluoromethyl)pyridin-3-yl)methyl)amino)pyrimidin-4-yl)amino)-N-methylcyclohexanecarboxamide 4-Chloro-2-(((4-(trifluoromethyl)pyridin-3-yl)methyl)amino)pyrimidine-5-carbonitrile (1.0 equiv.) was placed in a sealable flask with (1s,4s)-4-amino-N-methylcyclohexanecarboxamide (1.0 equiv.), 1,8-diazabicyclo[5.4.0]undec-7-ene (1.2 equiv.), and THF (0.1 M). The flask was purged with nitrogen and sealed. The reaction mixture was heated to 60° C. for 18 h. Standard work-up afforded cis-4-((5-cyano-2-(((4-(trifluoromethyl)pyridin-3-yl)methyl)amino)pyrimidin-4-yl)amino)-N-methylcyclohexanecarboxamide (48.2% yield) as a white solid. $^1$H NMR (400 MHz, DMSO-d$_6$) δ (ppm) 8.73 (d, J=5.08 Hz, 1H), 8.64-8.69 (m, 1H), 8.29 (t, J=5.66 Hz, 1H), 8.21 (s, 1H), 7.72 (d, J=5.08 Hz, 1H), 7.53-7.66 (m, 1H), 7.00-7.12 (m, 1H), 4.62-4.73 (m, 2H), 3.69 (br. s., 1H), 2.53-2.61 (m, 3H), 2.15-2.30 (m, 1H), 1.70-1.97 (m, 2H), 1.42-1.62 (m, 3H), 1.15-1.27 (m, 3H). MS (ESI) m/z 434.3 [M+1]$^+$ Example 14

3-((4-(3-Hydroxy-2,2,4,4-tetramethylcyclobutylamino)-5-(trifluoromethyl)pyrimidin-2-ylamino)methyl)-4-(trifluoromethyl)pyridine 1-oxide

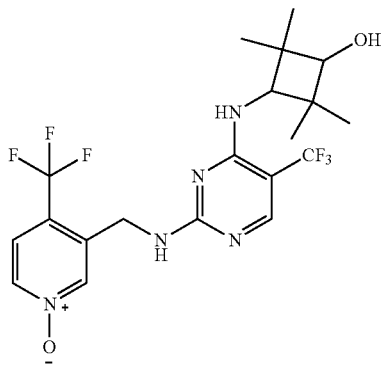 [SMILES: CC1(C)C(O)C(C)(C)C1Nc1nc(NCc2c[n+]([O-])ccc2C(F)(F)F)ncc1C(F)(F)F]

A. 3-((4-(3-Hydroxy-2,2,4,4-tetramethylcyclobutylamino)-5-(trifluoromethyl)pyrimidin-2-ylamino)methyl)-4-(trifluoromethyl)pyridine 1-oxide DIEA (3.0 equiv.) was placed in a sealable flask with 3-(((4-chloro-5-(trifluoromethyl)pyrimidin-2-yl)amino)methyl)-4-(trifluoromethyl)pyridine 1-oxide (1.0 equiv.), 3-amino-2,2,4,4-tetramethylcyclobutanol (2.0 equiv.)(See J. Med. Chem. 2011, 54, 7693-7704 for preparation), and ethanol. The flask was purged with nitrogen and sealed. The reaction mixture was heated to 80° C. for 9 h. Standard work-up afforded the following compounds. Stereochemistry was assigned based on similar activity as other compounds provided herein in the biochemical assays described herein.

3-((4-((1R,3R)-3-hydroxy-2,2,4,4-tetramethylcyclobutylamino)-5-(trifluoromethyl)pyrimidin-2-ylamino)methyl)-4-(trifluoromethyl)pyridine 1-oxide $^1$H NMR (400 MHz, DMSO-d$_6$) δ ppm 8.28 (d, J=6.25 Hz, 1H) 8.09-8.18 (m, 1H) 8.00-8.08 (m, 1H) 7.96 (s, 1H) 7.75 (m, 1H) 5.26 (m, 1H) 4.60 (m, 2H) 3.77 (m, 1H) 3.34 (s, 1H) 0.71-1.15 (m, 12H); MS (ESI) m/z 480.0 [M+1]$^+$.

3-((4-((1S,3S)-3-hydroxy-2,2,4,4-tetramethylcyclobutylamino)-5-(trifluoromethyl)pyrimidin-2-ylamino)methyl)-4-(trifluoromethyl)pyridine 1-oxide $^1$H NMR (400 MHz, DMSO-d$_6$) δ (ppm) 8.27 (d, J=6.64 Hz, 1H), 8.06-8.17 (m, 2H) 8.00 (s, 1H) 7.75 (m, 1H) 5.12 (m, 1H) 4.90 (br. s., 1H) 4.60 (m, 2H) 3.65-3.86 (m, 1H) 3.26 (br. s., 1H) 3.14 (m, 1H) 0.68-0.93 (m, 12H); MS (ESI) m/z 480.0 [M+1]$^+$.

Example 15

2-(((4-Ethylpyrimidin-5-yl)methyl)amino)-4-(((1S,3R)-3-hydroxy-2,2,3-trimethylcyclobutyl)amino)pyrimidine-5-carbonitrile, 2-(((4-ethylpyrimidin-5-yl)methyl)amino)-4-(((1R,3S)-3-hydroxy-2,2,3-trimethylcyclobutyl)amino)pyrimidine-5-carbonitrile

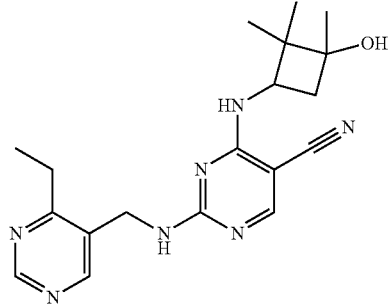 [SMILES: CCc1ncncc1CNc1ncc(C#N)c(NC2CC(C)(O)C2(C)C)n1]

A. 4-Ethylpyrimidine-5-carbonitrile

A mixture of 3-oxopentanenitrile (1.0 equiv.) and 1,1-dimethoxy-N,N-dimethylmethanamine (4.3 M) in THF (1.6 M) was stirred at room temperature overnight. After reaction completion, the solvent was removed under vacuum to give the crude 2-((dimethylamino)methylene)-3-oxopentanenitrile (0.98 equiv.), which was used for the next step without further purification. MS (ESI) m/z 152.1 [M+H]$^+$.

A mixture of crude 2-((dimethylamino)methylene)-3-oxopentanenitrile (0.98 equiv.), formamidine hydrochloride (2.0 equiv.) and triethyl amine (2.0 equiv.) in ethanol (1.0 M) was refluxed for 36 h. The solvent was removed and the residue was purified by silica column chromatography (20% ethyl acetate in petroleum ether) to afford the title product (35% yield). $^1$H-NMR (400 MHz, CDCl$_3$) δ (ppm) 9.20 (s, 1H), 8.83 (s 1H), 2.98 (d, J=7.6 Hz, 2H), 1.32 (t, J=7.6 Hz, 3H); MS (ESI) m/z 134.1 [M+H]$^+$.

B. (4-Ethylpyrimidin-5-yl)methanamine

To the solution of 4-ethylpyrimidine-5-carbonitrile (1.0 equiv.) in MeOH (0.4 M) was added ammonium hydroxide and Raney nickel. The mixture was stirred at room temperature under hydrogen atmosphere overnight and then the reaction mixture was filtered through celite. The filtrate was concentrated in vacuum to give the crude title compound (59%), which was used for the next step without further purification. MS (ESI) m/z 138.1/[M+H]$^+$.

C. 4-Chloro-2-(((4-ethylpyrimidin-5-yl)methyl)amino)pyrimidine-5-carbonitrile To a mixture of 2,4-dichloropyrimidine-5-carbonitrile (1.0 equiv. 61.4) and (4-ethylpyrimidin-5-yl)methanamine (1.0 equiv.) in isopropanol (0.2 M) was added DIEA (2.0 equiv.). The mixture was stirred at room temperature under nitrogen overnight. The reaction mixture was extracted with ethyl acetate, the organic layer was washed with a solution of ammonium chloride and concentrated under vacuum to give crude product, which was purified by silica gel chromatography (30% ethyl acetate in petroleum ether) to afford the title compound (11.4% yield) as brown solid. $^1$H-NMR (400 MHz, CD$_3$OD) δ (ppm) 9.95 (d, J=3.2 Hz, 1H), 8.64 (d, J=12.0 Hz, 1H), 8.58 (d, J=19.6 Hz, 1H), 4.70 (d, J=20.4 Hz, 2H), 2.97-2.87 (m, 2H), 1.33-1.27 (m, 3H); MS (ESI) m/z 275.1 [M+H]$^+$.

D. Methyl 2,2-dimethyl-3-oxocyclobutanecarboxylate

To a mixture of 1-chloro-N,N,2-trimethylprop-1-en-1-amine (1.0 equiv.) and zinc trifluoromethanesulfonate (1.3 equiv.) was added methyl acrylate (1.3 equiv.) with stirring under nitrogen atmosphere. Then the resulting mixture was sonicated for 12 h. The mixture was quenched with water and extracted with DCM. The combined organic layers were washed with brine, dried over anhydrous sodium sulfate and filtered. The filtrate was evaporated under reduced pressure and the residue was purified by silica gel chromatography (8% ethyl acetate in petroleum ether) to afford the title compound (37% yield) as a light yellow oil. $^1$H NMR (400 MHz, CDCl$_3$) δ (ppm) 3.76 (s, 3H), 3.59-3.51 (m, 1H), 3.15-3.06 (m, 1H), 2.99-2.94 (m, 1H), 1.32 (s, 3H), 1.12 (s, 3H).

E. 2,2-Dimethyl-3-oxocyclobutanecarboxylic acid

To a solution of methyl 2,2-dimethyl-3-oxocyclobutanecarboxylate (1.0 equiv.) in MeOH (1.1 M) was added aqueous solution of sodium hydroxide (4.48 N, 2.0 equiv.), and the resulting mixture was stirred at 50° C. for 2 h. After reaction completion, the excess MeOH was removed under reduced pressure, and the mixture was extracted with diethyl ether, then the aqueous solution was neutralized with hydrochloride acid (4 N, 2.9 equiv.). The mixture was extracted with ethyl acetate, the organic layer was washed with brine, dried over anhydrous sodium sulfate and filtered. The filtrate was concentrated under vacuum to afford the title product (88% yield) as white solid. $^1$H NMR (300 MHz, DMSO-d$_6$) δ (ppm) 12.4 (br, 1H), 3.31-3.23 (m, 1H), 3.17-3.08 (m, 1H), 2.97-2.91 (m, 1H), 1.22 (s, 3H), 1.04 (s, 3H).

F. tert-Butyl (2,2-dimethyl-3-oxocyclobutyl)carbamate

To a solution of 2,2-dimethyl-3-oxocyclobutanecarboxylic acid (1.0 equiv.) and triethylamine (1.5 equiv.) in toluene (0.2 M) was added diphenylphosphoryl azide (2.0 equiv.) slowly under ice-water bath. Then the mixture was stirred at 100° C. for 4 h. The reaction mixture was cooled down to room temperature, and tert-butanol (2.2 equiv.) was added. The resulting mixture was refluxed for 15 h. After the mixture cooled down, an aqueous solution of sodium bicarbonate and ethyl acetate were added. The organic layer was separated and the aqueous solution was extracted with ethyl acetate. The combined organic layer was washed with aqueous solution of sodium bicarbonate and brine, dried over anhydrous sodium sulfate and filtered. The filtrate was concentrated under vacuum, the residue was purified by silica gel column chromatography (7% ethyl acetate in petroleum ether) to afford the title product (16% yield). $^1$H NMR (300 MHz, CDCl$_3$) δ (ppm) 4.81-4.70 (m, 1H), 4.05-3.93 (m, 1H), 3.37 (dd, J$_1$=18.0 Hz, J$_2$=9.0 Hz, 1H), 2.89 (dd, J$_1$=18.0 Hz, J$_2$=6.9 Hz, 1H), 1.48 (s, 9H), 1.28 (s, 3H), 1.13 (s, 3H).

G. tert-Butyl (3-hydroxy-2,2,3-trimethylcyclobutyl)carbamate

To a solution of tert-butyl (2,2-dimethyl-3-oxocyclobutyl)carbamate (1.0 equiv.) in anhydrous THF (0.15 M) under nitrogen was added methyllithium (1.6 M in ether, 4.0 equiv.) drop-wise, keeping the temperature below −70° C. The mixture was stirred at this temperature for 1 h. The mixture was quenched with aqueous solution of ammonium chloride and the mixture was extracted with ethyl acetate, washed with aqueous solution of sodium bicarbonate and brine, dried over anhydrous sodium sulfate and filtered. The filtrate was concentrated under vacuum, the residue was purified by silica gel column chromatography (5% to 25% ethyl acetate in petroleum ether) to afford the title product (30% yield). $^1$H NMR (400 MHz, CDCl$_3$) δ (ppm) 4.65-4.52 (m, 1H), 3.60-3.49 (m, 1H), 2.37-2.28 (m, 1H), 1.84-1.76 (m, 1H), 1.66 (s, 1H), 1.44 (s, 9H), 1.28 (s, 3H), 1.06 (s, 3H), 1.01 (s, 3H); MS (ESI) m/z 230.2 [M+H]$^+$.

H. 3-Amino-1,2,2-trimethylcyclobutanol

To a solution of tert-butyl (3-hydroxy-2,2,3-trimethylcyclobutyl)carbamate (1.0 equiv.) in anhydrous DCM (0.5 M) was added trifluoroacetic acid (1.0 M) at 0° C. and the mixture was stirred at room temperature for 30 min. After removal of the volatile solvents, the residue was neutralized by ammonia MeOH solution and the final resulting mixture was concentrated to give the crude title product which was used for the next step without further purification. MS (ESI) m/z 130.1 [M+H]$^+$.

I. 2-(((4-Ethylpyrimidin-5-yl)methyl)amino)-4-(((1S,3R)-3-hydroxy-2,2,3-trimethylcyclobutyl)amino)pyrimidine-5-carbonitrile and 2-(((4-ethylpyrimidin-5-yl)methyl)amino)-4-(((1R,3S)-3-hydroxy-2,2,3-trimethylcyclobutyl)amino)pyrimidine-5-carbonitrile A mixture of ethyldiisopropylamine (2.0 equiv.), 3-amino-1,2,2-trimethylcyclobutanol (1.0 equiv) and 4-chloro-2-(((4-ethylpyrimidin-5-yl)methyl)amino)pyrimidine-5-carbonitrile (2.0 equiv.) in dioxane (0.2 M) was heated at 120° C. for 2 h in a microwave reactor. After reaction completion, the solvent was removed under reduced pressure, and the residue was purified by standard chiral separation methods to afford the title compounds. Stereochemistry was assigned based on similar activity as other compounds provided herein in the biochemical assays described herein.

2-(((4-Ethylpyrimidin-5-yl)methyl)amino)-4-(((1S, 3R)-3-hydroxy-2,2,3-trimethylcyclobutyl)amino) pyrimidine-5-carbonitrile (Chiral HPLC 100% e.e., retention time=2.63 min). $^1$H NMR (400 MHz, DMSO-$d_6$, T=323 K) δ (ppm) 8.96 (s, 1H), 8.48 (s, 1H), 8.19 (s, 1H), 7.98 (s, 1H), 6.91 (s, 1H), 4.55 (d, J=5.6 Hz, 2H), 4.37 (s, 1H), 3.92-3.83 (m, 1H), 2.81 (q, J=7.2 Hz, 2H), 2.24 (t, J=10.4 Hz, 1H), 2.02 (s, 1H), 1.23 (t, J=7.6 Hz, 3H), 1.13 (s, 3H), 0.87 (s, 3H), 0.80 (s, 3H); MS (ESI) m/z 368.2 [M+H]$^+$.

2-(((4-Ethylpyrimidin-5-yl)methyl)amino)-4-(((1R, 3S)-3-hydroxy-2,2,3-trimethylcyclobutyl)amino) pyrimidine-5-carbonitrile (Chiral HPLC 99% e.e., r.t.=6.16 min). $^1$H NMR (400 MHz, DMSO-$d_6$, T=323 K) δ 8.95 (s, 1H), 8.47 (s, 1H), 8.19 (s, 1H), 7.98 (s, 1H), 6.90 (s, 1H), 4.54 (d, J=6.4 Hz, 2H), 4.37 (s, 1H), 3.90-3.83 (m, 1H), 2.82 (q, J=7.6 Hz, 2H), 2.24 (t, J=10.0 Hz, 1H), 2.02 (s, 1H), 1.23 (t, J=7.6 Hz, 3H), 1.13 (s, 3H), 0.87 (s, 3H), 0.80 (s, 3H); MS (ESI) m/z 368.2 [M+H]$^+$.

Example 16

4-(((1R,3S)-3-(Hydroxymethyl)-2,2-dimethylcyclobutyl)amino)-2-(((4-(trifluoromethyl)pyridin-3-yl)methyl)amino)pyrimidine-5-carbonitrile

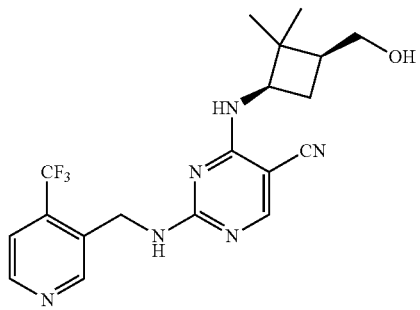 [SMILES: CC1(C)[C@@H](CO)C[C@H]1Nc1nc(NCc2cnccc2C(F)(F)F)ncc1C#N]

A. Methyl 2,2-dimethyl-3-oxocyclobutanecarboxylate

The suspension of methyl acrylate (1.3 equiv.), 1-chloro-N,N, 2-trimethylprop-1-en-1-amine (1.0 equiv.), and zinc trifluoromethanesulfonate (0.25 equiv.) was stirred to blend its contents for 15 min at room temperature under $N_2$. Then the mixture was sonicated (100 W) at 36-39° C. for 24 h. A mixture of THF: $H_2O$=10:1 was added to the mixture and sonicated. The mixture was concentrated and extracted with ethyl acetate. The combined organic layers were washed with brine, dried over anhydrous sodium sulfate and filtered. The filtrate was evaporated under reduced pressure and the residue was purified by silica gel chromatography (petroleum ether; petroleum ether: ethyl acetate=50:1, 10:1) to afford the title compound methyl 2,2-dimethyl-3-oxocyclobutanecarboxylate (29% yield) as a light yellow oil. $^1$H NMR (400 MHz, CDCl$_3$) δ (ppm) 3.73 (s, 3H), 3.51 (dd, J=7.6 Hz, 18.4 Hz, 1H), 3.07 (q, J=9.2 Hz, 18 Hz 1H), 2.94 (t, J=7.2 Hz, 8.8 Hz, 1H), 1.29 (s, 3H), 1.09 (s, 3H).

B. Methyl 3-(hydroxyimino)-2,2-dimethyl-cyclobutanecarboxylate

A mixture of methyl 2,2-dimethyl-3-oxocyclobutanecarboxylate (1.0 equiv.), hydroxylamine hydrochloride (1.4 equiv.) and sodium bicarbonate (2.5 equiv.) was suspended in MeOH (0.6 M) and stirred at 11° C. for 12 h. The solvent was removed under reduced pressure, and water was added. The mixture was extracted with ethyl acetate, washed with brine, dried over anhydrous sodium sulfate and filtered. The solvent was concentrated under reduced pressure to give the crude title product methyl 3-(hydroxyimino)-2,2-dimethyl-cyclobutanecarboxylate (92.7% yield) as a yellow oil, which was used in the next step without further purification. $^1$H NMR (400 MHz, CDCl$_3$) δ (ppm) 3.73 (s, 3H), 3.27 (dd, J=7.6 Hz, 18.4 Hz, 1H), 3.04 (q, J=9.2 Hz, 18 Hz 1H), 2.89 (t, J=7.2 Hz, 8.8 Hz, 1H), 1.57 (s, 1H), 1.40 (s, 2H), 1.28 (s, 1H), 1.19 (s, 2H).

C. Methyl 3-amino-2,2-dimethylcyclobutanecarboxylate

To a solution of methyl 3-(hydroxyimino)-2,2-dimethyl-cyclobutanecarboxylate (1.0 equiv.) in MeOH (0.4 M) was added ammonium hydroxide (0.2 M) and Raney nickel (20 wt percent). The mixture was stirred at 50° C. under 50 psi hydrogen atmospheres for about 6 h. After completion of the reaction, the mixture was filtered through celite. The filtrate was concentrated in vacuo to give the crude title compound methyl 3-amino-2,2-dimethylcyclobutanecarboxylate (82.3% yield) as green liquid. The product was used without further purification. $^1$H NMR (400 MHz, DMSO-$d_6$) δ (ppm) 3.56 (s, 3H), 2.50 (s, 0.4H), 2.14 (s, 0.24H), 1.94 (s, 0.35H), 1.71 (s, 0.73H), 1.05 (s, 2.0H), 0.76 (s, 2H).

D. (3-Amino-2,2-dimethylcyclobutyl)methanol

To a suspension of lithium aluminum hydride (2.8 equiv.) in dry THF (1.7 M) was added a solution of crude methyl 3-amino-2,2-dimethylcyclobutanecarboxylate (1.0 equiv.) in dry THF (0.7 M) at 0° C. Then the mixture was stirred under vigorously at 10° C. for 0.5 h, and then heated to 35-40° C. for 12 h. The reaction was quenched by addition of water, aqueous sodium hydroxide solution (3N) slowly at 0° C., and water. The mixture was stirred at 10° C. for 20 min, filtered through celite, and washed with ethyl acetate. The organic phase was dried over anhydrous sodium sulfate and filtered. The filtrate was concentrated in vacuo to give the crude title compound (3-amino-2,2-dimethylcyclobutyl)methanol as a racemic mixture (89.7% yield).

E. Benzyl 3-(hydroxymethyl)-2,2-dimethylcyclobutyl)carbamate

To a mixture of 4-amino-2,2-dimethylcyclohexanol (1.0 equiv.) in saturated aqueous sodium carbonate solution (1.3 equiv) in water (1.7 M) and THF (1.4 M) was added benzyl chloroformate (2.1 equiv.) slowly at 0° C. The reaction mixture was stirred at 10° C. for 0.5 h. The aqueous solvent was removed and the residue was dissolved in $H_2O$, extracted with ethyl acetate. The combined organic layers were washed with brine, dried over anhydrous sodium sulfate and filtered. The filtrate was concentrated under reduced pressure to give crude product, which was purified by silica gel column chromatography (5% MeOH in DCM) to afford benzyl 3-(hydroxymethyl)-2,2-dimethylcyclobutyl)carbamate as a racemic mixture (59% yield). The racemic mixture was purified by chiral supercritical fluid chromatography (column: ChiralPak AY-H, 300×50 mmI.D.) using 20% ethanol/CO$_2$, flow rate=200 mL/min, cycle time 3 min to separate the isomers. The first eluting peak was used in the next reaction.

F. 3-Amino-2,2-dimethylcyclobutyl)methanol hydrochloride

Benzyl 3-(hydroxymethyl)-2,2-dimethylcyclobutyl)carbamate (peak 1, obtained above) (1.0 equiv.) and palladium on carbon (10%) in MeOH (0.4 M) was stirred at room temperature under H$_2$ at 40 psi for 12 h. After reaction completion, the mixture was filtered through a celite pad and washed with MeOH. Evaporation of the solvents under reduced pressure provided the crude product 3-amino-2,2-dimethylcyclobutyl) MeOH as a white solid, which was used in the next step without purification. The crude product was dissolved in HCl/MeOH (4N, 10.0 equiv.) at 0° C., stirred at 18° C. for 2 h, and the solvent was removed to give a single isomer of 3-amino-2,2-dimethylcyclobutyl) MeOH hydrochloride (85% yield) as a solid. $^1$H NMR (400 MHz, DMSO-d$_6$) δ (ppm) 8.21 (s, 1H), 3.96 (s, 1H), 3.29-3.40 (m, 2H), 3.12-3.16 (m, 1H), 2.06-2.09 (m, 1H), 1.87-1.88 (m, 1H), 1.61-1.67 (m, 1H), 1.02 (d, J=25.2 Hz, 6H); MS(ESI) m/z (M+H)$^+$130.0

G. 4-(((1R,3S)-3-(Hydroxymethyl)-2,2-dimethylcyclobutyl)amino)-2-(methylthio)pyrimidine-5-carbonitrile The compound isolated above, 3-amino-2,2-dimethylcyclobutyl) MeOH hydrochloride (1.0 equiv.) and 4-chloro-2-(methylthio)pyrimidine-5-carbonitrile (1.0 equiv.) were dissolved in DIEA (3.0 equiv.) and ethanol (0.4 M). The solution was heated to 40° C. for 1 h. The reaction was concentrated under reduced pressure and the yellow residue purified via biotage chromatography (0-60% ethyl acetate in hexanes, then 60% ethyl acetate in hexanes) to afford the title compound (96% yield). MS(ESI) m/z 278.6[M]$^+$.

The single crystal X-ray diffraction studies were carried out on a Bruker D8 Smart APEX CCD diffractometer equipped with Cu K$_α$ radiation (λ=1.5478). Crystals of the subject compound were grown by vapor diffusion of pentane into a dichloroethane solution. A 0.115×0.087×0.082 mm colorless block was mounted on a Cryoloop with Paratone oil. Data were collected in a nitrogen gas stream at 100(2) K using φ and ω scans. Crystal-to-detector distance was 50 mm using variable exposure time (2 s-10 s) depending on θ with a scan width of 1.0°. Data collection was 98.2% complete to 68.00° in θ. A total of 23976 reflections were collected covering the indices, -13<=h<=13, -8<=k<=9, -28<=l<=28. 7222 reflections were found to be symmetry independent, with a R$_{int}$ of 0.0328. Indexing and unit cell refinement indicated a primitive, monoclinic lattice. The space group was found to be P2$_1$. The data were integrated using the Bruker SAINT software program and scaled using the SADABS software program. Solution by direct methods (SHELXS) produced a complete phasing model consistent with the proposed structure. The absolute stereochemisty was determined to be consistent with All nonhydrogen atoms were refined anisotropically by full-matrix least-squares (SHELXL-2013). All hydrogen atoms were placed using a riding model. Their positions were constrained relative to their parent atom using the appropriate HFIX command in SHELXL-2013. The absolute stereochemistry was determined to be consistent with 4-(((1R,3S)-3-hydroxymethyl)-2,2-dimethylcyclobutyl)amino)-2-(methylthio)pyrimidine-5-carbonitrile.

H. 4-(((1R,3S)-3-(Hydroxymethyl)-2,2-dimethylcyclobutyl)amino)-2-(methylsulfonyl)pyrimidine-5-carbonitrile and 4-(((1R,3S)-3-(hydroxymethyl)-2,2-dimethylcyclobutyl)amino)-2-(methylsulfinyl)pyrimidine-5-carbonitrile 4-(((1R,3S)-3-(Hydroxymethyl)-2,2-dimethylcyclobutyl)amino)-2-(methylthio)pyrimidine-5-carbonitrile (1.0 equiv.) and 3-chlorobenzoperoxoic acid (2.2 equiv.) were combined in DCM (0.2 M) and allowed to stir at ambient temperature. After 16 h, the solution was added to a separatory funnel with additional DCM and the organic layer was washed with saturated sodium bisulfate, followed by saturated sodium bicarbonate and finally saturated sodium chloride solution. The organic layer was dried over magnesium sulfate, filtered and the solvent was removed under reduced pressure to afford the title compound (71% yield). MS(ESI) m/z 311.3 [M+1]$^+$.

I. 4-(((1R,3S)-3-(Hydroxymethyl)-2,2-dimethylcyclobutyl)amino)-2-(((4-(trifluoromethyl)pyridin-3-yl)methyl)amino)pyrimidine-5-carbonitrile A mixture of 4-(((1R,3S)-3-(hydroxymethyl)-2,2-dimethylcyclobutyl)amino)-2-(methylsulfonyl)pyrimidine-5-carbonitrile and 4-(((1R,3S)-3-(hydroxymethyl)-2,2-dimethylcyclobutyl)amino)-2-(methylsulfinyl)pyrimidine-5-carbonitrile (1.0 equiv.), (4-(trifluoromethyl)pyridin-3-yl)methanamine hydrochloride (1.0 equiv.) and DIEA (3.0 equiv.) was combined in ethanol (0.1 M) and heated to 80° C. After 2 h, the reaction mixed was worked up using standard methods to afford the title compound (45% yield). $^1$H NMR (400 MHz, DMSO-d$_6$) δ (ppm) 8.71 (d, J=5.08 Hz, 1H), 8.57-8.65 (m, 1H), 8.15-8.25 (m, 2H), 7.65-7.75 (m, 1H), 7.19-7.32 (m, 1H), 4.70 (d, J=5.08 Hz, 2H), 4.23 (t, J=4.88 Hz, 1H), 3.96 (q, J=8.33 Hz, 1H), 3.20-3.29 (m, 1H), 1.73-1.96 (m, 2H), 1.53-1.68 (m, 1H), 1.20 (s, 1H), 0.86 (s, 1H), 0.62-0.77 (m, 6H): MS(ESI) m/z 407.3 [M+1]$^+$.

Example 17

2-(((4-(2,2-Difluoropropoxy)pyrimidin-5-yl)methyl)amino)-4-(((1R,4R)-4-hydroxy-3,3,4-trimethylcyclohexyl)amino)pyrimidine-5-carbonitrile

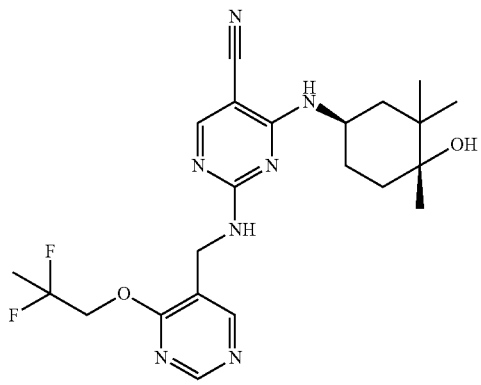 [SMILES: CC(F)(F)COc1ncncc1CNc1ncc(C#N)c(N[C@@H]2CC[C@@](C)(O)C(C)(C)C2)n1]

A. tert-butyl ((1R,4S)-4-Hydroxy-3,3-dimethylcyclohexyl)carbamate

To a solution of (1S,4R)-4-amino-2,2-dimethylcyclohexanol (1.00 g, 6.99 mmol) in THF (22 mL) was added di-tert-butyl bicarbonate (1.81 g, 8.39 mmol) slowly at 0° C. The resulting mixture was stirred at 55° C. for 2 h. The reaction mixture was diluted with water and extracted with ethyl acetate (2×200 mL). The combined organic layers were washed with brine (100 mL), dried over anhydrous sodium sulfate and filtered. The filtrate was evaporated under reduced pressure to give a crude product as a yellow oil (2.00 g crude), which was used directly in the next step without purification. MS (ESI) m/z 244.2 [M+H]$^+$.

B. (R)-tert-butyl (3,3-Dimethyl-4-oxocyclohexyl)carbamate

To a solution of tert-butyl ((1R,4S)-4-hydroxy-3,3-dimethylcyclohexyl)carbamate (2 g crude) in DCM (110 mL) was added Dess-Martin periodinane (4.24 g, 10 mmol) keeping the temperature below 5° C. The resulting mixture was stirred at room temperature for 1 h. The reaction was diluted with DCM and washed with saturated solution of sodium bicarbonate. The separated organic layer was dried over anhydrous sodium sulfate and filtered. The filtrate was evaporated under reduced pressure and the residue was purified by silica gel chromatography column (6% ethyl acetate in petroleum ether) to afford the title compound as a yellow oil (1.10 g, 4.56 mmol, 65% yield over two steps). MS (ESI) m/z 242.2 [M+H]$^+$.

C. tert-butyl ((1R)-4-Hydroxy-3,3,4-trimethylcyclohexyl)carbamate

To a solution of (R)-tert-butyl (3,3-dimethyl-4-oxocyclohexyl)carbamate (550 mg, 2.28 mmol) in diethyl ether (15 mL) was added methyl magnesium bromide (3 M, 3.00 mL) at −30° C. to −40° C. under nitrogen. The mixture was stirred at this temperature for 0.5 h and quenched with saturated aqueous ammonium chloride solution (150 mL). The aqueous layer was extracted with ethyl acetate (300 mL×3). The combined organic layers were washed with brine (150 mL), dried over anhydrous sodium sulfate and filtered. The filtrate was evaporated under reduced pressure. The residue was purified silica gel chromatography column (12% ethyl acetate in petroleum ether) to afford the title compound as a yellow oil (520 mg, 5.02 mmol, 88% yield). MS (ESI) m/z 258.2 [M+H]$^+$.

D. (4R)-4-Amino-1,2,2-trimethylcyclohexanol

To a solution of tert-butyl ((1R)-4-hydroxy-3,3,4-trimethylcyclohexyl)carbamate (520 mg, 2.15 mmol) in DCM (6.00 mL) was added TFA (3.00 mL) at 0° C. The resulting mixture was stirred at room temperature for 1 h. The reaction was concentrated in vacuo to give a crude product (450 mg, crude), which was used directly in the next step without further purification. MS (ESI) m/z 158.1 [M+H]$^+$.

E. 4-(((1R,4R)-4-Hydroxy-3,3,4-trimethylcyclohexyl)amino)-2-(methylthio)pyrimidine-5-carbonitrile and 4-(((1R,4S)-4-Hydroxy-3,3,4-trimethylcyclohexyl)amino)-2-(methylthio)pyrimidine-5-carbonitrile To a mixture of (4R)-4-amino-1,2,2-trimethylcyclohexanol (323 mg, 2.06 mmol) and 4-chloro-2-(methylthio)pyrimidine-5-carbonitrile (450 mg, crude) in iso-propanol (5.00 mL) was added DIEA (800 mg, 6.60 mmol). The resulting solution was stirred at 90° C. for 1.5 h. The solvent was evaporated and the residue was purified by silica gel chromatography (30% ethyl acetate in petroleum ether) to afford the title compound (380 mg, 1.24 mmol, 60% yield). The title compound was further separated by supercritical fluid chromatography (Column: AD, 0.46 cm I.D.×15 cm L; Mobile phase: CO$_2$/EtOH/DEA=70/30/0.1 (v/v/v); Flow: 1.5 ml/min; WL: UV 254 nm; T=35° C.) to afford the title compounds.

4-(((1R,4R)-4-hydroxy-3,3,4-trimethylcyclohexyl)amino)-2-(methylthio)pyrimidine-5-carbonitrile (120 mg, 0.391 mmol, chiral SFC: d.e.=100%).

4-(((1R,4S)-4-hydroxy-3,3,4-trimethylcyclohexyl)amino)-2-(methylthio)pyrimidine-5-carbonitrile (240 mg, 0.782 mmol, chiral SFC: d.e.=100%).

F. 4-(2,2-Difluoropropoxy)pyrimidine-5-carbonitrile

To a suspension of sodium hydride (60% dispersed in mineral oil, 315 mg, 7.88 mmol) in THF (20 mL) was added 2,2-difluoropropan-1-ol (757 mg, 7.88 mmol) at 0° C. and the resulting mixture was stirred for 1 h. Then 4-chloropyrimidine-5-carbonitrile (1.00 g, 7.16 mmol) was added in portions and the mixture was stirred at room temperature for 30 min. The reaction was quenched with saturated aqueous ammonium chloride solution and extracted with ethyl acetate (500 mL×2). The combined organic layers were dried and concentrated and the residue was purified by silica gel chromatography column (12% ethyl acetate in petroleum ether) to afford the title compound (850 mg, 4.27 mmol, 58% yield) as a yellow solid. MS (ESI) m/z 200.0 [M+H]$^+$.

G. (4-(2,2-Difluoropropoxy)pyrimidin-5-yl)methanamine

To a solution of 4-(2,2-difluoropropoxy)pyrimidine-5-carbonitrile (850 mg, 4.27 mmol) in THF (30 mL) was added Raney-nickel (600 mg). The mixture was de-gassed under vacuum for 10 minutes, and then hydrogenated under a fully-inflated balloon at room temperature overnight. The mixture was filtered through a pad of Celite and the cake was washed with ethyl acetate (200 mL). The filtrate was removed under vacuum and the residue was purified by preparative HPLC (5% to 60% acetonitrile in water) to give the product (260 mg, 1.28 mmol, 30% yield) as a yellow oil. MS (ESI) m/z 204.0 [M+H]$^+$.

H. 4-(((1R,4R)-4-Hydroxy-3,3,4-trimethylcyclohexyl)amino)-2-(methylsulfonyl)pyrimidine-5-carbonitrile To a solution of 4-(((1R,4R)-4-hydroxy-3,3,4-trimethylcyclohexyl)amino)-2-(methylthio)pyrimidine-5-carbonitrile (80 mg, 0.261 mmol) in DCM (3.00 mL) was added 3-chloroperbenzoic acid (85%, 114 mg, 0.653 mmol) under ice-water bath. The mixture was stirred at room temperature for 2 h. The reaction was diluted with DCM and washed with aqueous sodium thiosulfate solution, then aqueous potassium carbonate solution. The separated organic layers were dried over anhydrous sodium sulfate and concentrated to afford the crude title compound (90 mg crude). MS (ESI) m/z 323.1, 339.1 [M+H]$^+$.

I. 2-(((4-(2,2-Difluoropropoxy)pyrimidin-5-yl) methyl)amino)-4-(((1R,4R)-4-hydroxy-3,3,4-trimethylcyclohexyl)amino)pyrimidine-5-carbonitrile To a solution of 4-(((1R,4R)-4-hydroxy-3,3,4-trimethylcyclohexyl)amino)-2-(methylsulfonyl)pyrimidine-5-carbonitrile (90 mg, crude) in THF (2.8 mL) was added (4-(2,2-difluoropropoxy)pyrimidin-5-yl)methanamine (50 mg, 0.246 mmol) and DIEA (100 mg, 0.738 mmol). The resulting mixture was stirred at 100° C. in a microwave reactor for 2 h. The solvent was evaporated and the residue was purified via standard methods to afford the title compound (34.2 mg, 0.074 mmol, 30% yield). $^1$H NMR (400 MHz, CD$_3$OD) δ (ppm) 8.70 (s, 1H), 8.34-8.32 (m, 1H), 8.13 (s, 1H), 4.70 (t, J=12.0 Hz, 1H), 4.64-4.59 (m, 2H), 4.18-4.15 (m, 1H), 1.81-1.74 (m, 3H), 1.68-1.41 (m, 6H), 1.32-1.30 (s, 3H), 0.92-0.85 (s, 6H). MS (ESI) m/z 462.2 [M+H]$^+$.

Example 18

2-(((4-(2,2-Difluoropropoxy)pyrimidin-5-yl)methyl) amino)-4-(((1R,4S)-4-hydroxy-3,3,4-trimethylcyclohexyl)amino)pyrimidine-5-carbonitrile

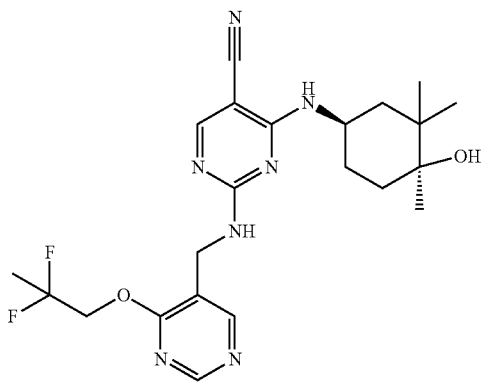 [SMILES: CC(F)(F)COc1ncncc1CNc1ncc(C#N)c(N[C@@H]2CC[C@](C)(O)C(C)(C)C2)n1]

A. tert-butyl ((1R,4S)-4-Hydroxy-3,3-dimethylcyclohexyl)carbamate

To a solution of (1S,4R)-4-amino-2,2-dimethylcyclohexanol (1.00 g, 6.99 mmol) in THF (22 mL) was added di-tert-butyl bicarbonate (1.81 g, 8.39 mmol) slowly at 0° C. The resulting mixture was stirred at 55° C. for 2 h. The reaction mixture was diluted with water and extracted with ethyl acetate (2×200 mL). The combined organic layers were washed with brine (100 mL), dried over anhydrous sodium sulfate and filtered. The filtrate was evaporated under reduced pressure to give the crude product as a yellow oil (2.00 g crude), which was used directly for next step without purification. MS (ESI) m/z 244.2 [M+H]$^+$.

B. (R)-tert-butyl (3,3-Dimethyl-4-oxocyclohexyl)carbamate

To a solution of tert-butyl ((1R,4S)-4-hydroxy-3,3-dimethylcyclohexyl)carbamate (2 g crude) in DCM (110 mL) was added Dess-Martin periodinane (4.24 g, 10 mmol) keeping the temperature below 5° C. The resulting mixture was stirred at room temperature for 1 h. The reaction was diluted with DCM and washed with saturated solution of sodium bicarbonate. The separated organic layers were dried over anhydrous sodium sulfate and filtered. The filtrate was evaporated under reduced pressure and the residue was purified by silica gel chromatography column (6% ethyl acetate in petroleum ether) to afford the title compound as a yellow oil (1.10 g, 4.56 mmol, 65% yield over two steps). MS (ESI) m/z 242.2 [M+H]$^+$.

C. tert-butyl ((1R)-4-Hydroxy-3,3,4-trimethylcyclohexyl)carbamate

To a solution of (R)-tert-butyl (3,3-dimethyl-4-oxocyclohexyl)carbamate (550 mg, 2.28 mmol) in diethyl ether (15 mL) was added methyl magnesium bromide (3 M, 3.00 mL) at −30° C. to −40° C. under nitrogen. The mixture was stirred at this temperature for 0.5 h and quenched with saturated aqueous ammonium chloride solution (150 mL). The aqueous layer was extracted with ethyl acetate (300 mL×3). The combined organic layers were washed with brine (150 mL), dried over anhydrous sodium sulfate and filtered. The filtrate was evaporated under reduced pressure. The residue was purified silica gel chromatography column (12% ethyl acetate in petroleum ether) to afford the title compound as a yellow oil (520 mg, 5.02 mmol, 88% yield). MS (ESI) m/z 258.2 [M+H]$^+$.

D. (4R)-4-Amino-1,2,2-trimethylcyclohexanol

To a solution of tert-butyl ((1R)-4-hydroxy-3,3,4-trimethylcyclohexyl)carbamate (520 mg, 2.15 mmol) in DCM (6.00 mL) was added TFA (3.00 mL) at 0° C. The result mixture was stirred at room temperature for 1 h. The reaction was concentrated in vacuo to give a crude product (450 mg, crude), which was used directly for next step without further purification. MS (ESI) m/z 158.1 [M+H]$^+$.

E. 4-(((1R,4R)-4-Hydroxy-3,3,4-trimethylcyclohexyl)amino)-2-(methylthio)pyrimidine-5-carbonitrile and 4-(((1R,4S)-4-Hydroxy-3,3,4-trimethylcyclohexyl)amino)-2-(methylthio)pyrimidine-5-carbonitrile To a mixture of (4R)-4-amino-1,2,2-trimethylcyclohexanol (323 mg, 2.06 mmol) and 4-chloro-2-(methylthio)pyrimidine-5-carbonitrile (450 mg, crude) in iso-propanol (5.00 mL) was added DIEA (800 mg, 6.60 mmol). The resulting solution was stirred at 90° C. for 1.5 h. The solvent was evaporated and the residue was purified by silica gel chromatography (30% ethyl acetate in petroleum ether) to afford the title compound (380 mg, 1.24 mmol, 60% yield). The title compound was further separated by supercritical fluid chromatography (Column: AD, 0.46 cm I.D.×15 cm L; Mobile phase: CO$_2$/EtOH/DEA=70/30/0.1 (v/v/v); Flow: 1.5 ml/min; WL: UV 254 nm; T=35° C.) to afford the title compounds.

4-(((1R,4R)-4-hydroxy-3,3,4-trimethylcyclohexyl) amino)-2-(methylthio)pyrimidine-5-carbonitrile (120 mg, 0.391 mmol, chiral SFC: d.e.=100%).

4-(((1R,4S)-4-hydroxy-3,3,4-trimethylcyclohexyl) amino)-2-(methylthio)pyrimidine-5-carbonitrile (240 mg, 0.782 mmol, chiral SFC: d.e.=100%).

F. 4-(2,2-Difluoropropoxy)pyrimidine-5-carbonitrile

To a suspension of sodium hydride (60% dispersed in mineral oil, 315 mg, 7.88 mmol) in THF (20 mL) was added 2,2-difluoropropan-1-ol (757 mg, 7.88 mmol) at 0° C. and the resulting mixture was stirred for 1 h. Then 4-chloropyrimidine-5-carbonitrile (1.00 g, 7.16 mmol) was added in portions and the mixture was stirred at room temperature for 30 min. The reaction was quenched with saturated aqueous ammonium chloride solution and extracted with ethyl acetate (500 mL×2). The combined organic layers were dried and concentrated and the residue was purified by silica gel chromatography column (12% ethyl acetate in petroleum ether) to afford the title compound (850 mg, 4.27 mmol, 58% yield) as a yellow solid. MS (ESI) m/z 200.0 [M+H]$^+$.

G. (4-(2,2-Difluoropropoxy)pyrimidin-5-yl)methanamine

To a solution of 4-(2,2-difluoropropoxy)pyrimidine-5-carbonitrile (850 mg, 4.27 mmol) in THF (30 mL) was added Raney-nickel (600 mg). The mixture was de-gassed under vacuum for 10 minutes, and then hydrogenated under a fully-inflated balloon at room temperature overnight. The mixture was filtered through a pad of Celite and the cake was washed with ethyl acetate (200 mL). The filtrate was removed under vacuum and the residue was purified by preparative HPLC (5% to 60% acetonitrile in water) to give the product (260 mg, 1.28 mmol, 30% yield) as a yellow oil. MS (ESI) m/z 204.0 [M+H]$^+$.

H. 4-(((1R,4S)-4-Hydroxy-3,3,4-trimethylcyclohexyl)amino)-2-(methylsulfonyl)pyrimidine-5-carbonitrile To a solution of 4-(((1R,4S)-4-hydroxy-3,3,4-trimethylcyclohexyl)amino)-2-(methylthio)pyrimidine-5-carbonitrile (80 mg, 0.261 mmol) in DCM (3.00 mL) was added 3-chloroperbenzoic acid (85%, 114 mg, 0.653 mmol) under ice-water bath. The mixture was stirred at room temperature for 2 h. The reaction was diluted with DCM and washed with aqueous sodium thiosulfate solution, then aqueous potassium carbonate solution. The separated organic layers were dried over anhydrous sodium sulfate and concentrated to afford a crude compound (90 mg crude). MS (ESI) m/z 323.1, 339.1 [M+H]$^+$.

I. 2-(((4-(2,2-Difluoropropoxy)pyrimidin-5-yl) methyl)amino)-4-(((1R,4S)-4-hydroxy-3,3,4-trimethylcyclohexyl)amino)pyrimidine-5-carbonitrile To a solution of 4-(((1R,4S)-4-hydroxy-3,3,4-trimethylcyclohexyl)amino)-2-(methylsulfonyl)pyrimidine-5-carbonitrile (90 mg, crude) in THF (2.8 mL) was added (4-(2,2-difluoropropoxy)pyrimidin-5-yl)methanamine (50 mg, 0.246 mmol) and DIEA (100 mg, 0.738 mmol). The resulting mixture was stirred at 100° C. in a microwave reactor for 2 h. The solvent was evaporated and the residue was purified by standard methods to afford the title compound (38.7 mg, 0.084 mmol, 34% yield). $^1$H NMR (400 MHz, CD$_3$OD) δ (ppm) 8.90 (s, 1H), 8.57-8.54 (s, 1H), 8.34 (s, 1H), 4.92 (t, J=12.0 Hz, 1H), 4.81-4.78 (m, 2H), 4.34-4.28 (m, 1H), 2.04-1.95 (m, 3H), 1.92-1.68 (m, 6H), 1.47-1.45 (m, 3H), 1.09-1.01 (m, 6H). MS (ESI) m/z 462.2 [M+H]$^+$.

Example 19

2-((4-Cyano-3-(trifluoromethoxy)phenethyl)amino)-4-(((1R,3S)-3-hydroxy-2,2-dimethylcyclobutyl) amino)pyrimidine-5-carbonitrile

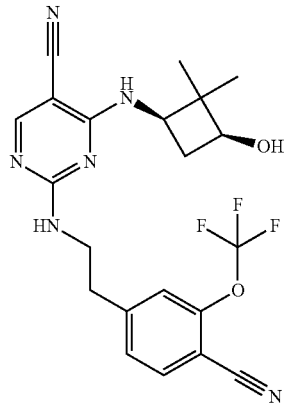 [SMILES: CC1(C)[C@@H](O)C[C@H]1Nc1nc(NCCc2ccc(C#N)c(OC(F)(F)F)c2)ncc1C#N]

A. Methyl 4-amino-3-(trifluoromethoxy)benzoate

A mixture of 4-amino-3-(trifluoromethoxy)benzoic acid (8.88 g 40.2 mmol), MeOH (142 mL) and hydrochloric acid in 1,4-dioxane (4.0 M, 142 mL, 568 mmol) was stirred at room temperature for 72 h. After removal of the organic solvent the pH of the residue was adjusted to pH 8 and the aqueous layer was extracted with ethyl acetate (50 mL×3). The combined organic layers were dried and concentrated under vacuum to afford the title compound (9.3 g, 39.6 mmol, 95% yield). MS (ESI) m/z 236.1 [M+1]$^+$.

B. Methyl 4-bromo-3-(trifluoromethoxy)benzoate

To a mixture of methyl 4-amino-3-(trifluoromethoxy) benzoate (9.3 g, 39.6 mmol) and tert-butylnitrite (6.77 mL, 57.6 mmol) in acetonitrile (300 mL) and water (30 mL) was added cupric bromide (10.3 g, 46.2 mmol). The resulting reaction mixture was stirred at 75° C. for 1.5 h. The reaction was treated with water and extracted with ethyl acetate. The combined organic layers were washed with saturated sodium bicarbonate, dried over anhydrous sodium sulfate and filtered. The filtrate was evaporated under vacuum to afford the title compound (10.6 g, 35.6 mmol, 90% yield). MS (ESI) m/z 299.1, 300.1 [M+1]$^+$.

C. (4-Bromo-3-(trifluoromethoxy)phenyl)methanol

To a solution of lithium borohydride (1.16 g, 53.4 mmol) in THF (100 mL) was added methyl 4-bromo-3-(trifluoromethoxy)benzoate (10.6 g, 35.6 mmol) at 0° C., and the resulting solution was heated at 70° C. for 3 h under nitrogen atmosphere. The reaction was quenched with water and the mixture was extracted with ethyl acetate. The combined organic layers were washed with saturated brine, dried over anhydrous sodium sulfate and filtered. The filtrate was evaporated under vacuum to afford the crude title product (9.17 g, 34 mmol). MS (ESI) m/z 270.1 [M]$^+$, 272.1 [M+2]$^+$.

D. 1-Bromo-4-(bromomethyl)-2-(trifluoromethoxy) benzene

To a mixture of (4-bromo-3-(trifluoromethoxy)phenyl) MeOH (5 g, 18.5 mmol) and triphenylphosphine (8.24 g, 31.45 mmol) in dry DCM (50 mL) was added N-bromosuccinimide (5.83 g, 32.92 mmol) at −10° C. The resulting reaction mixture was stirred at room temperature for 0.5 h under nitrogen. Water was added and the mixture was extracted with DCM (3×40 mL). The combined organic layers were washed with brine, dried over anhydrous sodium sulfate and filtered. The filtrate was evaporated under vacuum to afford the crude product, which was purified by silica gel column chromatography (5% ethyl acetate in petroleum ether) to afford the title compound (4.3 g, 12.9 mmol, 67% yield, over two steps). MS (ESI) m/z 332.8, 334.8, 336.8 [M+H]$^+$.

E. 2-(4-Bromo-3-(trifluoromethoxy)phenyl)acetonitrile

A mixture of 1-bromo-4-(bromomethyl)-2-(trifluoromethoxy)benzene (1 g, 3.0 mmol) in EtOH (20 mL) and water (5 mL) was added potassiumcyanide (390 mg, 6 mmol). The resulting mixture was stirred at 85° C. for 2 h. Sodium bicarbonate was added and the mixture was extracted with ethyl acetate. The organic layer was washed with brine, dried and concentrated to afford the crude title product (800 mg, 2.86 mmol). MS (ESI) m/z 279.9 [M]$^+$, 281.1 [M+2]$^+$.

F. 2-(4-Bromo-3-(trifluoromethoxy)phenyl)ethanamine

To a solution of 2-(4-bromo-3-(trifluoromethoxy)phenyl) acetonitrile (800 mg, 2.86 mmol) in THF (40 mL) was added a solution of borane dimethyl sulfide complex in THF (2 M, 2.15 mL, 4.3 mmol) at 0° C. The resulting solution was heated at 75° C. for 2 h under nitrogen atmosphere. The reaction was quenched with MeOH (10 mL) at 0° C. and concentrated under vacuum to afford the crude title product (720 mg, 2.54 mmol). MS (ESI) m/z 283.9 [M]$^+$, 291.1 [M+2]$^+$.

G. tert-butyl 4-Bromo-3-(trifluoromethoxy)phenethylcarbamate

To a solution of 2-(4-bromo-3-(trifluoromethoxy)phenyl) ethanamine (720 mg, 2.54 mmol) in THF (10 mL) was added di-tert-butyl dicarbonate (575 mg, 2.66 mmol). The resulting reaction mixture was stirred at 75° C. for 2 h. The reaction mixture was concentrated to afford the crude product, which was purified by silica gel column chromatography (5% ethyl acetate in petroleum ether) to afford the title compound as a yellow solid (460 mg, 1.2 mmol, 40% yield, over three steps). MS (ESI) m/z 384.1 [M+1]$^+$.

H. tert-butyl 4-Cyano-3-(trifluoromethoxy)phenethylcarbamate

A mixture of tert-butyl 4-bromo-3-(trifluoromethoxy) phenethylcarbamate (460 mg, 1.2 mmol), zinc cyanide (463 mg, 1.56 mmol) and tetrakis(triphenylphosphine)palladium (69 mg, 0.06 mmol) in DMF (10 mL) was stirred at 160° C. for 1 h under nitrogen. The reaction was treated with saturated sodium hydrogen carbonate and extracted with ethyl acetate (30 mL×3). The combined organic layers were washed with brine, dried, concentrated and purified by preparative thin layer chromatography (2.9% MeOH in DCM) to afford the title compound (150 mg, 0.45 mmol, 38% yield). MS (ESI) m/z 331.1 [M+1]$^+$.

I. 4-(2-Aminoethyl)-2-(trifluoromethoxy)benzonitrile

To a solution of tert-butyl 4-cyano-3-(trifluoromethoxy) phenethylcarbamate (150 mg, 0.45 mmol) in DCM (3 mL) was added TFA (1.5 mL). The resulting reaction mixture was stirred at room temperature for 1.5 h. The mixture was concentrated to afford the crude title product (120 mg, crude), which was used directly for next step without further purification. MS (ESI) m/z 231.1 [M+H]$^+$.

J. 4-(((1R,3S)-3-Hydroxy-2,2-dimethylcyclobutyl) amino)-2-(methylthio)pyrimidine-5-carbonitrile A mixture of (1S,3R)-3-amino-2,2-dimethylcyclobutanol (550 mg crude), 4-chloro-2-(methylthio)pyrimidine-5-carbonitrile (887 mg, 4.78 mmol) and DIEA (1.12 g, 8.7 mmol) in isopropanol (20 mL) was stirred at 85° C. for 3 h. After cooling to room temperature, the reaction mixture was concentrated and the residue was purified by silica gel column chromatography (0.6% MeOH in DCM) to afford the title compound (760 mg, 2.88 mmol, 66.3% yield). MS (ESI) m/z 265.1 [M+1]$^+$.

K. 4-(((1R,3S)-3-Hydroxy-2,2-dimethylcyclobutyl) amino)-2-(methylsulfonyl)pyrimidine-5-carbonitrile To a solution of 4-(((1R,3S)-3-hydroxy-2,2-dimethylcyclobutyl)amino)-2-(methylthio)pyrimidine-5-carbonitrile (760 mg, 2.88 mmol) in DCM (10 mL) was added m-chloroperoxybenzoic acid (85%, 1.25 g, 6.18 mmol). The resulting mixture was stirred at room temperature for 1 h. The reaction mixture was quenched with aqueous solution of sodium thiosulfate and extracted with DCM. The combined organic layers were washed with aqueous potassium carbonate and brine, dried over sodium sulfate and concentrated to afford the title compound (550 mg, crude), which was used directly in the next step without further purification. MS (ESI) m/z 281.1, 297.1 [M+1]$^+$.

L. 2-((4-Cyano-3-(trifluoromethoxy)phenethyl) amino)-4-(((1R,3S)-3-hydroxy-2,2-dimethylcyclobutyl)amino)pyrimidine-5-carbonitrile A mixture of 4-(((1R,3S)-3-hydroxy-2,2-dimethylcyclobutyl)amino)-2-(methylsulfonyl)pyrimidine-5-carbonitrile (80 mg, 0.27 mmol), 4-(2-aminoethyl)-2-(trifluoromethoxy)benzonitrile (60 mg, crude)) and DIEA (105 mg, 0.81 mmol) in THF (2 mL) was stirred at 100° C. in a microwave reactor for 1.5 h. After cooling to room temperature, the reaction mixture was concentrated and the residue purified by standard methods to afford the title compound (34.4 mg, 0.077 mmol, 40% yield, over two steps). $^1$H NMR (400 MHz, CD$_3$OD) δ 8.14-8.07 (m, 1H), 7.82-7.80 (m, 1H), 7.45-7.43 (m, 2H), 3.97-3.93 (m, 1H), 3.83-3.70 (m, 2H), 3.68-3.59 (m, 1H), 3.10-2.01 (m, 2H), 2.58-2.54 (m, 1H), 2.15-2.06 (m, 1H), 1.21 (s, 3H), 0.95 (s, 3H). MS (ESI) m/z 447.2 [M+1]$^+$.

Example 20

2-((4-(2,2-Difluoropropoxy)phenethyl)amino)-4-(((1R,4S)-4-hydroxy-3,3-dimethylcyclohexyl)amino) pyrimidine-5-carbonitrile

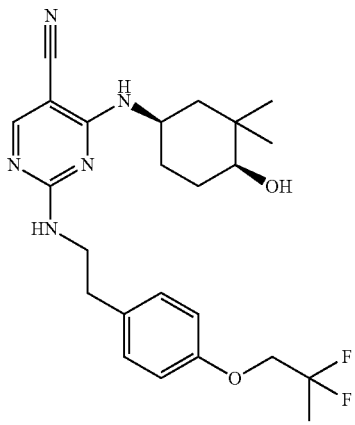 [SMILES: CC(F)(F)COc1ccc(CCNc2ncc(C#N)c(N[C@@H]3CC[C@H](O)C(C)(C)C3)n2)cc1]

A. tert-butyl 4-Hydroxyphenethylcarbamate

To a solution of 4-(2-aminoethyl)phenol (1.00 g, 7.30 mmol) in THF (10 mL) was added di-tert-butyl pyrocarbonate (1.89 g, 8.79 mmol). The resulting reaction mixture was stirred at room temperature for 16 h. The mixture was concentrated to remove the solvent, diluted with ethyl acetate, filtered and concentrated to give a crude title product (1.65 g, 6.96 mmol, 95% yield). MS (ESI) m/z 238.1 [M+H]$^+$.

B. 2,2-Difluoropropyl methanesulfonate

To a mixture of 2,2-difluoropropan-1-ol (2.00 g, 20.8 mmol) and TEA (3.16 g, 31.25 mmol) in dry DCM (20 mL) was added methanesulfonyl chloride (2.84 g, 24.96 mmol) at 0° C. The resulting reaction mixture was stirred at rt for 1.5 h. Water was added and the mixture was extracted with DCM (3×100 mL). The combined organic layers were washed with saturated aqueous ammonium chloride solution, brine, dried over anhydrous sodium sulfate and filtered. The filtrate was evaporated under vacuum to give the title product (2.70 g, 15.52 mmol, 75% yield), which was used directly in the next step without further purification.

C. tert-butyl 4-(2,2-Difluoropropoxy)phenethylcarbamate

A mixture of tert-butyl 4-hydroxyphenethylcarbamate (700 g, 2.94 mmol), 2,2-difluoropropyl methanesulfonate (668 mg, 3.84 mmol) and cesium carbonate (1.92 g, 5.88 mmol) in DMF (5 mL) was stirred at 115° C. in a microwave reactor for 3 h. After cooling to room temperature, water was added and extracted with ethyl acetate (3×100 mL). The combined organic layers were washed with brine, dried over anhydrous sodium sulfate and filtered. The filtrate was evaporated under vacuum to give the crude product, which was purified by preparative thin layer chromatography (22% ethyl acetate in petroleum ether) to afford the title compound (130 mg, 0.41 mmol, 14% yield). MS (ESI) m/z 316.1 [M+H]$^+$.

D. 2-(4-(2,2-Difluoropropoxy)phenyl)ethanamine

To a solution of tert-butyl 4-(2,2-difluoropropoxy)phenethylcarbamate (95 mg, 0.30 mmol) in DCM (2 mL) was added TFA (1 mL) at 0~5° C. The resulting reaction mixture was stirred at room temperature for 1.5 h. The reaction mixture was concentrated to give the crude product, which was used directly for next step without further purification (70 mg crude). MS (ESI) m/z 216.1 [M+H]$^+$.

E. 4-(((1R,4S)-4-Hydroxy-3,3-dimethylcyclohexyl) amino)-2-(methylthio)pyrimidine-5-carbonitrile A mixture of 4-chloro-2-(methylthio)pyrimidine-5-carbonitrile (2.15 g, 11.6 mmol)), (1S,4R)-4-amino-2,2-dimethylcyclohexanol (1.51 g, 10.5 mmol) and DIEA (2.72 mg, 21.1 mmol) in isopropanol (30 mL) was heated at 100° C. for 3 h. After removal of the organic solvent under reduced pressure, the residue was treated with water and extracted with ethyl acetate. The combined organic layers were washed with brine, dried over sodium sulfate and concentrated to give a crude product, which was purified by silica gel column chromatography (15% ethyl acetate in petroleum) to afford the title compound as a pale yellow solid (2.2 g, 7.53 mmol, yield: 72%). MS (ESI) m/z 293.2 [M+H]$^+$.

F. 4-(((1R,4S)-4-Hydroxy-3,3-dimethylcyclohexyl) amino)-2-(methylsulfonyl)pyrimidine-5-carbonitrile To a solution of 4-(((1R,4S)-4-hydroxy-3,3-dimethylcyclohexyl)amino)-2-(methylthio)pyrimidine-5-carbonitrile (1.02 g, 3.48 mmol) in dry DCM (20 mL) was added m-chloroperoxybenzoic acid (85%, 1.78 g, 8.79 mmol) under cooling in an ice-water bath. The resulting mixture was stirred at room temperature for 3 h. The reaction was quenched with aqueous sodium thiosulfate and extracted with DCM. The combined organic layers were washed with aqueous potassium carbonate and brine, dried over sodium sulfate and concentrated to give the title compound (0.9 g, crude) as a pale yellow solid. MS (ESI) m/z 309.2, 325.2 [M+H]$^+$.

J. 2-((4-(2,2-Difluoropropoxy)phenethyl)amino)-4-(((1R,4S)-4-hydroxy-3,3-dimethylcyclohexyl)amino)pyrimidine-5-carbonitrile A mixture of 4-(((1R,4S)-4-hydroxy-3,3-dimethylcyclohexyl)amino)-2-(methylsulfonyl)pyrimidine-5-carbonitrile (90 mg, 0.28 mmol), 2-(4-(2,2-difluoropropoxy)phenyl)ethanamine (70 mg crude) and DIEA (85 mg, 0.66 mmol) in THF (2 mL) was stirred at 100° C. in a microwave reactor for 1.5 h. After cooling to room temperature, the reaction mixture was concentrated and the residue was purified by standard methods to give the title product (38.6 mg, 0.084 mmol, 28% yield). $^1$H NMR (400 MHz, CD$_3$OD) δ (ppm) 8.15-7.97 (m, 1H), 7.15 (d, J=8.4 Hz, 2H), 6.87 (d, J=8.4 Hz, 2H), 4.39-4.22 (m, 1H), 4.12 (t, J=11.6 Hz, 2H), 3.66-3.49 (m, 2H), 3.41-3.35 (m, 1H), 2.88-2.77 (t, J=7.2 Hz, 2H), 1.96-1.82 (m, 1H), 1.80-1.42 (m, 8H), 1.03-0.95 (m, 6H). MS (ESI) m/z 460.2 [M+H]$^+$.

Example 21

3-Chloro-5-(2-((5-cyano-4-(((1R,4S)-4-hydroxy-3,3-dimethylcyclohexyl)amino)pyrimidin-2-yl)amino)ethyl)pyridine 1-oxide

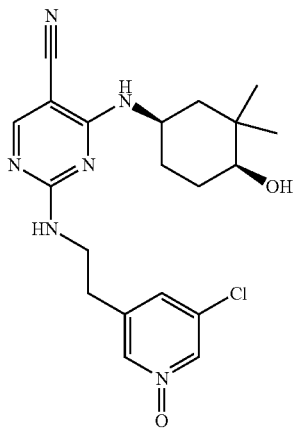 [SMILES: CC1(C)C[C@H](Nc2nc(NCCc3cc(Cl)c[n+]([O-])c3)ncc2C#N)CC[C@@H]1O]

A. (5-Chloro-pyridin-3-yl)-methanol

To a solution of 5-chloro-nicotinic acid (2 g, 12.7 mmol) and TEA (1.52 g, 15 mmol) in THF (30 mL) was added slowly methyl chloroformate (1.42 g, 15 mmol) at 0° C. The resulting mixture was stirred at room temperature overnight. The reaction was diluted with ethyl acetate, washed with saturated ammonia chloride and dried over anhydrous sodium sulfate. The organic layer was concentrated to give the crude product (2.8 g, crude), which was dissolved in THF (40 mL) and cooled to −78° C. Lithium aluminium hydride (570 mg, 15 mmol) was added portion-wise. The resulting mixture was stirred for 30 min. The reaction was quenched with aqueous sodium hydroxide and extracted with ethyl acetate. The combined organic layers were dried over anhydrous sodium sulfate and concentrated to give the crude product, which was purified by silica gel column chromatography (30% ethyl acetate in petroleum ether) to afford the title compound (1.4 g, 9.72 mmol, 76% yield). MS (ESI) m/z 144.1 [M+H]$^+$.

B. (5-Chloropyridin-3-yl)methyl methanesulfonate

To a mixture of (5-chloropyridin-3-yl) MeOH (1.60 g, 11.3 mmol) and TEA (1.7 g, 16.8 mmol) in dry DCM (30 mL) was added methanesulfonyl chloride (1.53 g, 13.4 mmol) at 0° C. The resulting reaction mixture was stirred at room temperature for 1.5 h. Water was added and the mixture was extracted with DCM (3×100 mL). The combined organic layers were washed with saturated aqueous ammonium chloride, brine, dried over anhydrous sodium sulfate and filtered. The filtrate was evaporated under vacuum to give a crude title compound (2.09 g, crude) as a yellow oil, which was used directly in the next step without further purification. MS (ESI) m/z 222.0 [M+H]$^+$.

C. 3-Chloro-5-(isocyanomethyl)pyridine

To a mixture of (5-chloropyridin-3-yl)methyl methanesulfonate (2.09 g, crude) in EtOH (45 mL) and water (5 mL) was added potassium cyanide (926 mg, 14.3 mmol), and the resulting mixture was stirred at 85° C. for 2 h. Sodium bicarbonate was added and the mixture was extracted with ethyl acetate, the organic layer was washed with brine, dried over anhydrous sodium sulfate and concentrated. The residue was purified by silica gel column chromatography (50% ethyl acetate in petroleum ether) to afford the title compound as a yellow solid (820 mg, 5.43 mmol, 48% yield, 2 steps). MS (ESI) m/z 153.1 [M+H]$^+$.

D. 2-(5-Chloropyridin-3-yl)ethanamine

To a solution of 3-chloro-5-(isocyanomethyl)pyridine (810 mg, 5.36 mmol) in MeOH (15 mL) was added Raney-nickel and ammonia. The resulting reaction mixture was stirred at room temperature for 5 h under hydrogen. The reaction mixture was filtered and the filtrate was concentrated to afford the crude title compound (780 mg, crude). MS (ESI) m/z 157.0 [M+H]$^+$.

E. tert-butyl (2-(5-Chloropyridin-3-yl)ethyl)carbamate

To a solution of 2-(5-chloropyridin-3-yl)ethanamine (780 mg, crude) in THF (10 mL) was added di-tert-butyl dicarbonate (1.1 g, 5.1 mmol) at 0° C. The resulting reaction mixture was stirred at room temperature for 2 h. The reaction mixture was concentrated in vacuum and the residue was purified by silica gel column chromatography (20% ethyl acetate in petroleum ether) to afford the title compound as a yellow solid (650 mg, 2.54 mmol, 48% yield, 2 steps). MS (ESI) m/z 257.1 [M+H]$^+$.

F. 3-(2-((tert-Butoxycarbonyl)amino)ethyl)-5-chloropyridine 1-oxide

To a solution of tert-butyl (2-(5-chloropyridin-3-yl)ethyl)carbamate (93 mg, 0.36 mmol) in DCM (4 mL) was added 3-chloroperbenzoic acid (85%, 94.8 mg, 0.54 mmol) at 0° C. The resulting reaction mixture was stirred at room temperature for 1.5 h. The reaction was quenched with aqueous solution of sodium thiosulfate and extracted with DCM. The combined organic layers were washed with aqueous solution of potassium carbonate and brine, dried over sodium sulfate and concentrate to give a crude product, which was used directly in the next step without further purification (90 mg, crude). MS (ESI) m/z 273.1 [M+H]+.

G. 3-(2-Aminoethyl)-5-chloropyridine 1-oxide

To a solution of 3-(2-((tert-butoxycarbonyl)amino)ethyl)-5-chloropyridine 1-oxide (90 mg, crude) in DCM (3 mL) was added TFA (1.5 mL) at 0° C. The resulting reaction mixture was stirred at room temperature for 1.5 h. The reaction mixture was concentrated to afford the crude title product, which was used directly in the next step without further purification (80 mg, crude). MS (ESI) m/z 173.1 [M+H]+.

H. 4-(((1R,4S)-4-Hydroxy-3,3-dimethylcyclohexyl)amino)-2-(methylthio)pyrimidine-5-carbonitrile A mixture of 4-chloro-2-(methylthio)pyrimidine-5-carbonitrile (2.15 g, 11.6 mmol)), (1S,4R)-4-amino-2,2-dimethylcyclohexanol (1.51 g, 10.5 mmol) and DIEA (2.72 mg, 21.1 mmol) in isopropanol (30 mL) was heated at 100° C. for 3 h. After removal of the organic solvents under reduced pressure, the residue was treated with water and extracted with ethyl acetate. The combined organic layers were washed with brine, dried over sodium sulfate and concentrated to give the crude product, which was purified by silica gel column chromatography (15% ethyl acetate in petroleum) to afford the title compound, as a pale yellow solid (2.2 g, 7.53 mmol, 72% yield). MS (ESI) m/z 293.2 [M+H]+.

I. 4-(((1R,4S)-4-Hydroxy-3,3-dimethylcyclohexyl)amino)-2-(methylsulfonyl)pyrimidine-5-carbonitrile To a solution of 4-(((1R,4S)-4-hydroxy-3,3-dimethylcyclohexyl)amino)-2-(methylthio)pyrimidine-5-carbonitrile (1.02 g, 3.48 mmol) in dry DCM (20 mL) was added m-chloroperoxybenzoic acid (85%, 1.78 g, 8.79 mmol) under cooling in an ice-water bath. The resulting mixture was stirred at room temperature for 3 h. The reaction was quenched with aqueous sodium thiosulfate and extracted with DCM. The combined organic layers were washed with aqueous solution of potassium carbonate and brine, dried over sodium sulfate and concentrate to afford the title compound (0.9 g, crude) as a pale yellow solid. MS (ESI) m/z 309.2, 325.2 [M+H]+.

J. 3-chloro-5-(2-((5-cyano-4-(((1R,4S)-4-hydroxy-3,3-dimethylcyclohexyl)amino)pyrimidin-2-yl)amino)ethyl)pyridine 1-oxide A mixture of 4-(((1R,4S)-4-hydroxy-3,3-dimethylcyclohexyl)amino)-2-(methylsulfonyl)pyrimidine-5-carbonitrile (80 mg, crude), 3-(2-aminoethyl)-5-chloropyridine 1-oxide (80 mg, crude) and DIEA (169 mg, 1.31 mmol) in THF (2 mL) was stirred at 85° C. in a microwave reactor for 1 h. After cooling to room temperature, the reaction mixture was concentrated and the residue purified by standard methods to afford the title product (32.6 mg, 0.08 mmol, 22% yield, over three steps). 1H NMR (400 MHz, CD3OD) δ (ppm) 8.30 (s, 1H), 8.16 (s, 1H), 8.08 (s, 1H), 7.51 (s, 1H), 4.32-4.25 (m, 1H), 3.77-3.65 (m, 2H), 3.42-3.40 (s, 1H), 2.99-2.93 (m, 2H), 1.95-1.50 (m, 6H), 1.03 (s, 3H), 0.99 (s, 3H). MS (ESI) m/z 417.2 [M+H]+.

Example 22

4-(((1S,3S)-3-Amino-2,2-dimethylcyclobutyl)amino)-2-((3-chlorophenethyl)amino)pyrimidine-5-carbonitrile

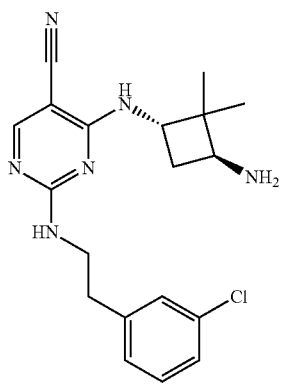 [SMILES: CC1(C)[C@@H](Nc2nc(NCCc3cccc(Cl)c3)ncc2C#N)C[C@@H]1N]

4-(((1R,3R)-3-Amino-2,2-dimethylcyclobutyl)amino)-2-((3-chlorophenethyl)amino)pyrimidine-5-carbonitrile

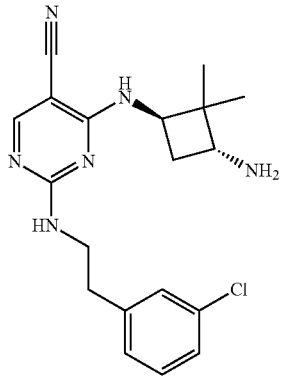 [SMILES: CC1(C)[C@H](N)C[C@H]1Nc1nc(NCCc2cccc(Cl)c2)ncc1C#N]

4-(((1S,3R)-3-Amino-2,2-dimethylcyclobutyl)amino)-2-((3-chlorophenethyl)amino)pyrimidine-5-carbonitrile

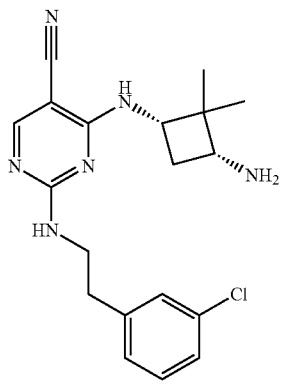

4-(((1R,3S)-3-Amino-2,2-dimethylcyclobutyl)amino)-2-((3-chlorophenethyl)amino)pyrimidine-5-carbonitrile

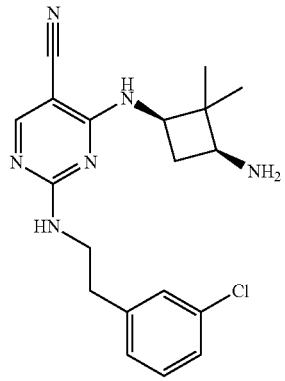 [SMILES: CC1(C)[C@@H](N)C[C@H]1Nc1nc(NCCc2cccc(Cl)c2)ncc1C#N]

A. Methyl 2,2-dimethyl-3-oxocyclobutanecarboxylate

To a mixture of 1-chloro-N,N,2-trimethylprop-1-en-1-amine (15 mL, 114 mmol) and zinc trifluoromethanesulfonate (9.3 g, 142 mmol) was added methyl acrylate (12.6 mL, 142 mmol) while stirring under nitrogen. Then the resulting mixture was ultrasonicated for 12 h. The reaction mixture was quenched with aqueous sodium bicarbonate and the mixture was extracted with ethyl acetate. The combined organic layers were washed with brine, dried over anhydrous sodium sulfate and filtered. The filtrate was concentrated under vacuum, and the residue was purified by silica gel column chromatography (5-8% ethyl acetate in petroleum ether) to afford the title compound (5.8 g, 37.2 mmol, 33% yield) as a yellow oil. $^1$H NMR (400 MHz, CHLOROFORM-d) δ 3.76 (s, 3H), 3.59-3.51 (m, 1H), 3.15-3.06 (m, 1H), 2.99-2.94 (m, 1H), 1.32 (s, 3H), 1.12 (s, 3H).

B. 2,2-Dimethyl-3-oxocyclobutanecarboxylic acid

To a solution of methyl 2,2-dimethyl-3-oxocyclobutanecarboxylate (5.0 g, 32.1 mmol) in MeOH (37.5 mL) was added an aqueous solution of sodium hydroxide (4.48 N, 18.5 mL, 84 mmol). The resulting mixture was stirred at 50° C. for 2 h. After completion, the excess MeOH was removed under reduced pressure and the mixture was extracted with diethyl ether (15 mL). The aqueous solution was neutralized with hydrochloric acid (4 N, 30 mL) and the mixture was extracted with ethyl acetate (100 mL×2). The combined organic layers were washed with brine (15 mL), dried over anhydrous sodium sulfate and filtered. The filtrate was concentrated under vacuum to afford the title product (3.9 g, 27.5 mmol, 86% yield) as a white solid. $^1$H NMR (300 MHz, DMSO-d$_6$) δ (ppm) 12.4 (br, 1H), 3.31-3.23 (m, 1H), 3.17-3.08 (m, 1H), 2.97-2.91 (m, 1H), 1.22 (s, 3H), 1.04 (s, 3H).

C. tert-butyl (2,2-Dimethyl-3-oxocyclobutyl)carbamate

To a solution of 2,2-dimethyl-3-oxocyclobutanecarboxylic acid (3.9 g, 27.5 mmol) and TEA (5.75 g, 57 mmol) in toluene (160 mL) was added diphenylphosphoryl azide (11.5 mL, 57 mmol) slowly under cooling in an ice-water bath. The mixture was stirred at 100° C. for 4 h. The reaction mixture was cooled down to room temperature, and tert-butanol (82 mL, 925 mmol) was added. The resulting mixture was refluxed overnight. The reaction mixture was treated with aqueous sodium bicarbonate (150 mL) and the aqueous solution was extracted with ethyl acetate (50 mL×3). The combined organic layers were washed with brine, dried over anhydrous sodium sulfate and filtered. The filtrate was concentrated under vacuum, the residue was purified by silica gel column chromatography (2-7% ethyl acetate in petroleum ether) to afford the title compound (650 mg, 3.05 mmol, 11% yield) as a yellow oil. $^1$H NMR (300 MHz, CDCl$_3$) δ (ppm) 4.81-4.70 (m, 1H), 4.05-3.93 (m, 1H), 3.37 (dd, $J_1$=18.0 Hz, $J_2$=9.0 Hz, 1H), 2.89 (dd, $J_1$=18.0 Hz, $J_2$=6.9 Hz, 1H), 1.48 (s, 9H), 1.28 (s, 3H), 1.13 (s, 3H).

D. tert-butyl (3-(Hydroxyimino)-2,2-dimethylcyclobutyl)carbamate oxime

A mixture of tert-butyl (2,2-dimethyl-3-oxocyclobutyl)carbamate (645 mg, 3.00 mmol), hydroxylamine hydrochloride (312 mg, 4.50 mmol) and sodium carbonate (240 mg, 2.25 mmol) in MeOH and water (7 mL and 7 mL) was stirred at room temperature overnight. The reaction was treated with water and extracted with ethyl acetate. The combined organic layers were dried over sodium sulfate and filtered. The filtrate was concentrated under vacuum to afford the crude title compound (730 mg, crude) as a white solid. MS (ESI) m/z 229.2 [M+H]$^+$.

E. tert-butyl (3-Amino-2,2-dimethylcyclobutyl)carbamate

To a solution of tert-butyl (3-(hydroxyimino)-2,2-dimethylcyclobutyl)carbamate oxime (730 mg, crude) in MeOH and ammonia (12.5 mL and 2.5 mL) was added Raney-Ni (430 mg, crude). The reaction mixture was stirred at room temperature under hydrogen atmosphere overnight. The reaction was filtered through celite and the filtrate was concentrated in vacuo. The residue was purified by silica gel column chromatography (2-5% MeOH in DCM) to afford the title compound (490 mg, 2.29 mmol, 76% yield two steps). MS (ESI) m/z 215.2 [M+H]$^+$.

F. 4-Chloro-2-((3-chlorophenethyl)amino)pyrimidine-5-carbonitrile

A mixture of 2,4-dichloropyrimidine-5-carbonitrile (5.0 g, 28.90 mmol), 2-(3-chlorophenyl)ethanamine (4.78 g, 28.9 mmol) and DIEA (7.45 g, 57.8 mmol) in THF (50 mL) was stirred at 50° C. for 3 h. After cooling to room temperature, water (80 mL) was added and the aqueous layer was extracted with ethyl acetate (3×100 mL). The combined organic layers were washed with saturated aqueous ammonium chloride, brine, dried over anhydrous sodium sulfate and filtered. The filtrate was evaporated in vacuum to give the crude product, which was treated with ethyl acetate (30 mL) and stirred for 30 min. The mixture was filtered and dried to afford the title compound (3.20 g, 10.92 mmol, 38% yield). MS (ESI) m/z 293.1, 294.1 [M+H]$^+$.

G. tert-butyl ((1S,3S)-3-((2-((3-Chlorophenethyl) amino)-5-cyanopyrimidin-4-yl)amino)-2,2-dimethylcyclobutyl)carbamate, tert-butyl ((1R,3R)-3-((2-((3-chlorophenethyl)amino)-5-cyanopyrimidin-4-yl) amino)-2,2-dimethylcyclobutyl)carbamate, tert-butyl ((1R,3S)-3-((2-((3-chlorophenethyl)amino)-5-cyanopyrimidin-4-yl)amino)-2,2-dimethylcyclobutyl)carbamate and tert-butyl ((1S,3R)-3-((2-((3-chlorophenethyl)amino)-5-cyanopyrimidin-4-yl)amino)-2, 2-dimethylcyclobutyl)carbamate To a mixture of 4-chloro-2-((3-chlorophenethyl)amino) pyrimidine-5-carbonitrile (600 mg, 2.04 mmol) and tert-butyl (3-amino-2,2-dimethylcyclobutyl)carbamate (490 mg, 2.29 mmol) in dioxane (20 mL) was added DIEA (738 mg, 5.73 mmol). The resulting mixture was stirred at 125° C. under microwave irradiation for 5 h. After removal of the organic solvent under reduced pressure, the residue was diluted with ethyl acetate and the organic layer was washed with aqueous solution of ammonia chloride. The organic layer was separated and dried over sodium sulfate and concentrated under vacuum to give the crude product, which was purified by silica gel chromatography (10% to 33% ethyl acetate in petroleum) to afford the title compound (610 mg, 1.30 mmol, 63% yield) as a pale yellow solid. The racemic product (500 mg, 1.06 mmol) was separated by chiral preparative supercritical fluid chromatography (chiral column: OJ, Column size: 0.46 cm I.D.×25 cm L, 5 um; Mobile phase: CO2:MeOH:DEA=60:40:0.1, Flow: 2.5 mL/min, 220 nm T=35° C.) to give four isomers: tert-butyl ((1S,3S)-3-((2-((3-chlorophenethyl)amino)-5-cyanopyrimidin-4-yl)amino)-2,2-dimethylcyclobutyl)carbamate (peak 1, 100 mg, 0.21 mmol, 20% yield, RT=7.88 min, d.e.=100%, e.e.=100%), tert-butyl ((1R,3R)-3-((2-((3-chlorophenethyl) amino)-5-cyanopyrimidin-4-yl)amino)-2,2-dimethylcyclobutyl)carbamate (peak 3, 102 mg, 0.22 mmol, 20% yield, RT=9.37 min, d.e.=100%, e.e.=100%), tert-butyl ((1R,3S)-3-((2-((3-chlorophenethyl)amino)-5-cyanopyrimidin-4-yl) amino)-2,2-dimethylcyclobutyl)carbamate (peak 2, 85 mg, 0.18 mmol, 17% yield, RT=8.29 min, d.e.=100%, e.e.=100%) and tert-butyl ((1S,3R)-3-((2-((3-chlorophenethyl)amino)-5-cyanopyrimidin-4-yl)amino)-2,2-dimethylcyclobutyl)carbamate (peak 4, 82 mg, 0.17 mmol, 17% yield, RT=10.96 min, d.e.=100%, e.e.=100%). MS (ESI) m/z 471.2 [M+H]$^+$

H. 4-(((1S,3S)-3-Amino-2,2-dimethylcyclobutyl) amino)-2-((3-chlorophenethyl)amino)pyrimidine-5-carbonitrile To a solution of tert-butyl ((1S,3S)-3-((2-((3-chlorophenethyl)amino)-5-cyanopyrimidin-4-yl)amino)-2,2-dimethylcyclobutyl)carbamate (100 mg, 0.21 mmol) in dry DCM (2 mL) was added TFA (1.5 mL) dropwise under cooling in an ice-water bath. The resulting mixture was stirred at room temperature for 30 min. After removal of the organic solvents, the residue was neutralized with ammonia and extracted with DCM. The combined organic layers were dried over anhydrous sodium sulfate and concentrated to give the crude product, which was purified by standard methods to afford the title compound (49.7 mg, 0.13 mmol, 64% yield). $^1$H NMR (400 MHz, CD$_3$OD) δ (ppm) 8.06 (s, 1H), 7.29-7.15 (m, 4H), 4.33 (dd, J$_1$=5.6 Hz, J$_2$=9.2 Hz, 1H), 3.72-3.50 (m, 2H), 3.18-3.12 (m, 1H), 2.93-2.86 (m, 2H), 2.45-2.39 (m, 1H), 2.17-2.12 (m, 1H), 1.20 (s, 3H), 0.98 (s 3H). MS (ESI) m/z 371.2 [M+H]$^+$.

4-(((1R,3R)-3-Amino-2,2-dimethylcyclobutyl) amino)-2-((3-chlorophenethyl)amino)pyrimidine-5-carbonitrile To a solution of tert-butyl ((1R,3R)-3-((2-((3-chlorophenethyl)amino)-5-cyanopyrimidin-4-yl)amino)-2,2-dimethylcyclobutyl)carbamate (102 mg, 0.22 mmol) in dry DCM (2 mL) was added TFA (1.5 mL) dropwise under cooling in an ice-water bath. The resulting mixture was stirred at room temperature for 30 min. After removal of the organic solvent, the residue was neutralized with ammonia and extracted with DCM. The combined organic layers were dried over anhydrous sodium sulfate and concentrated to give the crude, which was purified by standard methods to afford the title compound (43.8 mg, 0.118 mmol, 54% yield). $^1$H NMR (400 MHz, CD$_3$OD) δ (ppm) 8.06 (s, 1H), 7.29-7.15 (m, 4H), 4.33 (dd, J$_1$=5.6 Hz, J$_2$=9.2 Hz, 1H), 3.72-3.50 (m, 2H), 3.18-3.12 (m, 1H), 2.93-2.86 (m, 2H), 2.45-2.39 (m, 1H), 2.17-2.12 (m, 1H), 1.20 (s, 3H), 0.98 (s 3H). MS (ESI) m/z 371.2 [M+H]$^+$.

4-(((1S,3R)-3-Amino-2,2-dimethylcyclobutyl) amino)-2-((3-chlorophenethyl)amino)pyrimidine-5-carbonitrile To a solution of tert-butyl ((1S,3R)-3-((2-((3-chlorophenethyl)amino)-5-cyanopyrimidin-4-yl)amino)-2,2-dimethylcyclobutyl)carbamate (85 mg, 0.18 mmol) in dry DCM (2 mL) was added TFA (1.5 mL) dropwise under ice-water bath. The resulting mixture was stirred at room temperature for 30 min. After removal of the organic solvent, the residue was neutralized with ammonia and extracted with DCM. The combined organic layers were dried over anhydrous sodium sulfate and concentrated to give the crude product, which was purified by standard methods to afford the title compound (48.7 mg, 0.131 mmol, 73% yield). $^1$H NMR (400 MHz, CD$_3$OD) δ (ppm) 8.04 (s, 1H), 7.27-7.14 (m, 4H), 4.16-3.97 (m, 1H), 3.74-3.49 (m, 2H), 2.90-2.85 (m, 3H), 2.60-2.49 (m, 1H), 1.92-1.86 (m, 1H), 1.22 (s, 3H), 0.92 (s 3H). MS (ESI) m/z 371.2 [M+H]$^+$.

4-(((1R,3S)-3-Amino-2,2-dimethylcyclobutyl) amino)-2-((3-chlorophenethyl)amino)pyrimidine-5-carbonitrile To a solution of tert-butyl ((1R,3S)-3-((2-((3-chlorophenethyl)amino)-5-cyanopyrimidin-4-yl)amino)-2,2-dimethylcyclobutyl)carbamate (82 mg, 0.17 mmol) in dry DCM (2 mL) was added trifluoroacetic acid (1.5 mL) dropwise under cooling in an ice-water bath. The resulting mixture was stirred at room temperature for 30 min. After removal of the organic solvent, the residue was neutralized with ammonia and extracted with DCM. The combined organic layers were dried over anhydrous sodium sulfate and concentrated to give the crude product, which was purified by standard methods to afford the title compound (34.3 mg, 0.092 mmol, 55% yield). $^1$H NMR (400 MHz, CD$_3$OD) δ (ppm) 8.04 (s, 1H), 7.27-7.14 (m, 4H), 4.16-3.97 (m, 1H), 3.74-3.49 (m, 2H), 2.90-2.85 (m, 3H), 2.60-2.49 (m, 1H), 1.92-1.86 (m, 1H), 1.22 (s, 3H), 0.92 (s 3H). MS (ESI) m/z 371.2 [M+H]$^+$.

Example 23

4-((1R,4S)-4-Hydroxy-3,3-dimethylcyclohexy-lamino)-2-(3-(5-methyl-1H-tetrazol-1-yl)phenethyl-amino)pyrimidine-5-carbonitrile

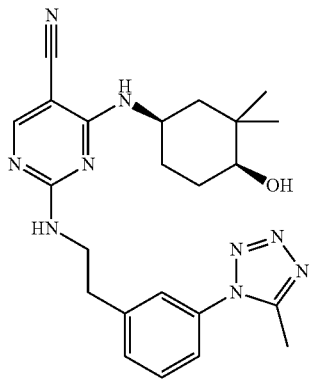 [SMILES: Cc1nnnn1-c1cccc(CCNc2ncc(C#N)c(N[C@@H]3CC[C@H](O)C(C)(C)C3)n2)c1]

A. (3-Amino-phenyl)-acetonitrile

A mixture of (3-nitro-phenyl)-acetonitrile (2.00 g, 12.35 mmol), iron dust (2.07 g, 37.03 mmol) and ammonia chloride (1.96 g, 37.03 mmol) in EtOH (20 mL) and water (4 mL) was refluxed at 85° C. for 1 h. The reaction mixture was filtered through celite and rinsed with EtOH. The combined filtrate was concentrated and the residue was purified by silica gel column chromatography (20% ethyl acetate in petroleum ether) to afford the title compound (1.57 g, 11.89 mmol, 96% yield) as a pale-yellow solid. MS (ESI) m/z 133.1 [M+H]$^+$.

B. N-(3-Cyanomethyl-phenyl)-acetamide

To a mixture of (3-amino-phenyl)-acetonitrile (500 mg, 3.79 mmol) and TEA (498 mg, 4.93 mmol) was added acetyl chloride (387 mg, 4.93 mmol) slowly at 0° C. The resulting mixture was stirred at room temperature for 10 min. The reaction mixture was quenched with saturated aqueous ammonium chloride and extracted with DCM twice. The combined organic layers were washed with aqueous ammonia chloride and brine, dried over anhydrous sodium sulfate and concentrated to afford the title compound (558 mg, 3.20 mmol, 85% yield) as a pale-yellow solid. MS (ESI) m/z 175.1 [M+H]$^+$.

C. [3-(5-Methyl-tetrazol-1-yl)-phenyl]-acetonitrile

To a solution of N-(3-cyanomethyl-phenyl)-acetamide (500 mg, 2.87 mmol) in anhydrous acetonitrile (5 mL) was added trifluoromethanesulfonic anhydride (1.62 g, 5.74 mmol) slowly at −5° C. The resulting mixture was stirred for 5 min, trimethylsilylazide (1.32 g, 11.48 mmol) was added slowly keeping the temperature below −5° C. The resulting mixture was stirred at −5° C. for 1 h. The reaction was poured into cooled aqueous ammonia chloride and extracted with ethyl acetate three times. The combined organic layers were dried over sodium sulfate and concentrated to give the crude product, which was purified by silica gel column chromatography (1-2% MeOH in DCM) to afford the title compound (260 mg, 1.31 mmol, 45% yield) as a yellow solid. MS (ESI) m/z 199.9 [M+H]$^+$.

D. 2-[3-(5-Methyl-tetrazol-1-yl)-phenyl]-ethylamine

To a solution of [3-(5-methyl-tetrazol-1-yl)-phenyl]-acetonitrile (180 mg, 0.90 mmol) in THF (3 mL) was added a solution of borane-methyl sulfide complex in THF (2M, 0.8 mL, 1.60 mmol) slowly at 0° C. and the resulting mixture was refluxed at 80° C. under nitrogen for 2 h. The reaction was quenched with MeOH and stirred at room temperature for 1 h. The mixture was concentrated to give the crude product, which was purified by silica gel column chromatography (10-26% ethyl acetate in petroleum ether) to afford the title compound (85 mg, 0.42 mmol, 46% yield). MS (ESI) m/z 204.1 [M+H]$^+$.

F. 4-(((1R,4S)-4-Hydroxy-3,3-dimethylcyclohexyl)amino)-2-(methylthio)pyrimidine-5-carbonitrile A mixture of 4-chloro-2-(methylthio)pyrimidine-5-carbonitrile (2.15 g, 11.6 mmol)), (1S,4R)-4-amino-2,2-dimethylcyclohexanol (1.51 g, 10.5 mmol) and DIEA (2.72 g, 21.1 mmol) in isopropanol (30 mL) was heated at 100° C. for 3 h. After removal of the organic solvent under reduced pressure, the residue was treated with water and extracted with ethyl acetate. The combined organic layers were washed with brine, dried over sodium sulfate and concentrated to give the crude product, which was purified by silica gel column chromatography (15% ethyl acetate in petroleum) to afford the title compound as a pale yellow solid (2.2 g, 7.53 mmol, 72% yield). MS (ESI) m/z 293.2 [M+H]$^+$.

G. 4-(((1R,4S)-4-Hydroxy-3,3-dimethylcyclohexyl)amino)-2-(methylsulfonyl)pyrimidine-5-carbonitrile and 4-(((1R,4S)-4-hydroxy-3,3-dimethylcyclohexyl)amino)-2-(methylsulfinyl)pyrimidine-5-carbonitrile To a solution of 4-(((1R,4S)-4-hydroxy-3,3-dimethylcyclohexyl)amino)-2-(methylthio)pyrimidine-5-carbonitrile (1.02 g, 3.48 mmol) in dry DCM (20 mL) was added m-chloroperoxybenzoic acid (85%, 1.78 g, 8.79 mmol) under cooling in an ice-water bath. The resulting mixture was stirred at room temperature for 3 h. The reaction was quenched with aqueous sodium thiosulfate and extracted with DCM. The combined organic layers were washed with aqueous potassium carbonate and brine, dried over sodium sulfate and concentrate to give the title compound (0.9 g, crude) as a pale yellow solid. MS (ESI) m/z 309.2, 325.2 [M+H]$^+$.

H. 4-((1R,4S)-4-Hydroxy-3,3-dimethylcyclohexy-lamino)-2-(3-(5-methyl-1H-tetrazol-1-yl)phenethyl-amino)pyrimidine-5-carbonitrile A mixture of 2-(2-(5-methyl-1H-tetrazol-1-yl)phenyl)ethanamine (85 mg, 0.42 mmol), 4-(((1R,4S)-4-hydroxy-3,3-dimethylcyclohexyl)amino)-2-(methylsulfonyl)pyrimidine-5-carbonitrile and 4-(((1R,4S)-4-hydroxy-3,3-dimethylcyclohexyl)amino)-2-(methylsulfinyl)pyrimidine-5-carbonitrile (90 mg, 0.27 mmol) and DIEA (105 mg, 0.81 mmol) was at 100° C. under microwave irradiation for 1.5 h. After cooling to room temperature, the reaction mixture was concentrated and the residue was purified by standard methods to give the title compound (44.3 mg, 0.073 mmol, 21% yield). $^1$H NMR (400 MHz, CD$_3$OD) δ (ppm) 7.92 (m, 1H), 7.50-7.40 (m, 2H), 7.34-7.25 (m, 2H), 4.25-

4.15 (m, 1H), 3.68-3.49 (m, 2H), 3.25-3.22 (m, 1H), 3.00-2.87 (m, 2H), 2.46 (s, 3H), 1.79-1.22 (m, 6H), 0.88-0.83 (m, 6H). MS (ESI) m/z 448.2 [M+H]+.

Example 24

2-((3-Chloro-2-(trifluoromethyl)phenethyl)amino)-4-(((1R,4S)-4-hydroxy-3,3-dimethylcyclohexyl)amino)pyrimidine-5-carbonitrile

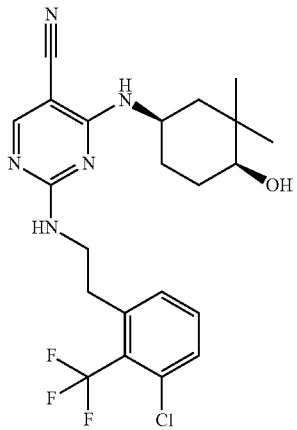 [SMILES: CC1(C)C[C@H](Nc2nc(NCCc3cccc(Cl)c3C(F)(F)F)ncc2C#N)CC[C@@H]1O]

A. (3-Chloro-2-(trifluoromethyl)phenyl)methanol

To a solution of 3-chloro-2-(trifluoromethyl)benzoic acid (0.15 g, 0.668 mmol) in THF (5 mL) was added dropwise a solution of borane dimethyl sulfide complex in THF (2 M, 0.70 mL, 1.40 mmol) at 0° C. to 5° C. The resulting solution was heated at 75° C. for 2 h under nitrogen atmosphere. The reaction was quenched with MeOH (1 mL) at 0° C. and concentrated under vacuum to give the crude title product (0.12 g). $^1$H NMR (400 MHz, CDCl$_3$) δ (ppm) 7.66-7.64 (m, 1H), 7.48-7.44 (m, 2H), 4.90 (d, J=2.0 Hz, 2H), 3.70 (t, J=2.0 Hz, 1H).

B. 3-Chloro-2-(trifluoromethyl)benzyl methanesulfonate

To a mixture of (3-chloro-2-(trifluoromethyl)phenyl)MeOH (0.12 g, crude) and TEA (0.115 g, 1.14 mmol) in dry DCM (5 mL) was added methanesulfonyl chloride (98.0 mg, 0.855 mmol) dropwise at 0° C. The resulting reaction mixture was stirred at room temperature for 2 h. Water was added and the mixture was extracted with DCM (10 mL×3). The combined organic layers were washed with saturated aqueous ammonium chloride, brine, dried over anhydrous sodium sulfate and filtered. The filtrate was evaporated under vacuum to give a crude title product (0.150 g). $^1$H NMR (300 MHz, CDCl$_3$) δ (ppm) 7.62-7.43 (m, 3H), 5.41 (d, J=1.8 Hz, 2H), 3.03 (s, 3H).

C. 2-(3-Chloro-2-(trifluoromethyl)phenyl)acetonitrile

To a mixture of 3-chloro-2-(trifluoromethyl)benzyl methanesulfonate (0.150 g, crude) and trimethylsilanecarbonitrile (119 mg, 1.2 mmol) in acetonitrile (5 mL) was added a solution of tetrabutylammonium fluoride in THF (1M, 1.2 mL, 1.2 mmol). The reaction was stirred at room temperature for 2 h. The reaction was treated with ethyl acetate and water, and the separated organic layer was washed with brine, dried and concentrated to give the crude product, which was purified by silica gel column chromatography (10% ethyl acetate in petroleum ether) to afford the title compound (0.10 g, 3.03 mmol, 68% yield over three steps) as a yellow solid. $^1$H NMR (400 MHz, CDCl$_3$) δ (ppm) 7.56-7.48 (m, 3H), 3.99 (d, J=2.0 Hz, 2H).

D. 2-(3-Chloro-2-(trifluoromethyl)phenyl)ethanamine

To a solution of 2-(3-chloro-2-(trifluoromethyl)phenyl)acetonitrile (0.10 g, 3.03 mmol) in MeOH (5 mL) was added Raney-nickel (100 mg). The mixture was degassed under vacuum for 10 min, and then hydrogenated under a fully-inflated balloon at room temperature overnight. The mixture was filtered through a pad of celite and the cake was washed with MeOH (10 mL). The filtrate was concentrated under vacuum to give the crude product (100 mg). MS (ESI) m/z 224.1 [M+H]+.

E. 4-(((1R,4S)-4-Hydroxy-3,3-dimethylcyclohexyl)amino)-2-(methylthio)pyrimidine-5-carbonitrile A mixture of 4-chloro-2-(methylthio)pyrimidine-5-carbonitrile (2.15 g, 11.6 mmol)), (1S,4R)-4-amino-2,2-dimethylcyclohexanol (1.51 g, 10.5 mmol) and DIEA (2.72 mg, 21.1 mmol) in isopropanol (30 mL) was heated at 100° C. for 3 h. After removal of the organic solvent under reduced pressure, the residue was treated with water and extracted with ethyl acetate. The combined organic layers were washed with brine, dried over sodium sulfate and concentrated to give the crude product, which was purified by silica gel column chromatography (15% ethyl acetate in petroleum) to afford the title compound as a pale yellow solid (2.2 g, 7.53 mmol, 72% yield). MS (ESI) m/z 293.2 [M+H]+.

F. 4-(((1R,4S)-4-Hydroxy-3,3-dimethylcyclohexyl)amino)-2-(methylsulfonyl)pyrimidine-5-carbonitrile To a solution of 4-(((1R,4S)-4-hydroxy-3,3-dimethylcyclohexyl)amino)-2-(methylthio)pyrimidine-5-carbonitrile (1.02 g, 3.48 mmol) in dry DCM (20 mL) was added m-chloroperoxybenzoic acid (85%, 1.78 g, 8.79 mmol) under cooling in an ice-water bath. The resulting mixture was stirred at room temperature for 3 h. The reaction was quenched with aqueous sodium thiosulfate and extracted with DCM. The combined organic layers were washed with aqueous solution of potassium carbonate and brine, dried over sodium sulfate and concentrate to give the title product (0.9 g, crude) as a pale yellow solid. MS (ESI) m/z 309.2, 325.2 [M+H]+.

G. 2-((3-Chloro-2-(trifluoromethyl)phenethyl)amino)-4-(((1R,4S)-4-hydroxy-3,3-dimethylcyclohexyl)amino)pyrimidine-5-carbonitrile A mixture of 4-(((1R,4S)-4-hydroxy-3,3-dimethylcyclohexyl)amino)-2-(methylsulfonyl)pyrimidine-5-carbonitrile (75 mg, 0.23 mmol), 2-(3-chloro-2-(trifluoromethyl)phenyl)ethanamine (100 mg, crude) and DIEA (85 mg, 0.66 mmol) in THF (2 mL) was stirred at 100° C. in a microwave reactor for 1.5 h. After cooling to room temperature, the reaction mixture was concentrated and the residue was purified by standard methods to afford the title compound (42.2 mg, 0.090 mmol, 39% yield). $^1$H NMR (400 MHz, CD$_3$OD) δ

(ppm) 8.10-8.03 (m, 1H), 7.48-4.41 (m, 2H), 7.30 (m, 1H), 4.31-4.28 (m, 1H), 3.73-3.69 (m, 1H), 3.63-3.56 (m, 1H), 3.39-3.37 (m, 1H), 3.17-3.14 (m, 2H), 1.88-1.44 (m, 6H), 0.97 (s, 3H), 0.96 (s, 3H). MS (ESI) m/z 468.1 [M+H]$^+$.

Example 25

4-Chloro-2-(2-(5-cyano-4-((1R,4S)-4-hydroxy-3,3-dimethylcyclohexylamino)pyrimidin-2-ylamino)ethyl)benzenesulfonamide

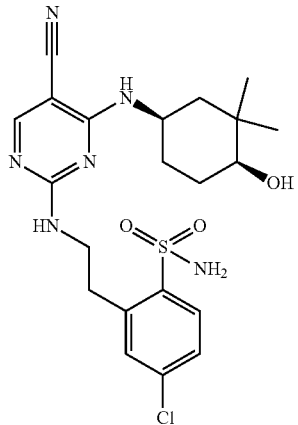 [SMILES: CC1(C)C[C@H](Nc2nc(NCCc3cc(Cl)ccc3S(N)(=O)=O)ncc2C#N)CC[C@@H]1O]

A. N-[2-(3-Chloro-phenyl)-ethyl]-acetamide

To a solution of 2-(3-chloro-phenyl)-ethylamine (3.00 g, 19.28 mmol) and TEA (2.9 g, 28.92 mmol) in anhydrous DCM (30 mL) was added acetyl chloride (2.27 g, 28.92 mmol) dropwise at 0° C. The resulting mixture was stirred at room temperature for 1 h. The reaction was quenched with water and the mixture was extracted with ethyl acetate. The combined organic layers were washed with saturated ammonium chloride aqueous solution, brine and concentrated to afford the title compound as yellow oil (3.60 g, 18.27 mmol, 94% yield). MS (ESI) m/z 198.1, 200.1 [M+H]$^+$.

B. 2-(2-Acetylamino-ethyl)-4-chloro-benzenesulfonyl chloride

N-[2-(3-Chloro-phenyl)-ethyl]-acetamide (400 mg, 2.02 mmol) was added to sulfurochloridic acid (4 mL) slowly at 0-5° C. The resulting mixture was stirred at room temperature for 2 h. The reaction mixture was poured into ice-water and stirred for 10 min. The mixture was extracted with DCM. The combined organic layers were washed with brine, dried over anhydrous sodium sulfate and concentrated to afford the title compound as a brown solid (288 mg, 0.97 mmol, 48% yield). MS (ESI) m/z 296.0, 298.0, 300.0 [M+H]$^+$.

C. N-[2-(5-Chloro-2-sulfamoyl-phenyl)-ethyl]-acetamide

To a solution of 2-(2-acetylamino-ethyl)-4-chloro-benzenesulfonyl chloride (288 mg, 1.04 mmol) in anhydrous DCM (4 mL) was added ammonia solution (2 mL) slowly at 0-5° C. The resulting reaction mixture was stirred at room temperature for 1 h. Water was added and the mixture was extracted with chloroform/isopropanol (3:1). The combined organic layers were dried over anhydrous sodium sulfate and concentrated to afford the crude product, which was purified by silica gel chromatography (209 mg, 0.76 mmol, 78% yield). MS (ESI) m/z 277.0, 279.0 [M+H]$^+$.

D. 2-(2-Amino-ethyl)-4-chloro-benzenesulfonamide

A mixture of N-[2-(5-chloro-2-sulfamoyl-phenyl)-ethyl]-acetamide (209 mg, 0.76 mmol) and potassium hydroxide aqueous solution (2 mol/L, 3 mL, 6 mmol) was stirred at 100° C. for 4 h. After cooling to room temperature, the reaction was neutralized with 2N of aqueous hydrochloric acid solution. The mixture was concentrated to dryness and the residue was diluted with solvent (3% MeOH in DCM, 200 mL) and stirred for 1 h. The mixture was filtered and the filtrate was concentrated to afford the title compound as a gray solid (150 mg, 0.64 mmol, 85% yield). MS (ESI) m/z 235.1, 237.1 [M+H]$^+$.

E. 4-(((1R,4S)-4-Hydroxy-3,3-dimethylcyclohexyl)amino)-2-(methylthio)pyrimidine-5-carbonitrile A mixture of 4-chloro-2-(methylthio)pyrimidine-5-carbonitrile (2.15 g, 11.6 mmol)), (1S,4R)-4-amino-2,2-dimethylcyclohexanol (1.51 g, 10.5 mmol) and DIEA (2.72 g, 21.1 mmol) in isopropanol (30 mL) was heated at 100° C. for 3 h. After removal of the organic solvents under reduced pressure, the residue was treated with water and extracted with ethyl acetate. The combined organic layers were washed with brine, dried over sodium sulfate and concentrated to give a crude product, which was purified by silica gel column chromatography (15% ethyl acetate in petroleum) to afford the title compound as a pale yellow solid (2.2 g, 7.53 mmol, 72% yield). MS (ESI) m/z 293.2 [M+H]$^+$.

F. 4-(((1R,4S)-4-Hydroxy-3,3-dimethylcyclohexyl)amino)-2-(methylsulfonyl)pyrimidine-5-carbonitrile To a solution of 4-(((1R,4S)-4-hydroxy-3,3-dimethylcyclohexyl)amino)-2-(methylthio)pyrimidine-5-carbonitrile (1.02 g, 3.48 mmol) in dry DCM (20 mL) was added m-chloroperoxybenzoic acid (85%, 1.78 g, 8.79 mmol) under cooling in an ice-water bath. The resulting mixture was stirred at room temperature for 3 h. The reaction was quenched with aqueous sodium thiosulfate and extracted with DCM. The combined organic layers were washed with aqueous solution of potassium carbonate and brine, dried over sodium sulfate and concentrate to give the title (0.9 g, crude) as a pale yellow solid. MS (ESI) m/z 309.2, 325.2 [M+H]$^+$.

4-Chloro-2-(2-(5-cyano-4-((1R,4S)-4-hydroxy-3,3-dimethylcyclohexylamino)pyrimidin-2-ylamino)ethyl)benzenesulfonamide A mixture of 4-(((1R,4S)-4-hydroxy-3,3-dimethylcyclohexyl)amino)-2-(methylsulfonyl)pyrimidine-5-carbonitrile (100 mg, 0.31 mmol), 2-(2-amino-ethyl)-4-chloro-benzenesulfonamide (150 mg, 0.64 mmol) and DIEA (80 mg, 0.62 mmol) in THF (4 mL) was stirred at 100° C. in a microwave reactor for 1 h. After cooling to room temperature, the reaction mixture was concentrated and the residue purified by standard methods to afford the title compound (53.3 mg, 0.060 mmol, 26% yield). $^1$H NMR (400 MHz, CD$_3$OD) δ (ppm) 8.18-8.00 (m, 1H), 7.96 (d, J=8.0 Hz, 1H), 7.50-7.34 (m, 2H), 4.41-4.23 (m, 1H), 3.89-3.51 (m, 2H), 3.41-3.33

(m, 2H), 3.29-3.22 (m, 1H), 2.04-1.80 (m, 1H), 1.80-1.68 (m, 2H), 1.67-1.38 (m, 3H), 1.05-0.93 (m, 6H). MS (ESI) m/z 479.1, 481.1 [M+H]+.

Example 26

2-Chloro-4-(2-(5-cyano-4-(((1R,4S)-4-hydroxy-3,3-dimethylcyclohexylamino)pyrimidin-2-ylamino)ethyl)benzenesulfonamide

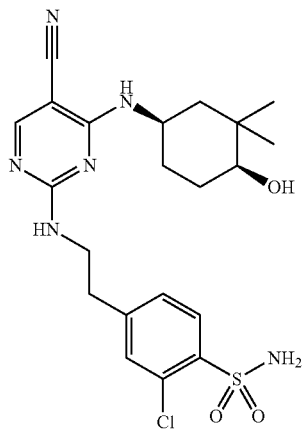 [SMILES: CC1(C)C[C@H](Nc2nc(NCCc3ccc(S(N)(=O)=O)c(Cl)c3)ncc2C#N)CC[C@@H]1O]

A. N-Phenethylacetamide

To a solution of 2-phenylethanamine (5.00 g, 41.32 mmol) and TEA (6.26 g, 61.98 mmol) in anhydrous DCM (50 mL) was added dropwise acetyl chloride (3.57 g, 45.45 mmol) at 0° C. The resulting reaction mixture was stirred at room temperature for 30 min. Water was added and the mixture was extracted with DCM. The combined organic layers were washed with saturated aqueous ammonium chloride, brine and concentrated to give the title product as a yellow oil (6.06 g, 37.19 mmol, 90% yield). MS (ESI) m/z 164.1 [M+H]+.

B. 4-(2-Acetamidoethyl)benzene-1-sulfonyl chloride

N-Phenethylacetamide (4.50 g, 27.6 mmol) was added to sulfurochloridic acid (30 mL) slowly at 0-5° C. The resulting reaction mixture was stirred at room temperature for 2 h. The reaction mixture was poured into ice-water and stirred for 10 min. The mixture was extracted with DCM. The combined organic layers were washed with brine, dried over anhydrous sodium sulfate and concentrated to afford the title compound as a brown solid (3.30 g, 12.64 mmol, 45% yield). MS (ESI) m/z 262.1 [M+H]+.

C. N-[2-(4-Sulfamoyl-phenyl)-ethyl]-acetamide

To a solution of 4-(2-acetamidoethyl)benzene-1-sulfonyl chloride (3.30 g, 12.64 mmol) in anhydrous DCM (30 mL) was added ammonia solution (15 mL) at 0-5° C. The resulting reaction mixture was stirred at room temperature for 1 h. Water was added and the mixture was extracted with chloroform/isopropanol (3:1). The combined organic layers were dried over anhydrous sodium sulfate and concentrated to afford the crude product, which was purified by silica gel chromatography (1-2% MeOH in DCM) as a brown solid (2.5 g, 10.33 mmol, 82% yield). MS (ESI) m/z 243.1 [M+H]+.

D. N-[2-(3-Chloro-4-sulfamoyl-phenyl)-ethyl]-acetamide

To a mixture of N-[2-(4-sulfamoyl-phenyl)-ethyl]-acetamide (780 mg, 3.21 mmol), N-chlorosuccinimide (216 mg, 1.60 mmol), sodium persulfate (573 mg, 2.41 mmol) and palladium diacetate (108 mg, 0.48 mmol) in dichloroethane (30 mL) was added trifluoromethanesulfonic acid (843 mg, 5.62 mmol) at 0° C. The resulting mixture was stirred at 75° C. in a sealed tube for 7 h. The reaction mixture was neutralized with ammonia and the mixture was extracted with DCM. The combined organic layers were dried over anhydrous sodium sulfate and concentrated to afford the crude product, which was purified by silica gel chromatography (1-3% MeOH in DCM) to afford the title compound as a brown solid (350 mg, 1.27 mmol, 39% yield). MS (ESI) m/z 276.0 [M+H]+.

E. 4-(2-Amino-ethyl)-2-chloro-benzenesulfonamide

A mixture of N-[2-(3-chloro-4-sulfamoyl-phenyl)-ethyl]-acetamide (350 mg, 1.27 mmol) and potassium hydroxide aqueous solution (2 mol/L, 8 mL, 16 mmol) was stirred at 100° C. for 4 h. After cooling to room temperature, the reaction was neutralized with 2N of aqueous hydrochloric acid solution. The mixture was concentrated to dryness and the residue was diluted with solvent (3% MeOH in DCM, 200 mL) and stirred for 1 h. The mixture was filtered and the filtrate was concentrated to afford the title compound as a pale green solid (240 mg, 1.03 mmol, 81% yield). MS (ESI) m/z 235.1 [M+H]+.

F. 4-(((1R,4S)-4-Hydroxy-3,3-dimethylcyclohexyl)amino)-2-(methylthio)pyrimidine-5-carbonitrile A mixture of 4-chloro-2-(methylthio)pyrimidine-5-carbonitrile (2.15 g, 11.6 mmol)), (1S,4R)-4-amino-2,2-dimethylcyclohexanol (1.51 g, 10.5 mmol) and DIEA (2.72 g, 21.1 mmol) in isopropanol (30 mL) was heated at 100° C. for 3 h. After removal of the organic solvent under reduced pressure, the residue was treated with water and extracted with ethyl acetate. The combined organic layers were washed with brine, dried over sodium sulfate and concentrated to give the crude product, which was purified by silica gel column chromatography (15% ethyl acetate in petroleum) to afford the title compound as a pale yellow solid (2.2 g, 7.53 mmol, 72% yield). MS (ESI) m/z 293.2 [M+H]+.

G. 4-(((1R,4S)-4-Hydroxy-3,3-dimethylcyclohexyl)amino)-2-(methylsulfonyl)pyrimidine-5-carbonitrile and 4-(((1R,4S)-4-hydroxy-3,3-dimethylcyclohexyl)amino)-2-(methylsulfinyl)pyrimidine-5-carbonitrile To a solution of 4-(((1R,4S)-4-hydroxy-3,3-dimethylcyclohexyl)amino)-2-(methylthio)pyrimidine-5-carbonitrile (1.02 g, 3.48 mmol) in dry DCM (20 mL) was added m-chloroperoxybenzoic acid (85%, 1.78 g, 8.79 mmol) under cooling in an ice-water bath. The resulting mixture was stirred at room temperature for 3 h. The reaction was quenched with aqueous sodium thiosulfate and extracted with DCM. The combined organic layers were washed with aqueous potassium carbonate and brine, dried over sodium sulfate and concentrate to give the title compound (0.9 g, crude) as a pale yellow solid. MS (ESI) m/z 309.2, 325.2 [M+H]+.

H. 2-Chloro-4-{2-[5-cyano-4-(4-hydroxy-3,3-dimethyl-cyclohexylamino)-pyrimidin-2-ylamino]-ethyl}-benzenesulfonamide A mixture of 4-(((1R,4S)-4-hydroxy-3,3-dimethylcyclohexyl)amino)-2-(methylsulfonyl)pyrimidine-5-carbonitrile (90 mg, 0.28 mmol) and 4-(((1R,4S)-4-hydroxy-3,3-dimethylcyclohexyl)amino)-2-(methylsulfinyl)pyrimidine-5-carbonitrile, 4-(2-amino-ethyl)-2-chloro-benzenesulfonamide (90 mg, 0.38 mmol) and DIEA (72 mg, 0.56 mmol) in THF (4 mL) was stirred at 100° C. in a microwave reactor for 1 h. After cooling to room temperature, the reaction mixture was concentrated and the residue was purified by standard methods to afford the title compound (28.6 mg, 0.060 mmol, 26% yield). $^1$H NMR (400 MHz, CD$_3$OD) δ (ppm) 7.93 (s, 1H), 7.85 (d, J=8.0 Hz, 1H), 7.35 (s, 1H), 7.20 (d, J=8.0 Hz, 1H), 4.26-4.12 (m, 1H), 3.66-3.46 (m, 2H), 3.31-3.25 (m, 1H), 2.87 (t, J=6.8 Hz, 2H), 1.86-1.35 (m, 6H), 0.90 (s, 3H), 0.88 (s, 3H). MS (ESI) m/z 479.1 [M+H]+.

Example 27

2-(((4-(2,2-Difluoropropoxy)pyrimidin-5-yl)methyl)amino)-4-(((1S,3R)-3-hydroxy-3-methylcyclohexyl)amino)pyrimidine-5-carbonitrile

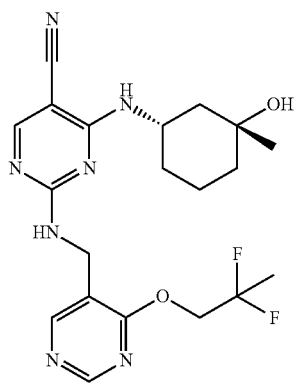 [SMILES: CC(F)(F)COc1ncncc1CNc1ncc(C#N)c(N[C@H]2CCC[C@@](C)(O)C2)n1]

A. 4-(2,2-Difluoropropoxy)pyrimidine-5-carbonitrile

To a suspension of sodium hydride (60% dispersed in mineral oil, 1.84 g, 46 mmol) in THF (30.0 mL) was added 2,2-difluoropropan-1-ol (4.42 g, 46.0 mmol) at 0° C. The resulting mixture was stirred at room temperature for 1 h, then 4-chloropyrimidine-5-carbonitrile (6 g, 43.2 mmol) was added in portions at 0° C. After addition, the reaction mixture was stirred at room temperature for 30 min. The reaction was quenched with saturated aqueous ammonium chloride solution and extracted with ethyl acetate. The combined organic layers were dried over sodium sulfate and concentrated to give a crude product, which was purified by silica gel column chromatography (10% ethyl acetate in petroleum ether) to afford the title compound (4.40 g, 22.1 mmol, 51% yield) as a yellow solid. MS (ESI) m/z 200.0 [M+H]+.

B. (4-(2,2-Difluoropropoxy)pyrimidin-5-yl)methanamine

To a solution of 4-(2,2-difluoropropoxy)pyrimidine-5-carbonitrile (1.7 g, 8.54 mmol) in THF (30 mL) was added Raney nickel (500 mg, crude). The resulting mixture was stirred at room temperature overnight under hydrogen atmosphere. The reaction was filtered and the filtrated was concentrated in vacuo and purified by silica gel column chromatography (5% MeOH in DCM) to afford the desired product (650 mg, 3.20 mmol, 37% yield) as a yellow solid. MS (ESI) m/z 204.1 [M+H]+.

C. tert-butyl(3-Hydroxycyclohexyl)carbamate

To a solution of 3-aminocyclohexanol (3.0 g, 26.0 mol) in THF (30 mL) was added di-tert-butyl dicarbonate (6.74 g, 31.2 mmol). The resulting mixture was stirred at 50° C. for 16 h. Then the reaction mixture was concentrated in vacuum and purified by silica gel column chromatography (30% ethyl acetate in petroleum ether) to afford the desired compound (4.40 g, 20.46 mmol, 78% yield). MS (ESI) m/z 216.1 [M+H]+.

D. tert-butyl(3-Oxocyclohexyl)carbamate

To a solution of tert-butyl (3-hydroxycyclohexyl)carbamate (4.40 g, 20.46 mmol) in DCM (250 mL) was added Dess-Martin periodinane (13.0 g, 30.70 mmol) in portions under cooling in an ice bath. The mixture was stirred at room temperature for 2 h. The reaction was diluted with DCM and washed with aqueous sodium carbonate. The separated organic layer was dried over anhydrous sodium sulfate and concentrated. The crude compound was purified by silica gel column chromatography (40% ethyl acetate in petroleum ether) to afford the title compound (4.0 g, 18.78 mmol, 91% yield). MS (ESI) m/z 214.1 [M+H]+.

E. tert-butyl(3-Hydroxycyclohexyl)carbamate

To a degassed suspension of tert-butyl(3-oxocyclohexyl)carbamate (4.0 g, 18.78 mmol) in dry THF 200 mL) was added a solution of methyllithium in THF (3M, 25.0 mL, 75 mmol) at −75° C. The resulting reaction mixture was stirred at −75° C. for 1 h. A solution of methyllithium in THF (3M, 25.0 mL, 75 mmol) was added at −75° C. and the mixture was stirred for 1 h. Aqueous ammonia chloride solution was added dropwise to quench the reaction. The resulting reaction mixture was continued to stir at room temperature for 2 h. The reaction mixture was extracted with ethyl acetate (150 mL×3). The combined organic layers were washed with brine, dried over anhydrous sodium sulfate and concentrated under vacuum to afford the crude product (4.0 g, crude), which was used directly in the next step without purification. MS (ESI) m/z 230.1 [M+H]+.

F. 3-Amino-1-methylcyclohexanol

To a solution of crude tert-butyl (3-hydroxycyclohexyl)carbamate (4.0 g, crude) in DCM (40 mL) was added TFA (20 mL) under cooling in an ice bath. The resulting reaction mixture was stirred at room temperature for 2 h. The mixture was concentrated to give a crude product (3.0 g, crude), which was used in the next step without further purification. MS (ESI) m/z 130.1 [M+H]+.

G. 4-(((1S,3R)-3-Hydroxy-3-methylcyclohexyl) amino)-2-(methylthio)pyrimidine-5-carbonitrile and 4-(((1R,3S)-3-hydroxy-3-methylcyclohexyl)amino)- 2-(methylthio)pyrimidine-5-carbonitrile A mixture of 4-chloro-2-(methylthio)pyrimidine-5-carbonitrile (3.71 g, 20 mmol)), 3-amino-1-methylcyclohexanol (3.0 g, crude), DIEA (3.23 g, 25 mmol) in isopropanol (30 mL) was heated at 100° C. for 3 h. The organic solvents were removed under reduced pressure. The residue was treated with water and extracted with ethyl acetate. The combined organic layers were washed with brine, dried over sodium sulfate and concentrated to give the crude product, which was purified by silica gel column chromatography (20% ethyl acetate in petroleum) to afford the cis-isomer (0.90 g, 3.24 mmol, 17% yield over 3 steps) and trans-isomer (1.80 g, 6.47 mmol, 34% yield over 3 steps). The cis-isomer (0.90 g, 3.24 mmol) was separated by chiral SFC (Column IF; method: 70-30-$CO_2$-MeOH; $CO_2$ Flow Rate: 2.1; Col. Temp.=40° C.) to give 4-(((1S,3R)-3-hydroxy-3-methylcyclohexyl)amino)-2-(methylthio)pyrimidine-5-carbonitrile (peak 1: 300 mg, 1.08 mmol, 33% yield, 100% e.e.) and 4-(((1R,3S)-3-hydroxy-3-methylcyclohexyl)amino)-2-(methylthio)pyrimidine-5-carbonitrile (peak 2: 310 mg, 1.12 mmol, 34% yield, 100% e.e.), MS (ESI) m/z 279.1 [M+H]+.

H. 4-(((1S,3R)-3-Hydroxy-3-methylcyclohexyl) amino)-2-(methylsulfonyl)pyrimidine-5-carbonitrile To a solution of 4-(((1S,3R)-3-hydroxy-3-methylcyclohexyl)amino)-2-(methylthio)pyrimidine-5-carbonitrile (peak 1: 250 mg, 0.90 mmol) in dry DCM (5 mL) was added m-chloroperoxybenzoic acid (85%, 366 mg, 1.80 mmol) under cooling in an ice-water bath. The resulting mixture was stirred at room temperature for 1 h. The reaction was quenched with aqueous sodium thiosulfate and extracted with DCM. The combined organic layers were washed with aqueous potassium carbonate and brine, dried over sodium sulfate and concentrated to give the title compound (230 mg, crude) as a pale yellow solid. MS (ESI) m/z 311.2 [M+H]+.

I. 2-(((4-(2,2-Difluoropropoxy)pyrimidin-5-yl) methyl)amino)-4-(((1S,3R)-3-hydroxy-3-methylcyclohexyl)amino)pyrimidine-5-carbonitrile A mixture of 4-(((1S,3R)-3-hydroxy-3-methylcyclohexyl)amino)-2-(methylsulfonyl)pyrimidine-5-carbonitrile (80 mg, crude), (4-(2,2-difluoropropoxy)pyrimidin-5-yl) methanamine (50 mg 0.246 mmol), and DIEA (85 mg, 0.66 mmol) in THF (2 mL) was stirred at 100° C. in a microwave reactor for 1 h. The reaction was cooled to room temperature and the mixture was concentrated. The residue was purified by standard methods to give the desired product (26.1 mg, 0.060 mmol, 24% yield). 1H NMR (400 MHz, CD3OD) δ (ppm) 8.69 (s, 1H), 8.41 (s, 1H), 8.11 (s, 1H), 4.73-4.50 (m, 4H), 4.34-4.23 (m, 1H), 1.92-1.08 (m, 14H). MS (ESI) m/z 434.2 [M+H]+.

Example 28

(1s,3s)-3-((2-((2-(1H-Indol-3-yl)ethyl)amino)-5-cyanopyrimidin-4-yl)amino)cyclobutanecarboxamide

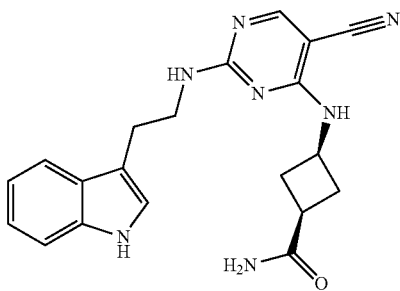 [SMILES: N#Cc1cnc(NCCc2c[nH]c3ccccc23)nc1N[C@H]1C[C@@H](C(N)=O)C1]

A. (1s,3s)-Methyl 3-((tert-butoxycarbonyl)amino) cyclobutane-carboxylate

To a mixture of (1s,3s)-3-((tert-butoxycarbonyl)amino) cyclobutane-carboxylic acid (600 mg, 2.79 mmol) and potassium carbonate (577 mg, 4.18 mmol) in DMF (4 mL) was added iodomethane (593 mg, 4.18 mmol) at 0° C., and the resulting mixture was stirred at room temperature for 3 h. The reaction mixture was treated with water and ethyl acetate. The separated organic layer was washed with brine, dried over sodium sulfate and concentrated to afford the title compound (590 mg, 2.58 mmol, 92% yield) as a yellow solid. 1H NMR (400 MHz, CDCl3) δ (ppm) 4.85-4.68 (brs, 1H), 4.16-4.08 (m, 1H), 3.68 (s, 3H), 2.82-2.71 (m, 1H), 2.67-2.54 (m, 2H), 2.14-2.04 (m, 2H).

B. (1s,3s)-Methyl 3-aminocyclobutanecarboxylate

To a solution of (1s,3s)-methyl 3-((tert-butoxycarbonyl) amino)cyclobutanecarboxylate (590 mg, 2.58 mmol) in DCM (5 mL) was added TFA (2.5 mL) at ~0° C. to 5° C. The resulting reaction mixture was stirred at room temperature for 1.5 h. The reaction mixture was concentrated to afford the product, which was used in the next step without further purification (300 mg, crude). MS (ESI) m/z 130.1 [M+H]+

C. 4-Chloro-2-[2-(1H-indol-3-yl)-ethylamino]-pyrimidine-5-carbonitrile

A mixture of 2,4-dichloro-pyrimidine-5-carbonitrile (2.0 g, 11.5 mmol), 2-(1H-indol-3-yl)-ethylamine (1.83 g, 11.4 mmol), and DIEA (1.94 g, 15.0 mmol) in THF (50 mL) was stirred at 50° C. for 3 h. After cooling to room temperature, the reaction mixture was concentrated and the residue was diluted with ethyl acetate (150 mL). The organic layer was washed with saturated aqueous ammonium chloride, brine, dried over anhydrous sodium sulfate and filtered. The filtrate was evaporated in vacuum to give the crude product, which was purified by silica gel column chromatography (20% ethyl acetate in petroleum ether) to afford the title compound as a brown solid (1.3 g, 4.38 mmol, 38% yield). MS (ESI) m/z 298.1 [M+H]+.

D. (1s,3s)-Methyl 3-((2-((2-(1H-indol-3-yl)ethyl) amino)-5-cyanopyrimidin-4-yl)amino)cyclobutanecarboxylate A mixture of 2-((2-(1H-indol-3-yl)ethyl)amino)-4-chloropyrimidine-5-carbonitrile (713 mg, 2.40 mmol), (1s,3s)- methyl 3-aminocyclobutanecarboxylate (300 mg, crude), and DIEA (619 mg, 4.80 mmol) in DMA (5 mL) was stirred at 125° C. in a microwave reactor for 4 h. After cooling to room temperature, the reaction mixture was concentrated and the residue was diluted with ethyl acetate (100 mL). The organic layer was washed with saturated aqueous ammonium chloride, brine, dried over anhydrous sodium sulfate and filtered. The filtrate was evaporated in vacuum to give the crude product, which was purified by silica gel column chromatography (0.6% MeOH in DCM) to afford the title compound as a brown solid (720 mg, 1.85 mmol, 75% yield). MS (ESI) m/z 391.1 [M+H]$^+$.

E. (1s,3s)-3-((2-((2-(1H-Indol-3-yl)ethyl)amino)-5-cyanopyrimidin-4-yl)amino)cyclobutanecarboxamide A solution of (1s,3s)-methyl 3-((2-((2-(1H-indol-3-yl)ethyl)amino)-5-cyanopyrimidin-4-yl)amino)cyclobutanecarboxylate (130 mg, 0.33 mmol) in a solution of ammonia in MeOH (5 mL, 5 mol/L) was stirred at 65° C. in a sealed tube for 72 h. After cooling to room temperature, the reaction mixture was concentrated and the residue was purified by standard methods to give the desired product (27.5 mg, 0.073 mmol, 22% yield). $^1$H NMR (400 MHz, CD$_3$OD) δ (ppm) 8.02 (s, 1H), 7.59 (d, J=8.0 Hz, 1H), 7.33 (J=7.2 Hz, 1H), 7.11-6.98 (m, 3H), 4.55-4.40 (m, 1H), 3.68 (t, J=7.2 Hz, 2H), 3.03 (t, J=7.2 Hz, 2H), 2.78-2.69 (m, 4H), 2.55-2.49 (m, 2H), 2.26-2.18 (m, 2H). MS (ESI) m/z 376.2 [M+H]$^+$.

Example 29

4-(((1R,4S)-4-Hydroxy-3,3-dimethylcyclohexyl)amino)-2-((2-(3-methyl-2-oxo-2,3-dihydro-1H-benzo[d]imidazol-1-yl)ethyl)amino)pyrimidine-5-carbonitrile

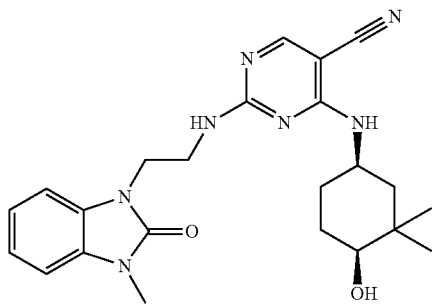 [SMILES: Cn1c(=O)n(CCNc2ncc(C#N)c(N[C@@H]3CC[C@H](O)C(C)(C)C3)n2)c2ccccc21]

A. tert-butyl (2-(2-Oxo-2,3-dihydro-1H-benzo[d]imidazol-1-yl)ethyl)carbamate

To a solution of 1-(2-aminoethyl)-1H-benzo[d]imidazol-2(3H)-one hydrochloride (180 mg, 0.84 mmol) and TEA (255 mg, 2.52 mmol) in THF (15 mL) was added di-tert-butyl pyrocarbonate (218 mg, 1.01 mmol) at 0° C. The resulting reaction mixture was stirred at 50° C. for 3 h. After cooling to room temperature, the mixture was concentrated to remove the solvent, the residue was diluted with ethyl acetate, which was filtered and concentrated to give the crude product, which was purified by silica gel column chromatography (20% ethyl acetate in petroleum ether) to afford the title compound (198 mg, 0.72 mmol, 85% yield). MS (ESI) m/z 278.1 [M+H]$^+$.

B. tert-butyl (2-(3-Methyl-2-oxo-2,3-dihydro-1H-benzo[d]imidazol-1-yl)ethyl)carbamate To a solution of tert-butyl (2-(2-oxo-2,3-dihydro-1H-benzo[d]imidazol-1-yl)ethyl)carbamate (190 mg, 0.69 mmol) in THF (10 mL) was added sodium hydride (34.5 mg, 0.86 mmol, 60% in mineral oil) at 0° C. under nitrogen in a sealed tube. After the resulting reaction mixture was stirred at room temperature for 20 min, iodomethane (112 mg, 0.79 mmol) in THF (2 mL) was added at 0° C. under nitrogen. The reaction was stirred at room temperature for 4 h. The reaction was quenched with saturated aqueous ammonium chloride solution and the aqueous layer was extracted with ethyl acetate. The combined organic layers were washed with brine, dried over anhydrous sodium sulfate and filtered. Concentration under vacuum gave the crude product, which was purified by silica gel column chromatography (20% ethyl acetate in petroleum ether) to afford the title compound (100 mg, 0.345 mmol, 50% yield). MS (ESI) m/z 292.1 [M+H]$^+$.

C. 1-(2-Amino-ethyl)-3-methyl-1,3-dihydro-benzo-imidazol-2-one

To a solution of tert-butyl (2-(3-methyl-2-oxo-2,3-dihydro-1H-benzo[d]imidazol-1-yl)ethyl)carbamate (100 mg, 0.345 mmol) in DCM (3 mL) was added TFA (1.5 mL) at 0° C. to 5° C. The resulting reaction mixture was stirred at room temperature for 2 h. The reaction mixture was concentrated to give the crude product, which was used in the next step without further purification (140 mg crude). MS (ESI) m/z 192.1 [M+H]$^+$.

D. 4-(((1R,4S)-4-Hydroxy-3,3-dimethylcyclohexyl)amino)-2-(methylthio)pyrimidine-5-carbonitrile A mixture of 4-chloro-2-(methylthio)pyrimidine-5-carbonitrile (2.15 g, 11.6 mmol)), (1S,4R)-4-amino-2,2-dimethylcyclohexanol (1.51 g, 10.5 mmol) and DIEA (2.72 mg, 21.1 mmol) in isopropanol (30 mL) was heated at 100° C. for 3 h. After removal of the organic solvent under reduced pressure, the residue was treated with water and extracted with ethyl acetate. The combined organic layers were washed with brine, dried over sodium sulfate and concentrated to give a crude product, which was purified by silica gel column chromatography (15% ethyl acetate in petroleum) to afford the desired compound as a pale yellow solid (2.2 g, 7.53 mmol, 72% yield). MS (ESI) m/z 293.2 [M+H]$^+$.

E. 4-(((1R,4S)-4-Hydroxy-3,3-dimethylcyclohexyl)amino)-2-(methylsulfonyl)pyrimidine-5-carbonitrile To a solution of 4-(((1R,4S)-4-hydroxy-3,3-dimethylcyclohexyl)amino)-2-(methylthio)pyrimidine-5-carbonitrile (1.02 g, 3.48 mmol) in dry DCM (20 mL) was added m-chloroperoxybenzoic acid (85%, 1.78 g, 8.79 mmol) under cooling in an ice-water bath. The resulting mixture was stirred at room temperature for 3 h. The reaction was quenched with aqueous sodium thiosulfate and extracted with DCM. The combined organic layers were washed with aqueous potassium carbonate and brine, dried over sodium sulfate and concentrate to give the desired (0.9 g, crude) as a pale yellow solid. MS (ESI) m/z 309.2, 325.2 [M+H]+.

F. 4-(((1R,4S)-4-Hydroxy-3,3-dimethylcyclohexyl)amino)-2-((2-(2-oxo-2,3-dihydro-1H-benzo[d]imidazol-1-yl)ethyl)amino)pyrimidine-5-carbonitrile A mixture of 4-(((1R,4S)-4-hydroxy-3,3-dimethylcyclohexyl)amino)-2-(methylsulfonyl)pyrimidine-5-carbonitrile (100 mg, 0.308 mmol), 1-(2-amino-ethyl)-3-methyl-1,3-dihydro-benzoimidazol-2-one (140 mg, crude), and DIEA (85 mg, 0.66 mmol) in THF (3 mL) was stirred at 100° C. in a microwave reactor for 1.5 h. After cooling to room temperature, the reaction mixture was concentrated and the residue was purified by preparative standard methods to afford the title compound (36.7 mg, 0.084 mmol, 24% yield over 2 steps). $^1$H NMR (400 MHz, CD$_3$OD) δ (ppm) 8.08-7.94 (m, 1H), 7.11-7.08 (m, 4H), 4.26-4.10 (m, 3H), 3.89-3.66 (m, 2H), 3.40-3.35 (m, 4H), 1.96-1.51 (m, 6H), 1.05-0.99 (m, 6H). MS (ESI) m/z 436.2 [M+H]+.

Example 30

4-(((1R,4S)-4-Hydroxy-3,3-dimethylcyclohexyl)amino)-2-((2-(1-methyl-1H-indol-3-yl)ethyl)amino)pyrimidine-5-carbonitrile

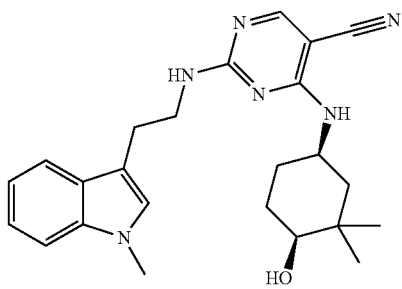 [SMILES: Cn1cc(CCNc2ncc(C#N)c(N[C@@H]3CC[C@H](O)C(C)(C)C3)n2)c2ccccc21]

A. tert-butyl (2-(1H-Indol-3-yl)ethyl)carbamate

To a solution of 2-(1H-indol-3-yl)ethanamine (1.00 g, 6.25 mmol) in THF (10 mL) was added di-tert-butyl dicarbonate (1.42 g, 6.56 mmol). The resulting reaction mixture was stirred at room temperature for 16 h. The mixture was concentrated to give the crude product, which was purified by silica gel column chromatography (20% ethyl acetate in petroleum ether) to afford the title compound (1.50 g, 5.77 mmol, 92% yield) as a yellow solid. MS (ESI) m/z 261.1 [M+H]+.

B. tert-butyl (2-(1-Methyl-1H-indol-3-yl)ethyl)carbamate

To a solution of tert-butyl (2-(1H-Indol-3-yl)ethyl)carbamate (1.50 g, 5.77 mmol) in anhydrous THF (15 mL) was added sodium hydride (300 mg, 7.50 mmol, 60% in mineral oil) at 0° C. under nitrogen. After the resulting reaction mixture was stirred at room temperature for 15 min, iodomethane (982 mg, 6.92 mmol) in THF (5 mL) was added slowly at 0° C. The resulting mixture was stirred at room temperature for 3 h and quenched with saturated aqueous ammonium chloride solution. The aqueous layer was extracted with ethyl acetate. The combined organic layers were washed with brine, dried over anhydrous sodium sulfate and filtered. The organic solvents were removed under reduced pressure and the residue was purified by silica gel column chromatography (0.6% MeOH in DCM) to afford the title compound (1.29 g, 4.71 mmol, 81% yield) as a brown solid. MS (ESI) m/z 275.1 [M+H]+.

C. 2-(1-Methyl-1H-indol-3-yl)ethanamine

To a solution of tert-butyl (2-(1-methyl-1H-indol-3-yl)ethyl)carbamate (1.29 g, 4.71 mmol) in DCM (15 mL) was added TFA (7 mL) at ~0° C. to 5° C. The resulting reaction mixture was stirred at room temperature for 1 h. The reaction mixture was concentrated to give the crude product which was diluted with DCM and washed with sodium bicarbonate aqueous solution. The organic layer was washed with brine, dried and concentrated to give the desired product (700 mg, 4.02 mmol, 85% yield) as yellow oil. MS (ESI) m/z 175.1 [M+H]+.

D. 4-(((1R,4S)-4-Hydroxy-3,3-dimethylcyclohexyl)amino)-2-(methylthio)pyrimidine-5-carbonitrile A mixture of 4-chloro-2-(methylthio)pyrimidine-5-carbonitrile (2.15 g, 11.6 mmol)), (1S,4R)-4-amino-2,2-dimethylcyclohexanol (1.51 g, 10.5 mmol) and DIEA (2.72 g, 21.1 mmol) in isopropanol (30 mL) was heated at 100° C. for 3 h. After removal of the organic solvent under reduced pressure, the residue was treated with water and extracted with ethyl acetate. The combined organic layers were washed with brine, dried over sodium sulfate and concentrated to give a crude product, which was purified by silica gel column chromatography (15% ethyl acetate in petroleum) to afford the title compound as a pale yellow solid (2.2 g, 7.53 mmol, 72% yield). MS (ESI) m/z 293.2 [M+H]+.

E. 4-(((1R,4S)-4-Hydroxy-3,3-dimethylcyclohexyl)amino)-2-(methylsulfonyl)pyrimidine-5-carbonitrile To a solution of 4-(((1R,4S)-4-hydroxy-3,3-dimethylcyclohexyl)amino)-2-(methylthio)pyrimidine-5-carbonitrile (1.02 g, 3.48 mmol) in dry DCM (20 mL) was added m-chloroperoxybenzoic acid (85%, 1.78 g, 8.79 mmol) under cooling in an ice-water bath. The resulting mixture was stirred at room temperature for 3 h. The reaction was quenched with aqueous sodium thiosulfate and extracted with DCM. The combined organic layers were washed with aqueous potassium carbonate and brine, dried over sodium sulfate and concentrate to give the desired (0.9 g, crude) as a pale yellow solid. MS (ESI) m/z 309.2, 325.2 [M+H]+.

F. 4-(((1R,4S)-4-Hydroxy-3,3-dimethylcyclohexyl)amino)-2-((2-(1-methyl-1H-indol-3-yl)ethyl)amino)pyrimidine-5-carbonitrile A mixture of 4-(((1R,4S)-4-hydroxy-3,3-dimethylcyclohexyl)amino)-2-(methylsulfonyl)pyrimidine-5-carbonitrile (90 mg, crude), 2-(1-methyl-1H-indol-3-yl)ethanamine (60 mg, 0.34 mmol), and DIEA (72 mg, 0.56 mmol) in THF (3 mL) was stirred at 100° C. in a microwave reactor for 1 h. After cooling to room temperature, the reaction mixture was concentrated and the residue was purified by standard methods to afford the title compound (21.5 mg, 0.051 mmol, 15% yield). $^1$H NMR (400 MHz, CD$_3$OD) δ (ppm) 8.00 (s, 1H), 7.52 (d, J=8.0 Hz, 1H), 7.30 (d, J=8.0 Hz, 1H), 7.14 (t, J=7.6 Hz, 1H), 7.00 (t, J=8.0 Hz, 1H), 6.94 (s, 1H), 4.28-4.23 (m, 1H), 3.75 (s, 3H), 3.75-3.62 (m, 2H), 3.02 (t, J=7.6 Hz, 1H), 1.82-1.26 (m, 6H), 1.02-0.87 (m, 6H). MS (ESI) m/z 419.2 [M+H]$^+$.

Example 31 cis-2-(((4-(2,2-Difluoropropoxy)pyrimidin-5-yl)methyl)amino)-4-((6-hydroxy-6-methylspiro[3.3]heptan-2-yl)amino)pyrimidine-5-carbonitrile

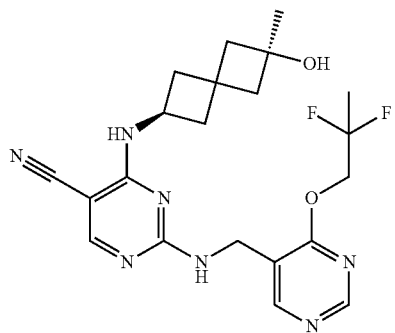 [SMILES: CC(F)(F)COc1ncncc1CNc1ncc(C#N)c(N[C@H]2CC3(C2)C[C@@](C)(O)C3)n1]

trans-2-(((4-(2,2-Difluoropropoxy)pyrimidin-5-yl)methyl)amino)-4-((6-hydroxy-6-methylspiro[3.3]heptan-2-yl)amino)pyrimidine-5-carbonitrile

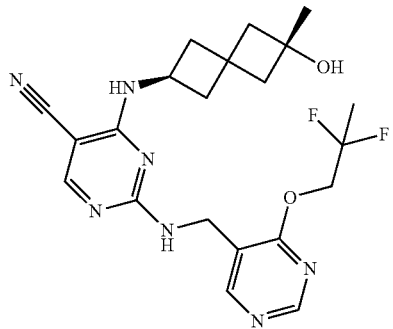 [SMILES: CC(F)(F)COc1ncncc1CNc1ncc(C#N)c(N[C@H]2CC3(C2)C[C@](C)(O)C3)n1]

A. tert-butyl (6-Oxospiro[3.3]heptan-2-yl)carbamate

To a solution of tert-butyl (6-hydroxyspiro[3.3]heptan-2-yl)carbamate (1.00 g, 4.40 mmol) in DCM (10 mL) was added Dess-Martin periodinane (2.80 g, 6.60 mmol) at ~0° C. to 10° C. The resulting reaction mixture was stirred at room temperature for 1.5 h. The reaction mixture was treated with aqueous sodium bicarbonate and extracted with DCM. The combined organic layers were washed with brine, dried over anhydrous sodium sulfate and filtered. Concentration under vacuum gave the crude product, which was purified by silica gel column chromatography (22% ethyl acetate in petroleum ether) to afford the title compound (800 mg, 3.55 mmol, 80% yield) as a pale yellow solid. MS (ESI) m/z 226.1 [M+H]$^+$.

B. tert-butyl (6-Hydroxy-6-methylspiro[3.3]heptan-2-yl)carbamate

To a solution of tert-butyl (6-oxospiro[3.3]heptan-2-yl)carbamate (800 mg, 3.55 mmol) in anhydrous THF (15 mL) was added a solution of methyl lithium in THF (2.36 mL, 3 mol/L, 7.50 mmol) at −78° C. under nitrogen. The resulting mixture was stirred at room temperature for 2 h. The reaction mixture was quenched with saturated aqueous ammonium chloride and the mixture was extracted with ethyl acetate. The combined organic layers were washed with brine, dried over anhydrous sodium sulfate, and concentrated under vacuum to afford the title compound (760 mg, crude) as a brown solid, which was which was used to next step without further purification. MS (ESI) m/z 242.2 [M+H]$^+$.

C. 6-Amino-2-methylspiro[3.3]heptan-2-ol

To a solution of tert-butyl (6-hydroxy-6-methylspiro[3.3]heptan-2-yl)carbamate (760 mg, crude) in DCM (7 mL) was added TFA (3.5 mL) at ~0° C. to 5° C. The resulting reaction mixture was stirred at room temperature for 1 h. The reaction mixture was concentrated to give the crude product (500 mg, crude) as a brown oil, which was used in the next step without further purification. MS (ESI) m/z 142.1 [M+H]$^+$.

D. cis-4-((6-Hydroxy-6-methylspiro[3.3]heptan-2-yl)amino)-2-(methylthio)pyrimidine-5-carbonitrile and trans-4-((6-Hydroxy-6-methylspiro[3.3]heptan-2-yl)amino)-2-(methylthio)pyrimidine-5-carbonitrile 6-Amino-2-methylspiro[3.3]heptan-2-ol (500 mg, crude), 4-chloro-2-(methylthio)pyrimidine-5-carbonitrile (656 mg, 3.54 mmol) and DIEA (913 mg, 7.08 mmol) in isopropanol (8 mL) was stirred at reflux for 2 h. After cooling to room temperature, the reaction mixture was concentrated and the residue was purified by silica gel column chromatography (22% ethyl acetate in petroleum ether) to give the racemic compound as a brown solid (700 mg, 2.41 mmol, 68% yield over three steps). MS (ESI) m/z 291.1 [M+H]$^+$. The racemic compound was separated by chiral preparative supercritical fluid chromatography (Column: Chiralpak IF 5 μm, Column size 4.6*250 mm; Mobile phase Hexane: Ethanol=70:30; Flow: 1.0 mL/min 230 nm, T=30° C.) to give cis-4-((6-hydroxy-6-methylspiro[3.3]heptan-2-yl)amino)-2-(methylthio)pyrimidine-5-carbonitrile (160 mg, 0.55 mmol, 100% e.e.) and trans-4-((6-hydroxy-6-methylspiro[3.3]heptan-2-yl)amino)-2-(methylthio)pyrimidine-5-carbonitrile (160 mg, 0.55 mmol, 99.4% e.e.).

E. 4-(2,2-Difluoropropoxy)pyrimidine-5-carbonitrile

To a suspension of sodium hydride (60% dispersed in mineral oil, 1.84 g, 46 mmol) in a THF (30.0 mL) was added 2,2-difluoropropan-1-ol (4.42 g, 46.0 mmol) at 0° C. The resulting mixture was stirred at room temperature for 1 hour, then 4-chloropyrimidine-5-carbonitrile (6 g, 43.2 mmol) was added in portions at 0° C. After addition, the reaction mixture was stirred at room temperature for 30 min. The reaction was quenched with saturated aqueous ammonium chloride solution and extracted with ethyl acetate. The combined organic layers were dried over sodium sulfate and concentrated to give the crude product, which was purified by silica gel column chromatography (10% ethyl acetate in petroleum ether) to afford the title compound (4.40 g, 22.1 mmol, 51% yield) as a yellow solid. MS (ESI) m/z 200.0 [M+H]$^+$.

F. (4-(2,2-Difluoropropoxy)pyrimidin-5-yl)methanamine

To a solution of 4-(2,2-difluoropropoxy)pyrimidine-5-carbonitrile (1.7 g, 8.54 mmol) in THF (30 mL) was added Raney nickel (500 mg, crude). The resulting mixture was stirred at room temperature overnight under hydrogen atmosphere. The reaction was filtered and the filtrate was concentrated in vacuo to give the crude product, which was purified by silica gel column chromatography (5% MeOH in DCM) to afford the title compound (650 mg, 3.20 mmol, 37% yield) as a yellow solid. MS (ESI) m/z 204.1 [M+H]$^+$.

G. cis-4-((6-Hydroxy-6-methylspiro[3.3]heptan-2-yl)amino)-2-(methylsulfonyl)pyrimidine-5-carbonitrile To a solution of cis-4-((6-hydroxy-6-methylspiro[3.3]heptan-2-yl)amino)-2-(methylthio)pyrimidine-5-carbonitrile (80 mg, 0.276 mmol) in DCM (3 mL) was added 3-chloroperbenzoic acid (85%, 113 mg, 0.552 mmol). The resulting reaction mixture was stirred at room temperature for 1 h. Aqueous sodium thiosulfate solution was added and the mixture was extracted with DCM (50 mL×2). The combined organic layers were washed with aqueous sodium carbonate solution and brine, dried over anhydrous sodium sulfate and concentrated to afford the title compound (80 mg, crude) as a grey solid. MS (ESI) m/z 323.1 [M+H]$^+$.

H. trans-4-((6-Hydroxy-6-methylspiro[3.3]heptan-2-yl)amino)-2-(methylsulfonyl)pyrimidine-5-carbonitrile To a solution of trans-4-((6-hydroxy-6-methylspiro[3.3]heptan-2-yl)amino)-2-(methylthio)pyrimidine-5-carbonitrile (80 mg, 0.276 mmol) in DCM (3 mL) was added 3-chloroperbenzoic acid (85%, 113 mg, 0.552 mmol). The resulting reaction mixture was stirred at room temperature for 1 h. Aqueous sodium thiosulfate solution was added and the mixture was extracted with DCM (50 mL×2). The combined organic layers were washed with aqueous sodium carbonate solution and brine, dried over anhydrous sodium sulfate and concentrated to afford the title compound (80 mg, crude) as a grey solid. MS (ESI) m/z 323.1 [M+H]$^+$.

I. cis-2-(((4-(2,2-Difluoropropoxy)pyrimidin-5-yl)methyl)amino)-4-((6-hydroxy-6-methylspiro[3.3]heptan-2-yl)amino)pyrimidine-5-carbonitrile To a solution of cis-4-((6-hydroxy-6-methylspiro[3.3]heptan-2-yl)amino)-2-(methylsulfonyl)pyrimidine-5-carbonitrile (80 mg, crude) in THF (2.0 mL) was added (4-(2,2-difluoropropoxy)pyrimidin-5-yl)methanamine (56 mg, 0.276 mmol), and DIEA (71 mg, 0.55 mmol). The resulting mixture was stirred at 100° C. in a microwave reactor for 1 h. The solvent was evaporated and the residue was purified by standard methods to afford the title compound (33.9 mg, 0.076 mmol, 28% yield over two steps). $^1$H NMR (400 MHz, CD$_3$OD) δ (ppm) 8.68 (s, 1H), 8.36 (s, 1H), 8.10 (s, 1H), 4.70 (t, J=12.0 Hz, 2H), 4.61 (s, 2H), 4.50-4.20 (m, 1H), 2.50-1.95 (m, 8H), 1.74 (t, J=18.8 Hz, 3H), 1.26 (s, 3H). MS (ESI) m/z 446.1 [M+H]$^+$.

J. trans-2-(((4-(2,2-Difluoropropoxy)pyrimidin-5-yl)methyl)amino)-4-((6-hydroxy-6-methylspiro[3.3]heptan-2-yl)amino)pyrimidine-5-carbonitrile To a solution of trans-4-((6-hydroxy-6-methylspiro[3.3]heptan-2-yl)amino)-2-(methylsulfonyl)pyrimidine-5-carbonitrile (80 mg, crude) in THF (2.0 mL) was added (4-(2,2-difluoropropoxy)pyrimidin-5-yl)methanamine (100 mg, crude), and DIEA (71 mg, 0.55 mmol). The resulting mixture was stirred at 100° C. in a microwave reactor for 1 h. The solvent was evaporated and the residue was purified by standard methods to afford the title compound (36.9 mg, 0.083 mmol, 30% yield over two steps). $^1$H NMR (400 MHz, CD$_3$OD) δ (ppm) 8.68 (s, 1H), 8.36 (s, 1H), 8.10 (s, 1H), 4.70 (t, J=12.0 Hz, 2H), 4.61 (s, 2H), 4.50-4.20 (m, 1H), 2.50-1.95 (m, 8H), 1.74 (t, J=18.8 Hz, 3H), 1.26 (s, 3H). MS (ESI) m/z 446.1 [M+H]$^+$.

Example 32

2-(((4-(2,2-Difluoropropoxy)pyrimidin-5-yl)methyl)amino)-4-(((1R,3S)-3-hydroxy-2,2-dimethylcyclohexyl)amino)pyrimidine-5-carbonitrile

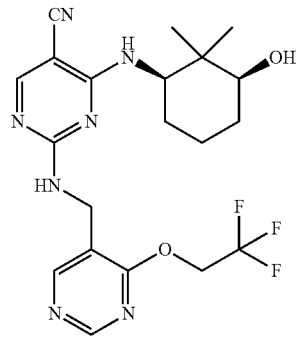 [SMILES: CC1(C)[C@@H](O)CCC[C@H]1Nc1nc(NCc2cncnc2OCC(F)(F)F)ncc1C#N]

A. 2,2-Dimethylcyclohexane-1,3-dione

A mixture of cyclohexane-1,3-dione (10.0 g, 89.3 mmol), potassium carbonate (24.6 g, 178.6 mmol), and iodomethane (28.5 g, 201 mmol) in acetone (50 mL) was refluxed overnight. The reaction mixture was concentrated and the residue was purified by silica gel column chromatography (5-10% ethyl acetate in petroleum ether) to afford the title compound (3.5 g, 25.0 mmol, 28% yield). $^1$H NMR (400 MHz, CDCl$_3$) δ (ppm) 2.69 (t, J=6.8 Hz, 4H), 1.52 (m, 2H) 1.31 (s, 6H).

B. 3-Hydroxy-2,2-dimethylcyclohexanone

To a solution of 2,2-dimethylcyclohexane-1,3-dione (2.00 g, 14.3 mmol) in MeOH (20 mL) was added sodium borohydride (135 mg, 3.58 mmol) portion-wise at 0° C. The resulting solution was stirred at room temperature for 1 h. The reaction was quenched with water and extracted with ethyl acetate. The combined organic layers were washed with brine, dried over anhydrous sodium sulfate and concentrated to afford the title compound (1.6 g, crude). MS (ESI) m/z 143.2 [M+H]$^+$.

C. 3-Hydroxy-2,2-dimethylcyclohexanone oxime

A mixture of 3-hydroxy-2,2-dimethylcyclohexanone (1.6 g, crude), hydroxylamine hydrochloride (2.98 g, 42.9 mmol) and sodium carbonate (4.54 g, 42.9 mmol) in EtOH (30 mL) and water (3 mL) was stirred at 25° C. for 6 h. The organic solvents were removed under reduced pressure and the residue was extracted with ethyl acetate (2×200 mL). The combined organic layers were washed with brine, dried over anhydrous sodium sulfate and concentrated to afford the title compound (1.8 g, crude). MS (ESI) m/z 158.2 [M+H]$^+$.

D. 3-Amino-2,2-dimethylcyclohexanol

A mixture of 3-hydroxy-2,2-dimethylcyclohexanone oxime (1.8 g, crude) and Raney nickel (1.5 g) in a MeOH (50 mL) and ammonia (5 mL) was stirred at 25° C. under hydrogen atmosphere overnight. The reaction mixture was filtered through celite and the filter cake was rinsed with MeOH (50 mL). The filtrate was concentrated to afford the title compound (1.30 g, crude). MS (ESI) m/z 144.2 [M+H]$^+$.

E. 4-((3-Hydroxy-2,2-dimethylcyclohexyl)amino)-2-(methylthio)pyrimidine-5-carbonitrile A mixture of 3-amino-2,2-dimethylcyclohexanol (1.30 g, crude) and 4-chloro-2-(methylthio)pyrimidine-5-carbonitrile (1.35 g, 7.27 mmol), and DIEA (1.93 g, 15.0 mmol) in isopropanol (14 mL) was stirred at 90° C. for 1 h. After removal of the solvent, the residue was purified by silica gel column chromatography (10%-30% ethyl acetate in petroleum ether) to afford the title compound (820 mg, 2.81 mmol, 38% yield), which was separated by chiral column (Superchiral S-AD, 0.46 cm I.D.×25 cm L, 5 μl, CO$_2$/MeOH/DEA=80/20/0.05 (v/v/v); Flow: 2.5 ml/min, 254 nm, T=35° C.), then by chiral column: Chiralpak IC, 0.46 cm I.D.×25 cm L, 5 μl, CO$_2$/MeOH/DEA=70/30/0.05 (v/v/v); Flow: 2.5 ml/min, 254 nm, T=35° C.) to give four isomers (peak 1: 90 mg, d.e.=100%, e.e.=100%, peak 2: 220 mg, d.e.=99.7%, e.e.=100%, peak 3: 210 mg, d.e.=100%, e.e.=97.3%, peak 4:125 mg, d.e.=99.6%, e.e.=100%. Peak 1 and peak 4 were determinated to be cis-isomers and peak 2 and peak 3 were determinated to be trans-isomers by 2D-NMR). MS (ESI) m/z 293.1 [M+H]$^+$ F. 4-(((1R,3S)-3-hydroxy-2,2-dimethylcyclohexyl)amino)-2-(methylsulfonyl)pyrimidine-5-carbonitrile To a solution of 4-(((1R,3S)-3-hydroxy-2,2-dimethylcyclohexyl)amino)-2-(methylthio)pyrimidine-5-carbonitrile (120 mg, 0.411 mmol) in DCM (2.00 mL) was added 3-chloroperbenzoic acid (85%, 168 mg, 0.822 mmol) under cooling in an ice-water bath. The mixture was stirred at room temperature for 2 h. The reaction was diluted with DCM and washed with aqueous sodium thiosulfate, then aqueous potassium carbonate. The separated organic was dried over anhydrous sodium sulfate and concentrated to afford the crude compound (130 mg crude), which was used directly in the next step without further purification. MS (ESI) m/z 325.1 [M+H]$^+$.

G. 2-(((4-(2,2-Difluoropropoxy)pyrimidin-5-yl)methyl)amino)-4-(((1R,3S)-3-hydroxy-2,2-dimethylcyclohexyl)amino)pyrimidine-5-carbonitrile To a solution of 4-(((1R,3S)-3-hydroxy-2,2-dimethylcyclohexyl)amino)-2-(methylthio)pyrimidine-5-carbonitrile (130 mg, crude) in THF (3.0 mL) was added (4-(2,2-difluoropropoxy)pyrimidin-5-yl)methanamine (84 mg, 0.411 mmol) and DIEA (158 mg, 1.23 mmol). The resulting mixture was stirred at 100° C. in a microwave reactor for 1 h. The solvent was evaporated and the residue was purified by standard methods to afford the title compound (33.6 mg, 0.075 mmol, 20% yield for two steps). $^1$H NMR (400 MHz, CD$_3$OD) δ (ppm) 8.69 (s, 1H), 8.40 (s, 1H), 8.13 (s, 1H), 4.72 (t, J=12.0 Hz, 2H), 4.57 (s, 2H), 4.05-3.91 (m, 1H), 3.45-3.42 (m, 1H), 1.82-1.72 (m, 5H), 1.70-1.50 (m, 2H), 1.50-1.30 (m, 2H), 1.03-0.91 (m, 6H). MS (ESI) m/z 448.2 [M+H]$^+$.

Example 33

4-(((1R,4S)-4-Hydroxy-3,3-dimethylcyclohexyl)amino)-2-((2-((S)-3-methyl-2-oxoindolin-3-yl)ethyl)amino)pyrimidine-5-carbonitrile

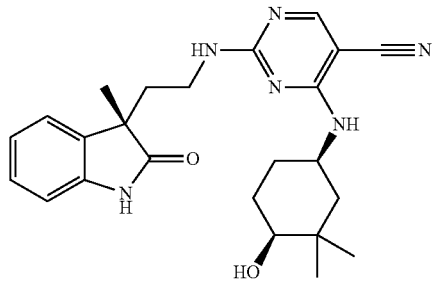 [SMILES: CC1(C)C[C@H](Nc2nc(NCC[C@]3(C)C(=O)Nc4ccccc43)ncc2C#N)CC[C@@H]1O]

4-(((1R,4S)-4-Hydroxy-3,3-dimethylcyclohexyl)amino)-2-((2-((R)-3-methyl-2-oxoindolin-3-yl)ethyl)amino)pyrimidine-5-carbonitrile

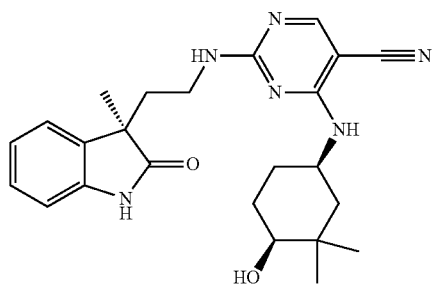 [SMILES: CC1(C)C[C@H](Nc2nc(NCC[C@@]3(C)C(=O)Nc4ccccc43)ncc2C#N)CC[C@@H]1O]

A. 2-(2-(2-Oxoindolin-3-yl)ethyl)isoindoline-1,3-dione

A mixture of 3-(2-aminoethyl)indolin-2-one hydrochloride (3.20 g, 15.06 mmol), phthalic anhydride (3.34 g, 22.59 mmol) and TEA (4.56 g, 45.18 mmol) in toluene/NMP (20 mL/10 mL). The mixture was heated under reflux for 3 h. The reaction mixture was concentrated and the resulting mixture was washed with saturated aqueous ammonium chloride and brine. The separated organic layer was dried over anhydrous sodium sulfate and filtered. Concentration under vacuum gave the crude product, which was purified by silica gel column chromatography (30% ethyl acetate in petroleum ether) to afford the title compound (2.60 g, 8.50 mmol, 56% yield) as a brown solid. MS (ESI) m/z 307.2 [M+H]$^+$.

B. tert-butyl 3-(2-(1,3-Dioxoisoindolin-2-yl)ethyl)-2-oxoindoline-1-carboxylate To a mixture of 2-(2-(2-oxoindolin-3-yl)ethyl)isoindoline-1,3-dione (2.60 g, 8.50 mmol) and sodium carbonate (1.35 g, 12.75 mmol) in anhydrous THF (30 mL) was added di-tert-butyl pyrocarbonate (2.02 g, 9.35 mmol). The resulting result mixture was stirred at room temperature for 20 h. The mixture was treated with water and extracted with ethyl acetate. The combined organic layers were dried over anhydrous sodium sulfate and concentrated under vacuum to give the crude product, which was purified by silica gel column chromatography (10-20% ethyl acetate in petroleum ether) to afford the title compound (2.00 g, 4.93 mmol, 58% yield) as a pale yellow solid. MS (ESI) m/z 407.1 [M+H]$^+$.

C. tert-butyl 3-(2-(1,3-Dioxoisoindolin-2-yl)ethyl)-3-methyl-2-oxoindoline-1-carboxylate To a mixture of tert-butyl 3-(2-(1,3-dioxoisoindolin-2-yl)ethyl)-2-oxoindoline-1-carboxylate (1.00 g, 2.46 mmol) and potassium carbonate (679 mg, 4.92 mmol) in DMF (5 mL) was added iodomethane (524 mg, 3.69 mmol) at ~0° C. to 5° C. The resulting reaction mixture was stirred at room temperature for 16 h. The resulting mixture was treated with water and extracted with ethyl acetate. The combined organic layers were washed with brine, dried over sodium sulfate and concentrated to give a crude product, which was purified by silica gel column chromatography (10-25% ethyl acetate in petroleum ether to afford the title compound (700 mg, 1.66 mmol, 67% yield) as a brown solid. MS (ESI) m/z 421.1 [M+H]$^+$.

D. 3-(2-Aminoethyl)-3-methylindolin-2-one hydrochloride

A mixture of tert-butyl 3-(2-(1,3-dioxoisoindolin-2-yl)ethyl)-3-methyl-2-oxoindoline-1-carboxylate (600 mg, 1.43 mmol) and hydrochloric acid (5 mL) in a sealed tube was stirred at 100° C. for 72 h. After cooling to room temperature, the reaction mixture was extracted with ethyl acetate. The aqueous layer was concentrated to dryness to give a crude product (350 mg, crude) as a yellow solid, which was used directly for next step without further purification. MS (ESI) m/z 191.1 [M+H]$^+$

E. 4-(((1R,4S)-4-Hydroxy-3,3-dimethylcyclohexyl)amino)-2-((2-((S)-3-methyl-2-oxoindolin-3-yl)ethyl)amino)pyrimidine-5-carbonitrile and 4-(((1R,4S)-4-hydroxy-3,3-dimethylcyclohexyl)amino)-2-((2-((R)-3-methyl-2-oxoindolin-3-yl)ethyl)amino)pyrimidine-5-carbonitrile A mixture of 4-(((1R,4S)-4-hydroxy-3,3-dimethylcyclohexyl)amino)-2-(methylsulfonyl)pyrimidine-5-carbonitrile (350 mg, 1.08 mmol), 3-(2-aminoethyl)-3-methylindolin-2-one (350 mg, crude) and DIEA (557 mg, 4.32 mmol) in DMA (4 mL) was stirred at 80° C. for 2 h. After cooling to room temperature, to the reaction mixture was added saturated aqueous ammonium chloride and the mixture was extracted with ethyl acetate. The combined organic layers were washed with brine, dried and concentrated to afford the crude product, which was purified by silica gel column chromatography (0.6% MeOH in DCM) to yield the racemic compound (340 mg, 0.78 mmol, 74% yield) as a brown solid. MS (ESI) m/z 435.2 [M+H]$^+$. The racemic compound (340 mg, 0.78 mmol) was separated by standard methods to afford 4-(((1R,4S)-4-hydroxy-3,3-dimethylcyclohexyl)amino)-2-((2-((S)-3-methyl-2-oxoindolin-3-yl)ethyl)amino)pyrimidine-5-carbonitrile (peak 1: 80.5 mg, 0.185 mmol, 24% yield, 100% e.e.). $^1$H NMR (400 MHz, CD$_3$OD) δ (ppm) 7.85 (s, 1H), 7.13 (d, J=7.6 Hz, 1H), 7.10 (t, J=7.2 Hz, 1H), 6.94 (t, J=7.6 Hz, 1H), 6.76 (d, J=8.0 Hz, 1H), 4.08-3.98 (m, 1H), 3.27-3.20 (m, 2H), 2.91-2.86 (m, 1H), 2.20-1.26 (m, 8H), 1.25 (s, 3H), 0.84-0.82 (m, 6H). MS (ESI) m/z 435.2 [M+H]$^+$ and 4-(((1R,4S)-4-hydroxy-3,3-dimethylcyclohexyl)amino)-2-((2-((R)-3-methyl-2-oxoindolin-3-yl)ethyl)amino)pyrimidine-5-carbonitrile (peak 2: 22.4 mg, 0.052 mmol, 6.6% yield, 99.1% e.e.). $^1$H NMR (400 MHz, CD$_3$OD) δ (ppm) 7.85 (s, 1H), 7.13 (d, J=7.6 Hz, 1H), 7.10 (t, J=7.2 Hz, 1H), 6.94 (t, J=7.6 Hz, 1H), 6.76 (d, J=8.0 Hz, 1H), 4.08-3.98 (m, 1H), 3.27-3.20 (m, 2H), 2.91-2.86 (m, 1H), 2.20-1.26 (m, 8H), 1.25 (s, 3H), 0.84-0.82 (m, 6H). MS (ESI) m/z 435.2 [M+H]$^+$.

Example 34

2-((2-(6-Fluoro-2-oxoindolin-3-yl)ethyl)amino)-4-(((1S,3S)-3-hydroxy-2,2-dimethylcyclohexyl)amino)pyrimidine-5-carbonitrile

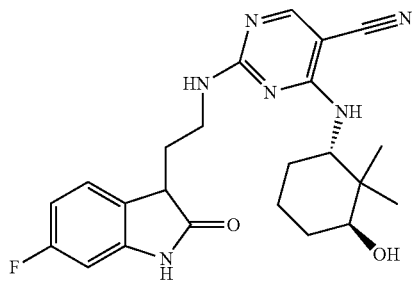 [SMILES: CC1(C)[C@@H](Nc2nc(NCCC3C(=O)Nc4cc(F)ccc43)ncc2C#N)CCC[C@@H]1O]

2-((2-(6-Fluoro-2-oxoindolin-3-yl)ethyl)amino)-4-(((1R,3R)-3-hydroxy-2,2-dimethylcyclohexyl)amino)pyrimidine-5-carbonitrile

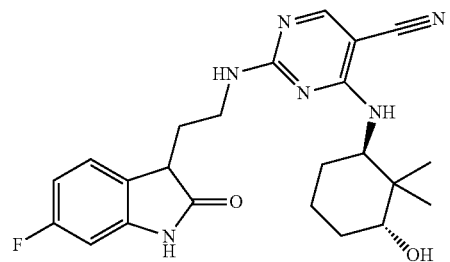 [SMILES: CC1(C)[C@H](O)CCC[C@H]1Nc1nc(NCCC2C(=O)Nc3cc(F)ccc32)ncc1C#N]

2-((2-(6-Fluoro-2-oxoindolin-3-yl)ethyl)amino)-4-(((1S,3R)-3-hydroxy-2,2-dimethylcyclohexyl)amino)pyrimidine-5-carbonitrile

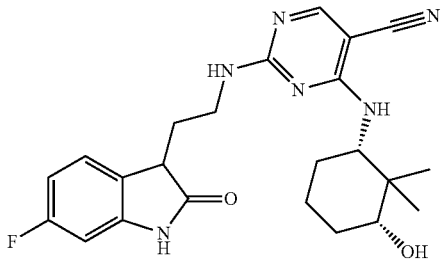 [SMILES: CC1(C)[C@H](O)CCC[C@@H]1Nc1nc(NCCC2C(=O)Nc3cc(F)ccc32)ncc1C#N]

2-((2-(6-Fluoro-2-oxoindolin-3-yl)ethyl)amino)-4-(((1R,3S)-3-hydroxy-2,2-dimethylcyclohexyl)amino)pyrimidine-5-carbonitrile

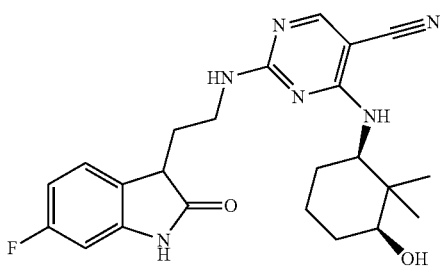 [SMILES: CC1(C)[C@@H](O)CCC[C@H]1Nc1nc(NCCC2C(=O)Nc3cc(F)ccc32)ncc1C#N]

A. 2,2-Dimethylcyclohexane-1,3-dione

A mixture of cyclohexane-1,3-dione (10.0 g, 89.3 mmol), potassium carbonate (24.6 g, 178.6 mmol) and iodomethane (28.5 g, 201 mmol) in acetone (50 mL) was refluxed overnight. After completion, the solvent was removed under reduced pressure and the residue was purified by silica gel column chromatography (5-10% ethyl acetate in petroleum ether) to afford the title compound (3.5 g, 25.0 mmol, 28% yield). $^1$H NMR (400 MHz, CDCl$_3$) δ (ppm) 2.69 (t, J=6.8 Hz, 4H), 1.52 (m, 2H) 1.31 (s, 6H).

B. 3-Hydroxy-2,2-dimethylcyclohexanone

To a solution of 2,2-dimethylcyclohexane-1,3-dione (2.00 g, 14.3 mmol) in MeOH (20 mL) was added sodium borohydride (135 mg, 3.58 mmol) portion-wise at 0° C. The resulting solution was stirred at room temperature for 1 hour. The reaction was quenched with water and the mixture was extracted with ethyl acetate. The combined organic layers were washed with brine, dried over anhydrous sodium sulfate and concentrated to afford the title compound (1.6 g, crude). MS (ESI) m/z 143.2 [M+H]$^+$.

C. 3-Hydroxy-2,2-dimethylcyclohexanone oxime

A mixture of 3-hydroxy-2,2-dimethylcyclohexanone (1.6 g, crude), hydroxylamine hydrochloride (2.98 g, 42.9 mmol) and sodium carbonate (4.54 g, 42.9 mmol) in EtOH (30 mL) and water (3 mL) was stirred at 25° C. for 6 h. After removal of EtOH, the residue was extracted with ethyl acetate (2×200 mL). The combined organic layers were washed with brine, dried over anhydrous sodium sulfate and concentrated to afford the title compound (1.8 g, crude). MS (ESI) m/z 158.2 [M+H]$^+$.

D. 3-Amino-2,2-dimethylcyclohexanol

A mixture of 3-hydroxy-2,2-dimethylcyclohexanone oxime (1.8 g, crude) and Raney nickel (1.5 g) in a MeOH (50 mL) and ammonia (5 mL) was stirred at 25° C. under hydrogen atmosphere overnight. The reaction mixture was filtered through celite and the filter cake was rinsed with MeOH (50 mL). The filtrate was concentrated to afford the title compound (1.30 g, crude). MS (ESI) m/z 144.2 [M+H]$^+$.

E. 4-(((1S,3S)-3-Hydroxy-2,2-dimethylcyclohexyl)amino)-2-(methylthio)pyrimidine-5-carbonitrile, 4-(((1R,3R)-3-hydroxy-2,2-dimethylcyclohexyl)amino)-2-(methylthio)pyrimidine-5-carbonitrile, 4-(((1S,3R)-3-hydroxy-2,2-dimethylcyclohexyl)amino)-2-(methylthio)pyrimidine-5-carbonitrile and 4-(((1R,3S)-3-hydroxy-2,2-dimethylcyclohexyl)amino)-2-(methylthio)pyrimidine-5-carbonitrile A mixture of 3-amino-2,2-dimethylcyclohexanol (1.30 g, crude) and 4-chloro-2-(methylthio)pyrimidine-5-carbonitrile (1.35 g, 7.27 mmol) and DIEA (1.93 g, 15.0 mmol) in isopropanol (14 mL) was stirred at 90° C. for 1 h. After removal of the solvent, the residue was purified by silica gel column chromatography (10%-30% ethyl acetate in petroleum ether) to afford the title compound (820 mg, 2.81 mmol, 38% yield), which was separated by chiral column (Superchiral S-AD, 0.46 cm I.D.×25 cm L, 5 μl, CO$_2$/MeOH/DEA=80/20/0.05 (v/v/v); Flow: 2.5 ml/min, 254 nm, T=35° C.), then by chiral column: (Chiralpak IC, 0.46 cm I.D.×25 cm L, 5 μl, CO$_2$/MeOH/DEA=70/30/0.05 (v/v/v); Flow: 2.5 ml/min, 254 nm, T=35° C.) to give four isomers (peak 1: 90 mg, d.e.=100%, e.e.=100%, peak 2: 220 mg, d.e.=99.7%, e.e.=100%, peak 3: 210 mg, d.e.=100%, e.e.=97.3%, peak 4:125 mg, d.e.=99.6%, e.e.=100%. Peak 1 and peak 4 were determinated to be cis-isomers and peak 2 and peak 3 were determinated to be trans-isomers by 2D-NMR). MS (ESI) m/z 293.1 [M+H]$^+$.

F. 4-(((1S,3S)-3-Hydroxy-2,2-dimethylcyclohexyl)amino)-2-(methylsulfonyl)pyrimidine-5-carbonitrile To a solution of 4-(((1S,3S)-3-hydroxy-2,2-dimethylcyclohexyl)amino)-2-(methylthio)pyrimidine-5-carbonitrile (peak 1: 85 mg, 0.291 mmol) in DCM (2.00 mL) was added 3-chloroperbenzoic acid (85%, 119 mg, 0.582 mmol) under cooling in an ice-water bath. The mixture was stirred at room temperature for 2 h. The reaction was diluted with DCM and washed with aqueous sodium thiosulfate, then aqueous potassium carbonate. The separated organic was dried over anhydrous sodium sulfate and concentrated to afford a crude compound (90 mg, crude). MS (ESI) m/z 325.1 [M+H]$^+$.

4-(((1R,3R)-3-Hydroxy-2,2-dimethylcyclohexyl)amino)-2-(methylsulfonyl)pyrimidine-5-carbonitrile To a solution of 4-(((1R,3R)-3-hydroxy-2,2-dimethylcyclohexyl)amino)-2-(methylthio)pyrimidine-5-carbonitrile (peak 4: 85 mg, 0.291 mmol) in DCM (2.00 mL) was added 3-chloroperbenzoic acid (85%, 119 mg, 0.582 mmol) under cooling in an ice-water bath. The mixture was stirred at room temperature for 2 h. The reaction was diluted with DCM and washed with aqueous sodium thiosulfate, then aqueous potassium carbonate. The separated organic was dried over anhydrous sodium sulfate and concentrated to afford a crude title compound (92 mg, crude). MS (ESI) m/z 325.1 [M+H]+.

4-(((1S,3R)-3-Hydroxy-2,2-dimethylcyclohexyl)amino)-2-(methylsulfonyl)pyrimidine-5-carbonitrile To a solution of 4-(((1S,3R)-3-hydroxy-2,2-dimethylcyclohexyl)amino)-2-(methylthio)pyrimidine-5-carbonitrile (peak 2: 100 mg, 0.342 mmol) in DCM (2.00 mL) was added 3-chloroperbenzoic acid (85%, 139 mg, 0.684 mmol) under cooling in an ice-water bath. The mixture was stirred at room temperature for 2 h. The reaction was diluted with DCM and washed with aqueous sodium thiosulfate, then aqueous potassium carbonate. The separated organic was dried over anhydrous sodium sulfate and concentrated to afford a crude title compound (110 mg, crude). MS (ESI) m/z 325.1 [M+H]+.

4-(((1R,3S)-3-Hydroxy-2,2-dimethylcyclohexyl)amino)-2-(methylsulfonyl)pyrimidine-5-carbonitrile To a solution of 4-(((1R,3S)-3-hydroxy-2,2-dimethylcyclohexyl)amino)-2-(methylthio)pyrimidine-5-carbonitrile (peak 3: 100 mg, 0.342 mmol) in DCM (2.00 mL) was added 3-chloroperbenzoic acid (85%, 139 mg, 0.684 mmol) under cooling in an ice-water bath. The mixture was stirred at room temperature for 2 h. The reaction was diluted with DCM and washed with aqueous sodium thiosulfate, then aqueous potassium carbonate. The separated organic was dried over anhydrous sodium sulfate and concentrated to afford a crude title compound (110 mg, crude). MS (ESI) m/z 325.1 [M+H]+.

G. 3-(2-Aminoethyl)-6-fluoroindolin-2-one hydrochloride

To a solution of 2-(6-fluoro-1H-indol-3-yl)ethanamine hydrochloride (500 mg, 2.3 mmol) in DMSO (0.8 mL) was added hydrochloric acid (36%, 1.3 g, 12.8 mmol). The resulting reaction mixture was stirred at 50° C. in a sealed tube for 6 h. After cooling to room temperature, the reaction mixture was filtered. The resulting cake was stirred in EtOH (5 mL). The mixture was filtered and dried to give the desired product (250 mg, 1.28 mmol, 47% yield) as a yellow solid. MS (ESI) m/z 195.1 [M+H]+.

H. 2-((2-(6-Fluoro-2-oxoindolin-3-yl)ethyl)amino)-4-(((1S,3S)-3-hydroxy-2,2-dimethylcyclohexyl)amino)pyrimidine-5-carbonitrile A mixture of 4-(((1S,3S)-3-hydroxy-2,2-dimethylcyclohexyl)amino)-2-(methylthio)pyrimidine-5-carbonitrile (90 mg, crude), 3-(2-aminoethyl)-6-fluoroindolin-2-one hydrochloride (95 mg, 0.41 mmol) and DIEA (122 mg, 0.94 mmol) in DMA (2 mL) was stirred at 90° C. for 1 h. The solvent was evaporated and the residue was purified by standard methods to afford the title compound (23.7 mg, 0.054 mmol, 19% yield for two steps). 1H NMR (400 MHz, CD3OD) δ (ppm) 8.05 (s, 1H), 7.34-7.29 (m, 1H), 6.79-6.69 (m, 1H), 6.69-6.61 (m, 1H), 4.67-4.59 (m, 1H), 3.60-3.44 (m, 4H), 2.29-2.08 (m, 2H), 1.93-1.67 (m, 3H), 1.67-1.49 (m, 3H), 1.02-0.97 (m, 6H). MS (ESI) m/z 439.2 [M+H]+.

2-((2-(6-Fluoro-2-oxoindolin-3-yl)ethyl)amino)-4-(((1R,3R)-3-hydroxy-2,2-dimethylcyclohexyl)amino)pyrimidine-5-carbonitrile A mixture of 4-(((1R,3R)-3-hydroxy-2,2-dimethylcyclohexyl)amino)-2-(methylthio)pyrimidine-5-carbonitrile (92 mg, crude), 3-(2-aminoethyl)-6-fluoroindolin-2-one hydrochloride (95 mg, 0.41 mmol) and DIEA (122 mg, 0.94 mmol) in DMA (2 mL) was stirred at 90° C. for 1 h. The solvent was evaporated and the residue was purified by standard methods to afford the title compound (36.7 mg, 0.083 mmol, 29% yield for two steps). 1H NMR (400 MHz, CD3OD) δ (ppm) 8.05 (s, 1H), 7.34-7.29 (m, 1H), 6.79-6.69 (m, 1H), 6.69-6.61 (m, 1H), 4.67-4.59 (m, 1H), 3.60-3.44 (m, 4H), 2.29-2.08 (m, 2H), 1.93-1.67 (m, 3H), 1.67-1.49 (m, 3H), 1.02-0.97 (m, 6H). MS (ESI) m/z 439.2 [M+H]+.

2-((2-(6-Fluoro-2-oxoindolin-3-yl)ethyl)amino)-4-(((1S,3R)-3-hydroxy-2,2-dimethylcyclohexyl)amino)pyrimidine-5-carbonitrile A mixture of 4-(((1S,3R)-3-hydroxy-2,2-dimethylcyclohexyl)amino)-2-(methylthio)pyrimidine-5-carbonitrile (110 mg, crude), 3-(2-aminoethyl)indolin-2-one hydrochloride (95 mg, 0.41 mmol) and DIEA (122 mg, 0.94 mmol) in N,N-dimethylacetamine (2 mL) was stirred at 90° C. for 1 h. The solvent was evaporated and the residue was purified by standard methods to afford the title compound (27.3 mg, 0.062 mmol, 18% yield for two steps). 1H NMR (400 MHz, CD3OD) δ (ppm) 8.05 (s, 1H), 7.31-7.28 (m, 1H), 6.77-6.73 (m, 1H), 6.68 (d, J=8.0 Hz, 1H), 4.11-4.08 (m, 1H), 3.56-3.46 (m, 4H), 2.23-2.10 (m, 2H), 1.84-1.31 (m, 6H), 1.02 (s, 3H), 1.00 (s, 3H). MS (ESI) m/z 439.2 [M+H]+.

2-((2-(6-Fluoro-2-oxoindolin-3-yl)ethyl)amino)-4-(((1R,3S)-3-hydroxy-2,2-dimethylcyclohexyl)amino)pyrimidine-5-carbonitrile A mixture of 4-(((1R,3S)-3-hydroxy-2,2-dimethylcyclohexyl)amino)-2-(methylthio)pyrimidine-5-carbonitrile (110 mg, crude), 3-(2-aminoethyl)indolin-2-one hydrochloride (95 mg, 0.41 mmol) and DIEA (122 mg, 0.94 mmol) in N,N-dimethylacetamine (2 mL) was stirred at 90° C. for 1 h. The solvent was evaporated and the residue was purified by standard methods to afford the title compound (27.3 mg, 0.062 mmol, 18% yield for two steps). 1H NMR (400 MHz, CD3OD) δ (ppm) 8.05 (s, 1H), 7.31-7.28 (m, 1H), 6.77-6.73 (m, 1H), 6.68 (d, J=8.0 Hz, 1H), 4.11-4.08 (m, 1H), 3.56-3.46 (m, 4H), 2.23-2.10 (m, 2H), 1.84-1.31 (m, 6H), 1.02 (s, 3H), 1.00 (s, 3H). MS (ESI) m/z 439.2 [M+H]+.

Example 35

4-(((1R,3S)-2,2-Dimethyl-3-(1H-1,2,4-triazol-3-yl)cyclobutyl)amino)-2-((2-(2-oxoindolin-3-yl)ethyl)amino)pyrimidine-5-carbonitrile

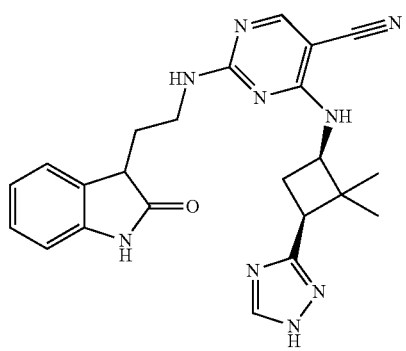 [SMILES: CC1(C)[C@@H](c2nc[nH]n2)C[C@H]1Nc1nc(NCCC2C(=O)Nc3ccccc32)ncc1C#N]

A. Benzyl ((1R,3S)-3-(hydroxymethyl)-2,2-dimethylcyclobutyl)carbamate

To a mixture of ((1S,3R)-3-amino-2,2-dimethylcyclobutyl) MeOH hydrochloride (1.8 g, 10.9 mmol) and sodium carbonate (2.31 g, 21.8 mmol) in ethyl acetate (54 mL) and water (18 mL) was added benzyl chloroformate (2.23 g, 13.1 mmol) slowly at 0° C. The resulting mixture was stirred at room temperature for 2 h. The organic layer was separated and the aqueous solution was extracted with ethyl acetate. The combined organic layers were washed with brine, dried over sodium sulfate and concentrated to give the crude product, which was purified by silica gel column chromatography (10%-20% ethyl acetate in petroleum ether) to afford the title compound (2.75 g, 10.4 mmol, 95% yield) as a white solid. MS (ESI) m/z 264.2 [M+H]$^+$.

B. (1S,3R)-3-(((Benzyloxy)carbonyl)amino)-2,2-dimethylcyclobutanecarboxylic acid To a solution of benzyl ((1R,3S)-3-(hydroxymethyl)-2,2-dimethylcyclobutyl)carbamate (2.75 g, 10.4 mmol) in carbon tetrachloride (14 mL) was added sodium periodate (6.68 g, 31.2 mmol), water (21 mL) and acetonitrile (14 mL), followed by ruthenium(III) chloride hydrate (52 mg, 0.2 mmol, in 0.5 mL of water) at room temperature. The resulting biphasic mixture was stirred vigorously at room temperature for 1 h. The reaction mixture was diluted with water and extracted with DCM (2×150 mL). The combined organic layers were dried over sodium sulfate and concentrated to give the title compound (2.6 g, crude), which was used directly in the next step without further purification. MS (ESI) m/z 278.1 [M+H]$^+$.

C. Benzyl ((1R,3S)-3-carbamoyl-2,2-dimethylcyclobutyl)carbamate

A mixture of (1S,3R)-3-(((benzyloxy)carbonyl)amino)-2,2-dimethylcyclobutanecarboxylic acid (2.6 g, 9.38 mmol), ammonium chloride (2.0 g, 37.5 mmol), TEA (2.84 g, 28.2 mmol) and 2-(7-aza-1H-benzotriazole-1-yl)-1,1,3,3-tetramethyluronium hexafluorophosphate (5.35 g, 14.1 mmol) in dry DMF (52 mL) was stirred at room temperature for 1 h. The reaction was quenched with water and extracted with ethyl acetate. The combined organic layers were washed with brine, dried over anhydrous sodium sulfate and concentrated to afford the crude product, which was purified by HPLC (10-50% acetonitrile in water) to afford the title compound (1.86 g, 6.71 mnmol, 66% yield for two steps). $^1$H NMR (400 MHz, CDCl$_3$): δ (ppm) 7.40-7.30 (m, 5H), 5.51-5.37 (m, 1H), 5.27-5.17 (m, 1H), 5.15-4.96 (m, 3H), 3.96-3.87 (m, 1H), 2.48-2.39 (m, 1H), 2.37-2.27 (m, 1H), 2.15-2.05 (m, 1H), 1.31 (s, 3H), 0.96 (s, 3H). MS (ESI) m/z 277.1 [M+H]$^+$.

D. Benzyl ((1R,3S)-3-((E)-((dimethylamino)methylene)carbamoyl)-2,2-dimethylcyclobutyl)carbamate A mixture of benzyl ((1R,3S)-3-carbamoyl-2,2-dimethylcyclobutyl)carbamate (638 mg, 2.30 mmol) in N,N-dimethylformamide dimethyl acetal (13 mL) was stirred at 120° C. overnight. The reaction mixture was concentrated at 50° C. in vacuo to give the crude product (850 mg) as a yellow oil, which was used directly in the next step without further purification. MS (ESI) m/z 332.2 [M+H]$^+$.

E. Benzyl ((1R,3S)-2,2-dimethyl-3-(1H-1,2,4-triazol-3-yl)cyclobutyl)-carbamate A mixture of ((1R,3S)-3-((E)-((dimethylamino)methylene)carbamoyl)-2,2-dimethylcyclobutyl)carbamate (850 mg, crude), hydrazine (0.5 mL) and acetic acid (0.5 mL) in EtOH (10 mL) was stirred at 80° C. for 2 h. The organic solvents were removed and the residual oil was purified by silica gel chromatography (10% MeOH in DCM) to afford the title compound (380 mg, 1.26 mmol, 55% yield for two steps). MS (ESI) m/z 301.4 [M+H]$^+$.

F. Benzyl ((1R,3S)-2,2-dimethyl-3-(1-(tetrahydro-2H-pyran-2-yl)-1H-1,2,4-triazol-3-yl)cyclobutyl)carbamate To a mixture of benzyl ((1R,3S)-2,2-dimethyl-3-(1H-1,2,4-triazol-3-yl)cyclobutyl)carbamate (380 mg, 1.26 mmol), and 3,4-dihydro-2H-pyran (127 mg, 1.51 mmol) in dry DCM (10 mL) was added pyridinium 4-methylbenzenesulfonate (476 mg, 1.89 mmol). The mixture was refluxed overnight. After removal of the solvent, the residue was purified by silica gel column chromatography (12% ethyl acetate in petroleum ether) to afford the title compound (438 mg, 1.14 mmol, 90% yield). MS (ESI) m/z 385.4 [M+H]$^+$.

G. (1R,3S)-2,2-Dimethyl-3-(1-(tetrahydro-2H-pyran-2-yl)-1H-1,2,4-triazol-3-yl)cyclobutanamine A mixture of ((1R,3S)-2,2-dimethyl-3-(1-(tetrahydro-2H-pyran-2-yl)-1H-1,2,4-triazol-3-yl)cyclobutyl)carbamate (438 mg, 1.14 mmol) and palladium on activated carbon (10% Pd, 50 mg) in MeOH (15 mL) was stirred at 25° C. under hydrogen atmosphere for 5 h. The reaction mixture was filtered through celite and the filtrate was concentrated to afford the crude title compound (340 mg, crude). MS (ESI) m/z 251.2 [M+H]$^+$.

H. 4-(((1R,3S)-2,2-Dimethyl-3-(1-(tetrahydro-2H-pyran-2-yl)-1H-1,2,4-triazol-3-yl)cyclobutyl)amino)-2-(methylthio)pyrimidine-5-carbonitrile A mixture of (1R,3S)-2,2-dimethyl-3-(1-(tetrahydro-2H-pyran-2-yl)-1H-1,2,4-triazol-3-yl)cyclobutanamine (340 mg, crude) and 4-chloro-2-(methylthio)pyrimidine-5-carbonitrile (210 mg, 1.14 mmol) and DIEA (450 mg, 3.50 mmol) in isopropanol (5 mL) was stirred at 90° C. for 1 h. After removal of the solvent, the residue was purified by silica gel column chromatography (10%-30% ethyl acetate in petroleum ether) to afford the title compound (290 mg, 0.727 mmol, 65% yield for two steps). MS (ESI) m/z 400.2 [M+H]$^+$.

I. 4-(((1R,3S)-2,2-Dimethyl-3-(1-(tetrahydro-2H-pyran-2-yl)-1H-1,2,4-triazol-3yl)cyclobutyl)amino)-2-(methylsulfonyl)pyrimidine-5-carbonitrile To a solution of 4-(((1R,3S)-2,2-dimethyl-3-(1-(tetrahydro-2H-pyran-2-yl)-1H-1,2,4-triazol-3-yl)cyclobutyl)amino)-2-(methylthio)pyrimidine-5-carbonitrile (150 mg, 0.376 mmol) in NMP (2.0 mL) was added 3-chloroperbenzoic acid (85%, 154 mg, 0.752 mmol) under cooling in an ice-water bath. The mixture was stirred at room temperature for 2 h. The reaction was diluted with DCM and washed with aqueous sodium thiosulfate, then aqueous potassium carbonate. The separated organic was dried over anhydrous sodium sulfate and concentrated to afford a crude title compound (140 mg, crude). MS (ESI) m/z 432.2 [M+H]+.

J. 3-(2-Aminoethyl)indolin-2-one hydrochloride

To a solution of 2-(1H-indol-3-yl)ethanamine (6.00 g, 37.50 mmol) in DMSO (8.0 mL, 112.50 mmol) was added concentrated hydrochloric acid (9.5 mL, 112.50 mmol) slowly. The resulting reaction mixture was stirred at 50° C. in a sealed tube for 16 h. After cooling to room temperature, the reaction mixture was filtered. The resulting cake was stirred in EtOH (15 mL). The mixture was filtered and dried to give the desired title compound as a brown solid (5.00 g, 23.64 mmol, 63% yield). MS (ESI) m/z 177.2 [M+H]+.

K. 4-(((1R,3S)-2,2-Dimethyl-3-(1H-1,2,4-triazol-3-yl)cyclobutyl)amino)-2-((2-(2-oxoindolin-3-yl)ethyl)amino)pyrimidine-5-carbonitrile A mixture of 4-(((1R,3S)-2,2-dimethyl-3-(1-(tetrahydro-2H-pyran-2-yl)-1H-1,2,4-triazol-3-yl)cyclobutyl)amino)-2-(methylsulfonyl)pyrimidine-5-carbonitrile (140 mg, crude), 3-(2-aminoethyl)indolin-2-one hydrochloride (80 mg, 0.376 mmol) and DIEA (194 mg, 1.50 mmol) in NMP (2.0 mL) was stirred at 100° C. for 1 h. The reaction was diluted with water and extracted with ethyl acetate. The combined organic layers were dried over anhydrous sodium sulfate and concentrated to give a crude product, which was dissolved in a solution of hydrochloride in MeOH (2N, 5 mL) and stirred at room temperature for 5 h. The reaction was neutralized with ammonia and concentrated. The residue was purified by standard methods to afford the title compound (33.4 mg, 0.075 mmol, 20% yield for two steps). $^1$H NMR (400 MHz, DMSO-$d_6$) δ (ppm) 13.49 (brs, 1H), 10.24 (s, 1H), 8.52-7.41 (m, 3H), 7.29 (t, J=7.6 Hz, 1H), 7.25-7.07 (m, 2H), 7.01-6.93 (m, 1H), 6.87-6.82 (m, 1H), 4.41-4.29 (m, 1H), 3.59-3.43 (m, 2H), 3.42-3.25 (m, 1H), 3.10-2.96 (m, 1H), 2.81-2.66 (m, 1H), 2.49-2.34 (m, 1H), 2.16-1.94 (m, 2H), 1.49-1.00 (m, 3H), 0.63-0.62 (m, 3H). MS (ESI) m/z 444.2 [M+H]+.

Example 36

(1S,3R)-3-(5-Cyano-2-(2-(1-methyl-2-oxoindolin-3-yl)ethylamino)pyrimidin-4-ylamino)-2,2-dimethyl-cyclobutanecarboxamide

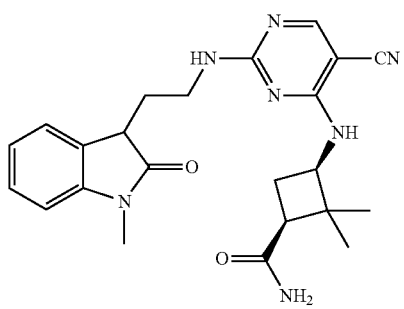 [SMILES: CN1C(=O)C(CCNc2ncc(C#N)c(N[C@@H]3C[C@H](C(N)=O)C3(C)C)n2)c2ccccc21]

A. tert-butyl (2-(1H-Indol-3-yl)ethyl)carbamate

To a solution of 2-(1H-indol-3-yl)ethanamine (3.00 g, 18.75 mmol) in THF (30 mL) was added di-tert-butyl pyrocarbonate (4.36 g, 20 mmol). The resulting reaction mixture was stirred at room temperature for 16 h. The mixture was concentrated to give the crude product, which was purified by silica gel column chromatography (20% ethyl acetate in petroleum ether) to give the title compound (4.70 g, 18.01 mmol, 95% yield) as a yellow solid. MS (ESI) m/z 261.1 [M+H]+.

B. tert-butyl (2-(1-Methyl-1H-indol-3-yl)ethyl)carbamate

To a solution of tert-butyl (2-(1H-indol-3-yl)ethyl)carbamate (4.70 g, 18.01 mmol) in anhydrous THF (50 mL) was added sodium hydride (800 mg, 20 mmol, 60% in mineral oil) at 0° C. under nitrogen. After the resulting reaction mixture was stirred at room temperature for 15 min, iodomethane (2.84 g, 20 mmol) in THF (15 mL) was added slowly at 0° C. The resulting mixture was stirred at room temperature for 3 h and quenched with saturated aqueous ammonium chloride solution. The aqueous layer was extracted with ethyl acetate. The combined organic layers were washed with brine, dried over anhydrous sodium sulfate and filtered. Concentration under vacuum gave the crude product, which was purified by silica gel column chromatography (0.6% MeOH in DCM) to afford the title compound (4 g, 14.6 mmol, 80% yield) as a brown solid. MS (ESI) m/z 275.1 [M+H]+.

C. 2-(1-Methyl-1H-indol-3-yl)ethanamine

To a solution of tert-butyl (2-(1-methyl-1H-indol-3-yl)ethyl)carbamate (4 g, 14.6 mmol) in DCM (30 mL) was added TFA (15 mL) at ~0° C. to 5° C. The resulting reaction mixture was stirred at room temperature for 1 h. The reaction mixture was concentrated to give a crude title compound (2.5 g, crude) as yellow oil. MS (ESI) m/z 175.1 [M+H]+.

D. 3-(2-Aminoethyl)-1-methylindolin-2-one hydrochloride

To a solution of 2-(1-methyl-1H-indol-3-yl)ethanamine (2.5 g crude) in DMSO (1.33 g, 17.0 mmol) was added concentrated hydrochloric acid (1.2 mL) slowly. The resulting reaction mixture was stirred at room temperature in a sealed reactor for 16 h. The reaction mixture was concentrated and the residue was purified by preparative HPLC to afford the title compound (1.5 g, 6.59 mmol, 45% yield over two steps) as a yellow solid. MS (ESI) m/z 191.1 [M+H]+.

E. Benzyl ((1R,3S)-3-(hydroxymethyl)-2,2-dimethylcyclobutyl)carbamate

To a mixture of ((1S,3R)-3-amino-2,2-dimethylcyclobutyl) MeOH hydrochloride (1.8 g, 10.9 mmol) and sodium carbonate (2.31 g, 21.8 mmol) in ethyl acetate (54 mL) and water (18 mL) was added benzyl chloroformate (2.23 g, 13.1 mmol) slowly at 0° C. The resultant mixture was stirred at room temperature for 2 h. The organic layer was separated and the aqueous solution was extracted with ethyl acetate. The combined organic layers were washed with brine, dried over sodium sulfate and concentrated to give the crude product, which was purified by silica gel column chromatography (10%-20% ethyl acetate in petroleum ether) to afford the title compound (2.75 g, 10.4 mmol, 95% yield) as a white solid. MS (ESI) m/z 264.2 [M+H]+.

F. (1S,3R)-3-(((Benzyloxy)carbonyl)amino)-2,2-dimethylcyclobutanecarboxylic acid To a solution of benzyl ((1R,3S)-3-(hydroxymethyl)-2,2-dimethylcyclobutyl)carbamate (2.75 g, 10.4 mmol) in carbon tetrachloride (14 mL) was added sodium periodate (6.68 g, 31.2 mmol), water (21 mL) and acetonitrile (14 mL), followed by ruthenium(III) chloride hydrate (52 mg, 0.2 mmol, in 0.5 mL of water) at room temperature. The resulting biphasic mixture was stirred vigorously at room temperature for 1 h. The reaction mixture was diluted with water and extracted with DCM (2×150 mL). The combined organic layers was dried over sodium sulfate and concentrated to afford the title compound (2.6 g, crude), which was used directly in the next step without further purification. MS (ESI) m/z 278.1 [M+H]$^+$.

G. Benzyl ((1R,3S)-3-carbamoyl-2,2-dimethylcyclobutyl)carbamate

A mixture of (1S,3R)-3-(((benzyloxy)carbonyl)amino)-2,2-dimethylcyclobutanecarboxylic acid (2.6 g, 9.38 mmol), ammonium chloride (2.0 g, 37.5 mmol), TEA (2.84 g, 28.2 mmol) and 2-(7-aza-1H-benzotriazole-1-yl)-1,1,3,3-tetramethyluronium hexafluorophosphate (5.35 g, 14.1 mmol) in dry DMF (52 mL) was stirred at room temperature for 1 h. The reaction was quenched with water and extracted with ethyl acetate. The combined organic layers were washed with brine, dried over anhydrous sodium sulfate and concentrated to afford the crude product, which was purified by HPLC (10-50% acetonitrile in water) to afford the title compound (1.86 g, 6.71 mnmol, 66% yield for two steps). $^1$H NMR (400 MHz, CDCl$_3$): δ (ppm) 7.40-7.30 (m, 5H), 5.51-5.37 (m, 1H), 5.27-5.17 (m, 1H), 5.15-4.96 (m, 3H), 3.96-3.87 (m, 1H), 2.48-2.39 (m, 1H), 2.37-2.27 (m, 1H), 2.15-2.05 (m, 1H), 1.31 (s, 3H), 0.96 (s, 3H). MS (ESI) m/z 277.1 [M+H]$^+$.

H. (1S,3R)-3-Amino-2,2-dimethylcyclobutanecarboxamide

A mixture of benzyl ((1R,3S)-3-carbamoyl-2,2-dimethylcyclobutyl)carbamate (193 mg, 0.70 mmol) and palladium on activated carbon (10% Pd, 30 mg) in MeOH (5 mL) was stirred at 25° C. under hydrogen atmosphere for 5 h. The reaction mixture was filtered through celite and the filtrate was concentrated to afford the crude title compound (120 mg, crude). MS (ESI) m/z 143.1 [M+H]$^+$.

I. (1S,3R)-3-((5-Cyano-2-(methylthio)pyrimidin-4-yl)amino)-2,2-dimethylcyclobutanecarboxamide A mixture of (1S,3R)-3-amino-2,2-dimethylcyclobutanecarboxamide. (120 mg, crude), chloro-2-(methylthio)pyrimidine-5-carbonitrile (130 mg, 0.70 mmol) and DIEA (129 mg, 1.0 mmol) in isopropanol (5 mL) was stirred at 80° C. for 2 h. After removal of the solvent, the residue was purified by silica gel column chromatography (10%-30% ethyl acetate in petroleum ether) to afford the title compound (160 mg, 0.55 mmol, 78% yield for two steps). MS (ESI) m/z 292.2 [M+H]$^+$.

J. (1S,3R)-3-((5-Cyano-2-(methylsulfonyl)pyrimidin-4-yl)amino)-2,2-dimethylcyclobutanecarboxamide To a solution of (1S,3R)-3-((5-cyano-2-(methylthio)pyrimidin-4-yl)amino)-2,2-dimethylcyclobutanecarboxamide (150 mg, 0.51 mmol) in NMP (1.5 mL) was added 3-chloroperbenzoic acid (85%, 230 mg, 1.12 mmol) under cooling in an ice-water bath. The mixture was stirred at room temperature for 2 h. The reaction mixture was used directly in the next step without further purification. MS (ESI) m/z 324.2 [M+H]$^+$.

K. (1S,3R)-3-(5-Cyano-2-(2-(1-methyl-2-oxoindolin-3-yl)ethylamino)pyrimidin-4-ylamino)-2,2-dimethylcyclobutanecarboxamide 3-(2-Aminoethyl)-1-methylindolin-2-one (231 mg, 1.02 mmol) and DIEA (197 mg, 1.53 mmol) were added to the reaction mixture of (1S,3R)-3-(5-cyano-2-(methylsulfonyl)pyrimidin-4-ylamino)-2,2-dimethylcyclobutanecarboxamide (prepared as described above) at 0° C. and stirred at 90° C. for 1 h. The reaction was diluted with water and extracted with ethyl acetate. The combined organic layers were dried over sodium sulfate and concentrated to afford the crude product, which was purified by standard methods to afford the title compound (17.7 mg, 0.041 mmol, 8% yield over two steps). $^1$H NMR (400 MHz, CD$_3$OD) δ (ppm) 8.12-8.01 (m, 1H), 7.42-7.33 (m, 2H), 7.17-6.93 (m, 2H), 4.36-4.09 (m, 1H), 3.62-3.60 (m, 2H), 3.23-3.13 (m, 4H), 2.60-2.25 (m, 5H), 1.39-0.88 (m, 6H). MS (ESI) m/z 433.8 [M+H]$^+$.

Example 37

4-(((1R,4S)-4-Hydroxy-3,3-dimethylcyclohexyl)amino)-2-((2-(5-methoxypyridin-3-yl)ethyl)amino)pyrimidine-5-carbonitrile

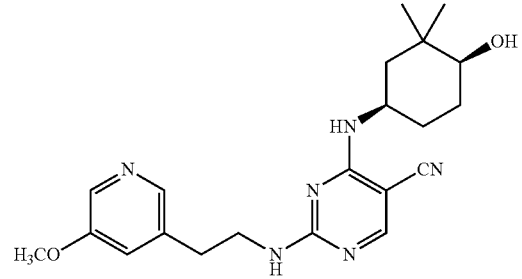 [SMILES: COc1cncc(CCNc2ncc(C#N)c(N[C@@H]3CC[C@H](O)C(C)(C)C3)n2)c1]

A. tert-butyl (2-(5-Methoxypyridin-3-yl)ethyl)carbamate

A 20 mL vial equipped with a septum cap and stir bar was charged with cesium carbonate (977 mg, 3.00 mmol), 3-bromo-5-methoxypyridine (188 mg, 1.00 mmol), potassium[2-(tert-butoxycarbonylamino)ethyl]trifluoroborate (301 mg, 1.20 mmol), di-(1-adamantyl)-n-butylphosphine (35.8 mg, 0.100 mmol) and palladium (II) acetate (11.2 mg, 0.050 mmol). Toluene (3 mL) and water (2 mL) were added, and the vial was purged with nitrogen gas and sealed. The mixture was stirred vigorously at 80° C. for 24 h, cooled to room temperature and the aqueous layer was removed. The organic layer was dried with sodium sulfate and the crude product solution was purified by silica gel chromatography (0-10% MeOH in DCM) to provide tert-butyl (2-(5-methoxypyridin-3-yl)ethyl)carbamate as a colorless syrup (153 mg, 0.606 mmol, 61%). $^1$H NMR (CDCl$_3$, 500 MHz): δ (ppm) 8.21 (d, J=6.14 Hz, 1H), 8.09 (d, J=1.58 Hz, 1H), 6.98-7.16 (m, 1H), 4.53-4.90 (m, 1H), 3.87 (s, 3H), 3.33-3.47 (m, 2H), 2.82 (t, J=6.78 Hz, 2H), 1.46 ppm (s, 9H).

B. 2-(5-methoxypyridin-3-yl)ethan-1-amine dihydrochloride

To a solution of tert-butyl (2-(5-methoxypyridin-3-yl)ethyl)carbamate (153 mg, 0.606 mmol) in isopropanol (2 mL) was added 4M HCl in dioxane (2 mL) and the mixture was stirred at room temperature for 16 h. The mixture was concentrated, the residual solid was washed with diethyl ether and dried in vacuum to provide the title compound as a white solid (103 mg, 0.458 mmol, 75%). $^1$H NMR (500 MHz, CD$_3$OD): δ (ppm) 8.56 (d, J=2.52 Hz, 1H), 8.51 (s, 1H), 8.27 (s, 1H), 4.15 (s, 3H), 3.23-3.38 ppm (m, 4H).

C. 4-(((1R,4S)-4-hydroxy-3,3-dimethylcyclohexyl)amino)-2-((2-(5-methoxypyridin-3-yl)ethyl)amino)pyrimidine-5-carbonitrile A 1 dram vial equipped with a septum cap was charged with 4-(((1R,4S)-4-hydroxy-3,3-dimethylcyclohexyl)amino)-2-(methylsulfinyl)pyrimidine-5-carbonitrile (55.0 mg, 0.178 mmol), 2-(5-methoxypyridin-3-yl)ethan-1-amine dihydrochloride (56.3 mg, 0.214 mmol) and DMSO (1.4 mL). The resulting solution was treated with DIEA (0.125 mL, 0.715 mmol), and the vial was sealed and shaken (250 rpm) at 60° C. for 14 h. The mixture was cooled to room temperature, diluted with DMSO (1.5 mL), and filtered. The solution was purified by standard methods to provide the title compound. MS (ESI) m/z 379.2 [M+1]$^+$.

Assays

Biochemical Assays

PKC-Theta Assay.
A 384-well time resolved fluorescence assay was used to monitor PKC-theta activity. The PKC-theta assay was run in the following assay buffer: 50 mM HEPES pH 7.6, 10 mM MgCl$_2$, 1 mM DTT, 0.01% Triton X-100, 0.01% BSA and 0.1 mM EDTA. To initiate the reaction, 200 nM of Fam-labeled S6-derived peptide (Molecular Devices) and 10 μM of ATP were mixed with 142 pM of His-PKC-theta (Invitrogen) for a total assay volume of 25 μL in each well. The assay was incubated at room temperature for 2 hours and terminated using a 60 μL/well mixture of Detection Binding Solution: 70% IMAP Progressive Binding Buffer A, 30% IMAP Progressive Binding Buffer B, 1:600 Progressive Binding Reagent, and 1:400 TR-FRET Tb Donor (Molecular Devices). The assay plates were then incubated overnight at room temperature and read on a Perkin-Elmer Envision Reader. The IC$_{50}$ values were calculated as the concentration of compound at which the level of fluorescence signal was reduced to 50% of the signal window.

PKC Delta Assay.
A 384-well time resolved fluorescence assay was used to monitor PKC delta activity. The PKC delta assay was run in the following assay buffer: 50 mM HEPES pH 7.6, 10 mM MgCl$_2$, 1 mM DTT, 0.01% Triton X-100, 0.01% BSA and 0.1 mM EDTA. To initiate the reaction, 200 nM of Fam-labeled S6-derived peptide (Molecular Devices) and 10 μM of ATP were mixed with 1.5 nM of PKC delta (Invitrogen), for a total assay volume of 25 μL in each well. The assay was incubated at room temperature for 2 hours and terminated using a 60 μL/well mixture of Detection Binding Solution: 70% IMAP Progressive Binding Buffer A, 30% IMAP Progressive Binding Buffer B, 1:600 Progressive Binding Reagent, and 1:400 TR-FRET Tb Donor (Molecular Devices). The assay plates were then incubated overnight at room temperature and read on the Perkin-Elmer Envision Reader. The IC$_{50}$ values were calculated as the concentration of compound at which the level of fluorescence signal was reduced to 50% of the signal window.

Table 1 shows the effect of Diaminopyrimidyl Compounds in PKC Kinase Enzymatic Assays. Certain Diaminopyrimidyl Compounds of Table 1 show an effect in the PKC Kinase Enzymatic Assays with an IC$_{50}$ value ranging from 0.0001-10 μM for PKC-theta and a selectivity for PKC-theta over PKC-delta ranging from 5 to >100-fold.

Table 2 shows the effect of certain compounds in PKC Kinase Enzymatic Assays. Certain compounds of Table 2 show an effect in the PKC Kinase Enzymatic Assays with an IC$_{50}$ value ranging from 0.001-10 μM for PKC-theta and a selectivity for PKC-theta over PKC-delta ranging from 5 to >100-fold.

Cell Assays

Jurkat Cellular Assay: CD3/CD8-Stimulated IL-2 Secretion.
The intracellular inhibition of PKCtheta over a range of test compound concentrations was evaluated in human Jurkat cells by measuring IL-2 cytokine production. Human Jurkat clone E6-1 from ATCC was used for these studies. The cells were activated in vitro with anti-CD3 (Life Technologies/Invitrogen) and anti-human CD28 (BD Biosciences) to express pro-inflammatory cytokines. Jurkat cells were cultured in RPMI 1640 medium supplemented with 1.0 mM sodium pyruvate, 2 mM L-glutamine, 10 mM Hepes, 1.0 mM non-essential amino acids, 100 IU/mL Penicillin, 100 μg/mL Streptomycin and 10% fetal calf serum. The cells were plated at a density of 0.5 million cells per well in RPMI complete culture media onto a clear 96-well round bottom plate (200 μL per well).

Compound dilutions were prepared from 10 mM stock by first diluting to the appropriate concentrations in 100% DMSO and then diluted 1:50 into serum-free RPMI media. Next, compounds were added to designated wells at dilution of 1:10; the final dilution of compound was 1:500 and final DMSO concentration of 0.2% in each well. The cells were exposed to compound dosed at 0, 0.01, 0.03, 0.1, 0.3, 1, 3 and 10 μM in triplicate for 30 minutes at 37° C. Finally, the cells were activated by adding 25 μL per well containing 15 μL anti-CD3 Dynabeads and 2 μg/mL purified anti-CD28 antibody prepared in serum-free RPMI media and incubated for 20 hours at 37° C. After incubation, 100 μL of culture media was collected from each well. The level of secreted IL-2 was measured using the MesoScale Discovery (MSD) single-plex cytokine assay for human IL-2 according to manufacture's protocol. The raw data was analyzed using XLfit from IDBS to calculate percentage of inhibition at each concentration. The formula used for determining IC$_{50}$ in XLfit was model number 205, which utilizes a sigmoidal dose-response model to calculate IC$_{50}$ values. The IC$_{50}$ values obtained from multiple experiments had to be within 2 fold of each other to be accepted (for n=3) as a valid IC$_{50}$. The IC$_{50}$ values were reported as an average.

Certain Diaminopyrimidyl Compounds from Table 1 and Table 2 have an $IC_{50}$ value ranging from 0.01-10 µM in this assay.

Human Whole Blood: CD3/CD8-Stimulated IL-2 Secretion.

The intracellular inhibition of PKCtheta over a range of test compound concentrations was evaluated in human whole blood by measuring IL-2 cytokine production. Human whole blood was obtained from normal healthy donors under IRB protocol. The whole blood was activated in vitro with crosslinking antibodies of CD3ε (R&D Systems) and CD28 (BD Biosciences) to express pro-inflammatory cytokines.

To prepare CD3ε coated plates, 50 µL with 1 µg/ml anti-human CD3ε (clone UCHT1) in sterile D-PBS ($Ca^{++}$/$Mg^{++}$ free) was added to each well of the 96-well Cova-LinkNH module plates (Fisher Scientific) and incubated for 16-20 hours at 4° C. The CD3 was removed and the wells were washed with 100 µL of D-PBS before transferring pretreated blood to the plate.

To prepare human whole blood, the blood was diluted 1:1 with serum-free RPMI media and mixed gently. The diluted blood was plated into 96 well U-bottom plates (160 µL per well). Compound dilutions were prepared from 10 mM stock by first diluting to the appropriate concentrations in 100% DMSO and then diluting 1:50 into serum-free RPMI media. Next, compound was added to designated well at dilution of 1:10. The final dilution of compound was 1:500 and final DMSO concentration of 0.2% in each well. The diluted whole blood was exposed to compound dosed at 0, 0.01, 0.03, 0.1, 0.3, 1, 3 and 10 µM in triplicate for 30 minutes at 37° C. The pre-treated blood was transferred to the designated wells of the pre-coated CD3ε plate. Finally, the blood was activated by adding 20 µL per well of 2 µg/mL purified anti-CD28 antibody prepared in serum-free RPMI media and incubated for 20 hours at 37° C. After incubation, 100 µL of culture media was collected from each well. Level of IL-2 was measured using the MesoScale Discovery (MSD) Ultrasensitive single-plex cytokine assay for human IL-2 according to manufacturer's protocol. The raw data was analyzed using XLfit from IDBS to calculate percentage of inhibition at each concentration. The formula used for determining $IC_{50}$ in XLfit was model number 205, which utilizes a sigmoidal dose-response model to calculate $IC_{50}$ values. The $IC_{50}$ values obtained from multiple experiments had to be within 2 fold of each other to be accepted (for n=3) as a valid $IC_{50}$. The $IC_{50}$ values were reported as an average.

Certain diaminopyrimidyl compounds from Table 1 and Table 2 have an $IC_{50}$ value ranging from 0.01-10 µM in this assay.

Animal Models

Acute T Cell Activation Model:

SEB mediated cytokine release in mice. Staphylococcal Enterotoxins (SEA, B, C, D and E) are termed superantigens (sAgs) because of their profound effect on a broad spectrum of T cells. They are mitogenic to humans, murine and rabbit T cells and cause a massive release of cytokines such as IL-2, IFN-g and IL-6. The SEB mediated T cell activation model in mice and rats is a fast and robust model that identifies compounds that inhibit T-cell activation.

Test articles or vehicle were administered up to 24 hrs prior by either oral, intravenous (i.v.), intraperitoneal (i.p.), or subcutaneous (s.c.) routes. Male C57/Bl6 mice were injected with 25-100 µg of SEB i.p. Plasma or lymphoid organs such as spleen or lymph node (LN) were collected 2 hrs after SEB and IL-2 cytokine levels measured using standard commercial ELISA kits.

Certain Diaminopyrimidyl Compounds as described herein have, or are expected to have an $ED_{50}$ value of <100 mg/kg, with some compounds having an $ED_{50}$ of <10 mg/kg, and others an $ED_{50}$ of <1 mg/kg.

Graft Vs Host Disease Model.

Unwanted immune reactions known as graft versus host disease (GVHD), mediated primarily by T cells, are a major cause of graft failure in allogeneic organ transplant recipients. This phenomenon is modeled in rodents by injection of allogeneic spleen or isolated T cells into a donor, and subsequent measurement of that GVHD response, which allows for identification of therapeutic compounds that suppress T cell activation.

C57Bl/6 mice were used as a source of donor cells and B6D2F1 (F1 of C57Bl/6×DBA/2) were used as recipients. Spleens were removed from the donor animals (C57Bl/6) and cell suspensions were prepared in phosphate buffered saline. A total of 20-30×10$^6$ cells were injected into the loose plantar subcutaneous tissues at the base of the toes on the left foot of the recipient (B6D2F1) animal. Cell suspensions from recipient animal strain were prepared and injected similarly in the right foot of the recipient animals as the syngeneic control group. The popliteal lymph nodes from both the left and right sides were removed 4 days after the injection, stripped of adherent adipose tissue and weighed. Test articles or vehicle were administered up to 24 hrs prior to spleen cell injections by either oral, i.v., i.p. or s.c. routes. The difference in lymph node enlargement when treated with a test article compared to lymph node enlargement with vehicle treatment is expressed as % inhibition.

Certain Diaminopyrimidyl Compounds as described herein have, or are expected to have an $ED_{50}$ value of <100 mg/kg, with some compounds having an $ED_{50}$ of <10 mg/kg, and others an $ED_{50}$ of <1 mg/kg.

Activity Tables

Each of the compounds in Tables 1 and 2 was tested in one or more of the biochemical assays and was found to have activity therein, with all of the compounds having an $IC_{50}$ below 10 µM in the PKC-theta Assay, with some compounds having an $IC_{50}$ below 100 nM (activity level D), some an $IC_{50}$ between 100 nM and 800 nM (activity level C), some an $IC_{50}$ between 800 nM and 2 µM (activity level B), and others having an $IC_{50}$ between 2 µM and 10 µM (activity level A). The compounds were also found to have selectivity for PKC-theta over PKC-delta, which some compounds showing selectivity (Sel. Level=ratio of IC$_{50}$ PKC-delta/IC$_{50}$ PKC-theta) of >100-fold (selectivity level E), some a selectivity of between 20- and 100-fold (selectivity level F), some a selectivity between 5- and 20-fold (selectivity level G) and others having a selectivity level of 5-fold or less (selectivity level H).
TABLE 1
| Cmpd No. | Cmpd Structure | MS (ESI) m/z | Act. Level | Sel. Level |
|---|---|---|---|---|
| 1 | 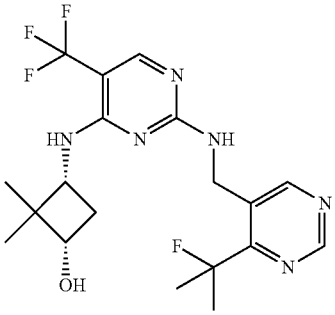 [SMILES: CC(C)(F)c1ncncc1CNc1ncc(C(F)(F)F)c(N[C@@H]2C[C@H](O)C2(C)C)n1] | 429.3 | D | E |
| 2 | 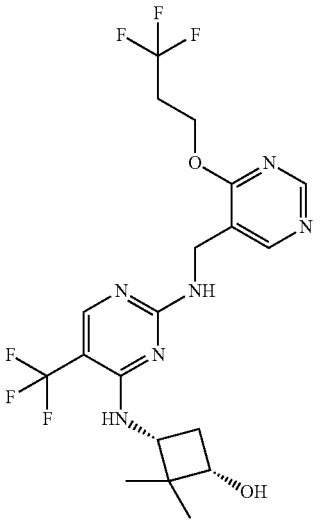 [SMILES: CC1(C)[C@@H](O)C[C@H]1Nc1nc(NCc2cncnc2OCCC(F)(F)F)ncc1C(F)(F)F] | 481.4 | D | E |
| 3 | 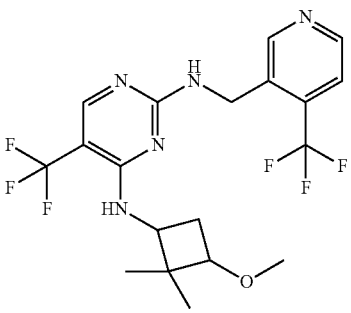 [SMILES: COC1CC(Nc2nc(NCc3cnccc3C(F)(F)F)ncc2C(F)(F)F)C1(C)C] | 450.1 | D | E |

TABLE 1-continued

| Cmpd No. | Cmpd Structure | MS (ESI) m/z | Act. Level | Sel. Level |
|---|---|---|---|---|
| 4 | (structure) | 438.2 | D | E |
| 5 | (structure) | 386.1 | D | E |
| 6 | (structure) | 466.2 | D | E |

TABLE 1-continued

| Cmpd No. | Cmpd Structure | MS (ESI) m/z | Act. Level | Sel. Level |
|---|---|---|---|---|
| 7 | | 448.2 | D | E |
| 8 | | 509.2 | D | E |
| 9 | | 466.2 | D | E |

TABLE 1-continued

| Cmpd No. | Cmpd Structure | MS (ESI) m/z | Act. Level | Sel. Level |
|---|---|---|---|---|
| 10 | | 414.2 | D | E |
| 11 | | 479.5 | D | E |
| 12 | | 406.1 | D | E |

TABLE 1-continued

| Cmpd No. | Cmpd Structure | MS (ESI) m/z | Act. Level | Sel. Level |
|---|---|---|---|---|
| 13 | | 463.4 | D | E |
| 14 | | 457.4 | D | E |
| 15 | | 400.4 | D | E |

TABLE 1-continued
| Cmpd No. | Cmpd Structure | MS (ESI) m/z | Act. Level | Sel. Level |
|---|---|---|---|---|
| 16 | 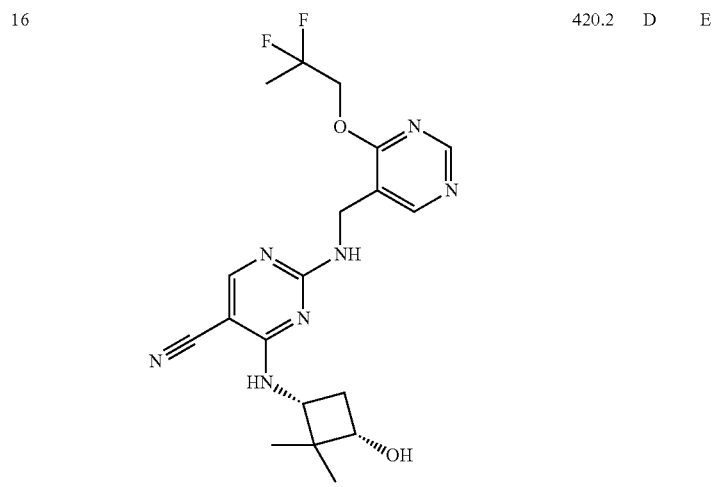 | 420.2 | D | E |
| 17 | 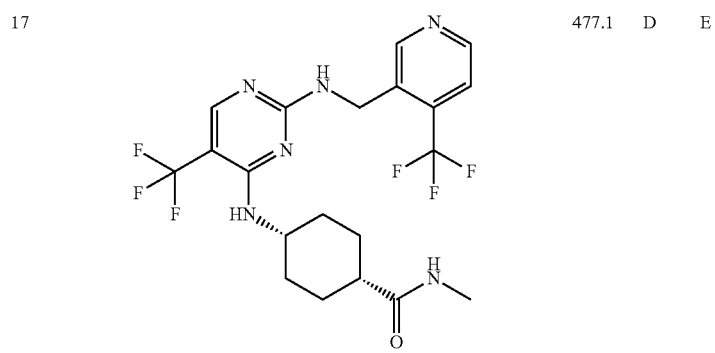 | 477.1 | D | E |
| 18 | 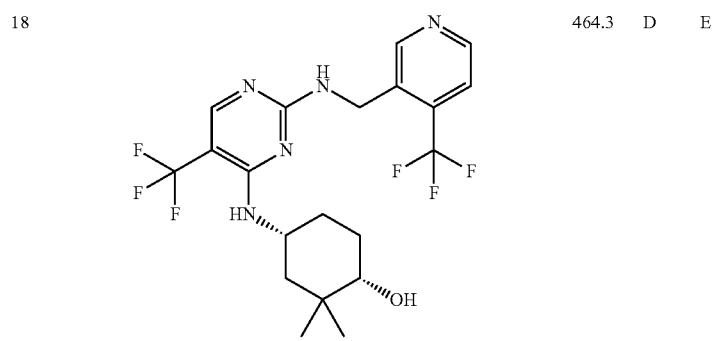 | 464.3 | D | E |

TABLE 1-continued

| Cmpd No. | Cmpd Structure | MS (ESI) m/z | Act. Level | Sel. Level |
| --- | --- | --- | --- | --- |
| 19 | | 475.3 | D | E |
| 20 | | 411.3 | D | E |
| 21 | | 416.2 | D | E |

TABLE 1-continued

| Cmpd No. | Cmpd Structure | MS (ESI) m/z | Act. Level | Sel. Level |
|---|---|---|---|---|
| 22 | | 473.3 | D | E |
| 23 | | 421.2 | D | E |
| 24 | | 436.1 | D | E |

TABLE 1-continued

| Cmpd No. | Cmpd Structure | MS (ESI) m/z | Act. Level | Sel. Level |
|---|---|---|---|---|
| 25 | (structure) | 441.2 | D | E |
| 26 | (structure) | 432.2 | D | E |
| 27 | (structure) | 393.1 | D | E |
| 28 | (structure) | 446.3 | D | E |

TABLE 1-continued

| Cmpd No. | Cmpd Structure | MS (ESI) m/z | Act. Level | Sel. Level |
|---|---|---|---|---|
| 29 | | 491.2 | D | E |
| 30 | | 465 | D | E |
| 31 | | 489.3 | D | E |

TABLE 1-continued

| Cmpd No. | Cmpd Structure | MS (ESI) m/z | Act. Level | Sel. Level |
|---|---|---|---|---|
| 32 | | 450.2 | D | E |
| 33 | | 436.1 | D | E |
| 34 | | 434.1 | D | E |
| 35 | | 368.1 | D | E |

TABLE 1-continued
| Cmpd No. | Cmpd Structure | MS (ESI) m/z | Act. Level | Sel. Level |
|---|---|---|---|---|
| 36 | 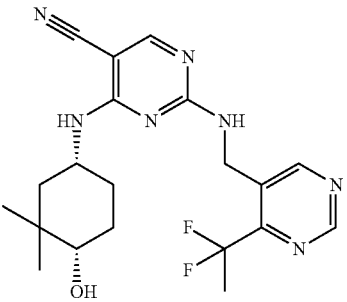 [SMILES: CC(F)(F)c1ncncc1CNc1ncc(C#N)c(N[C@@H]2CC[C@H](O)C(C)(C)C2)n1] | 418.2 | D | E |
| 37 | 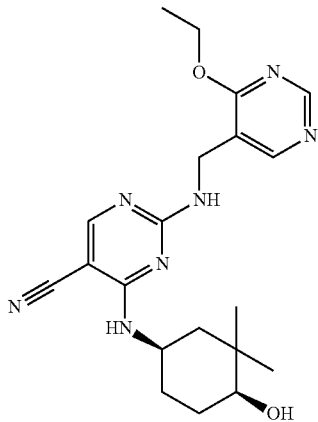 [SMILES: CCOc1ncncc1CNc1ncc(C#N)c(N[C@@H]2CC[C@H](O)C(C)(C)C2)n1] | 398.1 | D | E |
| 38 | 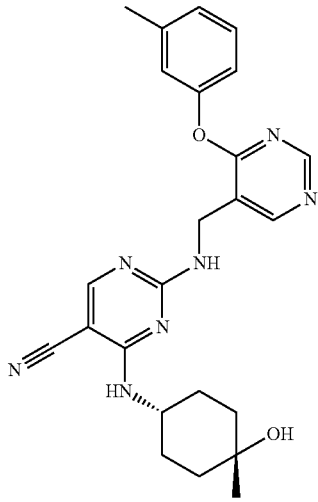 [SMILES: Cc1cccc(Oc2ncncc2CNc2ncc(C#N)c(N[C@H]3CC[C@@](C)(O)CC3)n2)c1] | 446.2 | D | E |

TABLE 1-continued

| Cmpd No. | Cmpd Structure | MS (ESI) m/z | Act. Level | Sel. Level |
|---|---|---|---|---|
| 39 | | 448.2 | D | E |
| 40 | | 480.1 | D | E |
| 41 | | 452.1 | D | E |
| 42 | | 437.2 | D | E |

TABLE 1-continued

| Cmpd No. | Cmpd Structure | MS (ESI) m/z | Act. Level | Sel. Level |
|---|---|---|---|---|
| 43 | | 422.2 | D | E |
| 44 | | 491.2 | D | E |
| 45 | | 432.3 | D | E |

TABLE 1-continued

| Cmpd No. | Cmpd Structure | MS (ESI) m/z | Act. Level | Sel. Level |
|---|---|---|---|---|
| 46 | | 450.1 | D | E |
| 47 | | 409 | D | E |
| 48 | | 466.2 | D | E |
| 49 | | 420.1 | D | E |

TABLE 1-continued

| Cmpd No. | Cmpd Structure | MS (ESI) m/z | Act. Level | Sel. Level |
|---|---|---|---|---|
| 50 | | 400.2 | D | E |
| 51 | | 407.4 | D | E |
| 52 | | 402.3 | D | E |
| 53 | | 423.2 | D | E |

TABLE 1-continued

| Cmpd No. | Cmpd Structure | MS (ESI) m/z | Act. Level | Sel. Level |
|---|---|---|---|---|
| 54 | | 382.2 | D | E |
| 55 | | 494.3 | D | E |
| 56 | | 382.2 | D | E |
| 57 | | 413.1 | D | F |

TABLE 1-continued

| Cmpd No. | Cmpd Structure | MS (ESI) m/z | Act. Level | Sel. Level |
|---|---|---|---|---|
| 58 | | 370.2 | D | F |
| 59 | | 387.3 | D | F |
| 60 | | 437.5 | D | F |

TABLE 1-continued

| Cmpd No. | Cmpd Structure | MS (ESI) m/z | Act. Level | Sel. Level |
|---|---|---|---|---|
| 61 | | 394.1 | D | F |
| 62 | | 399.2 | D | F |
| 63 | | 450.2 | D | F |
| 64 | | 407.3 | D | F |

TABLE 1-continued

| Cmpd No. | Cmpd Structure | MS (ESI) m/z | Act. Level | Sel. Level |
|---|---|---|---|---|
| 65 | | 368.2 | D | F |
| 66 | | 450.2 | D | F |
| 67 | | 354.2 | D | F |

TABLE 1-continued

| Cmpd No. | Cmpd Structure | MS (ESI) m/z | Act. Level | Sel. Level |
|---|---|---|---|---|
| 68 | | 434.3 | D | F |
| 69 | | 436 | D | F |
| 70 | | 463.1 | D | F |
| 71 | | 407.3 | D | F |

TABLE 1-continued

| Cmpd No. | Cmpd Structure | MS (ESI) m/z | Act. Level | Sel. Level |
|---|---|---|---|---|
| 72 | | 479.5 | D | F |
| 73 | | 437.5 | D | F |
| 74 | | 450.1 | D | F |
| 75 | | 393.2 | D | F |

TABLE 1-continued

| Cmpd No. | Cmpd Structure | MS (ESI) m/z | Act. Level | Sel. Level |
|---|---|---|---|---|
| 76 | | 445.5 | D | F |
| 77 | | 438.4 | D | F |
| 78 | | 541 | D | F |

TABLE 1-continued

| Cmpd No. | Cmpd Structure | MS (ESI) m/z | Act. Level | Sel. Level |
|---|---|---|---|---|
| 79 | | 420.2 | D | F |
| 80 | | 459.4 | D | F |
| 1p;4p 81 | | 437 | D | F |

TABLE 1-continued

| Cmpd No. | Cmpd Structure | MS (ESI) m/z | Act. Level | Sel. Level |
|---|---|---|---|---|
| 82 | | 466.3 | D | F |
| 83 | | 481.4 | D | F |
| 84 | | 416.4 | D | F |

TABLE 1-continued

| Cmpd No. | Cmpd Structure | MS (ESI) m/z | Act. Level | Sel. Level |
|---|---|---|---|---|
| 85 | | 481.4 | D | F |
| 86 | | 434.1 | D | F |
| 87 | | 407.3 | D | F |

TABLE 1-continued

| Cmpd No. | Cmpd Structure | MS (ESI) m/z | Act. Level | Sel. Level |
|---|---|---|---|---|
| 88 | | 420.4 | D | F |
| 89 | | 438.4 | D | F |
| 90 | | 365.2 | D | F |

TABLE 1-continued

| Cmpd No. | Cmpd Structure | MS (ESI) m/z | Act. Level | Sel. Level |
|---|---|---|---|---|
| 91 | | 450.2 | C | F |
| 92 | | 386.1 | C | F |
| 93 | | 420.2 | C | F |
| 94 | | 408.2 | C | F |

TABLE 1-continued

| Cmpd No. | Cmpd Structure | MS (ESI) m/z | Act. Level | Sel. Level |
|---|---|---|---|---|
| 95 | | 408.2 | C | F |
| 96 | | 394 | C | F |
| 97 | | 463.1 | C | F |
| 98 | | 479.5 | C | F |

TABLE 1-continued

| Cmpd No. | Cmpd Structure | MS (ESI) m/z | Act. Level | Sel. Level |
|---|---|---|---|---|
| 99 | | 420.4 | C | F |
| 100 | | 423.4 | C | F |
| 101 | | 435.1 | C | F |
| 102 | | 450.1 | C | F |

TABLE 1-continued

| Cmpd No. | Cmpd Structure | MS (ESI) m/z | Act. Level | Sel. Level |
|---|---|---|---|---|
| 103 | | 450.1 | C | F |
| 104 | | 393.1 | C | F |
| 105 | | 452.1 | C | F |
| 106 | | 408 | C | F |

TABLE 1-continued

| Cmpd No. | Cmpd Structure | MS (ESI) m/z | Act. Level | Sel. Level |
|---|---|---|---|---|
| 107 | | 438.4 | C | F |
| 108 | | 365.2 | C | F |
| 109 | | 400.2 | C | F |
| 110 | | 414.2 | C | F |

TABLE 1-continued

| Cmpd No. | Cmpd Structure | MS (ESI) m/z | Act. Level | Sel. Level |
|---|---|---|---|---|
| 111 | | 420.2 | C | F |
| 112 | | 433.2 | C | F |
| 113 | | 393.1 | C | F |
| 114 | | 437.5 | C | F |

TABLE 1-continued
| Cmpd No. | Cmpd Structure | MS (ESI) m/z | Act. Level | Sel. Level |
|---|---|---|---|---|
| 115 | 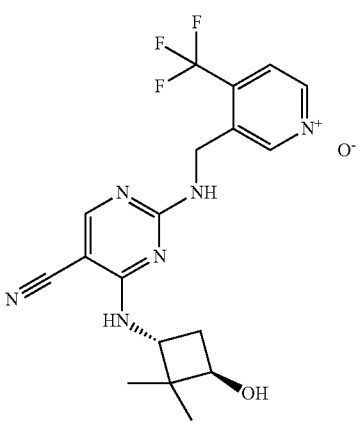 | 409 | C | F |
| 116 | 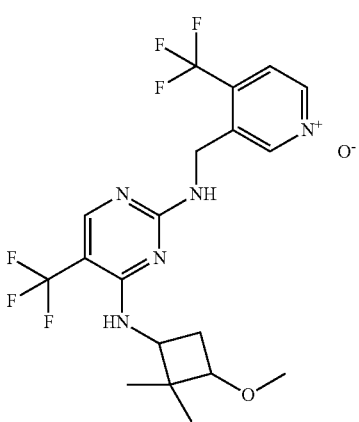 | 466.4 | C | F |
| 117 | 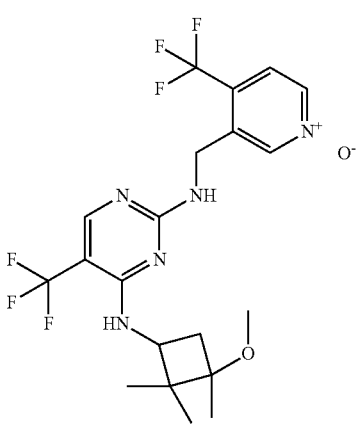 | 479.5 | C | F |

TABLE 1-continued

| Cmpd No. | Cmpd Structure | MS (ESI) m/z | Act. Level | Sel. Level |
|---|---|---|---|---|
| 118 | | 416.1 | C | F |
| 119 | | 368.1 | C | F |
| 120 | | 436.1 | C | F |
| 121 | | 420.4 | C | F |

TABLE 1-continued

| Cmpd No. | Cmpd Structure | MS (ESI) m/z | Act. Level | Sel. Level |
|---|---|---|---|---|
| 122 | | 407.4 | C | F |
| 123 | | 354.2 | C | F |
| 124 | | 445.2 | B | F |

TABLE 1-continued

| Cmpd No. | Cmpd Structure | MS (ESI) m/z | Act. Level | Sel. Level |
|---|---|---|---|---|
| 125 | | 481.4 | D | G |
| 126 | | 480 | D | G |
| 127 | | 480 | D | G |

TABLE 1-continued

| Cmpd No. | Cmpd Structure | MS (ESI) m/z | Act. Level | Sel. Level |
|---|---|---|---|---|
| 128 | | 354.2 | C | G |
| 129 | | 381.3 | C | G |
| 130 | | 420.8 | C | G |

TABLE 1-continued

| Cmpd No. | Cmpd Structure | MS (ESI) m/z | Act. Level | Sel. Level |
|---|---|---|---|---|
| 131 | | 450.4 | C | G |
| 132 | | 393.1 | C | G |
| 133 | | 420.2 | C | G |
| 134 | | 409 | C | G |

TABLE 1-continued
| Cmpd No. | Cmpd Structure | MS (ESI) m/z | Act. Level | Sel. Level |
|---|---|---|---|---|
| 135 | 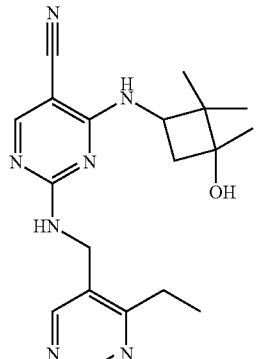 | 368.2 | C | G |
| 136 | 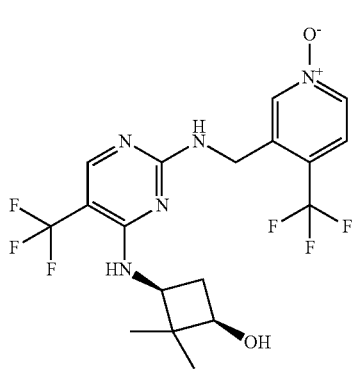 [SMILES: CC1(C)[C@H](O)C[C@@H]1Nc1nc(NCc2c[n+]([O-])ccc2C(F)(F)F)ncc1C(F)(F)F] | 452.1 | C | G |
| 137 | 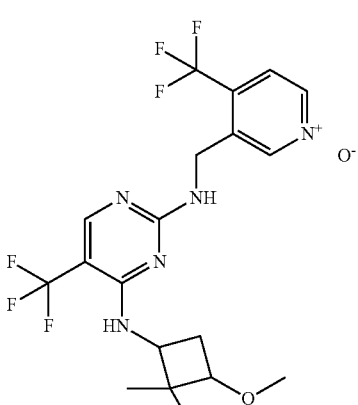 | 466.4 | C | G |
| 138 | 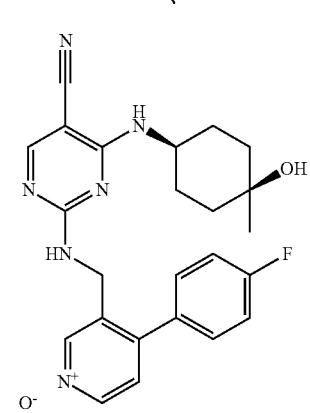 | 449.3 | C | G |

TABLE 1-continued

| Cmpd No. | Cmpd Structure | MS (ESI) m/z | Act. Level | Sel. Level |
|---|---|---|---|---|
| 139 | | 452.1 | C | G |
| 140 | | 382.3 | C | G |
| 141 | | 466.2 | B | G |
| 142 | | 354.2 | B | G |

TABLE 1-continued

| Cmpd No. | Cmpd Structure | MS (ESI) m/z | Act. Level | Sel. Level |
|---|---|---|---|---|
| 143 | | 436.1 | B | G |
| 144 | | 437.5 | B | G |
| 145 | | 423.2 | B | G |
| 146 | | 437.4 | B | G |

TABLE 1-continued
| Cmpd No. | Cmpd Structure | MS (ESI) m/z | Act. Level | Sel. Level |
|---|---|---|---|---|
| 147 | 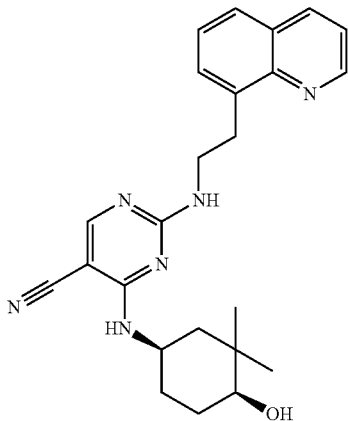 [SMILES: CC1(C)C[C@H](Nc2nc(NCCc3cccc4cccnc34)ncc2C#N)CC[C@@H]1O] | 416.4 | C | G |
| 148 | 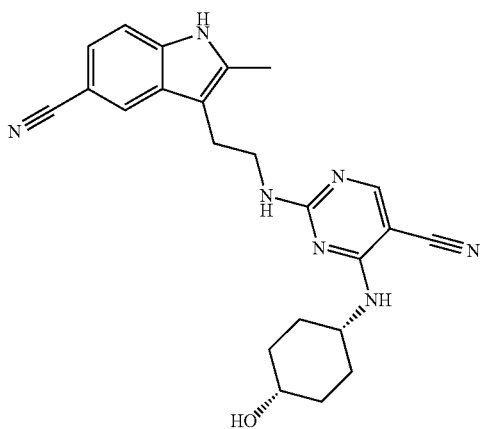 [SMILES: Cc1[nH]c2ccc(C#N)cc2c1CCNc1ncc(C#N)c(N[C@H]2CC[C@@H](O)CC2)n1] | 416.2 | A | H |
| 149 | 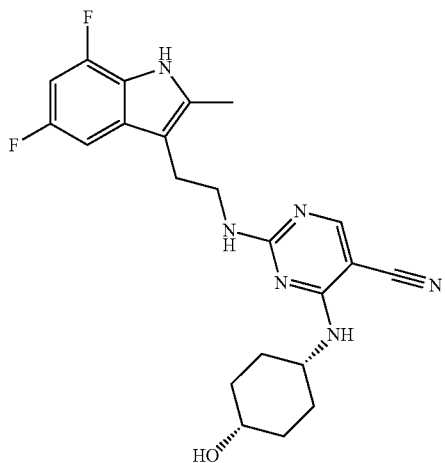 [SMILES: Cc1[nH]c2c(F)cc(F)cc2c1CCNc1ncc(C#N)c(N[C@H]2CC[C@@H](O)CC2)n1] | 426.4 | A | H |

TABLE 1-continued

| Cmpd No. | Cmpd Structure | MS (ESI) m/z | Act. Level | Sel. Level |
|---|---|---|---|---|
| 150 | | 388.4 | A | H |
| 151 | | 407.2 | A | H |
| 152 | | 353.4 | A | H |

TABLE 1-continued
| Cmpd No. | Cmpd Structure | MS (ESI) m/z | Act. Level | Sel. Level |
|---|---|---|---|---|
| 153 | 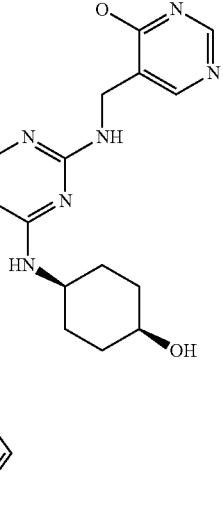 | 420.2 | D | |
| 154 |  | 377.2 | C | |
| 155 | 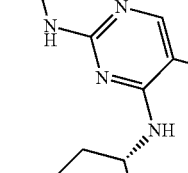 | 393.2 | C | |

TABLE 1-continued

| Cmpd No. | Cmpd Structure | MS (ESI) m/z | Act. Level | Sel. Level |
|---|---|---|---|---|
| 156 | | 446.2 | B | G |
| 157 | | 434.2 | C | F |
| 158 | | 421.2 | C | G |
| 159 | | 422.2 | C | F |

TABLE 1-continued

| Cmpd No. | Cmpd Structure | MS (ESI) m/z | Act. Level | Sel. Level |
|---|---|---|---|---|
| 160 | | 461.2 | D | E |
| 161 | | 448.5 | C | F |
| 162 | | 409.2 | A | H |
| 163 | | 402.2 | A | H |

TABLE 1-continued

| Cmpd No. | Cmpd Structure | MS (ESI) m/z | Act. Level | Sel. Level |
|---|---|---|---|---|
| 164 | | 407.2 | B | G |
| 165 | | 395.2 | B | G |
| 166 | | 407.2 | B | G |

TABLE 1-continued

| Cmpd No. | Cmpd Structure | MS (ESI) m/z | Act. Level | Sel. Level |
|---|---|---|---|---|
| 167 | | 455.2 | C | |
| 168 | | 419.2 | C | |
| 169 | | 439.2 | C | |

TABLE 1-continued

| Cmpd No. | Cmpd Structure | MS (ESI) m/z | Act. Level | Sel. Level |
|---|---|---|---|---|
| 170 | | 489.2 | C | |
| 171 | | 489.2 | A | |
| 172 | | 419.2 | C | F |

TABLE 1-continued

| Cmpd No. | Cmpd Structure | MS (ESI) m/z | Act. Level | Sel. Level |
|---|---|---|---|---|
| 173 | | 439.2 | C | F |
| 174 | | 419.2 | B | H |
| 175 | | 435.2 | C | G |

TABLE 1-continued
| Cmpd No. | Cmpd Structure | MS (ESI) m/z | Act. Level | Sel. Level |
|---|---|---|---|---|
| 176 | 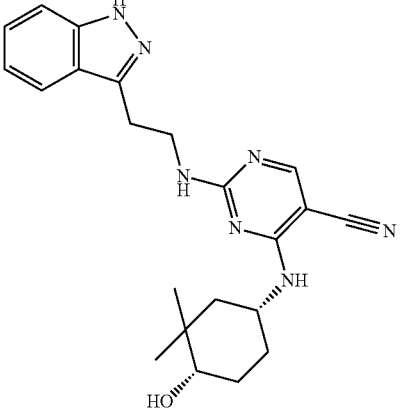 | 406.2 | B | |
| 177 | 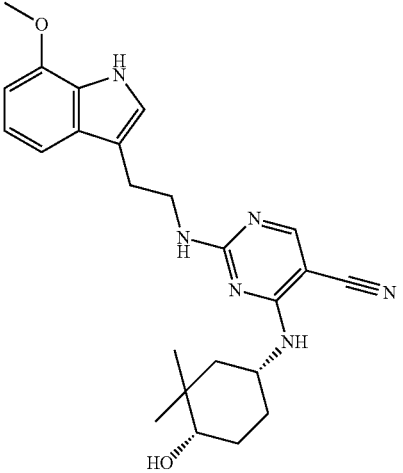 [SMILES: COc1cccc2c(CCNc3ncc(C#N)c(N[C@@H]4CC[C@H](O)C(C)(C)C4)n3)c[nH]c12] | 435.2 | C | |
| 178 | 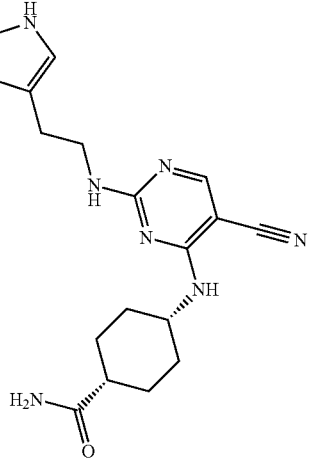 | 422.2 | D | F |

TABLE 1-continued

| Cmpd No. | Cmpd Structure | MS (ESI) m/z | Act. Level | Sel. Level |
|---|---|---|---|---|
| 179 | | 420.2 | D | E |
| 180 | | 448.2 | D | E |
| 181 | | 423.2 | C | |

TABLE 1-continued
| Cmpd No. | Cmpd Structure | MS (ESI) m/z | Act. Level | Sel. Level |
|---|---|---|---|---|
| 182 | 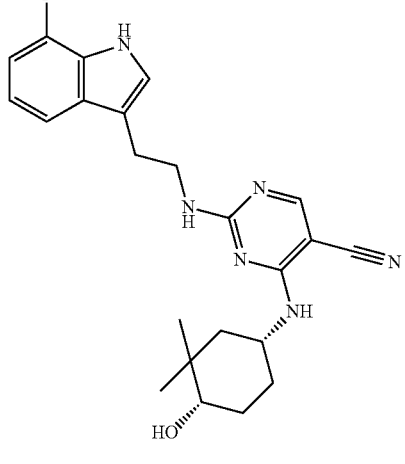 | 423.2 | D | |
| 183 | 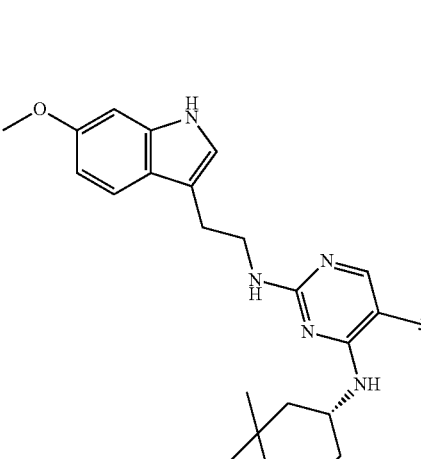 | 435.3 | D | |
| 184 | 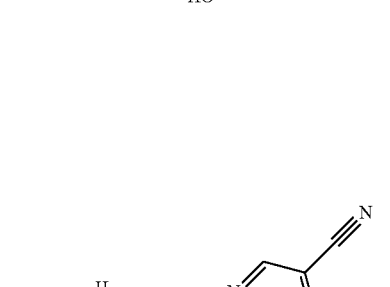 | 437.2 | C | |

TABLE 1-continued
| Cmpd No. | Cmpd Structure | MS (ESI) m/z | Act. Level | Sel. Level |
|---|---|---|---|---|
| 185 | 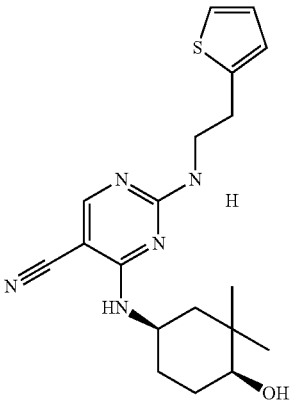 | 372.2 | C | F |
| 186 | 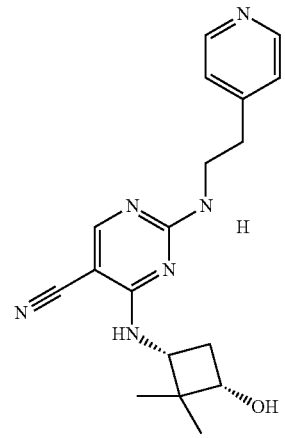 | 339.2 | B | G |
| 187 | 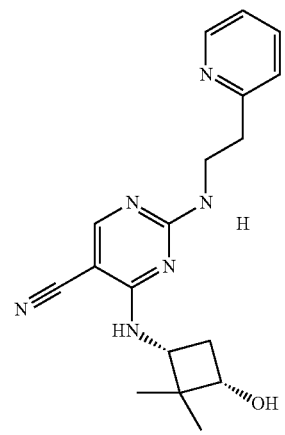 | 339.2 | A | H |

TABLE 1-continued

| Cmpd No. | Cmpd Structure | MS (ESI) m/z | Act. Level | Sel. Level |
|---|---|---|---|---|
| 188 | | 342.2 | A | H |
| 189 | | 344.2 | C | H |
| 190 | | 389.2 | A | H |

TABLE 1-continued
| Cmpd No. | Cmpd Structure | MS (ESI) m/z | Act. Level | Sel. Level |
|---|---|---|---|---|
| 191 | 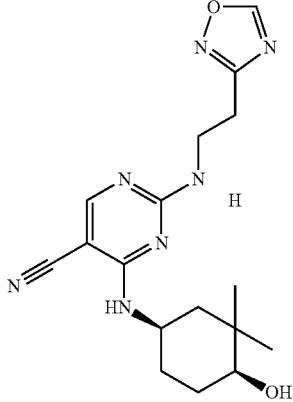 | 358.2 | A | H |
| 192 | 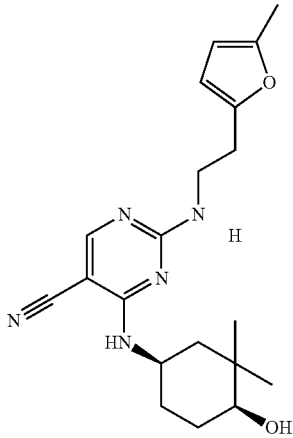 | 370.2 | C | F |
| 193 | 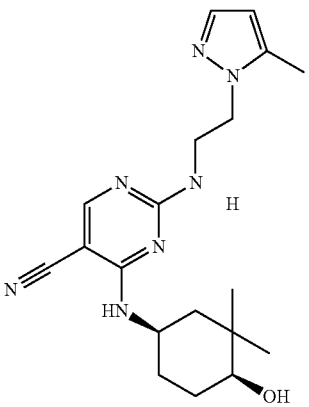 | 370.2 | A | H |

TABLE 1-continued

| Cmpd No. | Cmpd Structure | MS (ESI) m/z | Act. Level | Sel. Level |
|---|---|---|---|---|
| 194 | | 370.2 | A | H |
| 195 | | 372.2 | A | H |
| 196 | | 356.2 | C | G |

TABLE 1-continued

| Cmpd No. | Cmpd Structure | MS (ESI) m/z | Act. Level | Sel. Level |
|---|---|---|---|---|
| 197 | | 381.2 | B | G |
| 198 | | 384.2 | A | H |
| 199 | | 402.2 | A | H |

TABLE 1-continued

| Cmpd No. | Cmpd Structure | MS (ESI) m/z | Act. Level | Sel. Level |
|---|---|---|---|---|
| 200 | | 405.2 | B | G |
| 201 | | 355.2 | C | F |
| 202 | | 406.2 | A | H |
| 203 | | 405.2 | D | F |

TABLE 1-continued

| Cmpd No. | Cmpd Structure | MS (ESI) m/z | Act. Level | Sel. Level |
|---|---|---|---|---|
| 204 | | 406.2 | C | F |
| 205 | | 407.2 | A | H |
| 206 | | 419.2 | C | F |
| 207 | | 420.2 | A | H |

TABLE 1-continued

| Cmpd No. | Cmpd Structure | MS (ESI) m/z | Act. Level | Sel. Level |
|---|---|---|---|---|
| 208 | | 356.2 | C | G |
| 209 | | 432.2 | A | H |
| 210 | | 438.2 | B | G |

TABLE 1-continued

| Cmpd No. | Cmpd Structure | MS (ESI) m/z | Act. Level | Sel. Level |
|---|---|---|---|---|
| 211 | | 356.2 | A | H |
| 212 | | 370.2 | A | H |
| 213 | | 381.2 | A | H |

TABLE 1-continued

| Cmpd No. | Cmpd Structure | MS (ESI) m/z | Act. Level | Sel. Level |
|---|---|---|---|---|
| 214 | | 381.2 | A | H |
| 215 | | 397.2 | B | G |
| 216 | | 356.2 | B | G |

TABLE 1-continued

| Cmpd No. | Cmpd Structure | MS (ESI) m/z | Act. Level | Sel. Level |
|---|---|---|---|---|
| 217 | | 405.2 | C | G |
| 218 | | 408.2 | A | H |
| 219 | | 426.2 | B | G |

TABLE 1-continued

| Cmpd No. | Cmpd Structure | MS (ESI) m/z | Act. Level | Sel. Level |
|---|---|---|---|---|
| 220 | | 357.2 | B | G |
| 221 | | 356.2 | A | H |
| 222 | | 357.2 | B | G |

TABLE 1-continued
| Cmpd No. | Cmpd Structure | MS (ESI) m/z | Act. Level | Sel. Level |
|---|---|---|---|---|
| 223 | 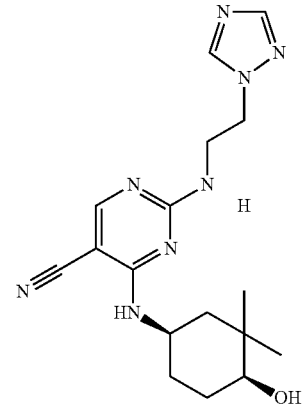 | 357.2 | A | H |
| 224 | 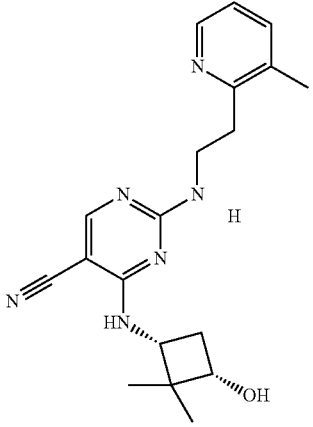 | 353.2 | A | H |
| 225 | 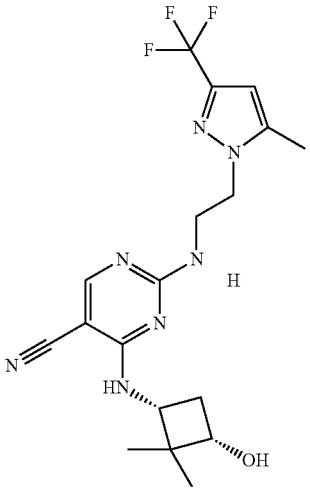 | 410.2 | A | H |

TABLE 1-continued

| Cmpd No. | Cmpd Structure | MS (ESI) m/z | Act. Level | Sel. Level |
|---|---|---|---|---|
| 226 | | 340.2 | A | H |
| 227 | | 369.2 | B | G |
| 228 | | 329.2 | B | G |

TABLE 1-continued

| Cmpd No. | Cmpd Structure | MS (ESI) m/z | Act. Level | Sel. Level |
|---|---|---|---|---|
| 229 | | 377.2 | B | G |
| 230 | | 330.2 | A | H |
| 231 | | 339.2 | B | G |

TABLE 1-continued

| Cmpd No. | Cmpd Structure | MS (ESI) m/z | Act. Level | Sel. Level |
|---|---|---|---|---|
| 232 | | 342.2 | C | F |
| 233 | | 344.2 | A | H |
| 234 | | 327.2 | B | G |

TABLE 1-continued

| Cmpd No. | Cmpd Structure | MS (ESI) m/z | Act. Level | Sel. Level |
|---|---|---|---|---|
| 235 | | 353.2 | A | H |
| 236 | | 374.2 | A | H |
| 237 | | 377.2 | B | G |

TABLE 1-continued

| Cmpd No. | Cmpd Structure | MS (ESI) m/z | Act. Level | Sel. Level |
|---|---|---|---|---|
| 238 | | 328.2 | C | G |
| 239 | | 378.2 | A | H |
| 240 | | 377.2 | D | G |

TABLE 1-continued

| Cmpd No. | Cmpd Structure | MS (ESI) m/z | Act. Level | Sel. Level |
|---|---|---|---|---|
| 241 | | 378.2 | B | G |
| 242 | | 379.2 | A | H |
| 243 | | 391.2 | B | G |
| 244 | | 328.2 | C | G |

TABLE 1-continued

| Cmpd No. | Cmpd Structure | MS (ESI) m/z | Act. Level | Sel. Level |
|---|---|---|---|---|
| 245 | | 328.2 | B | G |
| 246 | | 329.2 | A | H |
| 247 | | 421.2 | D | |
| 248 | | 435.2 | D | F |

TABLE 1-continued

| Cmpd No. | Cmpd Structure | MS (ESI) m/z | Act. Level | Sel. Level |
|---|---|---|---|---|
| 249 | | 449.2 | D | E |
| 250 | | 381.2 | B | G |
| 251 | | 430.2 | C | G |
| 252 | | 423.2 | D | E |

TABLE 1-continued

| Cmpd No. | Cmpd Structure | MS (ESI) m/z | Act. Level | Sel. Level |
|---|---|---|---|---|
| 253 | | 465.2 | C | F |
| 254 | | 488.2 | C | G |
| 255 | | 406.2 | A | H |
| 256 | | 417.2 | B | G |
| 257 | | 411.2 | B | G |

TABLE 1-continued

| Cmpd No. | Cmpd Structure | MS (ESI) m/z | Act. Level | Sel. Level |
|---|---|---|---|---|
| 258 | | 381.2 | C | F |
| 259 | | 393.2 | D | E |
| 260 | | 407.2 | D | F |
| 261 | | 421.2 | D | |
| 262 | | 353.2 | A | H |

TABLE 1-continued

| Cmpd No. | Cmpd Structure | MS (ESI) m/z | Act. Level | Sel. Level |
|---|---|---|---|---|
| 263 | | 411.2 | C | G |
| 264 | | 402.2 | C | G |
| 265 | | 395.2 | C | G |
| 266 | | 484.2 | A | H |
| 267 | | 383.2 | B | G |

TABLE 1-continued

| Cmpd No. | Cmpd Structure | MS (ESI) m/z | Act. Level | Sel. Level |
|---|---|---|---|---|
| 268 | | 353.2 | B | G |
| 269 | | 462.2 | C | F |
| 270 | | 462.2 | D | E |
| 271 | | 435.3 | B | G |

TABLE 1-continued

| Cmpd No. | Cmpd Structure | MS (ESI) m/z | Act. Level | Sel. Level |
|---|---|---|---|---|
| 272 | | 435.2 | C | G |
| 273 | | 407.2 | B | G |
| 274 | | 407.1 | B | G |

TABLE 1-continued
| Cmpd No. | Cmpd Structure | MS (ESI) m/z | Act. Level | Sel. Level |
|---|---|---|---|---|
| 275 | 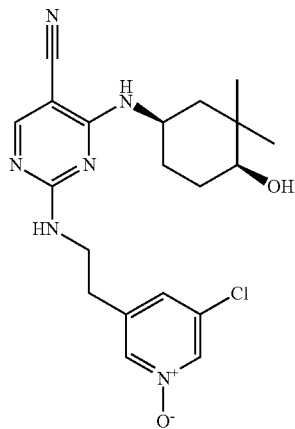 [SMILES: CC1(C)C[C@H](Nc2nc(NCCc3cc(Cl)c[n+]([O-])c3)ncc2C#N)CC[C@@H]1O] | 417.2 | B | G |
| 276 | 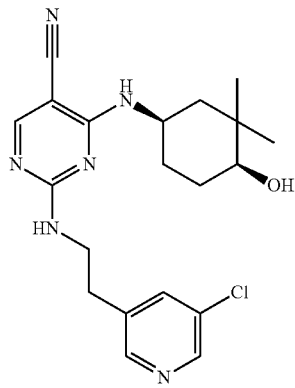 [SMILES: CC1(C)C[C@H](Nc2nc(NCCc3cncc(Cl)c3)ncc2C#N)CC[C@@H]1O] | 401.2 | C | F |
| 277 | 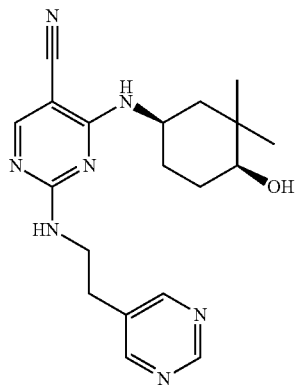 [SMILES: CC1(C)C[C@H](Nc2nc(NCCc3cncnc3)ncc2C#N)CC[C@@H]1O] | 368.2 | A | H |

TABLE 1-continued

| Cmpd No. | Cmpd Structure | MS (ESI) m/z | Act. Level | Sel. Level |
|---|---|---|---|---|
| 278 | | 368.2 | A | H |
| 279 | | 368.2 | A | H |
| 280 | | 367.2 | C | G |
| 281 | | 367.2 | B | G |

TABLE 1-continued
| Cmpd No. | Cmpd Structure | MS (ESI) m/z | Act. Level | Sel. Level |
|---|---|---|---|---|
| 282 | 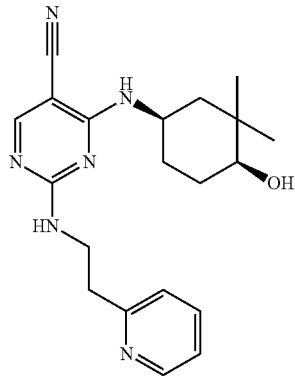 [SMILES: CC1(C)C[C@H](Nc2nc(NCCc3ccccn3)ncc2C#N)CC[C@@H]1O] | 367.2 | A | H |
| 283 | 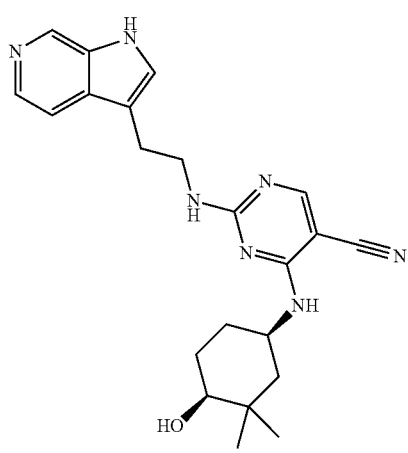 [SMILES: CC1(C)C[C@H](Nc2nc(NCCc3c[nH]c4cnccc34)ncc2C#N)CC[C@@H]1O] | 406.2 | C | F |
| 284 | 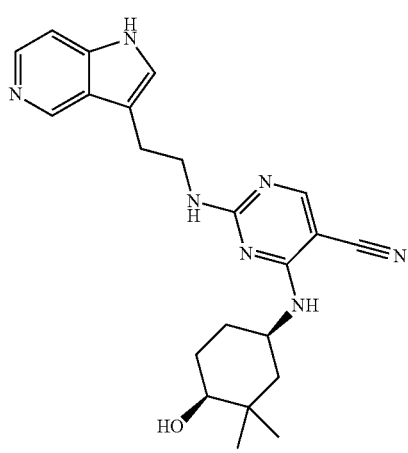 [SMILES: CC1(C)C[C@H](Nc2nc(NCCc3c[nH]c4ccncc34)ncc2C#N)CC[C@@H]1O] | 406.2 | A | H |

TABLE 1-continued

| Cmpd No. | Cmpd Structure | MS (ESI) m/z | Act. Level | Sel. Level |
|---|---|---|---|---|
| 285 | | 434.5 | A | H |
| 286 | | 434.5 | C | F |
| 287 | | 434.2 | C | F |
| 288 | | 404.2 | C | G |

TABLE 1-continued

| Cmpd No. | Cmpd Structure | MS (ESI) m/z | Act. Level | Sel. Level |
|---|---|---|---|---|
| 289 | | 390.2 | B | G |
| 290 | | 376.2 | C | F |
| 291 | | 436.2 | A | H |
| 292 | | 419.2 | D | F |
| 293 | | 422.2 | A | |

TABLE 1-continued

| Cmpd No. | Cmpd Structure | MS (ESI) m/z | Act. Level | Sel. Level |
|---|---|---|---|---|
| 294 | | 446.1 | C | F |
| 295 | | 446.1 | C | F |
| 296 | | 448.2 | C | F |
| 297 | | 448.2 | C | F |

TABLE 1-continued

| Cmpd No. | Cmpd Structure | MS (ESI) m/z | Act. Level | Sel. Level |
|---|---|---|---|---|
| 298 | | 448.2 | D | E |
| 299 | | 448.2 | D | E |
| 300 | | 435.2 | B | G |
| 301 | | 419.2 | C | F |

TABLE 1-continued

| Cmpd No. | Cmpd Structure | MS (ESI) m/z | Act. Level | Sel. Level |
|---|---|---|---|---|
| 302 | | 419.2 | B | G |
| 303 | | 435.2 | A | H |
| 304 | | 435.2 | C | F |
| 305 | | 421.2 | C | G |
| 306 | | 421.2 | C | H |

TABLE 1-continued

| Cmpd No. | Cmpd Structure | MS (ESI) m/z | Act. Level | Sel. Level |
|---|---|---|---|---|
| 307 | | 421.2 | C | G |
| 308 | | 421.2 | C | H |
| 309 | | 439.2 | B | G |
| 310 | | 439.2 | B | H |
| 311 | | 439.2 | C | G |

TABLE 1-continued

| Cmpd No. | Cmpd Structure | MS (ESI) m/z | Act. Level | Sel. Level |
|---|---|---|---|---|
| 312 | | 439.2 | C | G |
| 313 | | 439.2 | C | F |
| 314 | | 439.2 | C | H |
| 315 | | 439.2 | C | G |
| 316 | | 439.2 | D | F |

TABLE 1-continued

| Cmpd No. | Cmpd Structure | MS (ESI) m/z | Act. Level | Sel. Level |
|---|---|---|---|---|
| 317 | | 444.2 | D | E |
| 318 | | 420.2 | D | E |
| 319 | | 380.8 | A | H |
| 320 | | 404.8 | C | F |

TABLE 1-continued

| Cmpd No. | Cmpd Structure | MS (ESI) m/z | Act. Level | Sel. Level |
|---|---|---|---|---|
| 321 | | 380.8 | A | H |
| 322 | | 380.2 | C | G |
| 323 | | 382.2 | C | G |

TABLE 1-continued

| Cmpd No. | Cmpd Structure | MS (ESI) m/z | Act. Level | Sel. Level |
|---|---|---|---|---|
| 324 | | 368.2 | B | G |
| 325 | | 433.8 | C | F |
| 326 | | 435.2 | C | G |

TABLE 1-continued

| Cmpd No. | Cmpd Structure | MS (ESI) m/z | Act. Level | Sel. Level |
|---|---|---|---|---|
| 327 | | 369.2 | A | H |
| 328 | | 383.2 | A | H |
| 329 | | 397.2 | C | G |

TABLE 1-continued

| Cmpd No. | Cmpd Structure | MS (ESI) m/z | Act. Level | Sel. Level |
|---|---|---|---|---|
| 330 | | 411.2 | C | G |
| 331 | | 369.2 | A | H |
| 332 | | 420.2 | D | E |

TABLE 1-continued
| Cmpd No. | Cmpd Structure | MS (ESI) m/z | Act. Level | Sel. Level |
|---|---|---|---|---|
| 333 | | 434.2 | D | E |
| 334 | | 452.2 | D | E |
TABLE 2
| Cmpd No. | Cmpd Structure | MS (ESI) m/z | Act. Level | Sel. Level |
|---|---|---|---|---|
| 1 | 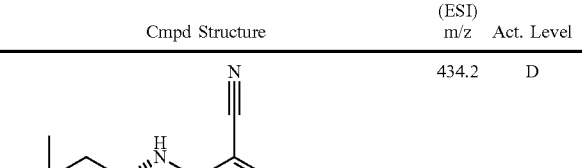 | 434.2 | D | E |

TABLE 2-continued

| Cmpd No. | Cmpd Structure | MS (ESI) m/z | Act. Level | Sel. Level |
|---|---|---|---|---|
| 2 | | 477.1 | D | E |
| 3 | | 410.2 | D | F |
| 4 | | 390.2 | C | F |

TABLE 2-continued
| Cmpd No. | Cmpd Structure | MS (ESI) m/z | Act. Level | Sel. Level |
|---|---|---|---|---|
| 5 | 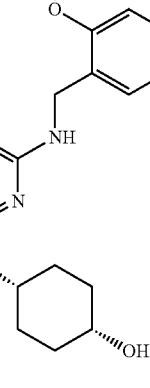 | 382.1 | C | F |
| 6 | 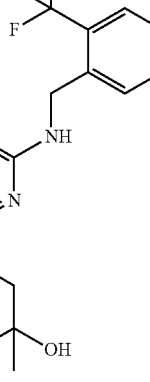 | 367.3 | C | F |
| 7 | 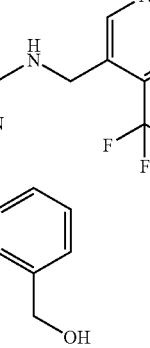 | 415.4 | C | F |

TABLE 2-continued

| Cmpd No. | Cmpd Structure | MS (ESI) m/z | Act. Level | Sel. Level |
|---|---|---|---|---|
| 8 | | 392.4 | C | G |
| 9 | | 358.4 | C | G |
| 10 | | 400.2 | C | G |

TABLE 2-continued

| Cmpd No. | Cmpd Structure | MS (ESI) m/z | Act. Level | Sel. Level |
|---|---|---|---|---|
| 11 | | 418.5 | B | G |
| 12 | | 434.3 | B | G |
| 13 | | 409.5 | B | G |

TABLE 2-continued

| Cmpd No. | Cmpd Structure | MS (ESI) m/z | Act. Level | Sel. Level |
|---|---|---|---|---|
| 14 | | 477.1 | B | G |
| 15 | | 367.2 | C | G |
| 16 | | 376.5 | C | H |

TABLE 2-continued
| Cmpd No. | Cmpd Structure | MS (ESI) m/z | Act. Level | Sel. Level |
|---|---|---|---|---|
| 17 | 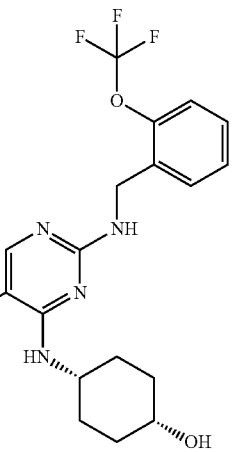 | 408.3 | B | H |
| 18 | 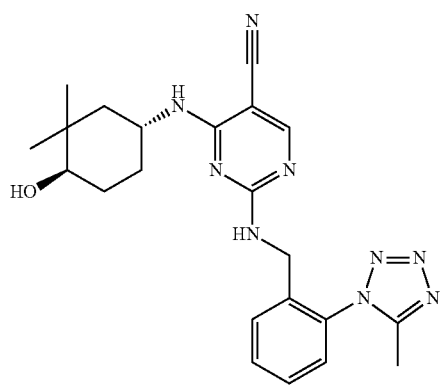 [SMILES: Cc1nnnn1-c1ccccc1CNc1ncc(C#N)c(N[C@@H]2CC[C@@H](O)C(C)(C)C2)n1] | 434.2 | A | H |
| 19 | 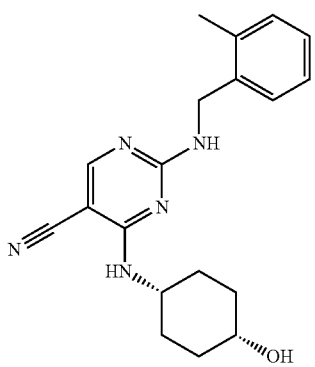 [SMILES: Cc1ccccc1CNc1ncc(C#N)c(N[C@H]2CC[C@@H](O)CC2)n1] | 338.4 | A | H |
| 20 | 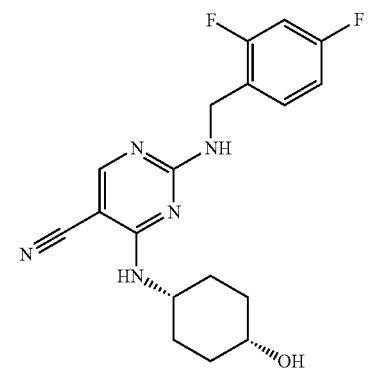 [SMILES: N#Cc1cnc(NCc2ccc(F)cc2F)nc1N[C@H]1CC[C@@H](O)CC1] | 360.2 | A | H |

TABLE 2-continued
| Cmpd No. | Cmpd Structure | MS (ESI) m/z | Act. Level | Sel. Level |
|---|---|---|---|---|
| 21 | 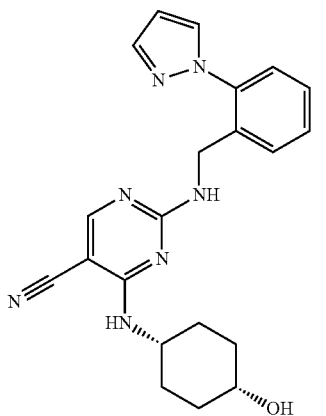 [SMILES: N#Cc1cnc(NCc2ccccc2-n2cccn2)nc1N[C@H]1CC[C@@H](O)CC1] | 390.4 | A | H |
| 22 | 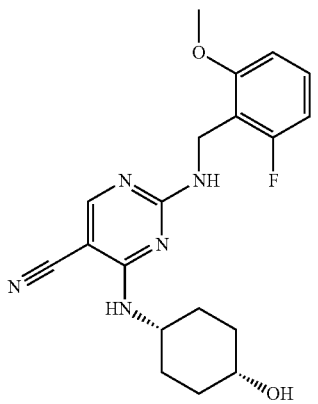 [SMILES: COc1cccc(F)c1CNc1ncc(C#N)c(N[C@H]2CC[C@@H](O)CC2)n1] | 372.4 | A | H |
| 23 | 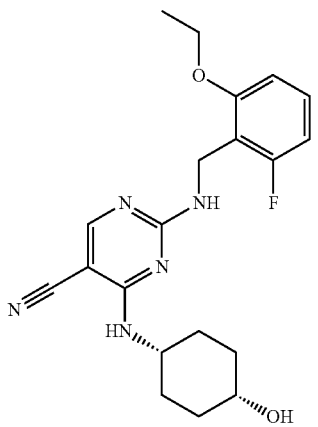 [SMILES: CCOc1cccc(F)c1CNc1ncc(C#N)c(N[C@H]2CC[C@@H](O)CC2)n1] | 386.6 | A | H |

TABLE 2-continued
| Cmpd No. | Cmpd Structure | MS (ESI) m/z | Act. Level | Sel. Level |
|---|---|---|---|---|
| 24 | 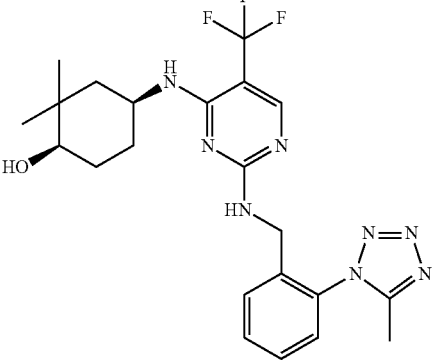 | 477.1 | A | H |
| 25 | 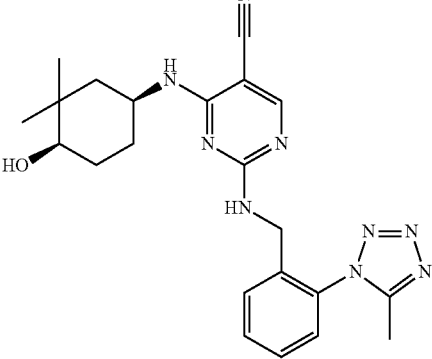 | 434.2 | A | H |
| 26 | 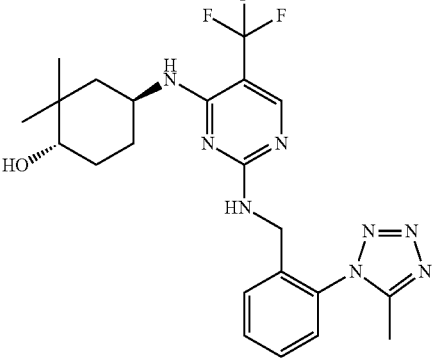 | 477.1 | A | H |
| 27 | 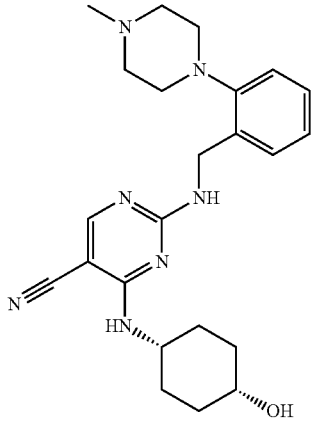 [SMILES: CN1CCN(c2ccccc2CNc2ncc(C#N)c(N[C@H]3CC[C@@H](O)CC3)n2)CC1] | 42204 | A | H |

TABLE 2-continued
| Cmpd No. | Cmpd Structure | MS (ESI) m/z | Act. Level | Sel. Level |
|---|---|---|---|---|
| 28 | 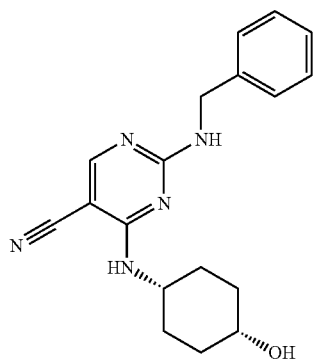 [SMILES: N#Cc1cnc(NCc2ccccc2)nc1N[C@H]1CC[C@@H](O)CC1] | 324.4 | A | H |
| 29 | 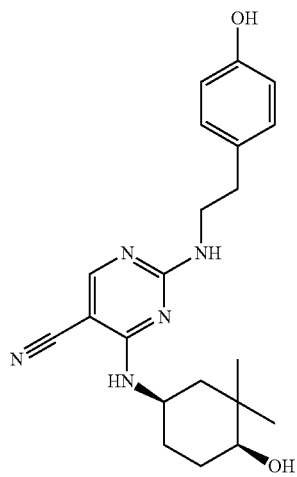 [SMILES: CC1(C)C[C@H](Nc2nc(NCCc3ccc(O)cc3)ncc2C#N)CC[C@@H]1O] | 382.4 | D | H |
| 30 | 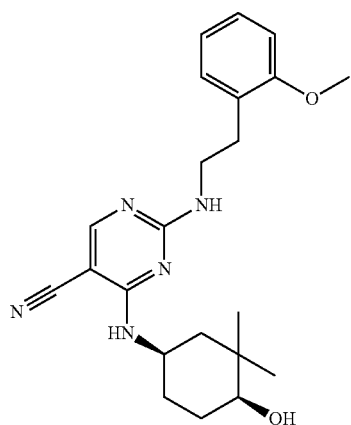 [SMILES: COc1ccccc1CCNc1ncc(C#N)c(N[C@@H]2CC[C@H](O)C(C)(C)C2)n1] | 396.3 | C | F |

TABLE 2-continued

| Cmpd No. | Cmpd Structure | MS (ESI) m/z | Act. Level | Sel. Level |
|---|---|---|---|---|
| 31 | | 396.3 | D | F |
| 32 | | 400.2 | D | E |
| 33 | | 400.2 | C | F |

TABLE 2-continued

| Cmpd No. | Cmpd Structure | MS (ESI) m/z | Act. Level | Sel. Level |
|---|---|---|---|---|
| 34 | | 394.2 | C | F |
| 35 | | 394.2 | D | F |
| 36 | | 426.2 | C | G |

TABLE 2-continued

| Cmpd No. | Cmpd Structure | MS (ESI) m/z | Act. Level | Sel. Level |
|---|---|---|---|---|
| 37 | | 391.2 | C | F |
| 38 | | 363.2 | C | G |
| 39 | | 480.4 | A | H |

TABLE 2-continued

| Cmpd No. | Cmpd Structure | MS (ESI) m/z | Act. Level | Sel. Level |
|---|---|---|---|---|
| 40 | | 400.2 | A | H |
| 41 | | 352.4 | B | G |
| 42 | | 352.3 | C | H |

TABLE 2-continued

| Cmpd No. | Cmpd Structure | MS (ESI) m/z | Act. Level | Sel. Level |
|---|---|---|---|---|
| 43 | | 374.2 | C | H |
| 44 | | 406.2 | C | G |
| 45 | | 406.2 | C | G |

TABLE 2-continued

| Cmpd No. | Cmpd Structure | MS (ESI) m/z | Act. Level | Sel. Level |
|---|---|---|---|---|
| 46 | | 406.2 | B | G |
| 47 | | 354.3 | C | H |
| 48 | | 404.2 | D | F |

TABLE 2-continued

| Cmpd No. | Cmpd Structure | MS (ESI) m/z | Act. Level | Sel. Level |
|---|---|---|---|---|
| 49 | | 381.2 | C | F |
| 50 | | 448.2 | A | H |
| 51 | | 450.2 | C | G |

TABLE 2-continued

| Cmpd No. | Cmpd Structure | MS (ESI) m/z | Act. Level | Sel. Level |
|---|---|---|---|---|
| 52 | | 462.2 | C | G |
| 53 | | 450.2 | C | F |
| 54 | | 502.2 | B | G |

TABLE 2-continued

| Cmpd No. | Cmpd Structure | MS (ESI) m/z | Act. Level | Sel. Level |
|---|---|---|---|---|
| 55 | | 450.2 | C | G |
| 56 | | 393.3 | B | G |
| 57 | | 396.2 | C | H |

TABLE 2-continued

| Cmpd No. | Cmpd Structure | MS (ESI) m/z | Act. Level | Sel. Level |
|---|---|---|---|---|
| 58 | | 442.3 | B | G |
| 59 | | 462.2 | C | F |

TABLE 2-continued
| Cmpd No. | Cmpd Structure | MS (ESI) m/z | Act. Level | Sel. Level |
|---|---|---|---|---|
| 60 | 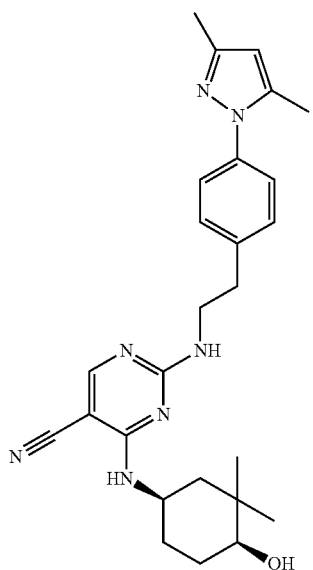 [SMILES: Cc1cc(C)n(-c2ccc(CCNc3ncc(C#N)c(N[C@@H]4CC[C@H](O)C(C)(C)C4)n3)cc2)n1] | 459.2 | B | G |
| 61 | 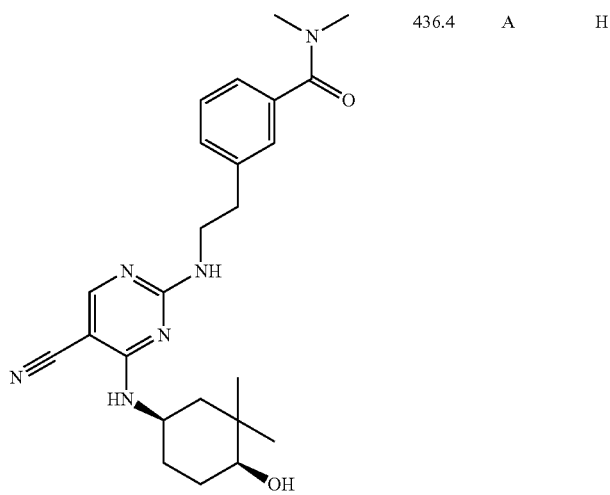 | 436.4 | A | H |

TABLE 2-continued
| Cmpd No. | Cmpd Structure | MS (ESI) m/z | Act. Level | Sel. Level |
|---|---|---|---|---|
| 62 | 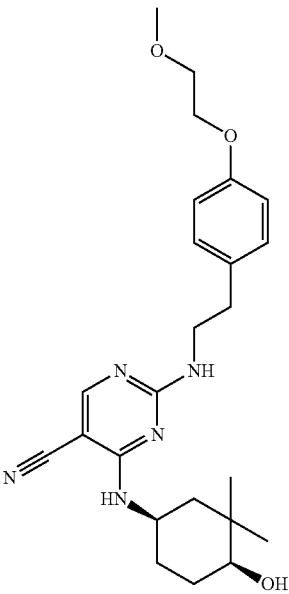 [SMILES: COCCOc1ccc(CCNc2ncc(C#N)c(N[C@@H]3CC[C@H](O)C(C)(C)C3)n2)cc1] | 439.5 | C | F |
| 63 | 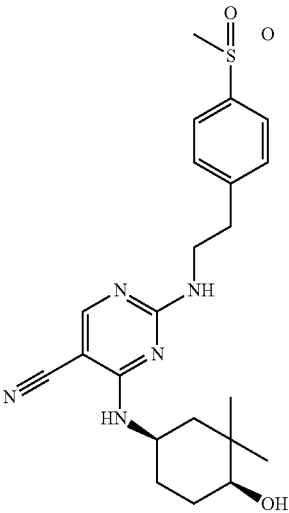 | 443 | C | F |

TABLE 2-continued

| Cmpd No. | Cmpd Structure | MS (ESI) m/z | Act. Level | Sel. Level |
|---|---|---|---|---|
| 64 | | 462 | D | E |
| 65 | | 444.3 | C | F |
| 66 | | 415.4 | C | F |

TABLE 2-continued
| Cmpd No. | Cmpd Structure | MS (ESI) m/z | Act. Level | Sel. Level |
|---|---|---|---|---|
| 67 | 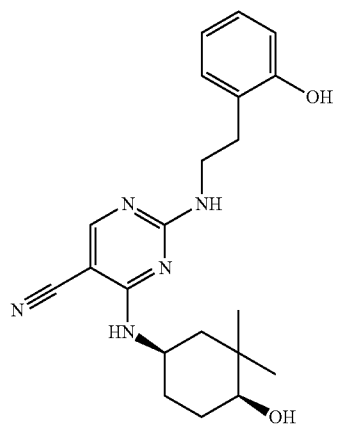 [SMILES: CC1(C)C[C@H](Nc2nc(NCCc3ccccc3O)ncc2C#N)CC[C@@H]1O] | 381.5 | C | F |
| 68 | 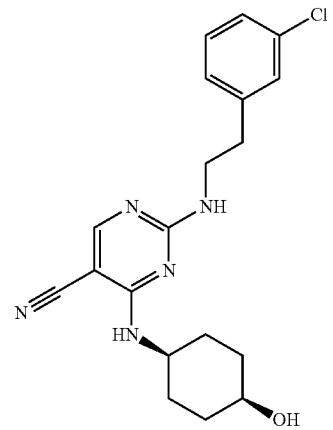 [SMILES: N#Cc1cnc(NCCc2cccc(Cl)c2)nc1N[C@H]1CC[C@@H](O)CC1] | 372.2 | C | F |
| 69 | 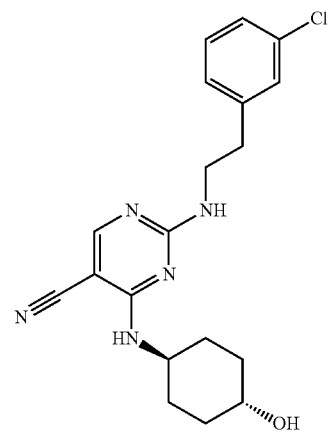 [SMILES: N#Cc1cnc(NCCc2cccc(Cl)c2)nc1N[C@H]1CC[C@H](O)CC1] | 372.2 | B | G |

TABLE 2-continued

| Cmpd No. | Cmpd Structure | MS (ESI) m/z | Act. Level | Sel. Level |
|---|---|---|---|---|
| 70 | | 344.2 | B | G |
| 71 | | 344 | A | H |
| 72 | | 415.4 | C | F |

TABLE 2-continued

| Cmpd No. | Cmpd Structure | MS (ESI) m/z | Act. Level | Sel. Level |
|---|---|---|---|---|
| 73 | | 363.2 | B | G |
| 74 | | 386.2 | D | F |
| 75 | | 386.2 | B | G |
| 76 | | 386.2 | D | F |

TABLE 2-continued
| Cmpd No. | Cmpd Structure | MS (ESI) m/z | Act. Level | Sel. Level |
|---|---|---|---|---|
| 77 | 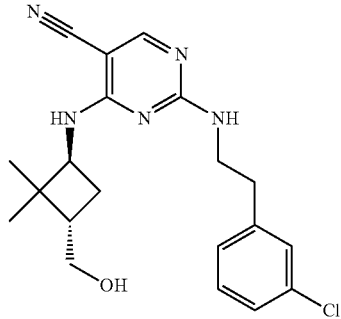 [SMILES: CC1(C)[C@@H](CO)C[C@@H]1Nc1nc(NCCc2cccc(Cl)c2)ncc1C#N] | 386.2 | A | H |
| 78 | 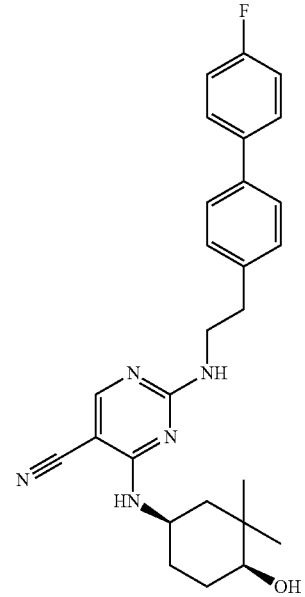 [SMILES: CC1(C)C[C@H](Nc2nc(NCCc3ccc(-c4ccc(F)cc4)cc3)ncc2C#N)CC[C@@H]1O] | 459 | C | F |
| 79 | 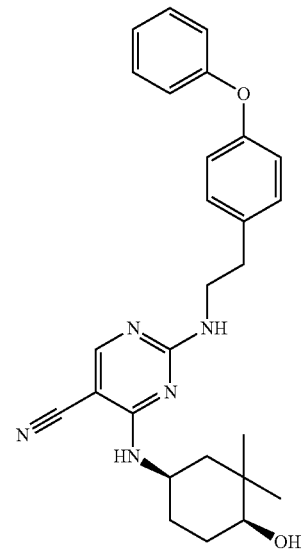 [SMILES: CC1(C)C[C@H](Nc2nc(NCCc3ccc(Oc4ccccc4)cc3)ncc2C#N)CC[C@@H]1O] | 457.3 | C | F |

TABLE 2-continued

| Cmpd No. | Cmpd Structure | MS (ESI) m/z | Act. Level | Sel. Level |
|---|---|---|---|---|
| 80 | | 397.3 | A | H |
| 81 | | 413.2 | C | F |
| 82 | | 441.2 | D | E |

TABLE 2-continued

| Cmpd No. | Cmpd Structure | MS (ESI) m/z | Act. Level | Sel. Level |
|---|---|---|---|---|
| 83 | | 448.4 | C | F |
| 84 | | 354.2 | C | H |
| 85 | | 368.2 | C | G |

TABLE 2-continued
| Cmpd No. | Cmpd Structure | MS (ESI) m/z | Act. Level | Sel. Level |
|---|---|---|---|---|
| 86 | 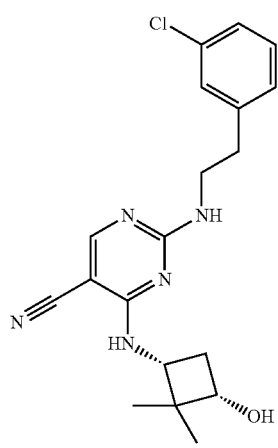 [SMILES: CC1(C)[C@@H](O)C[C@H]1Nc1nc(NCCc2cccc(Cl)c2)ncc1C#N] | 372.2 | D | G |
| 87 | 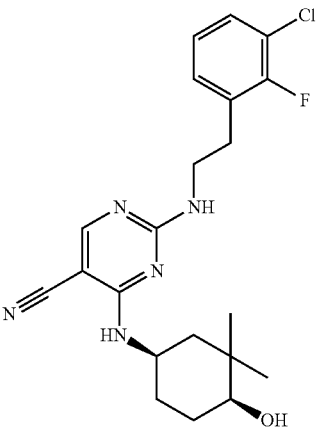 [SMILES: CC1(C)C[C@H](Nc2nc(NCCc3cccc(Cl)c3F)ncc2C#N)CC[C@@H]1O] | 419.2 | D | E |
| 88 | 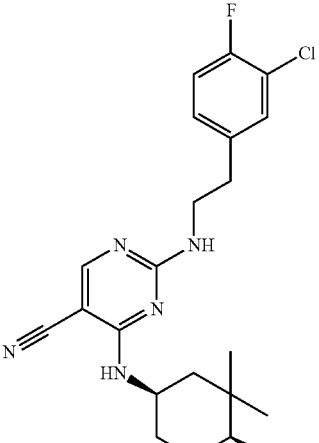 | 418.2 | D | E |

TABLE 2-continued

| Cmpd No. | Cmpd Structure | MS (ESI) m/z | Act. Level | Sel. Level |
|---|---|---|---|---|
| 89 | | 427.2 | D | F |
| 90 | | 417.2 | D | F |
| 91 | | 383.2 | C | F |

TABLE 2-continued

| Cmpd No. | Cmpd Structure | MS (ESI) m/z | Act. Level | Sel. Level |
|---|---|---|---|---|
| 92 | | 390.2 | C | G |
| 93 | | 384.2 | C | F |
| 94 | | 396.2 | C | F |

TABLE 2-continued

| Cmpd No. | Cmpd Structure | MS (ESI) m/z | Act. Level | Sel. Level |
|---|---|---|---|---|
| 95 | | 412.2 | C | G |
| 96 | | 426.2 | C | G |
| 97 | | 434.2 | C | F |

TABLE 2-continued
| Cmpd No. | Cmpd Structure | MS (ESI) m/z | Act. Level | Sel. Level |
|---|---|---|---|---|
| 98 | 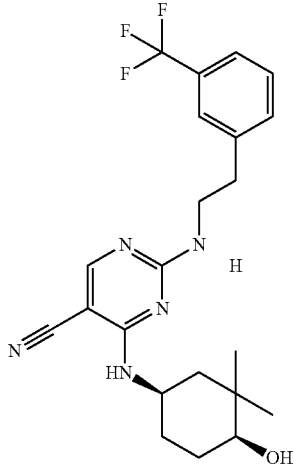 | 434.2 | C | F |
| 99 | 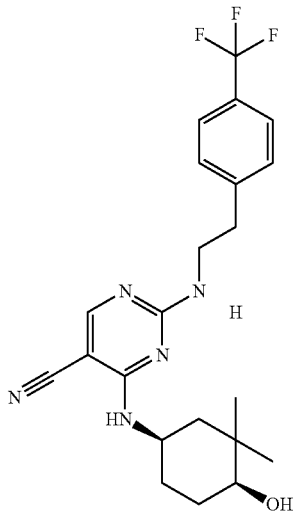 | 434.2 | C | G |
| 100 | 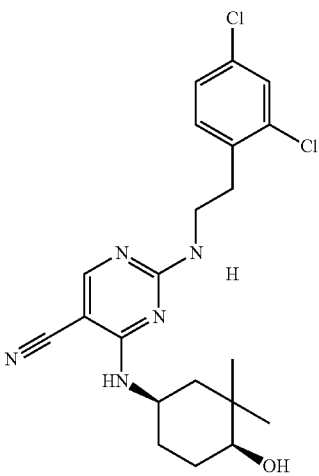 | 434.2 | C | F |

TABLE 2-continued

| Cmpd No. | Cmpd Structure | MS (ESI) m/z | Act. Level | Sel. Level |
| --- | --- | --- | --- | --- |
| 101 | | 434.2 | C | F |
| 102 | | 356.2 | C | G |
| 103 | | 368.2 | C | G |

TABLE 2-continued

| Cmpd No. | Cmpd Structure | MS (ESI) m/z | Act. Level | Sel. Level |
|---|---|---|---|---|
| 104 | | 384.2 | A | H |
| 105 | | 398.2 | B | G |
| 106 | | 406.2 | C | F |

TABLE 2-continued

| Cmpd No. | Cmpd Structure | MS (ESI) m/z | Act. Level | Sel. Level |
|---|---|---|---|---|
| 107 | (3,4-dichlorophenethylamino-pyrimidine-5-carbonitrile with (1,1-dimethyl-3-hydroxycyclobutyl)amino substituent) | 406.2 | C | G |
| 108 | (2-hydroxyphenethylamino-pyrimidine-5-carbonitrile with (1,1-dimethyl-3-hydroxycyclobutyl)amino substituent) | 354.2 | B | G |
| 109 | (4-(2-methoxyethoxy)phenethylamino-pyrimidine-5-carbonitrile with (1,1-dimethyl-3-hydroxycyclobutyl)amino substituent) | 412.2 | C | G |

TABLE 2-continued

| Cmpd No. | Cmpd Structure | MS (ESI) m/z | Act. Level | Sel. Level |
|---|---|---|---|---|
| 110 | | 414.2 | C | H |
| 111 | | 414.2 | C | F |
| 112 | | 416.2 | B | G |

TABLE 2-continued
| Cmpd No. | Cmpd Structure | MS (ESI) m/z | Act. Level | Sel. Level |
|---|---|---|---|---|
| 113 | 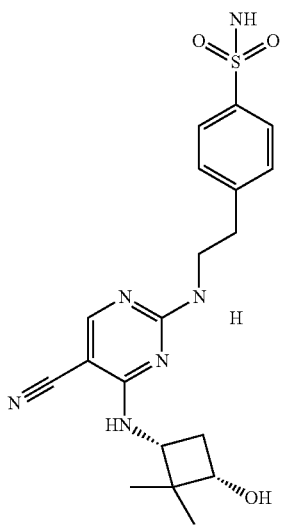 | 417.2 | C | G |
| 114 | 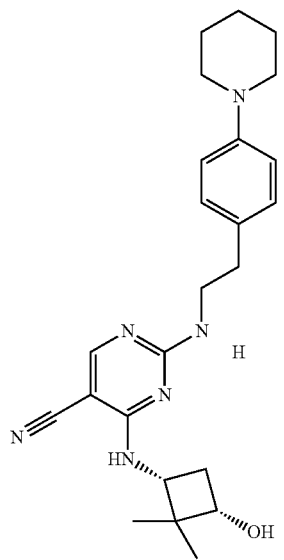 | 421.2 | B | G |

TABLE 2-continued

| Cmpd No. | Cmpd Structure | MS (ESI) m/z | Act. Level | Sel. Level |
|---|---|---|---|---|
| 115 | | 422.2 | B | G |
| 116 | | 422.2 | C | G |
| 117 | | 368.2 | C | G |

TABLE 2-continued
| Cmpd No. | Cmpd Structure | MS (ESI) m/z | Act. Level | Sel. Level |
|---|---|---|---|---|
| 118 | 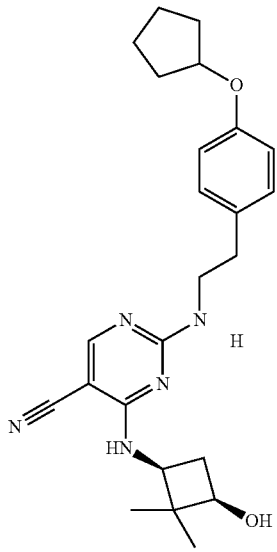 | 422.2 | B | G |
| 119 | 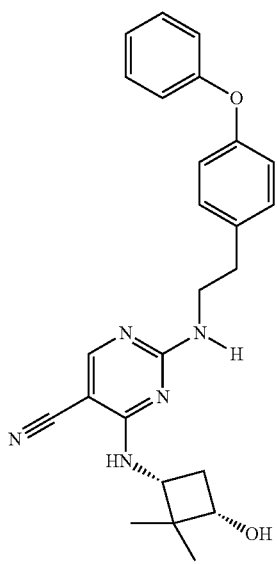 [SMILES: CC1(C)[C@@H](O)C[C@H]1Nc1nc(NCCc2ccc(Oc3ccccc3)cc2)ncc1C#N] | 430.2 | C | F |

TABLE 2-continued
| Cmpd No. | Cmpd Structure | MS (ESI) m/z | Act. Level | Sel. Level |
|---|---|---|---|---|
| 120 | 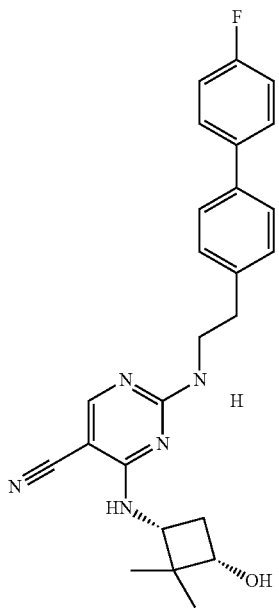 | 432.2 | C | F |
| 121 | 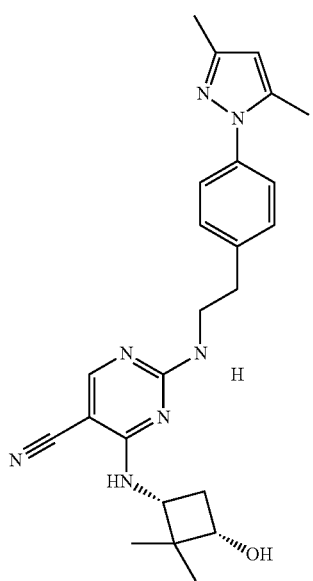 | 432.2 | B | G |

TABLE 2-continued

| Cmpd No. | Cmpd Structure | MS (ESI) m/z | Act. Level | Sel. Level |
|---|---|---|---|---|
| 122 | | 343.2 | C | G |
| 123 | | 435.2 | B | G |

TABLE 2-continued

| Cmpd No. | Cmpd Structure | MS (ESI) m/z | Act. Level | Sel. Level |
|---|---|---|---|---|
| 124 | | 435.2 | C | F |
| 125 | | 474.2 | C | F |
| 126 | | 386.2 | C | G |

TABLE 2-continued

| Cmpd No. | Cmpd Structure | MS (ESI) m/z | Act. Level | Sel. Level |
|---|---|---|---|---|
| 127 | | 388.2 | C | F |
| 128 | | 388.2 | C | F |
| 129 | | 409.2 | C | F |

TABLE 2-continued

| Cmpd No. | Cmpd Structure | MS (ESI) m/z | Act. Level | Sel. Level |
|---|---|---|---|---|
| 130 | | 423.2 | C | F |
| 131 | | 423.2 | B | G |
| 132 | | 432.2 | C | F |

TABLE 2-continued
| Cmpd No. | Cmpd Structure | MS (ESI) m/z | Act. Level | Sel. Level |
|---|---|---|---|---|
| 133 | 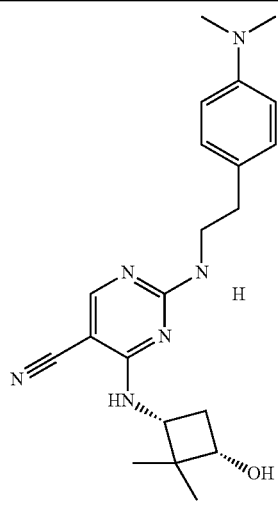 | 381.2 | C | G |
| 134 | 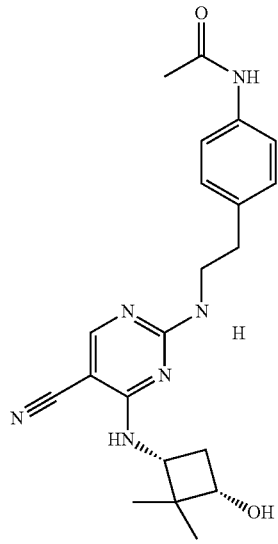 | 395.2 | C | G |
| 135 | 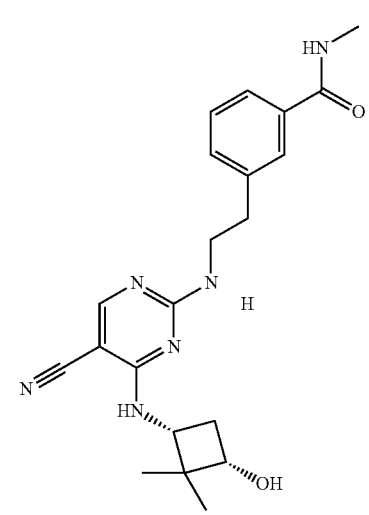 | 396.2 | B | G |

TABLE 2-continued

| Cmpd No. | Cmpd Structure | MS (ESI) m/z | Act. Level | Sel. Level |
|---|---|---|---|---|
| 136 | | 404.2 | C | G |
| 137 | | 421.2 | C | G |
| 138 | | 393.2 | B | G |

TABLE 2-continued

| Cmpd No. | Cmpd Structure | MS (ESI) m/z | Act. Level | Sel. Level |
|---|---|---|---|---|
| 139 | | 425.2 | C | F |
| 140 | | 459.2 | C | G |
| 141 | | 431.2 | C | G |

TABLE 2-continued

| Cmpd No. | Cmpd Structure | MS (ESI) m/z | Act. Level | Sel. Level |
| --- | --- | --- | --- | --- |
| 142 | | 397.1 | C | G |
| 143 | | 447.2 | B | G |
| 144 | | 475.2 | B | G |

TABLE 2-continued
| Cmpd No. | Cmpd Structure | MS (ESI) m/z | Act. Level | Sel. Level |
|---|---|---|---|---|
| 145 | 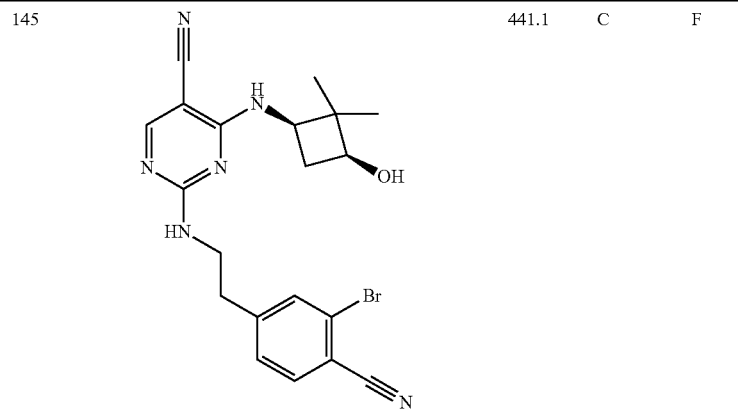 | 441.1 | C | F |
| 146 | 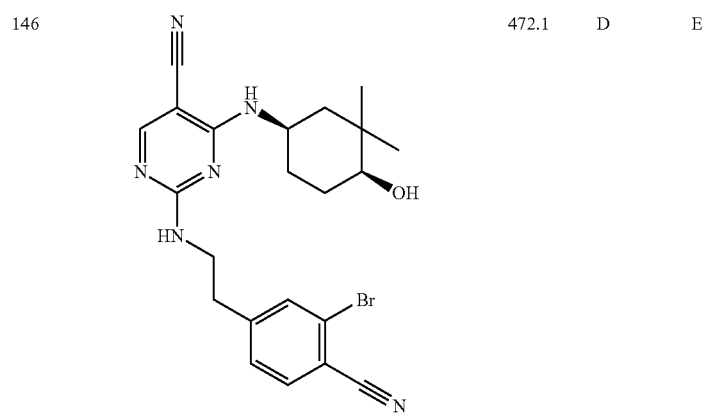 | 472.1 | D | E |
| 147 | 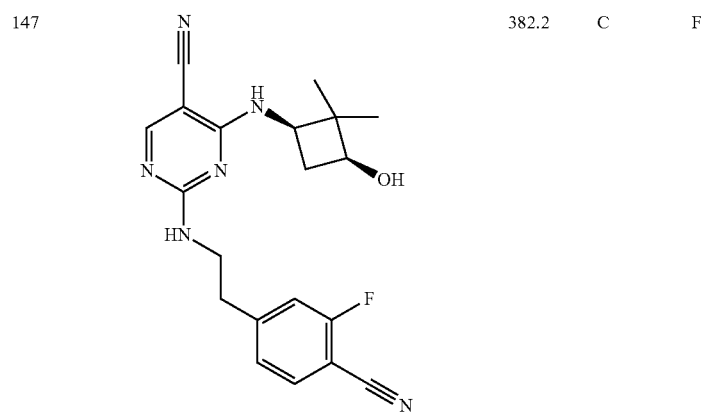 | 382.2 | C | F |

TABLE 2-continued

| Cmpd No. | Cmpd Structure | MS (ESI) m/z | Act. Level | Sel. Level |
|---|---|---|---|---|
| 148 | | 410.2 | C | G |
| 149 | | 339.2 | C | G |
| 150 | | 366.2 | D | F |

TABLE 2-continued

| Cmpd No. | Cmpd Structure | MS (ESI) m/z | Act. Level | Sel. Level |
|---|---|---|---|---|
| 151 | | 460.2 | D | F |
| 152 | | 460.2 | B | H |
| 153 | | 410.2 | B | G |

TABLE 2-continued

| Cmpd No. | Cmpd Structure | MS (ESI) m/z | Act. Level | Sel. Level |
|---|---|---|---|---|
| 154 | | 409.2 | C | F |
| 155 | | 460.3 | C | F |
| 156 | | 391.2 | C | G |

TABLE 2-continued

| Cmpd No. | Cmpd Structure | MS (ESI) m/z | Act. Level | Sel. Level |
|---|---|---|---|---|
| 157 | | 371.2 | C | G |
| 158 | | 371.2 | B | H |
| 159 | | 371.2 | D | G |
| 160 | | 371.2 | B | G |

TABLE 2-continued

| Cmpd No. | Cmpd Structure | MS (ESI) m/z | Act. Level | Sel. Level |
|---|---|---|---|---|
| 161 | | 434.2 | C | F |
| 162 | | 399.1 | C | G |
| 163 | | 399.1 | A | H |
| 164 | | 399.1 | C | G |

TABLE 2-continued

| Cmpd No. | Cmpd Structure | MS (ESI) m/z | Act. Level | Sel. Level |
|---|---|---|---|---|
| 165 | | 399.1 | D | E |
| 166 | | 392.1 | B | G |
| 167 | | 448.2 | C | F |

TABLE 2-continued

| Cmpd No. | Cmpd Structure | MS (ESI) m/z | Act. Level | Sel. Level |
|---|---|---|---|---|
| 168 | | 448.2 | A | H |
| 169 | | 448.2 | C | F |
| 170 | | 446.2 | D | E |

TABLE 2-continued

| Cmpd No. | Cmpd Structure | MS (ESI) m/z | Act. Level | Sel. Level |
|---|---|---|---|---|
| 171 | | 428.2 | D | E |
| 172 | | 445.2 | C | G |
| 173 | | 444.2 | C | G |
| 174 | | 499.1 | C | F |

TABLE 2-continued

| Cmpd No. | Cmpd Structure | MS (ESI) m/z | Act. Level | Sel. Level |
|---|---|---|---|---|
| 175 | | 473.2 | C | F |
| 176 | | 482.2 | C | F |
| 177 | | 515.2 | C | F |

TABLE 2-continued

| Cmpd No. | Cmpd Structure | MS (ESI) m/z | Act. Level | Sel. Level |
|---|---|---|---|---|
| 178 | | 513.3 | C | F |
| 179 | | 528.2 | C | F |
| 180 | | 466.2 | D | |

TABLE 2-continued

| Cmpd No. | Cmpd Structure | MS (ESI) m/z | Act. Level | Sel. Level |
|---|---|---|---|---|
| 181 | | 466.2 | D | E |
| 182 | | 468.1 | C | |
| 183 | | 468.2 | C | F |

TABLE 2-continued

| Cmpd No. | Cmpd Structure | MS (ESI) m/z | Act. Level | Sel. Level |
|---|---|---|---|---|
| 184 | | 418.2 | D | E |
| 185 | | 498.1 | C | F |
| 186 | | 479.1 | D | E |

TABLE 2-continued

| Cmpd No. | Cmpd Structure | MS (ESI) m/z | Act. Level | Sel. Level |
|---|---|---|---|---|
| 187 | | 400.2 | A | H |
| 188 | | 400.2 | C | F |
| 189 | | 400.2 | B | G |

TABLE 2-continued

| Cmpd No. | Cmpd Structure | MS (ESI) m/z | Act. Level | Sel. Level |
|---|---|---|---|---|
| 190 | | 400.2 | D | F |
| 191 | | 434.2 | A | |
| 192 | | 362.2 | A | H |

TABLE 2-continued

| Cmpd No. | Cmpd Structure | MS (ESI) m/z | Act. Level | Sel. Level |
|---|---|---|---|---|
| 193 | | 479.1 | C | |
| 194 | | 390.2 | C | F |
| 195 | | 449.2 | D | F |

TABLE 2-continued

| Cmpd No. | Cmpd Structure | MS (ESI) m/z | Act. Level | Sel. Level |
|---|---|---|---|---|
| 196 | | 384.2 | D | E |
| 197 | | 402.2 | C | F |
| 198 | | 356.2 | C | G |

A number of references have been cited, the disclosures of which are incorporated herein by reference in their entirety.

What is claimed is:

1. A compound of formula (I):

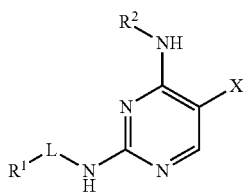

or a pharmaceutically acceptable salt, tautomer, or stereoisomer thereof,
wherein:
X is CN or $CF_3$;
L is ($C_{1-4}$ alkyl);
$R^1$ is substituted or unsubstituted heteroaryl; and
$R^2$ is substituted or unsubstituted cycloalkyl.

2. The compound of claim 1, wherein X is CN.

3. The compound of claim 1, wherein X is $CF_3$.

4. The compound of claim 1, wherein L is $CH_2$, $CH_2CH_2$ or $CH_2CH_2CH_2$.

5. The compound of claim 1, wherein $R^1$ is a substituted or unsubstituted pyridyl, pyridyl-1-oxide, or pyrimidyl.

6. The compound of claim 5, wherein $R^1$ is substituted with one or more halogen, $—OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl.

7. The compound of claim 5, wherein $R^1$ is substituted with one or more F, Cl, Br, I, methyl, ethyl, propyl, isopropyl, butyl, isobutyl, t-butyl, phenyl, naphthyl, $—CH_2F$, $—CHF_2$, $—CF_3$, $—CHFCH_3$, $—CF_2CH_3$, $—C(CH_3)_2F$, $—OCH_3$, $—OCH_2F$, $—OCHF_2$, $—OCF_3$, $—OCH_2CH_3$, $—OCH_2CH_2F$, $—OCH_2CHF_2$, $—OCH_2CF_3$, $—OCH_2CH(CH_3)F$, $—OCH_2C(CH_3)_2F$, $—OCH_2C(CH_3)F_2$, $—OCH_2CH_2CF_3$, or $—O$-phenyl, wherein each phenyl is optionally substituted with halogen or substituted or unsubstituted $C_{1-4}$ alkyl.

8. The compound of claim 5, wherein $R^1$ is substituted with one or more F, Cl, methyl, ethyl, isopropyl, phenyl, $—CF_3$, $—CF_2CH_3$, $—C(CH_3)_2F$, $—OCH_3$, $—OCH_2CH_3$, $—OCH_2CF_3$, $—OCH_2CH_2F$, $—OCH_2CHF_2$, $—OCH_2C(CH_3)F_2$, $—OCH_2CH_2CF_3$, or $—O$-phenyl, wherein each phenyl is optionally substituted with F or methyl.

9. The compound of claim 1, wherein $R^1$ is a substituted or unsubstituted indolyl, indolinonyl, benzoxazolyl, pyrrolopyridyl, indazolyl, benzimidazolyl, dihydrobenzimidazolonyl, or quinolyl.

10. The compound of claim 9, wherein $R^1$ is substituted with one or more halogen, CN, $—OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl.

11. The compound of claim 9, wherein $R^1$ is substituted with one or more F, Cl, CN, methyl, ethyl, $—CH_2SO_2NHCH_3$, $—OH$, $—OCH_3$, or $OCF_3$.

12. The compound of claim 1, wherein $R^1$ is a substituted or unsubstituted furanyl, pyrrolyl, thiophenyl, oxazolyl, pyrazolyl, imidazolyl, oxadiazolyl, or triazolyl.

13. The compound of claim 12, wherein $R^1$ is substituted with one or more halogen, CN, $—OR^3$, substituted or unsubstituted $C_{1-4}$ alkyl, or substituted or unsubstituted aryl, wherein each $R^3$ is independently H, substituted or unsubstituted $C_{1-6}$ alkyl, or substituted or unsubstituted aryl.

14. The compound of claim 12, wherein $R^1$ is substituted with one or more CN, methyl, ethyl, $—CF_3$, or $—CH_2OCH_3$.

15. The compound of claim 1, wherein $R^2$ is substituted or unsubstituted $C_{3-12}$ cycloalkyl.

16. The compound of claim 15, wherein $R^2$ is substituted or unsubstituted cyclopropyl, cyclobutyl, cyclopentyl, cyclohexyl, cycloheptyl, or adamantyl.

17. The compound of claim 15, wherein $R^2$ is substituted with one or more $C_{1-4}$ alkyl, $—OR^4$, or $—C(=O)NR_2$, wherein each $R^4$ is independently H or $C_{1-6}$ alkyl, and each R is independently H or $C_{1-4}$ alkyl.

18. The compound of claim 15, wherein $R^2$ is substituted with one or more methyl, ethyl, propyl, isopropyl, $—CH_2OH$, $—CH(CH_3)OH$, $—C(CH_3)_2OH$, $—OH$, $—OCH_3$, $—OCH_2CH_3$, $—C(=O)NH_2$, $—C(=O)NHCH_3$, or $—C(=O)N(CH_3)_2$.

19. The compound of claim 15, wherein $R^2$ is substituted with one or more methyl, $—CH_2OH$, $—C(CH_3)_2OH$, $—OH$, $—OCH_3$, or $—C(=O)NHCH_3$.

20. The compound of claim 15, wherein $R^2$ is substituted or unsubstituted spiro[3.3]heptyl, or bicyclooctyl.

21. The compound of claim 15, wherein $R^2$ is substituted with one or more $C_{1-4}$ alkyl, $—OR^4$, $—C(=O)NR_2$, or triazolyl, wherein each $R^4$ is independently H or $C_{1-6}$ alkyl, and each R is independently H or $C_{1-4}$ alkyl.

22. The compound of claim 15, wherein $R^2$ is substituted with one or more methyl, triazolyl, $—CH_2OH$, $—C(CH_3)_2OH$, $—OH$, $—OCH_3$, $—C(=O)NH_2$, $—C(=O)NHCH_3$, or $—C(=O)N(CH_3)_2$.

23. The compound of claim 1, wherein the compound at a concentration of 10 μM inhibits PKC-theta by at least about 50%.

24. The compound of claim 1, wherein the compound is

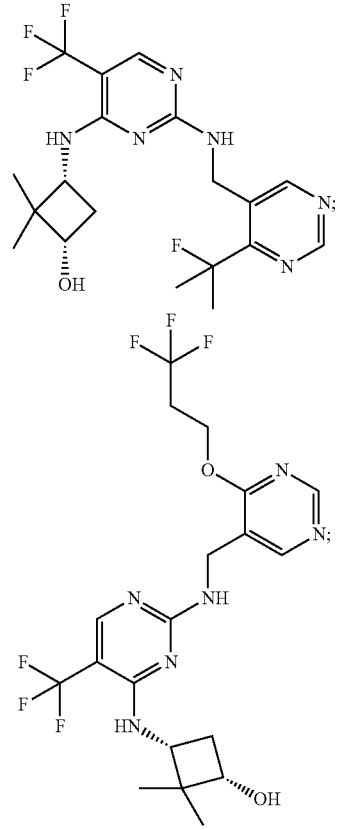

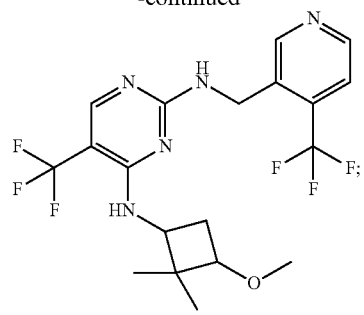
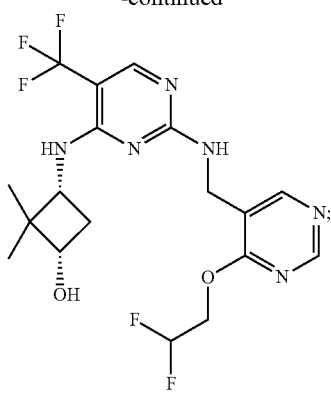
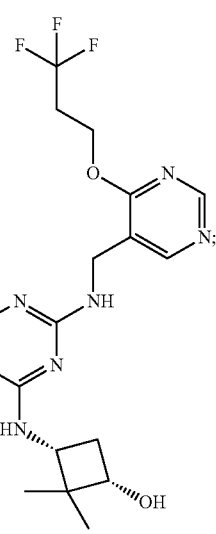
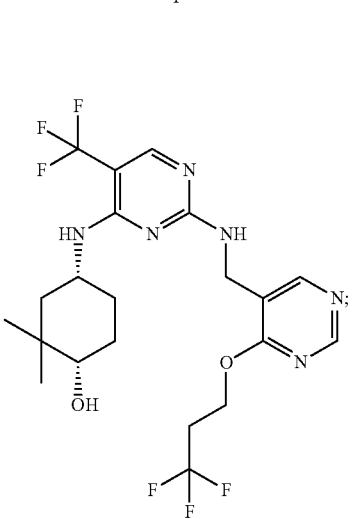
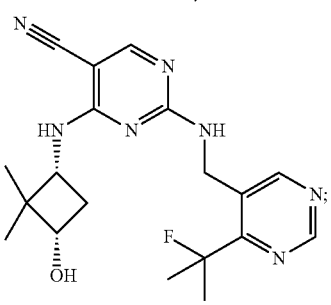
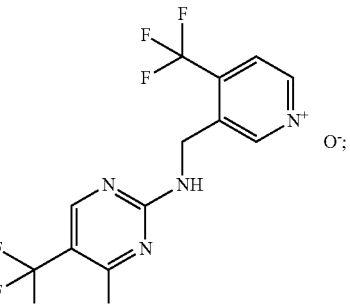
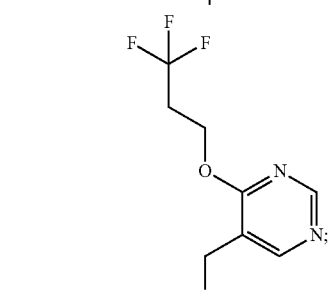
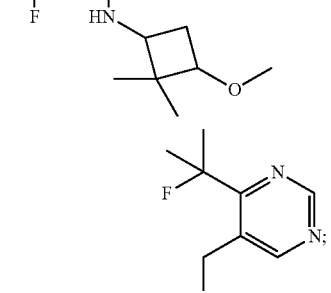
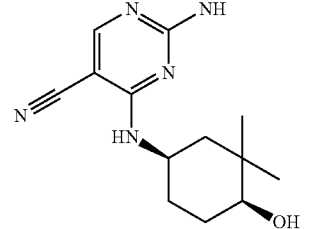
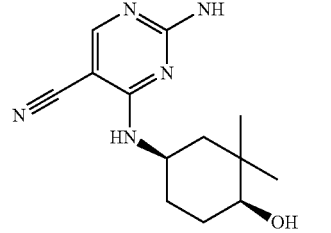

443
-continued
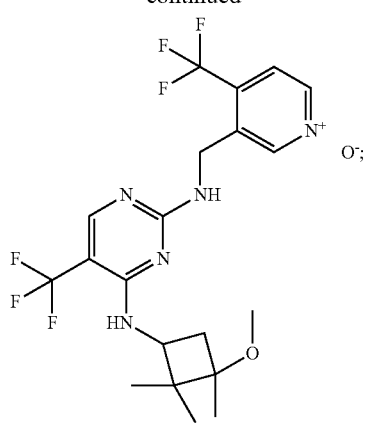
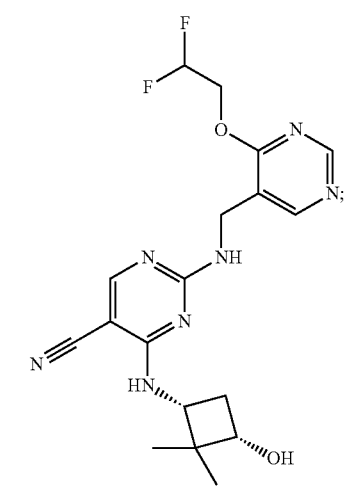
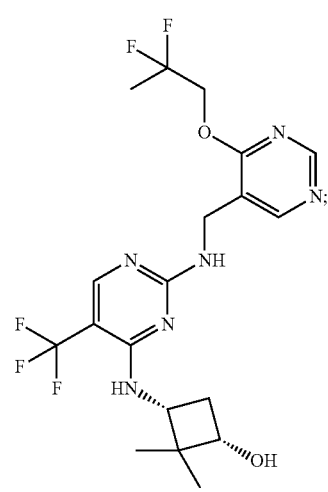
444
-continued
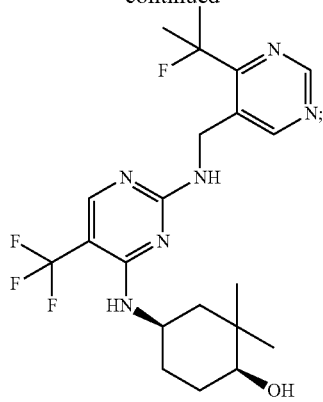
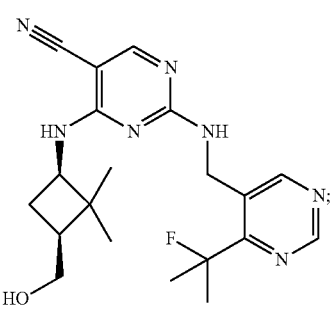
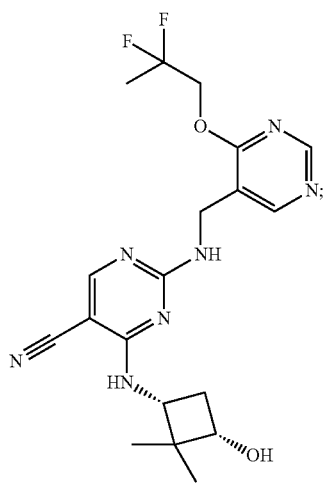
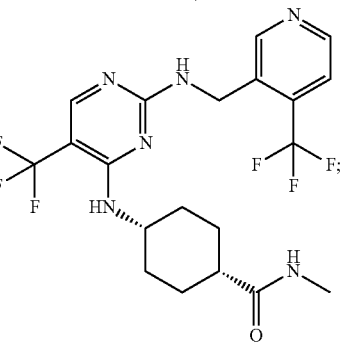

445
-continued
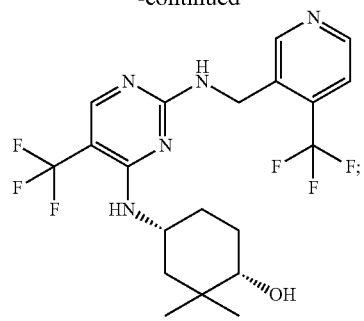
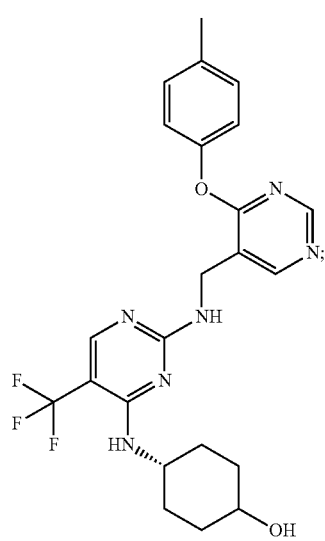
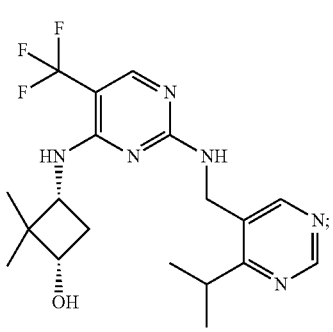
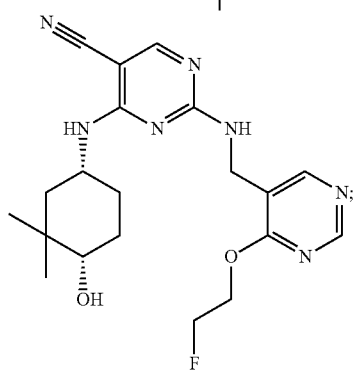
446
-continued
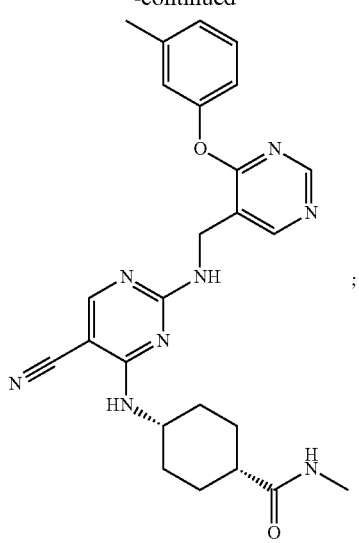
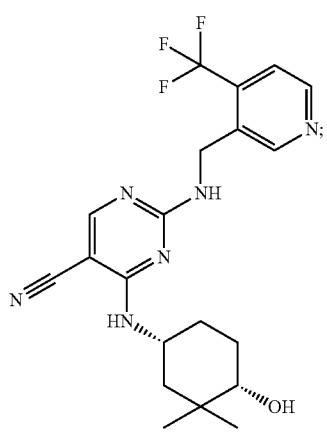
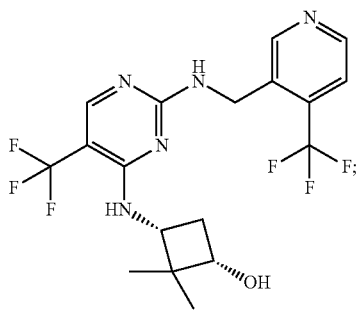
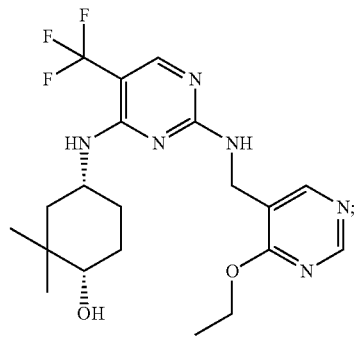

447
-continued
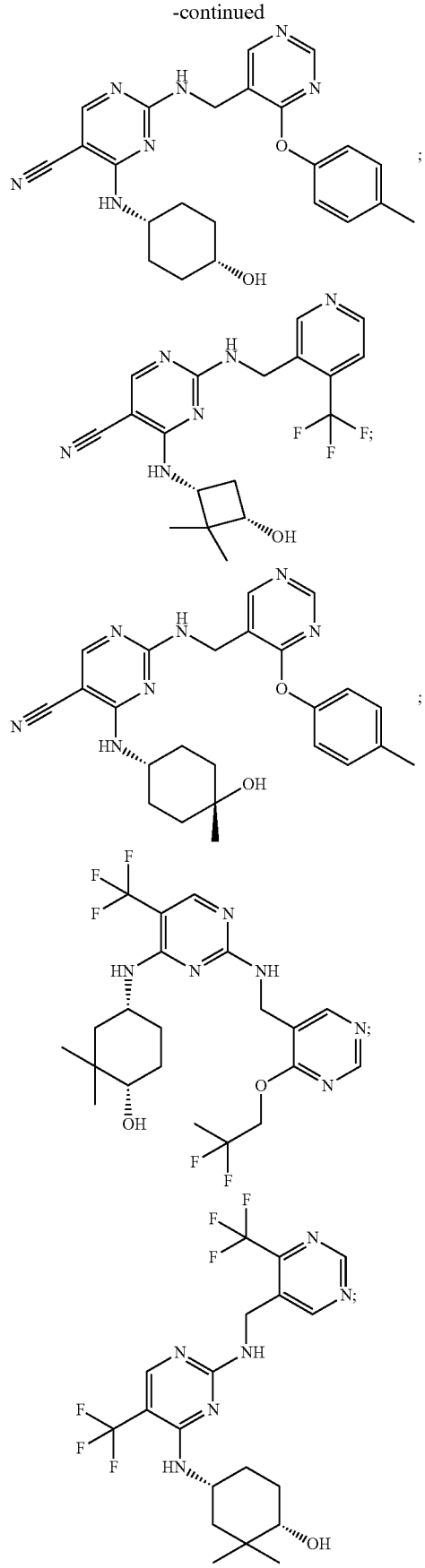
448
-continued
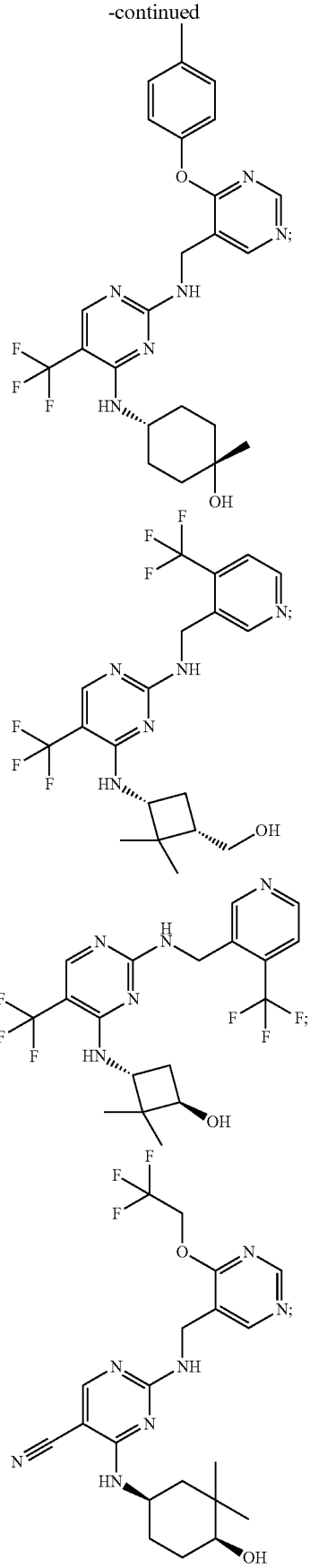

449
-continued
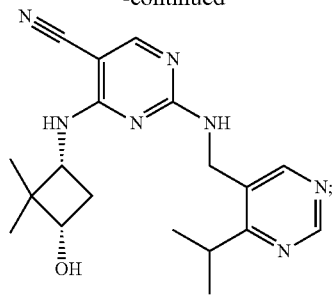
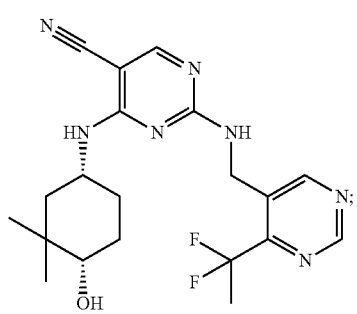
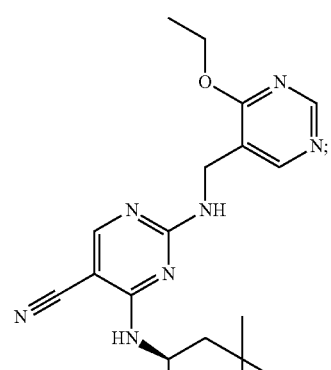
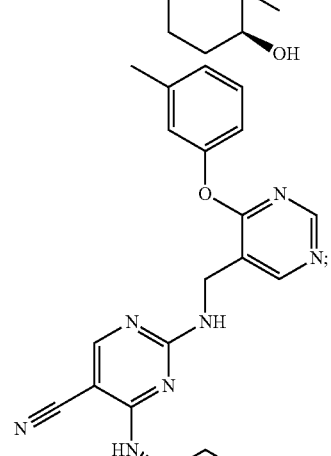
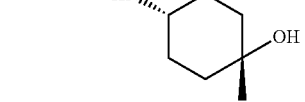
450
-continued
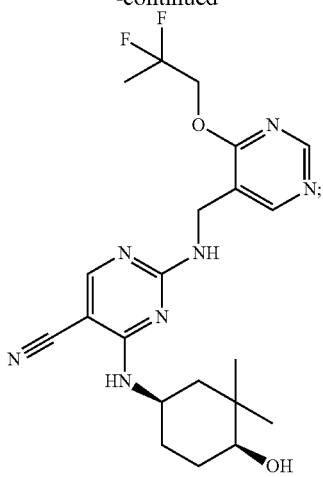
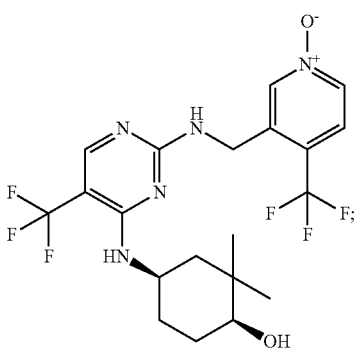
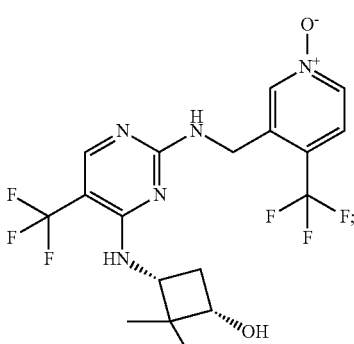
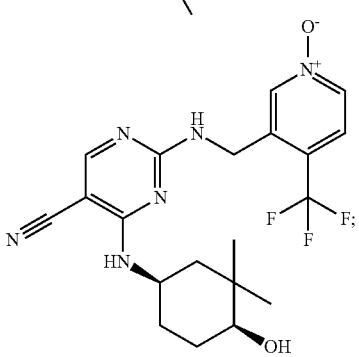

451
-continued
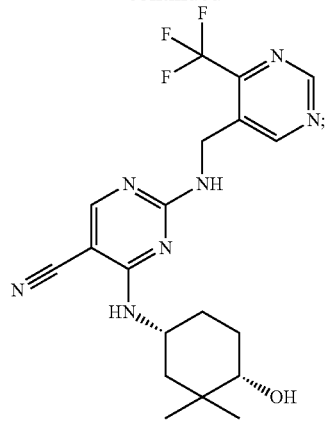
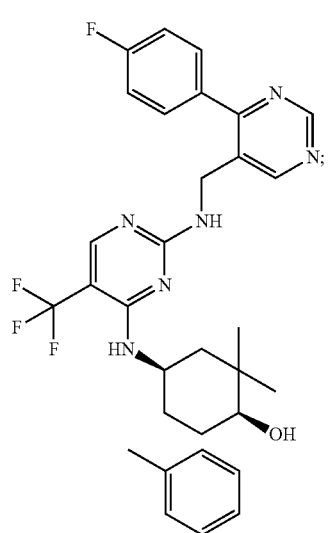
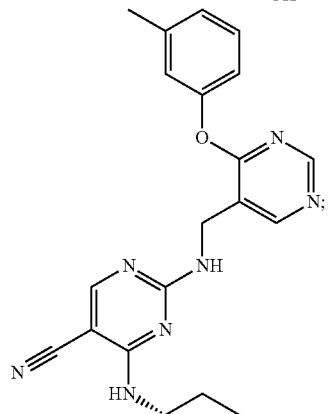
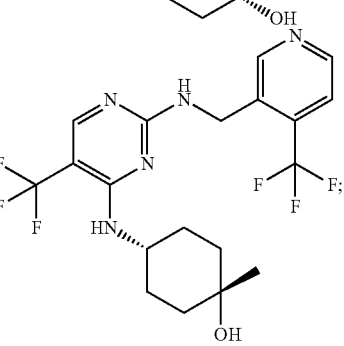
452
-continued
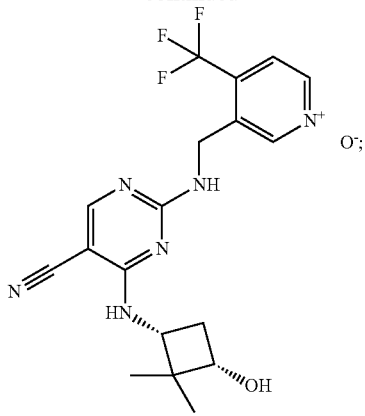
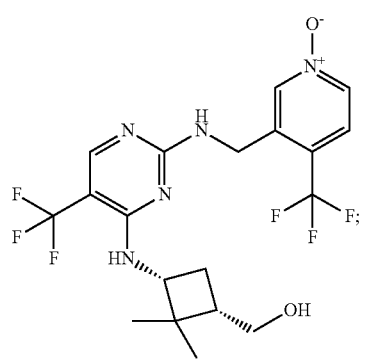
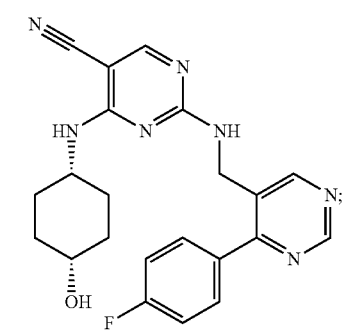
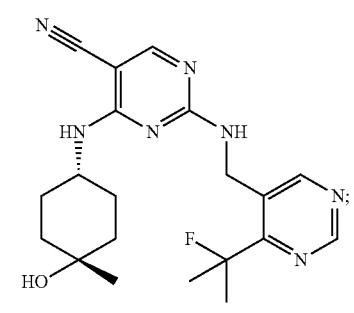

453
-continued
454
-continued
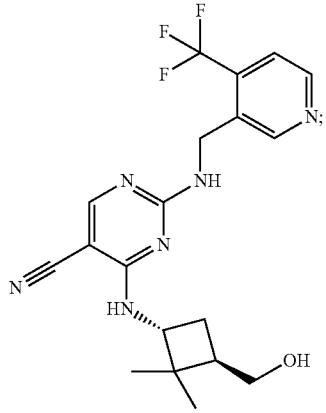
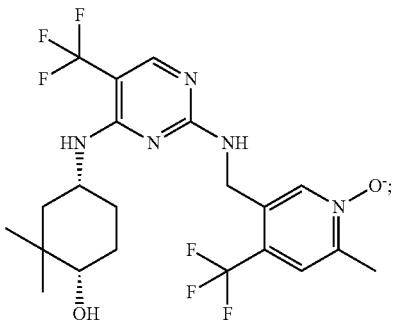
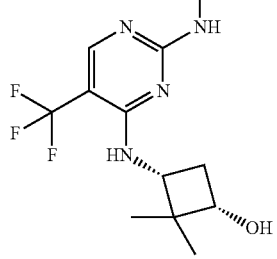
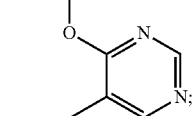
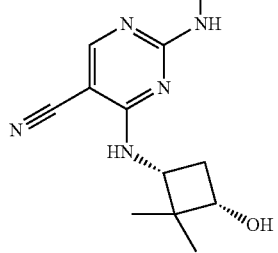

455
-continued
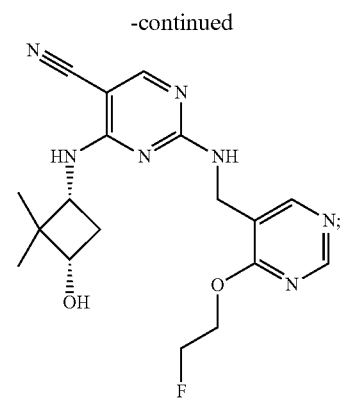
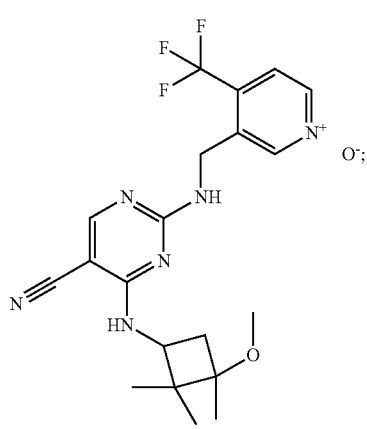
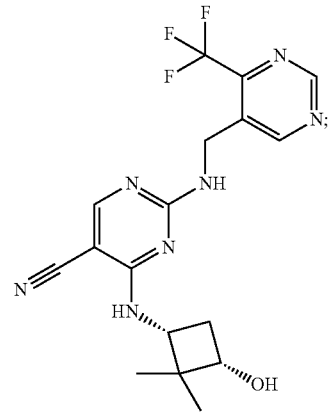
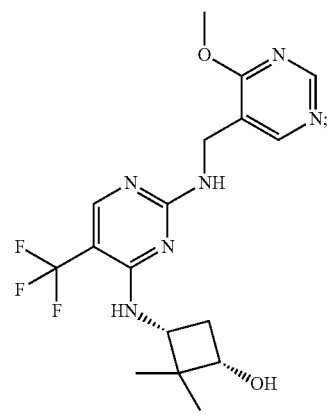
456
-continued
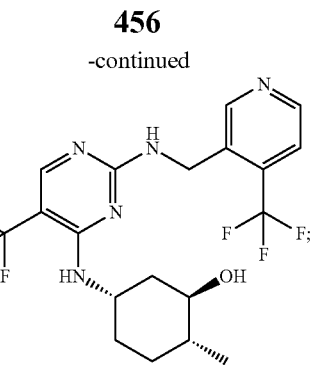
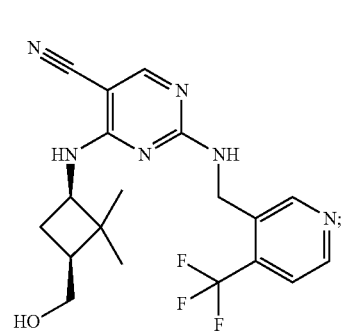
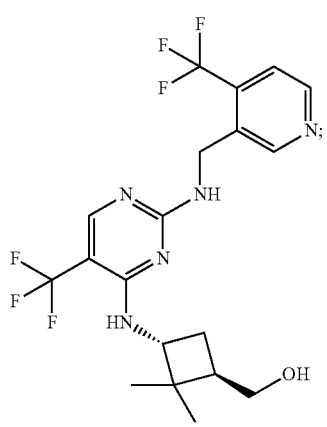

457
-continued
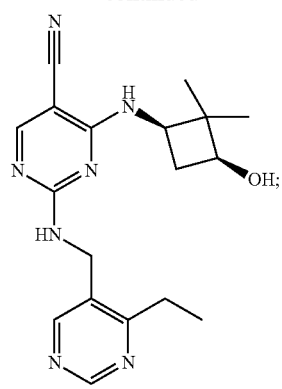
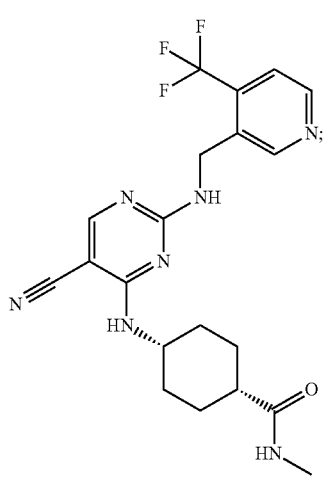
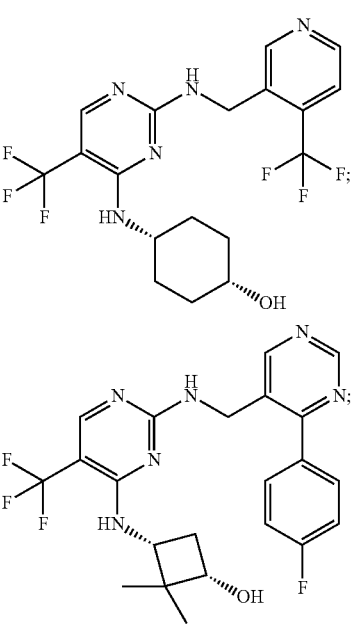
458
-continued
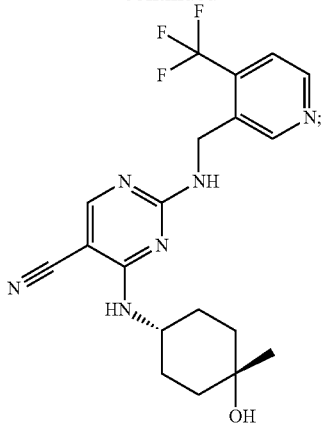
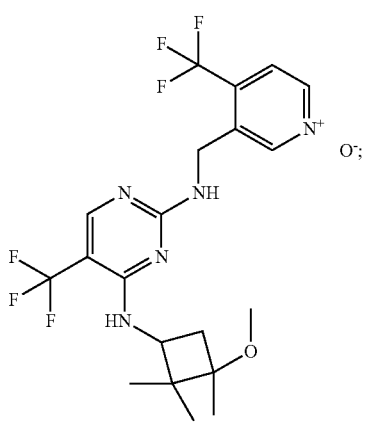
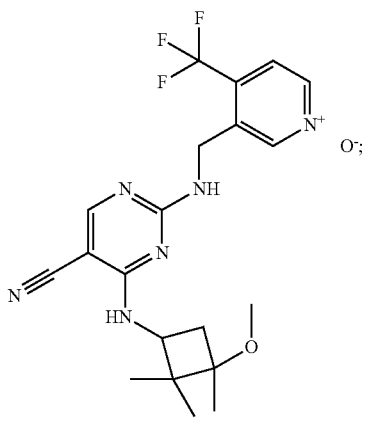
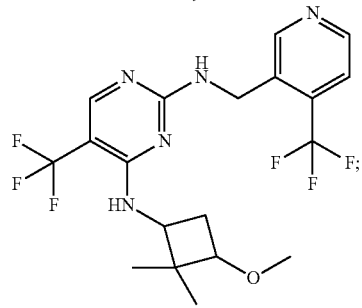

-continued
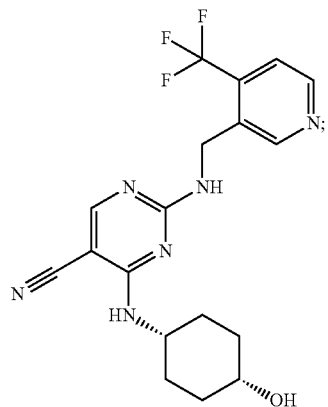
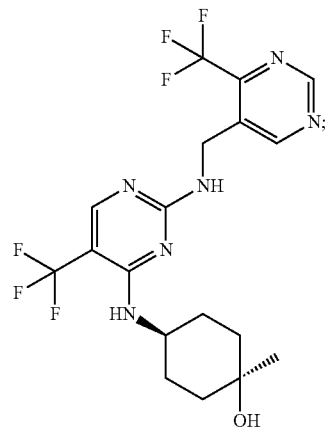
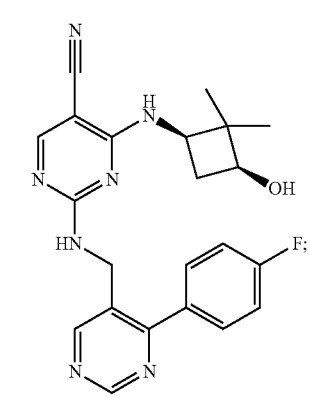
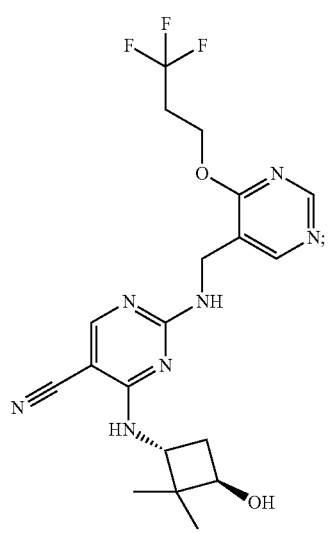
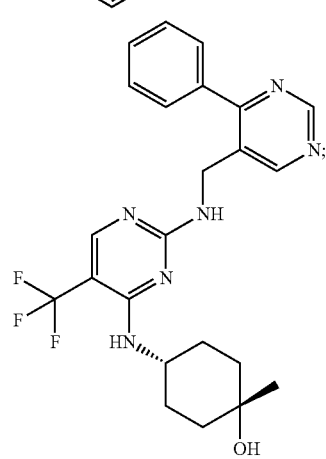
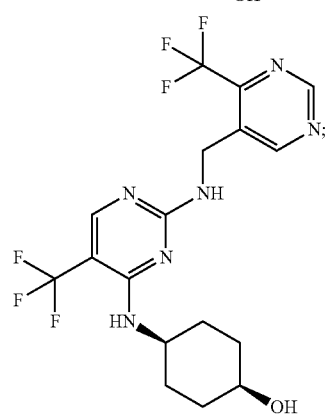

461
-continued
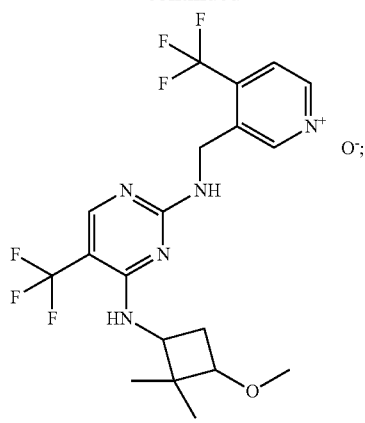
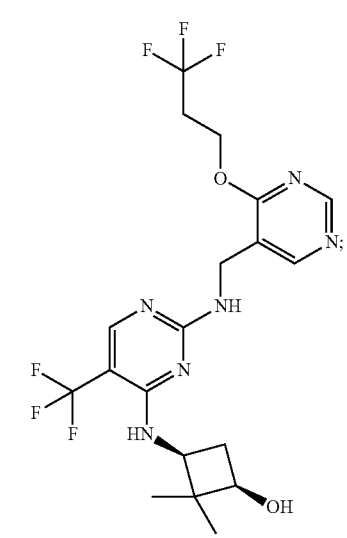
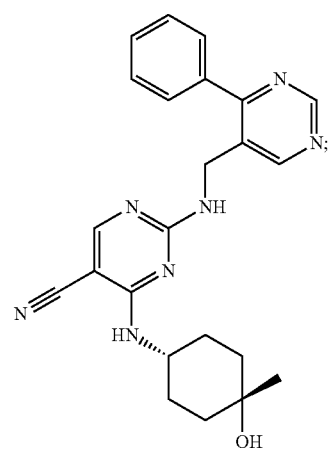
462
-continued
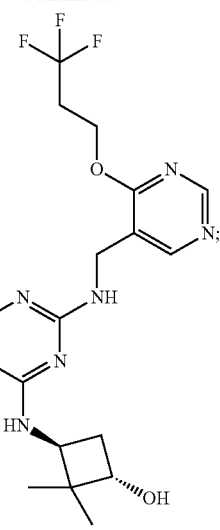
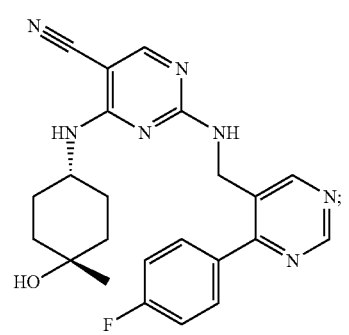
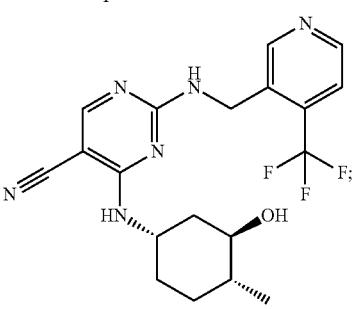
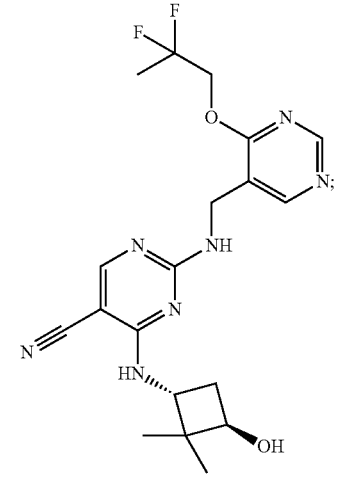

463
-continued
464
-continued
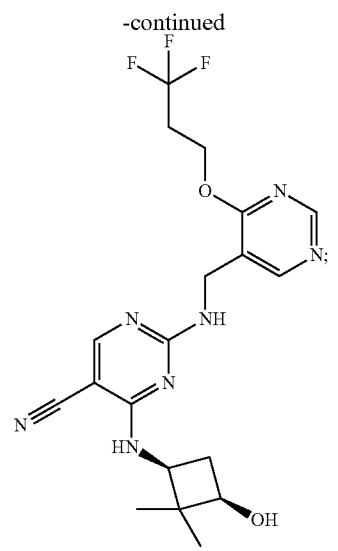
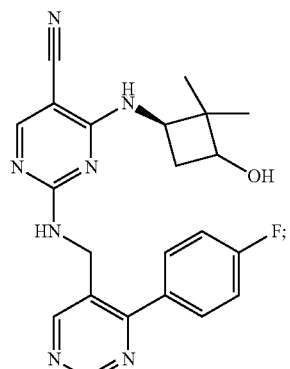
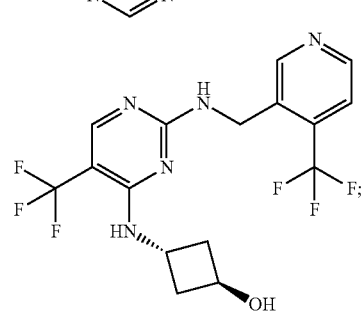
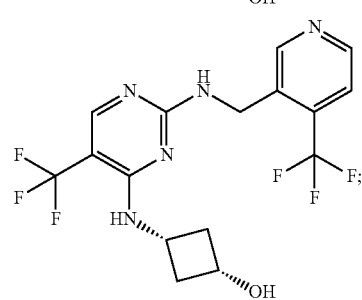
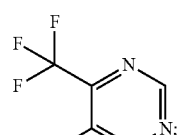
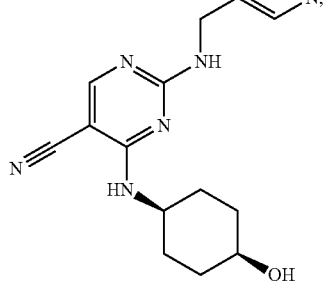
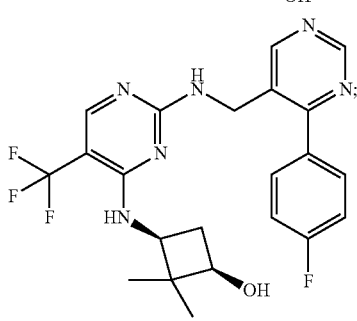

465
-continued
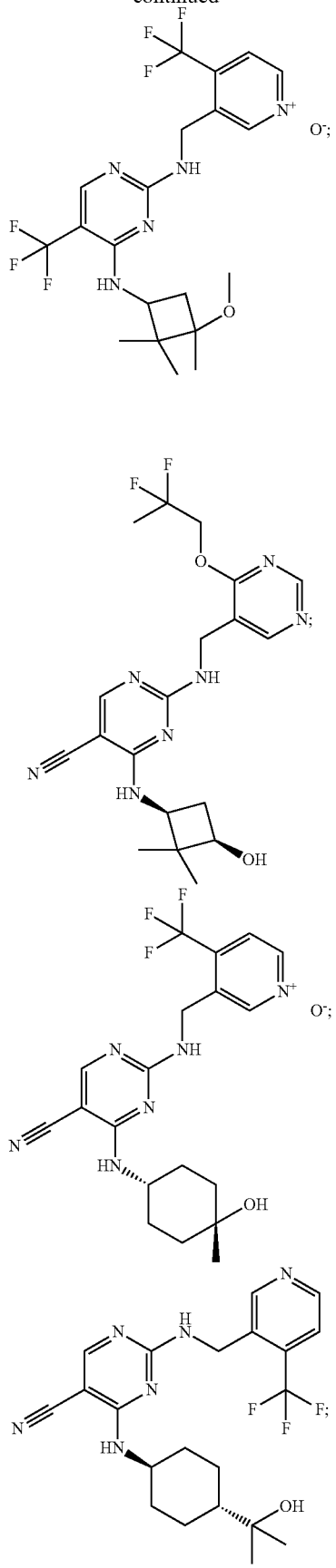
466
-continued
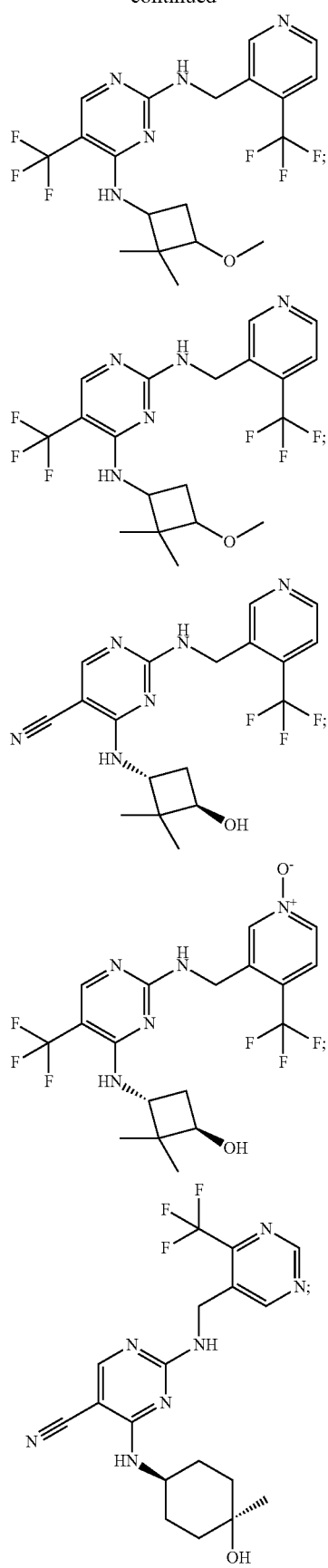

467
-continued
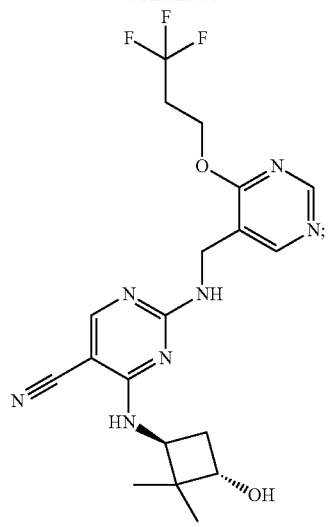
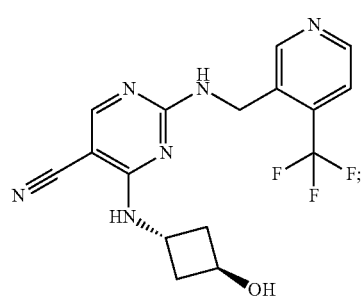
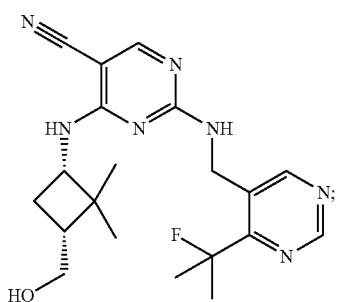
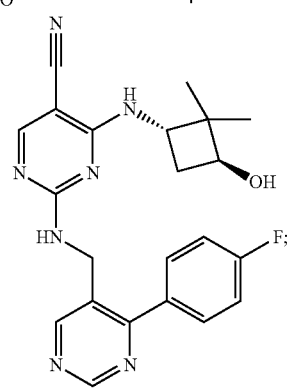
468
-continued
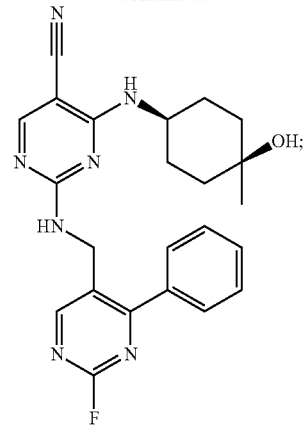
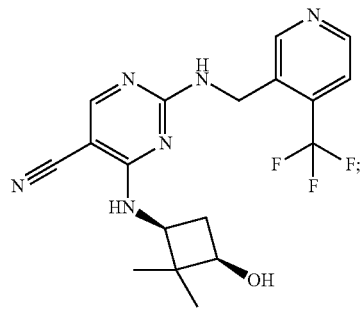
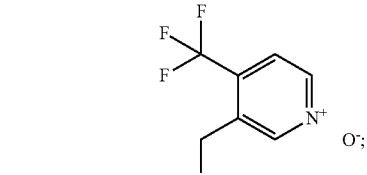
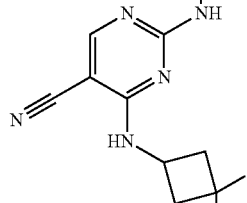
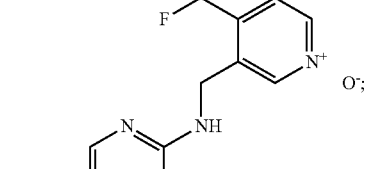
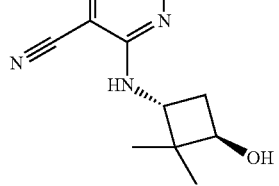

469
-continued
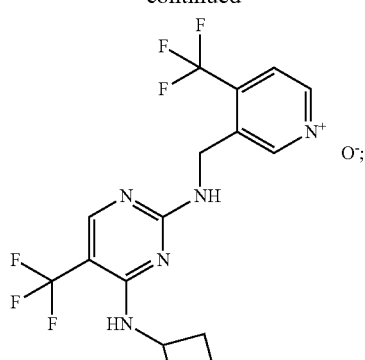
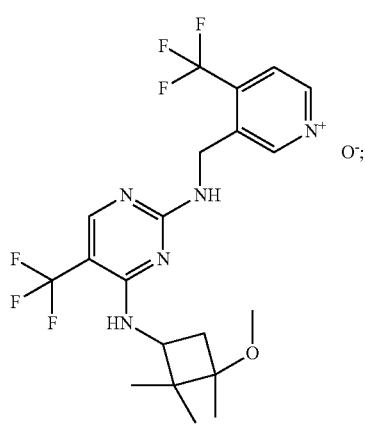
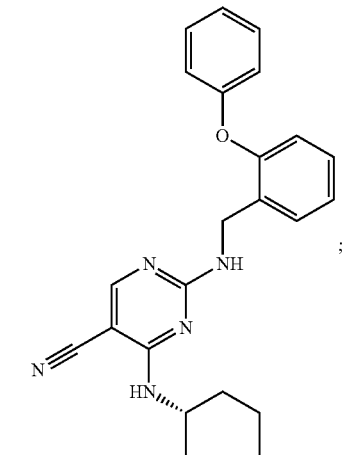
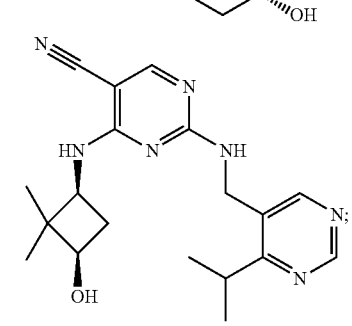
470
-continued
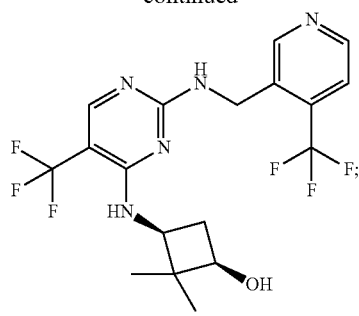
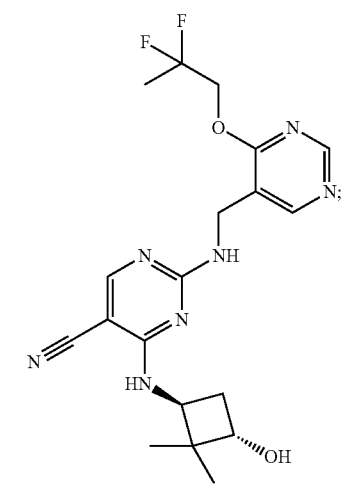
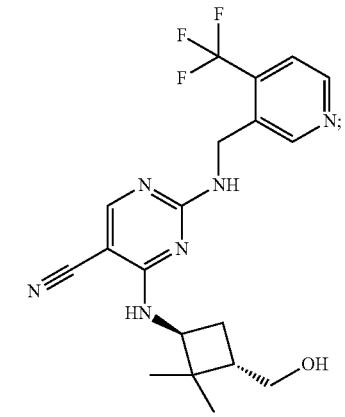
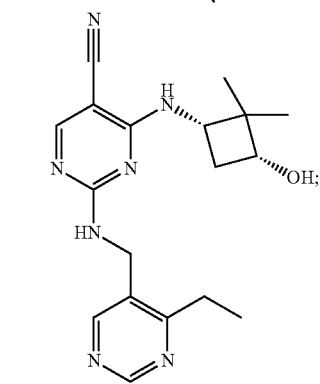

471
-continued
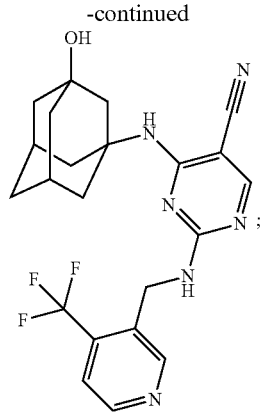
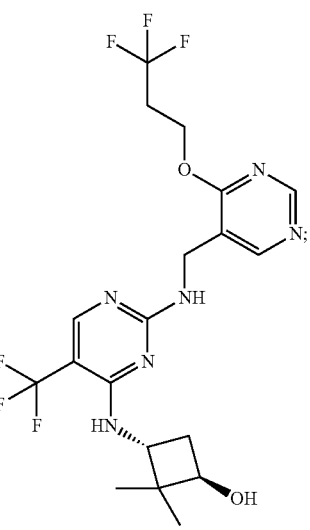
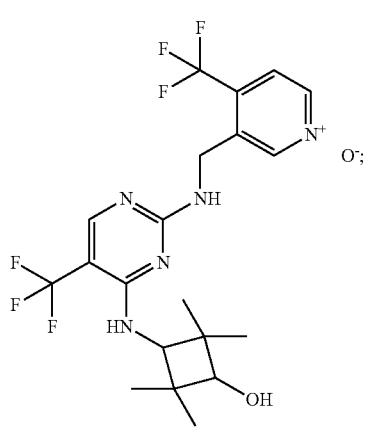
472
-continued
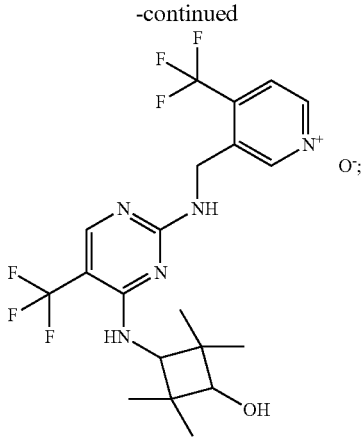
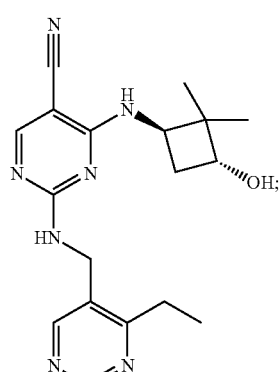
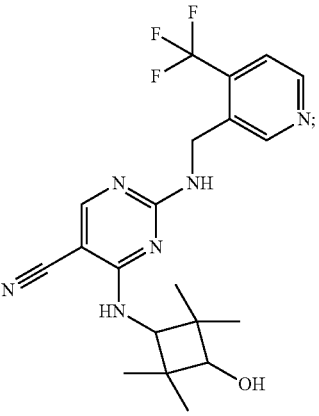
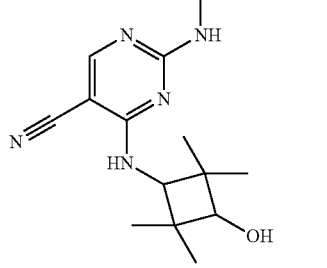
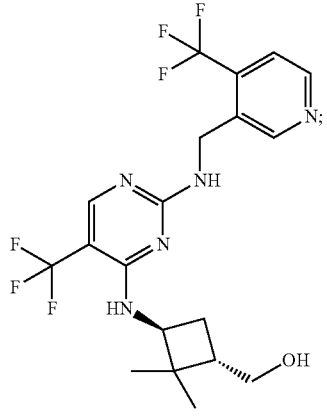

473
-continued
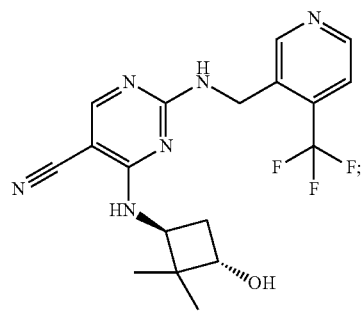
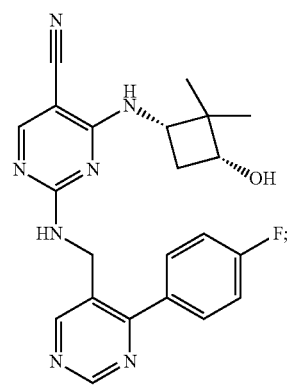
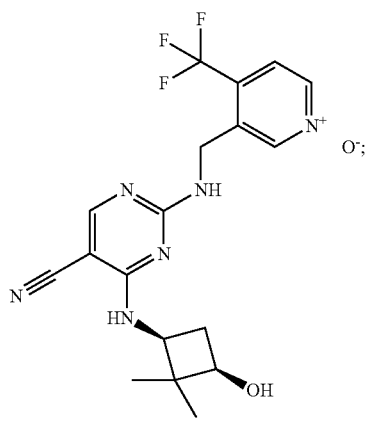
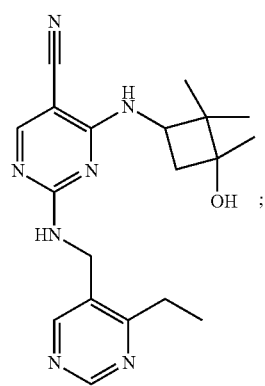
474
-continued
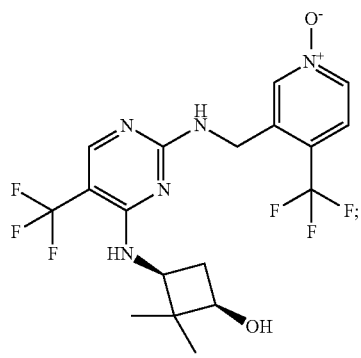
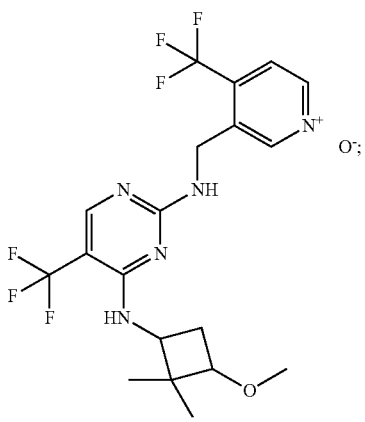
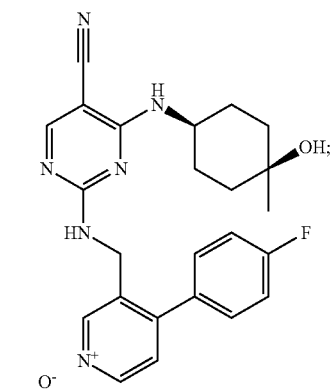
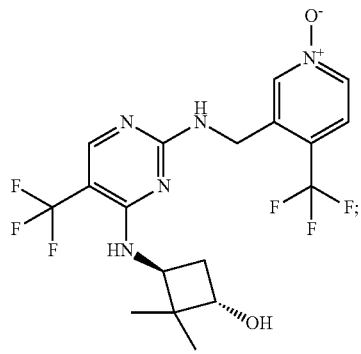

475
-continued
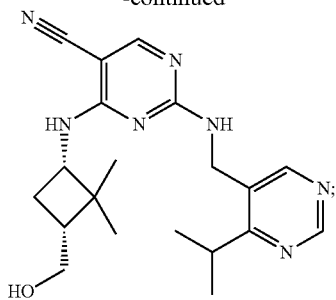
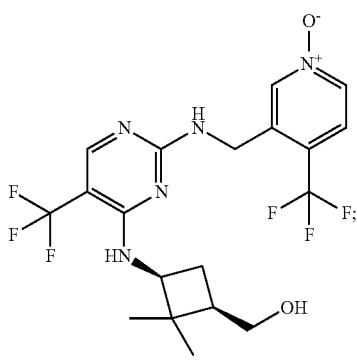
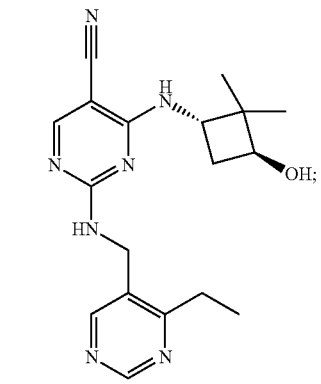
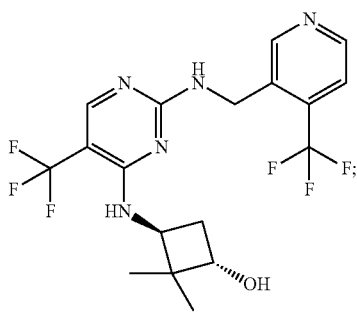
476
-continued
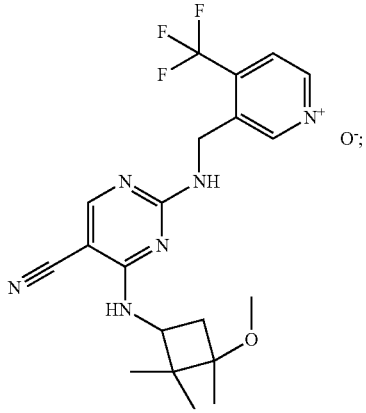
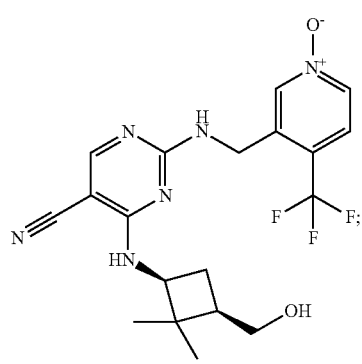
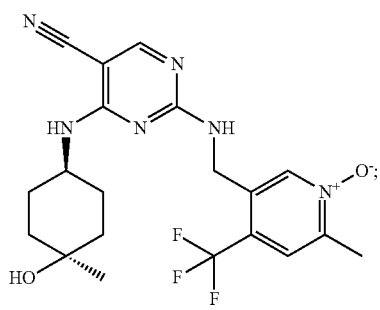

477
-continued
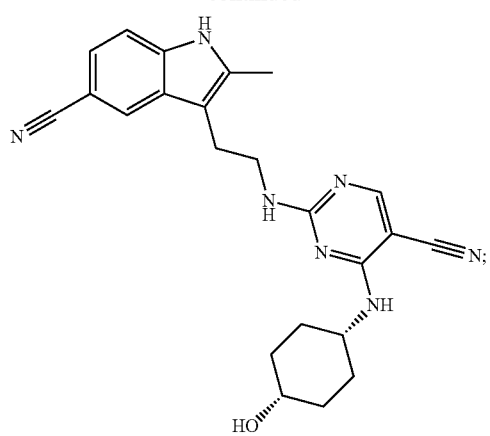
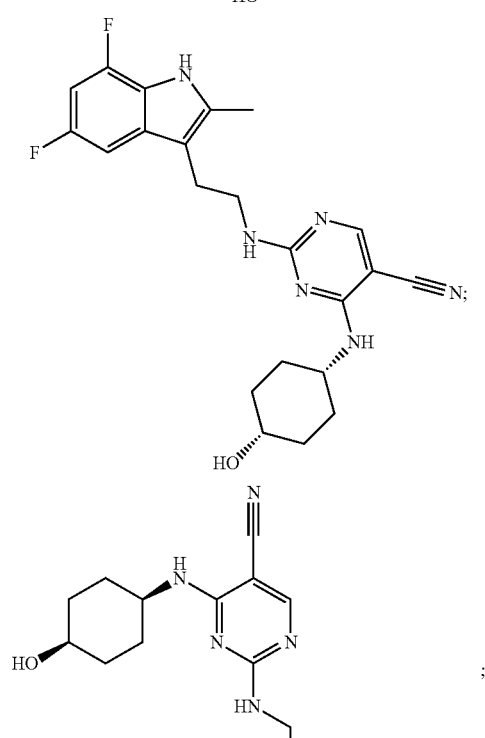
478
-continued
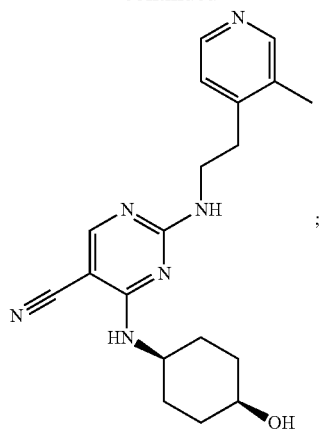
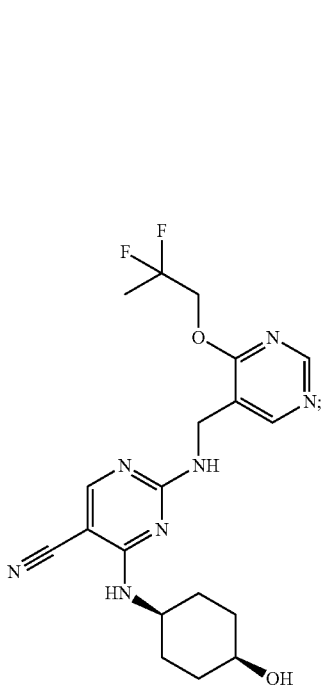
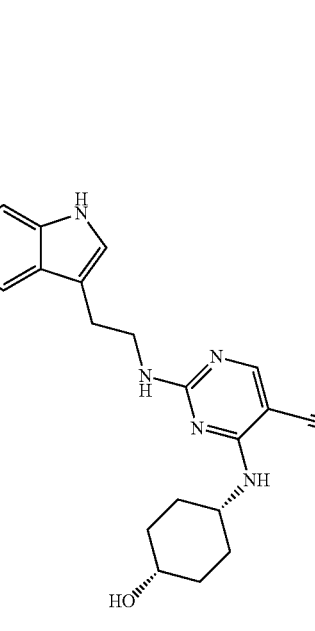

479
-continued
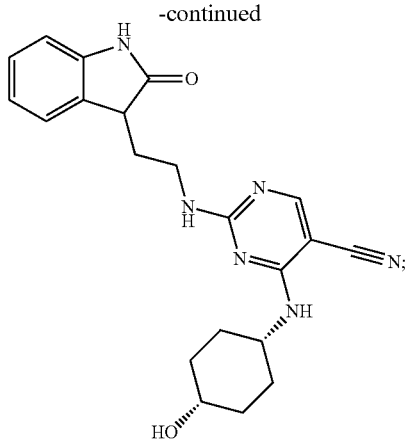
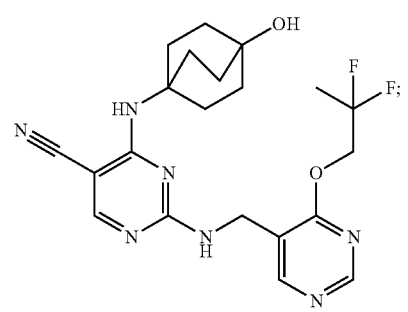
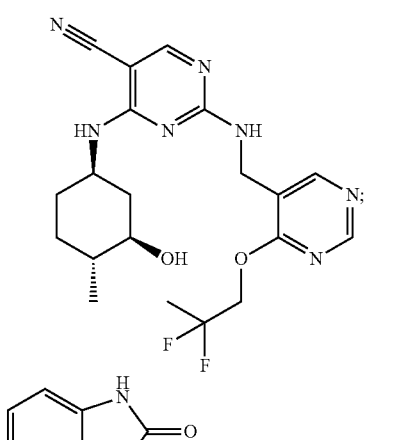
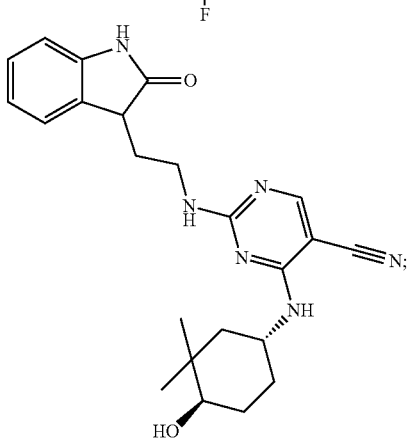
480
-continued
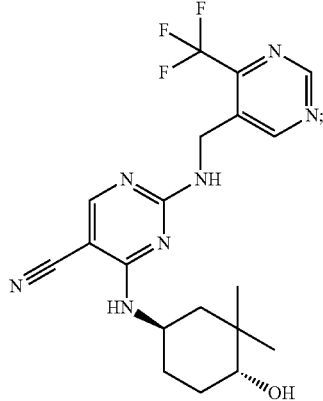
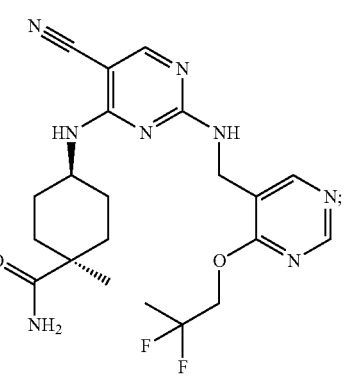
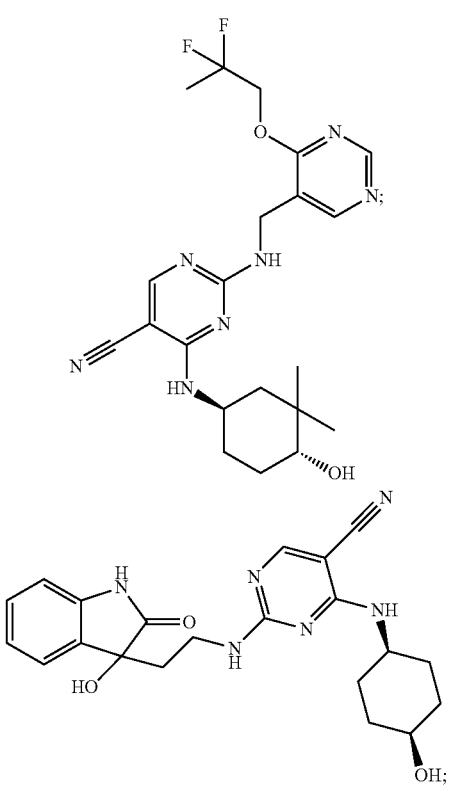

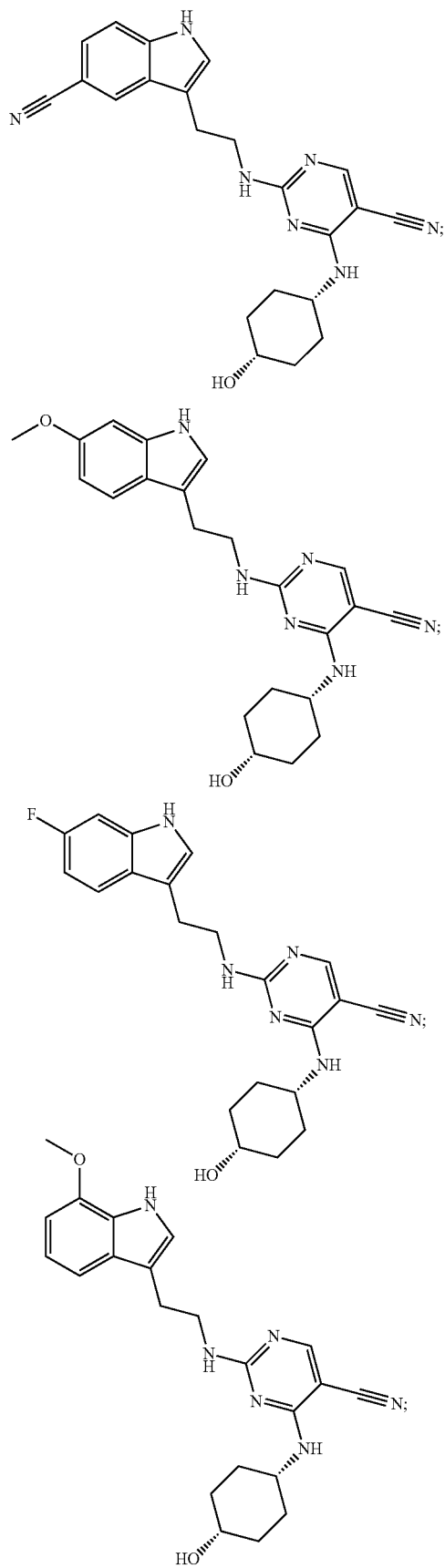
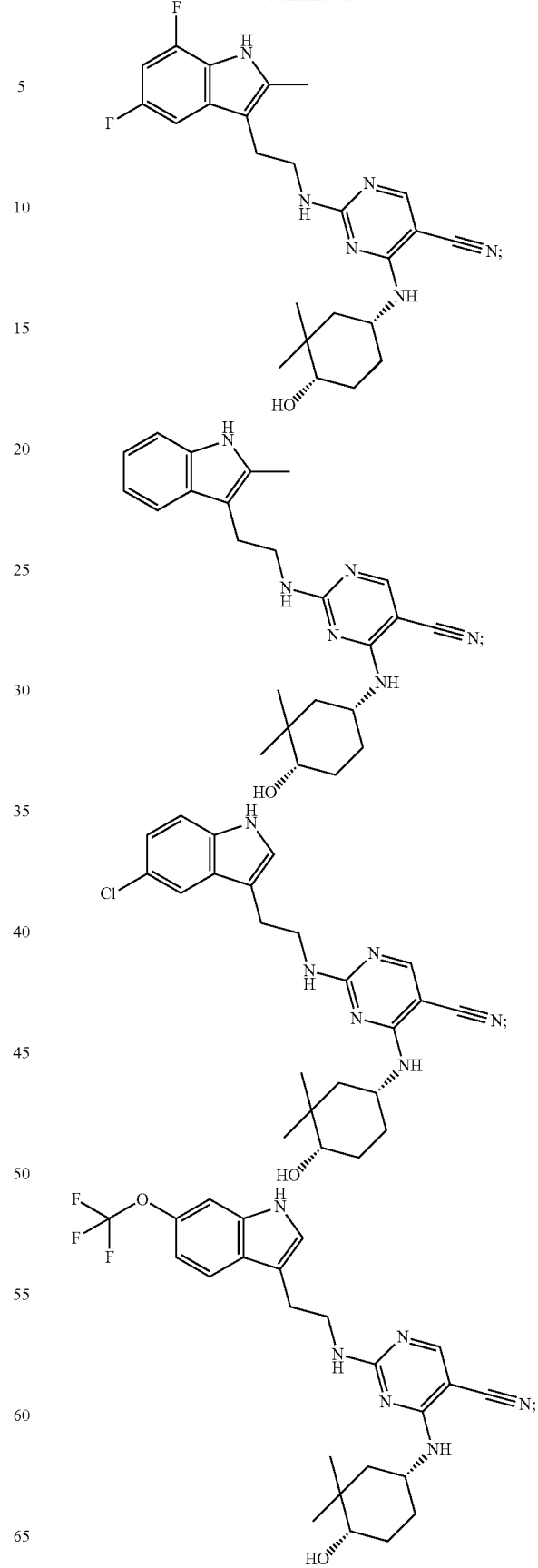

483 -continued
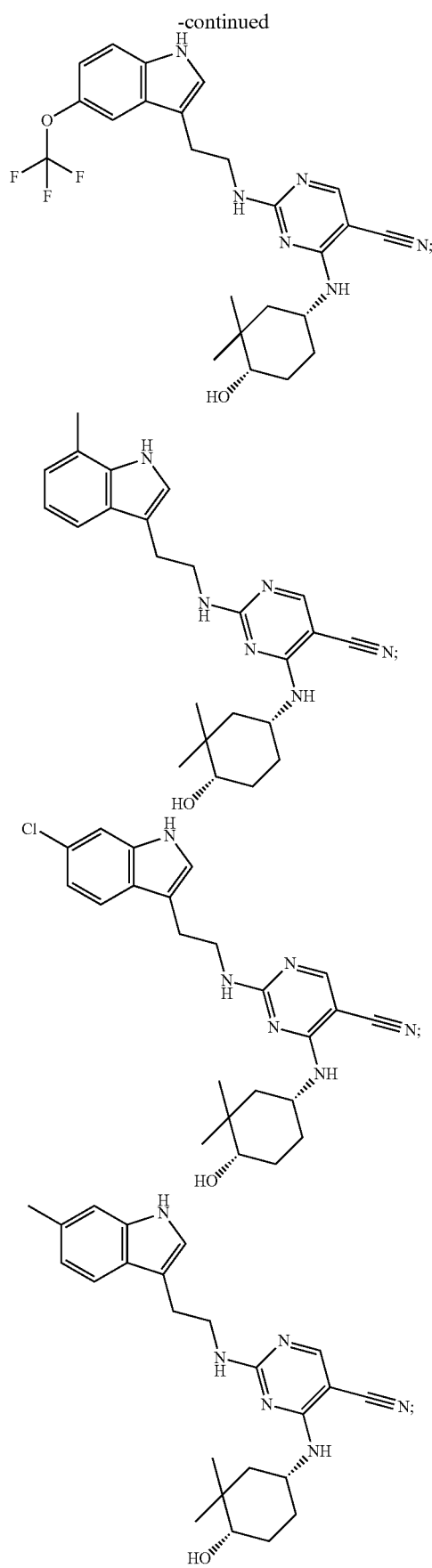
484 -continued
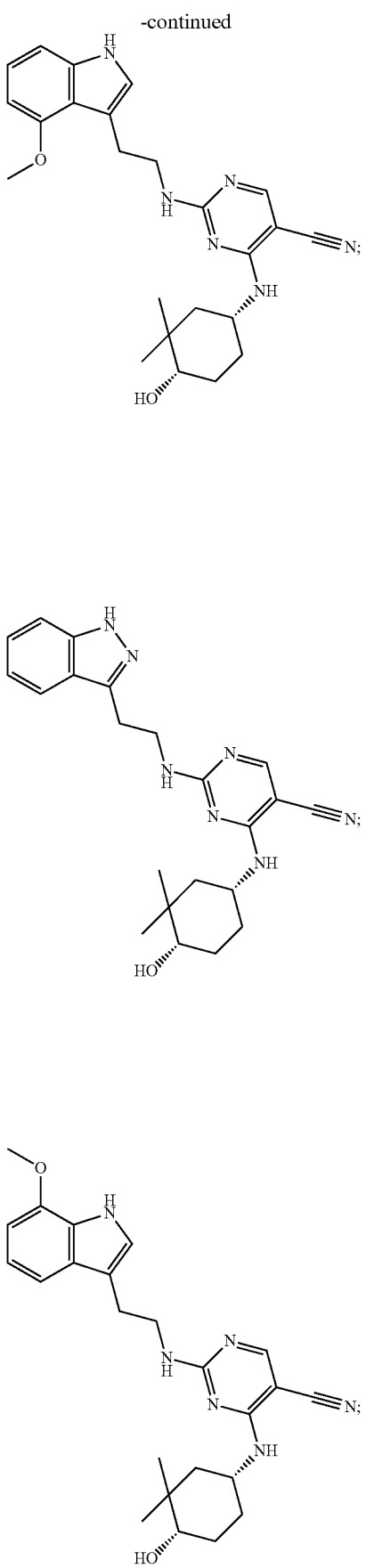

485
-continued
486
-continued
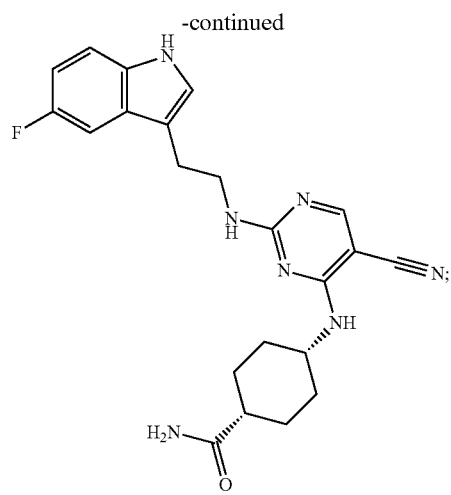
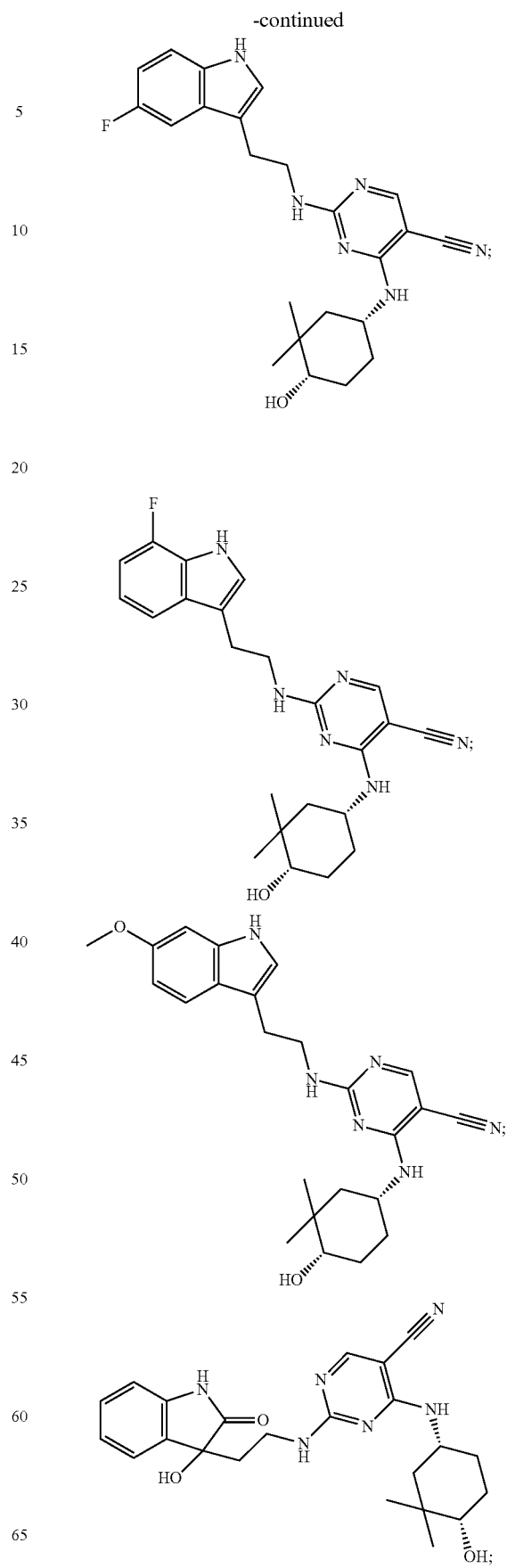

487
-continued
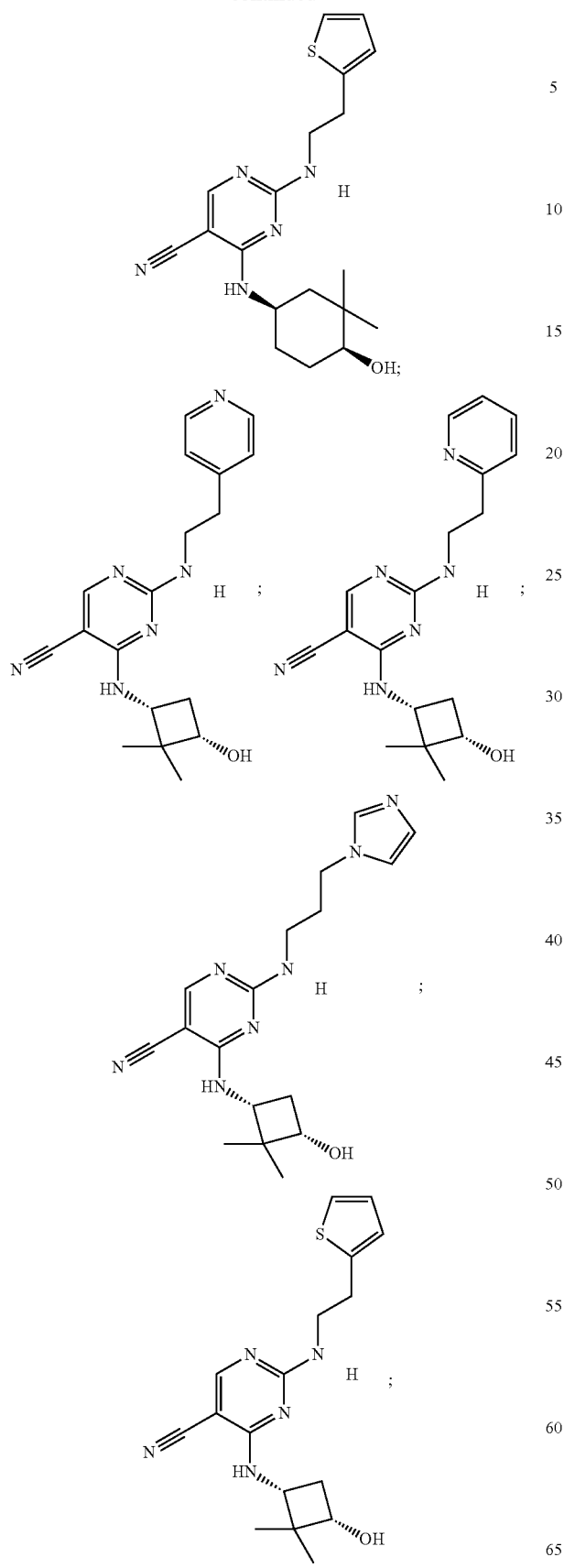
488
-continued
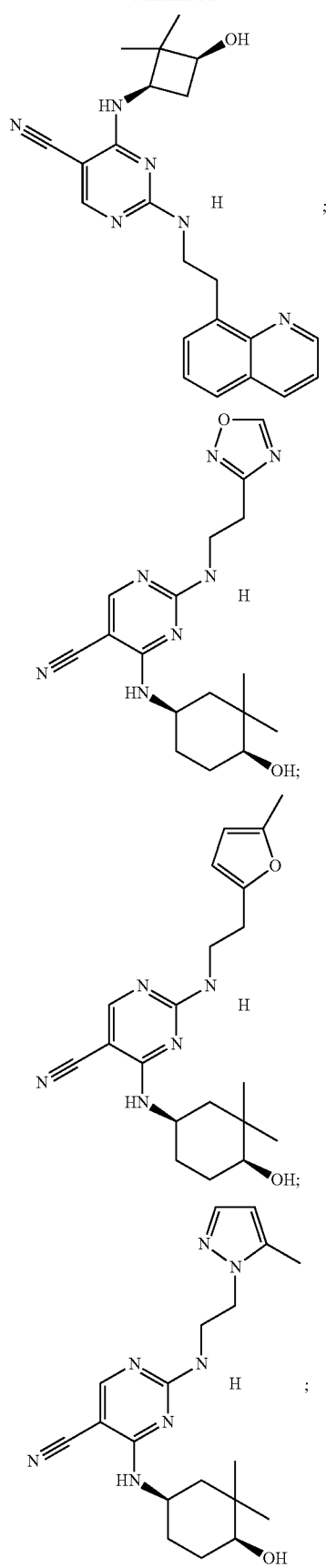

489
-continued
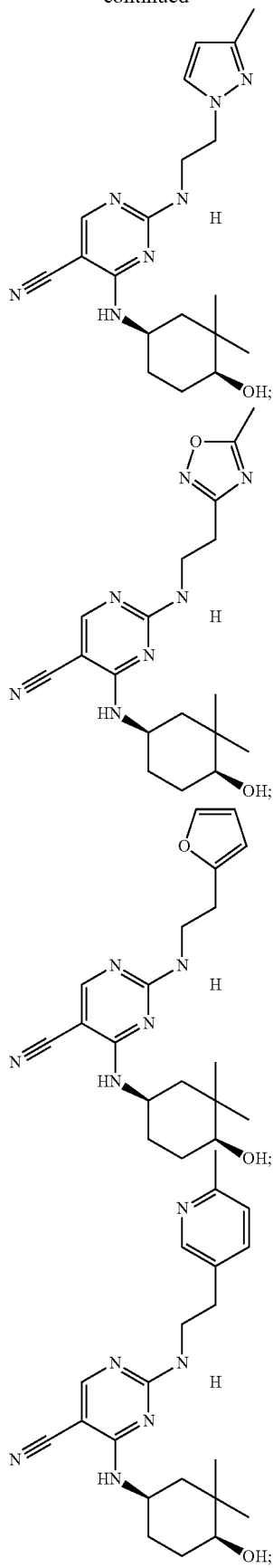
490
-continued
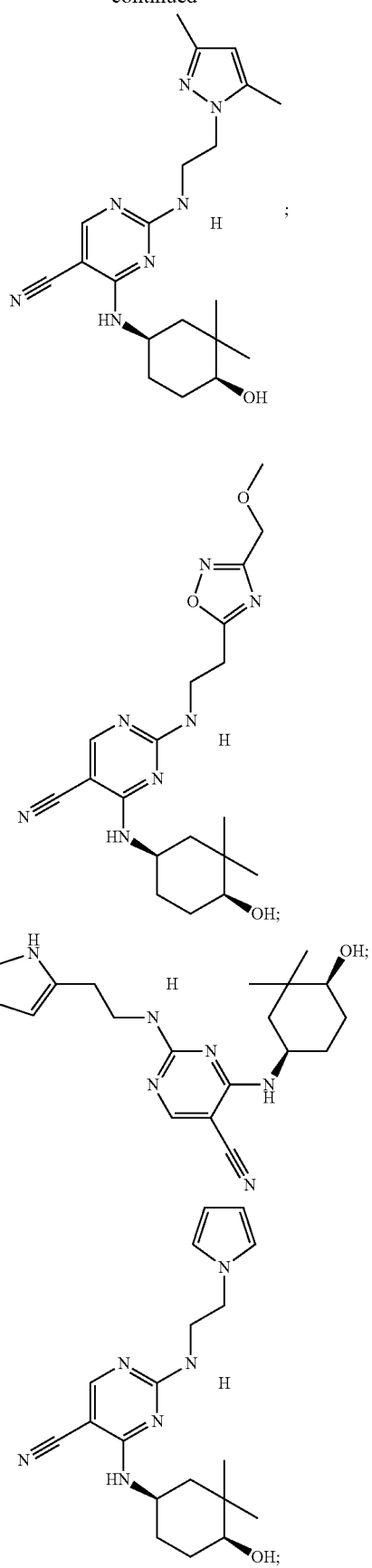

491
-continued
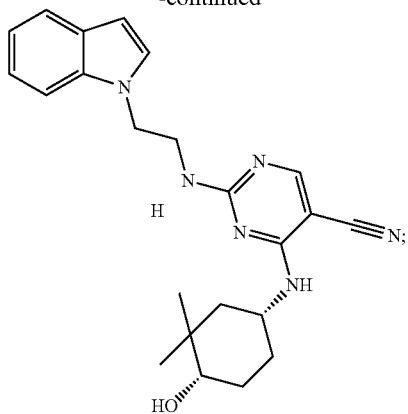
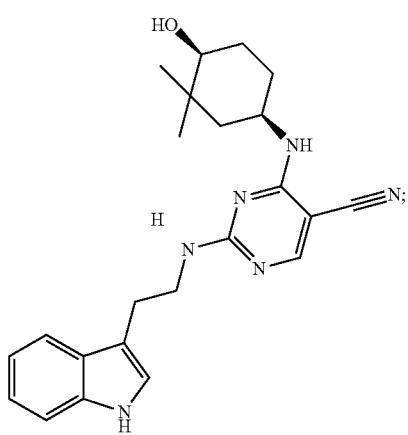
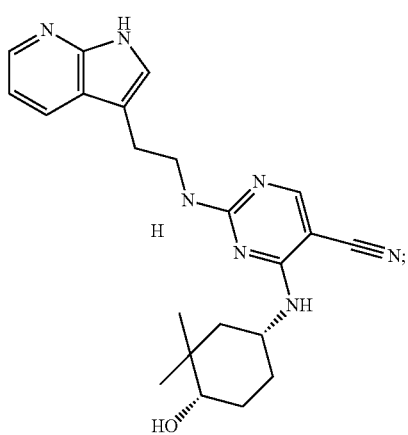
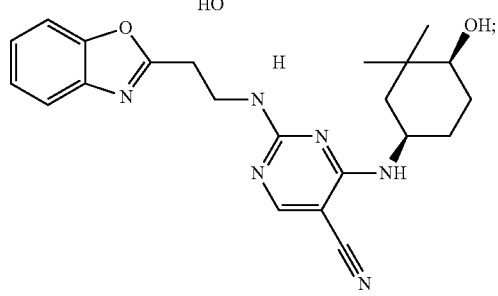
492
-continued
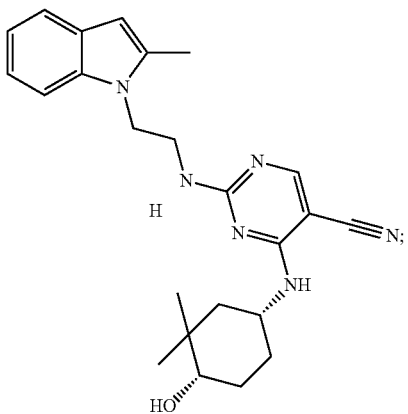
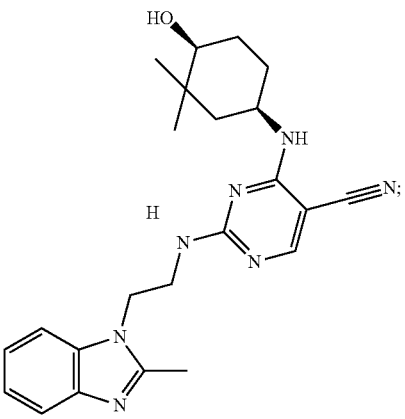
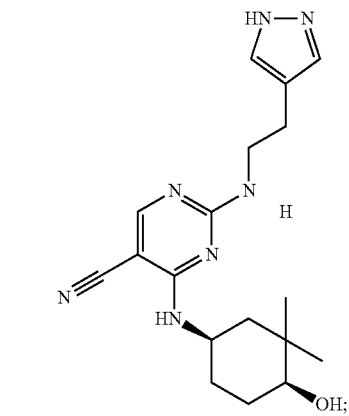

493
-continued
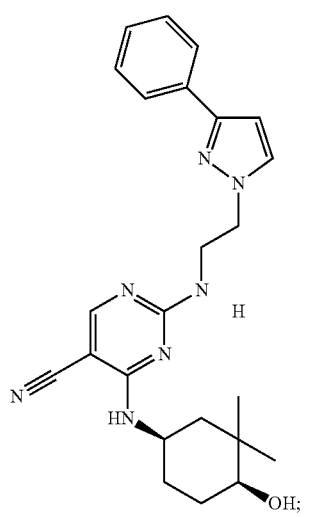
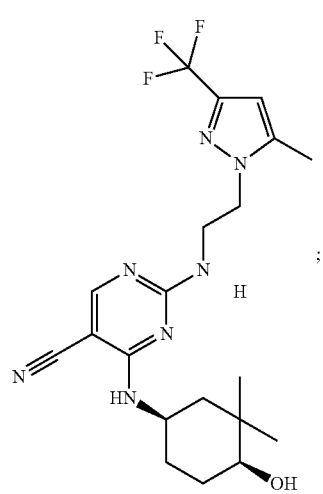
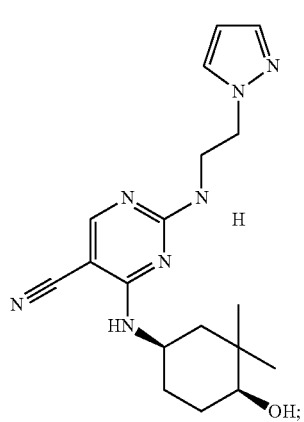
494
-continued
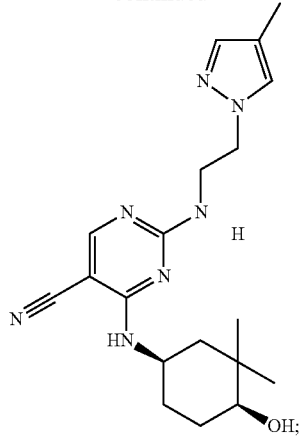
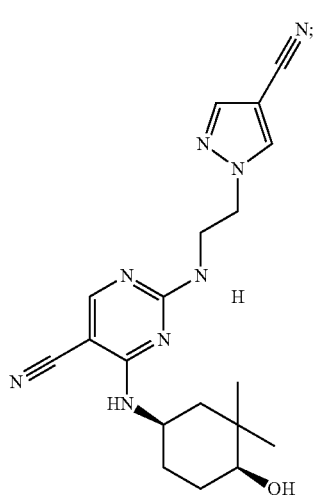
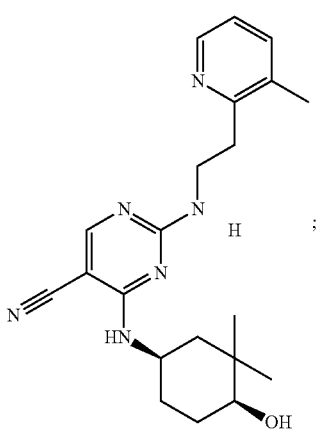

495
-continued
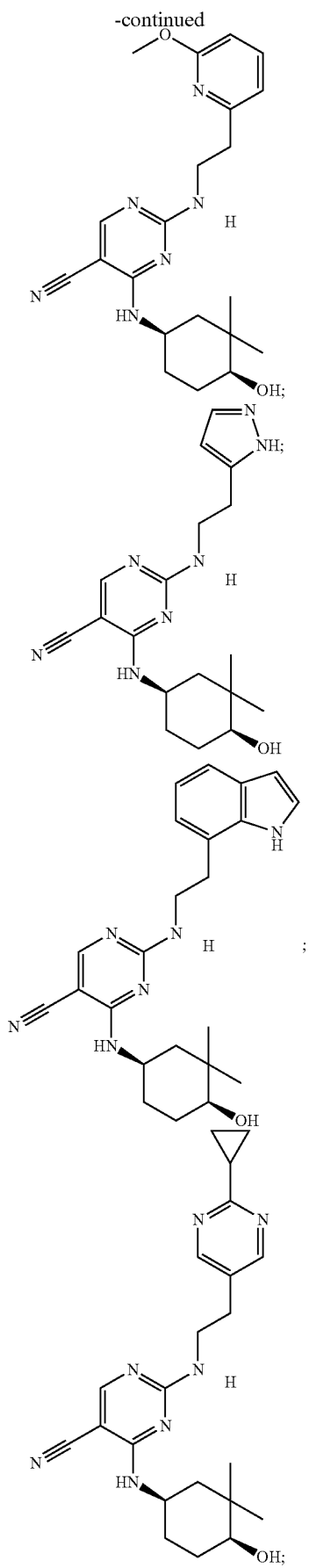
496
-continued
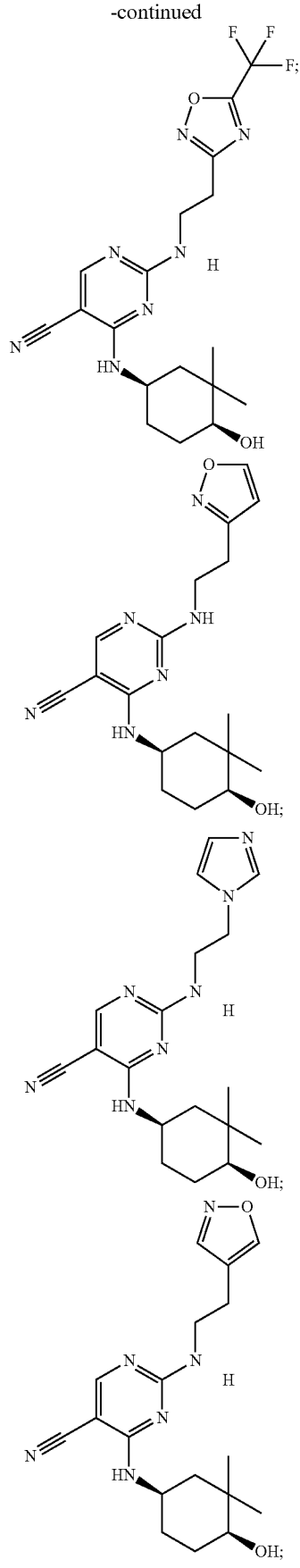

497
-continued
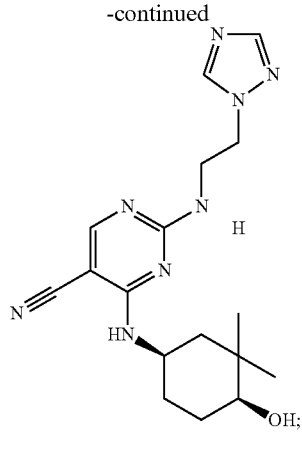
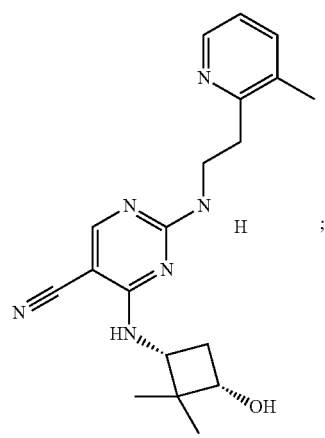
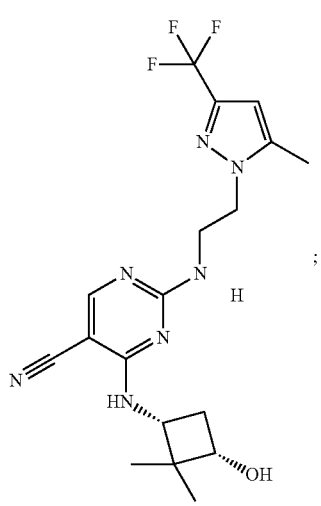
498
-continued
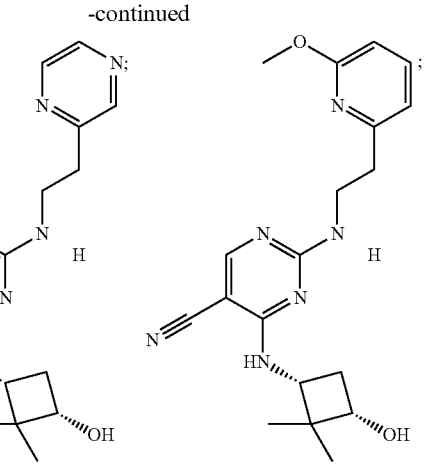
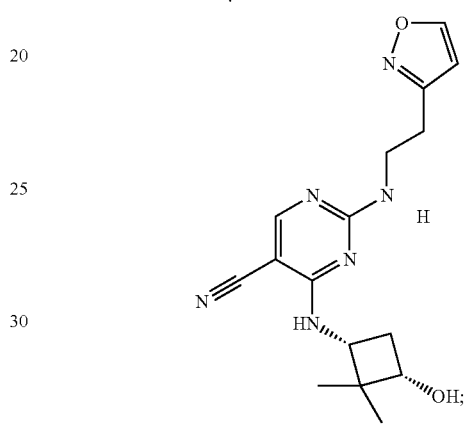
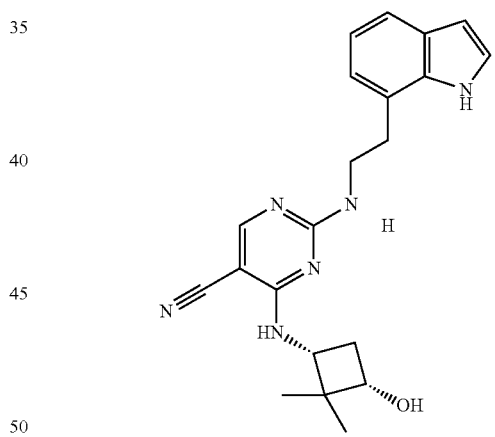
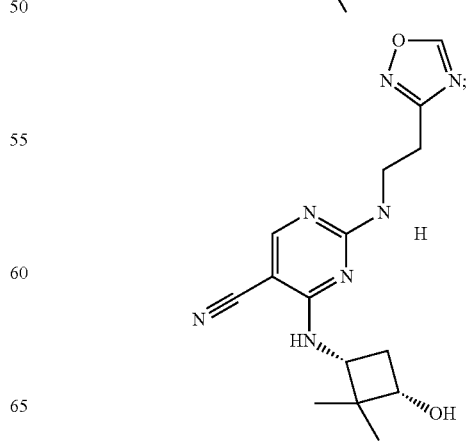

499
-continued
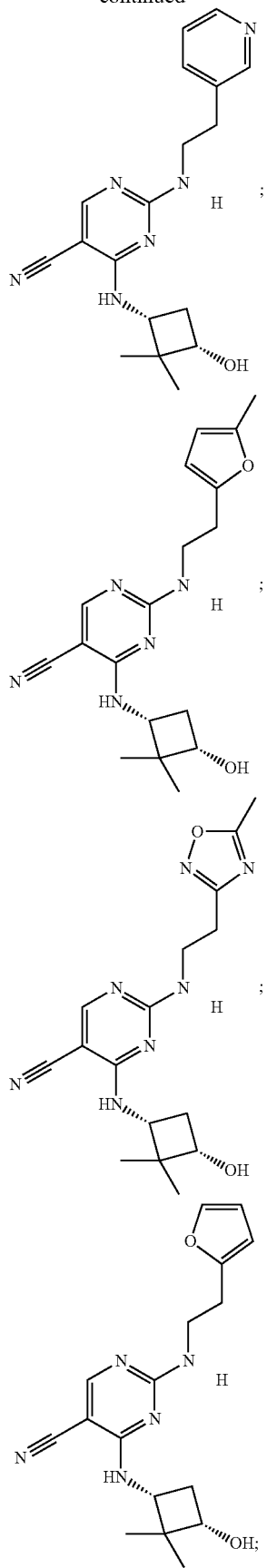
500
-continued
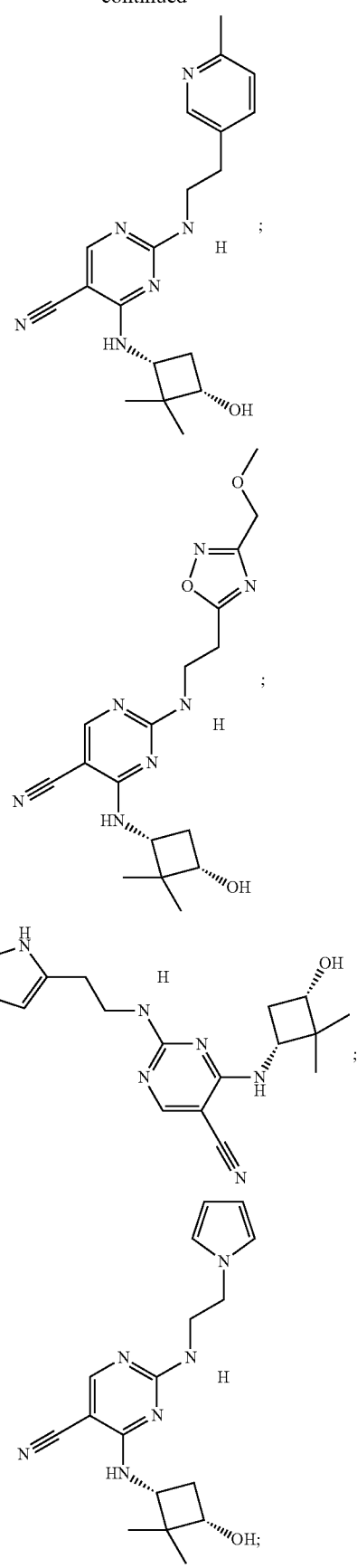

501
-continued

502
-continued

503
-continued
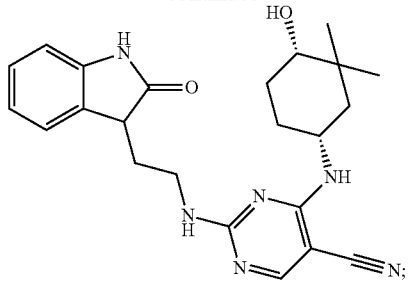
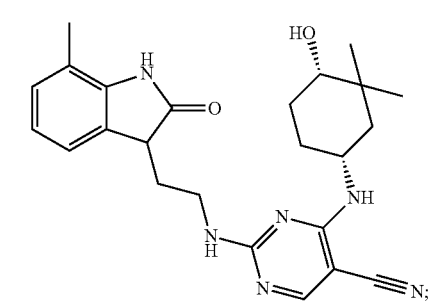
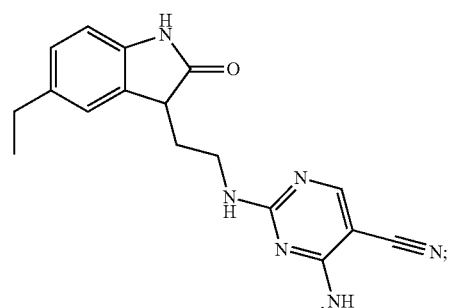
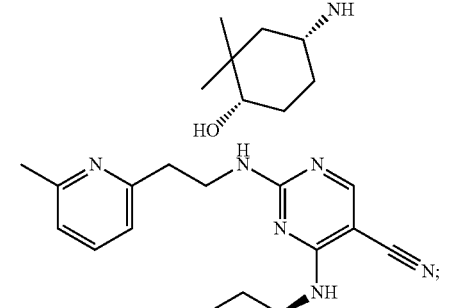
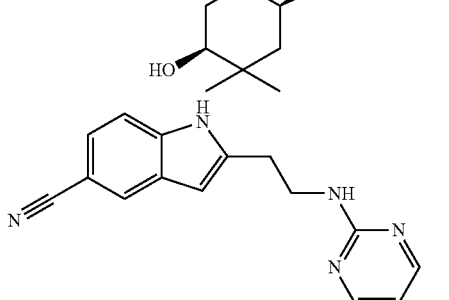
504
-continued
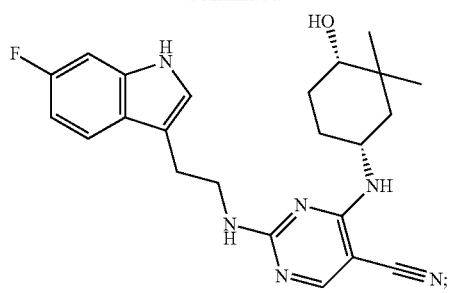
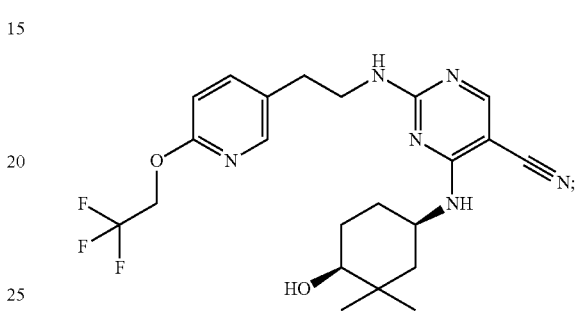
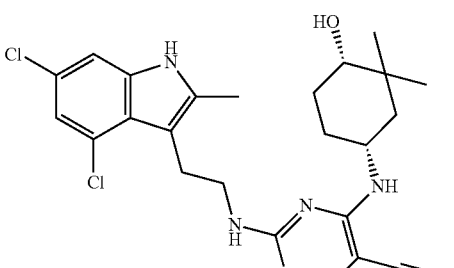
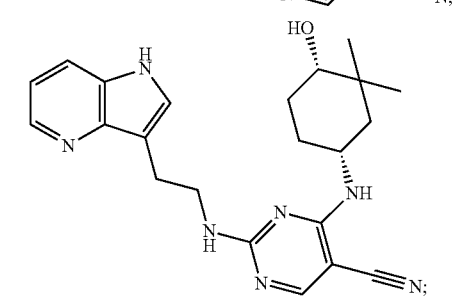
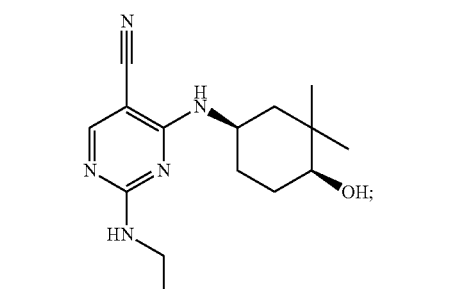

505
-continued
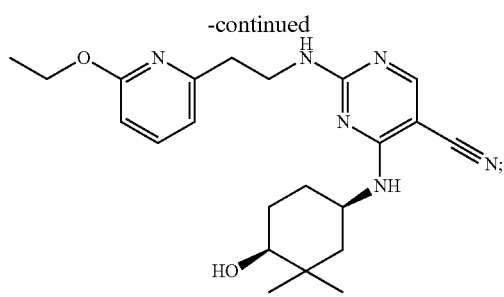
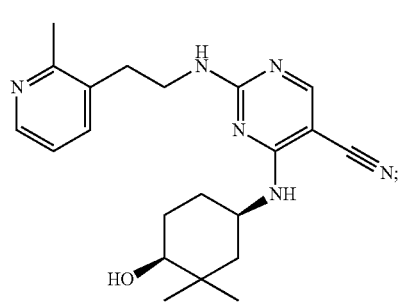
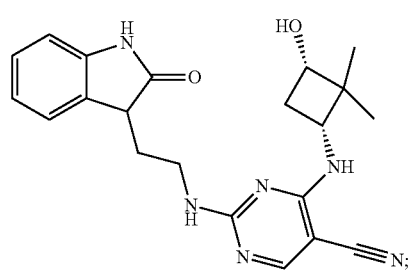
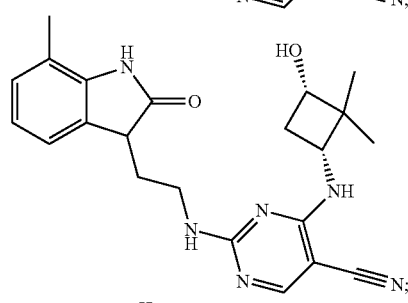
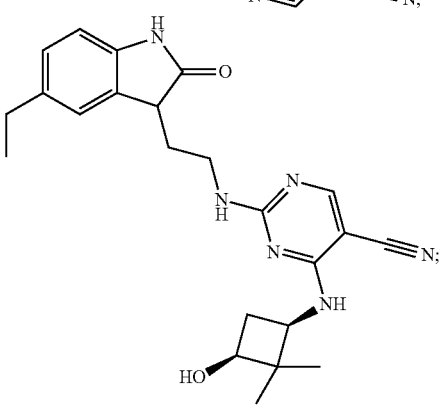
506
-continued
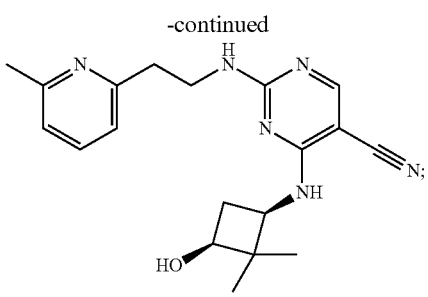
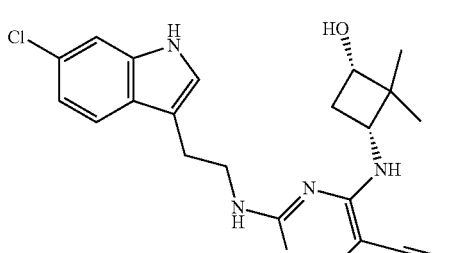
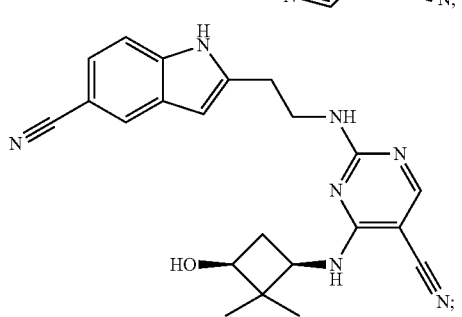
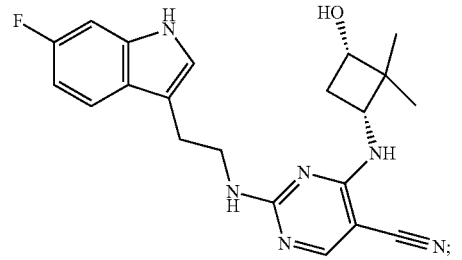
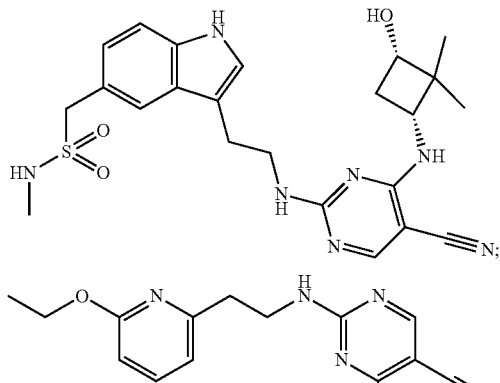
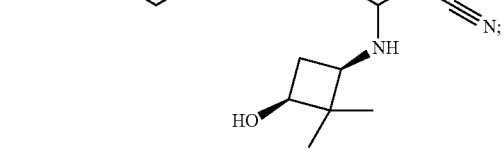

507
-continued
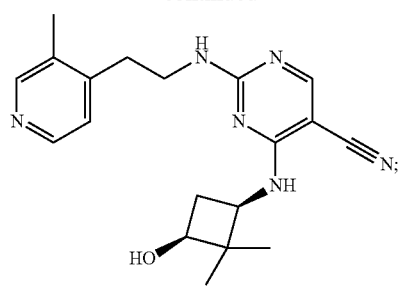
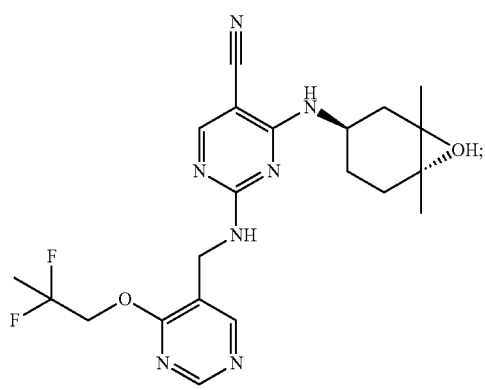
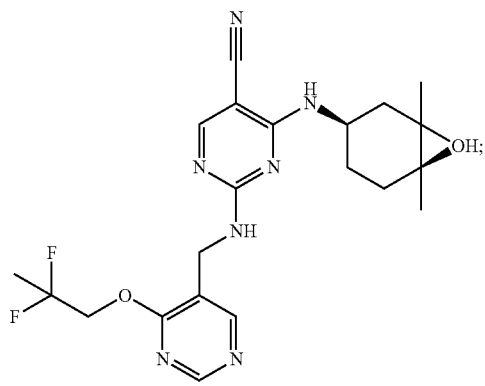
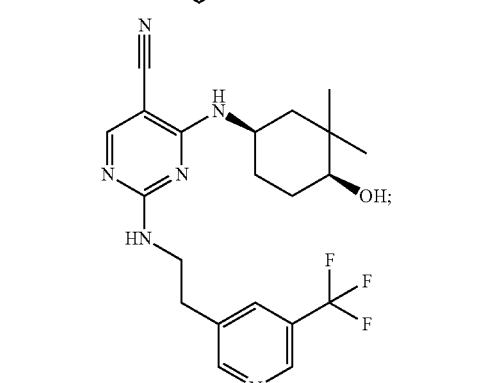
508
-continued
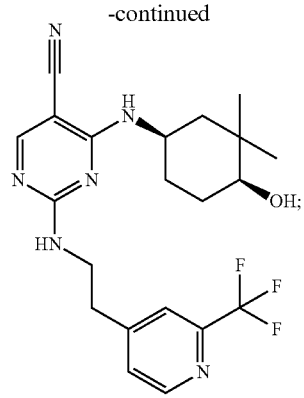
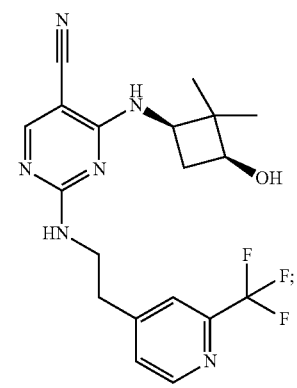
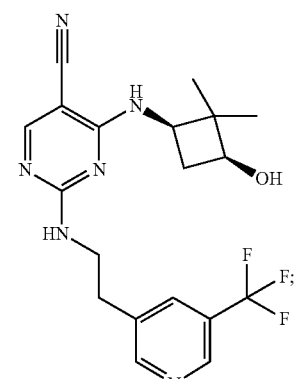
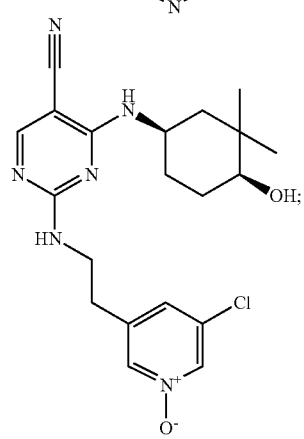

509
-continued
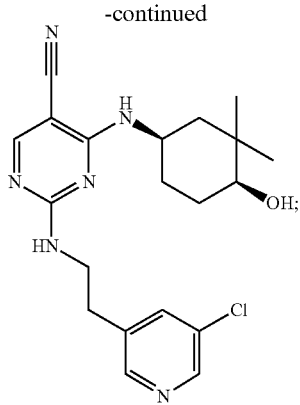
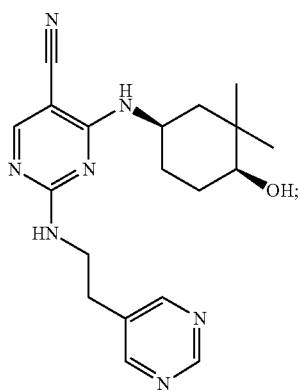
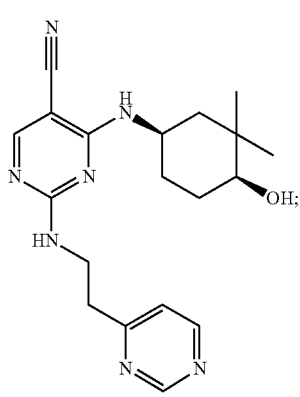
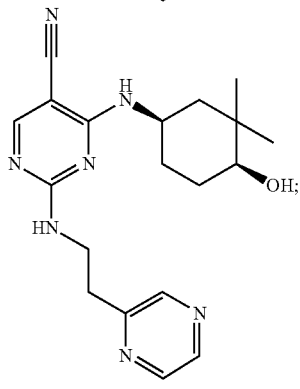
510
-continued
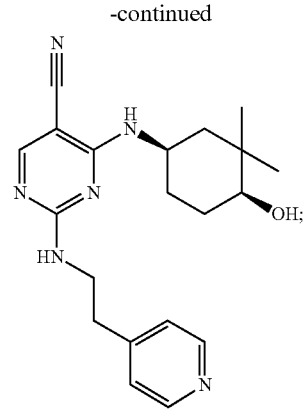
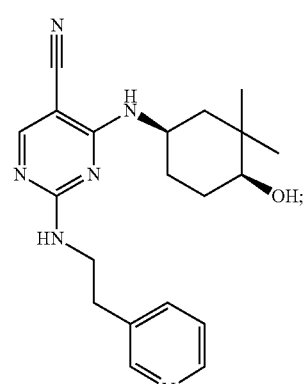
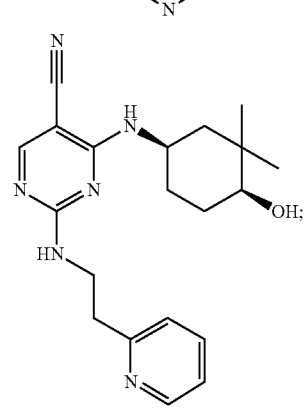
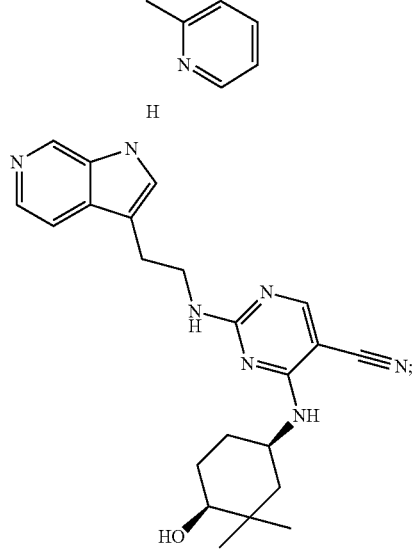

511
-continued
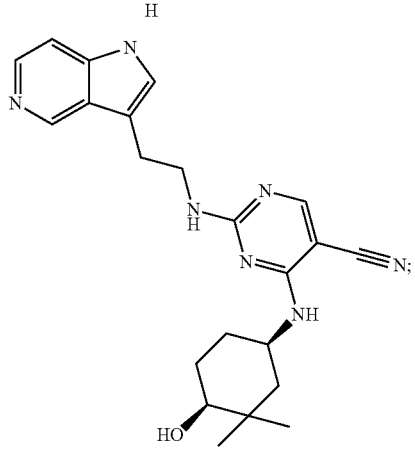
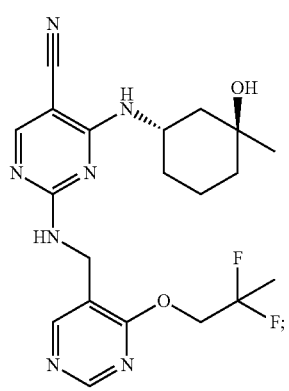
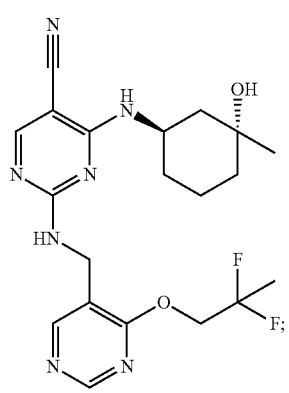
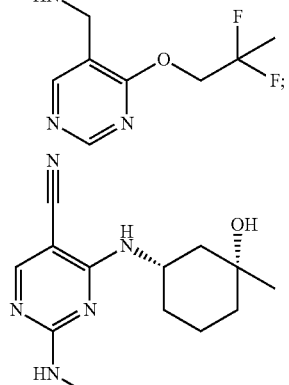
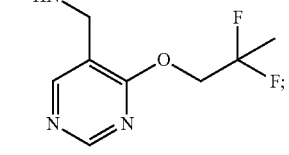
512
-continued
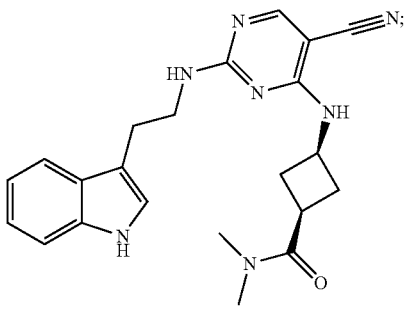
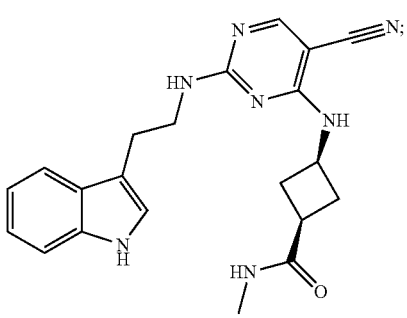
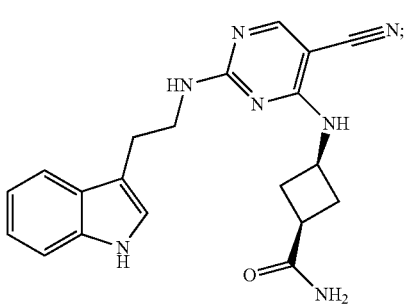
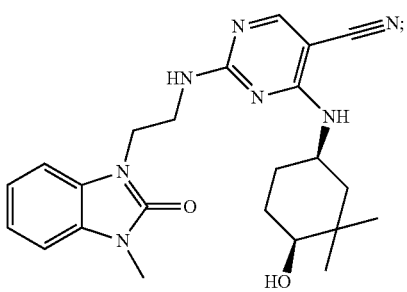
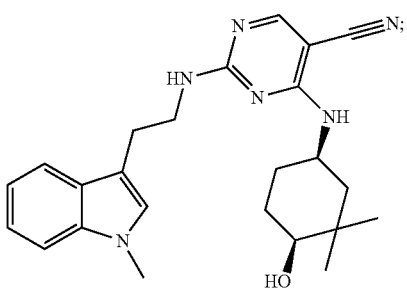

513
-continued
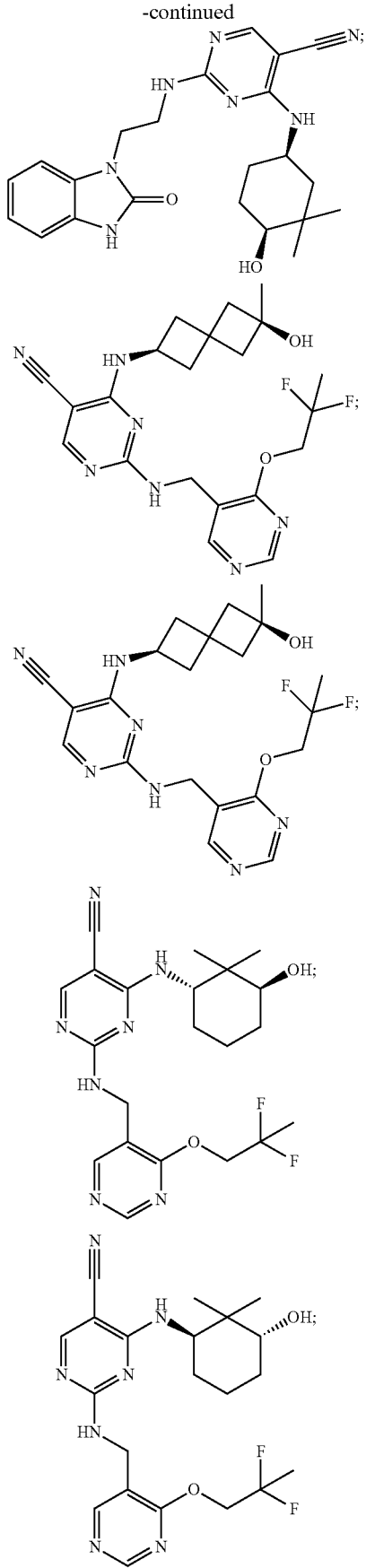
514
-continued
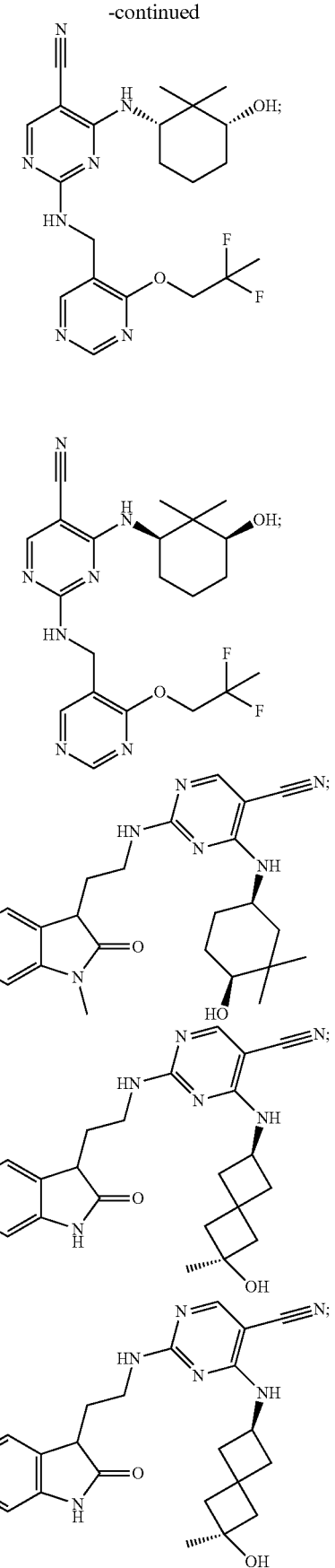

515
-continued
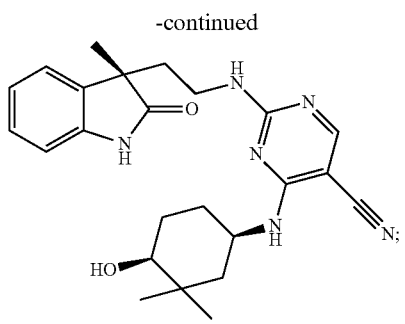
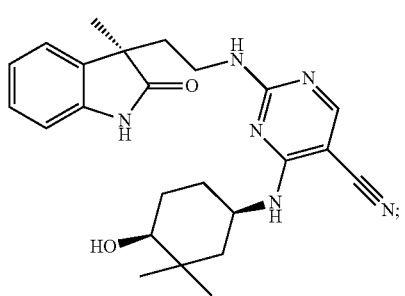
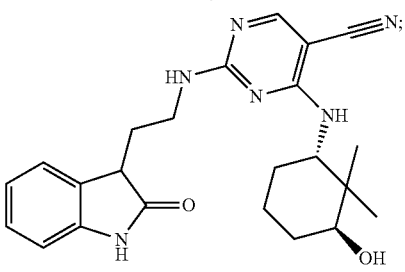
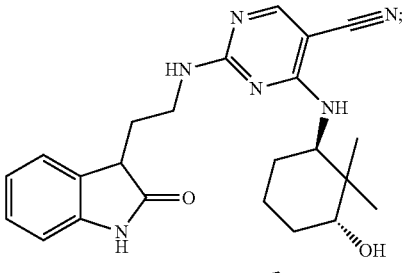
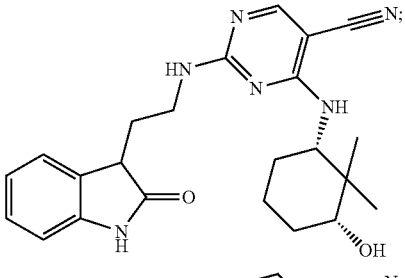
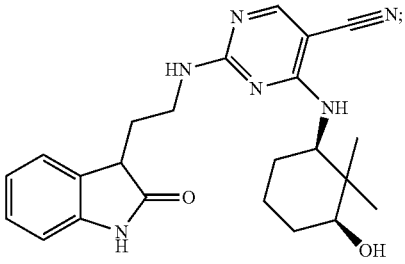
516
-continued
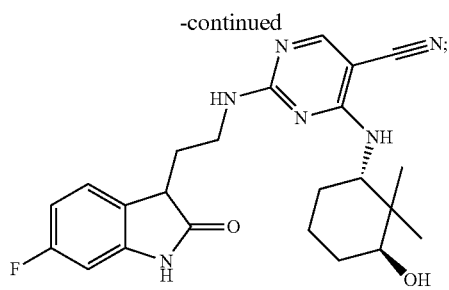
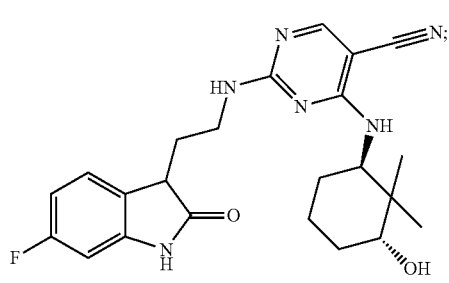
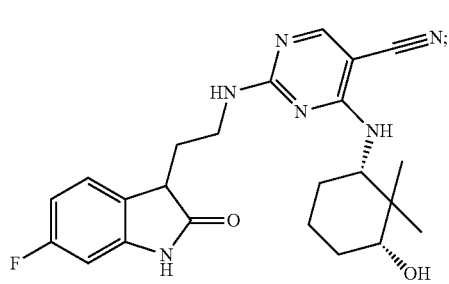
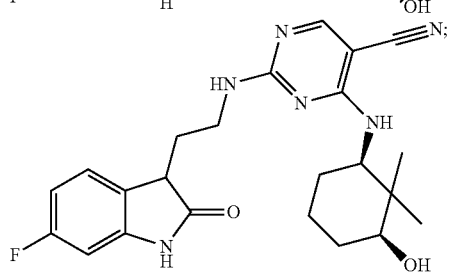
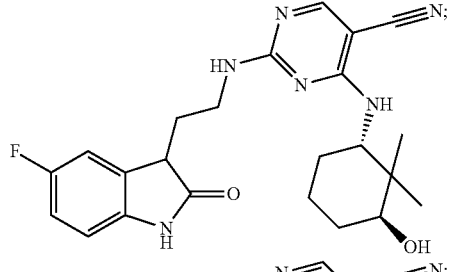
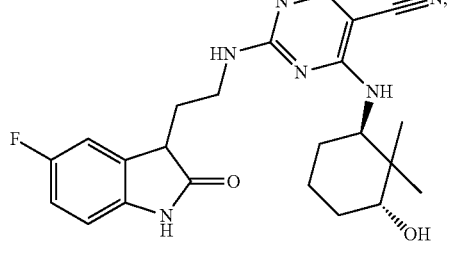

517
-continued
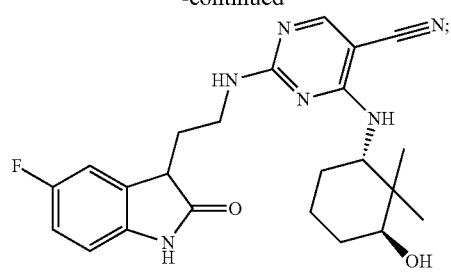
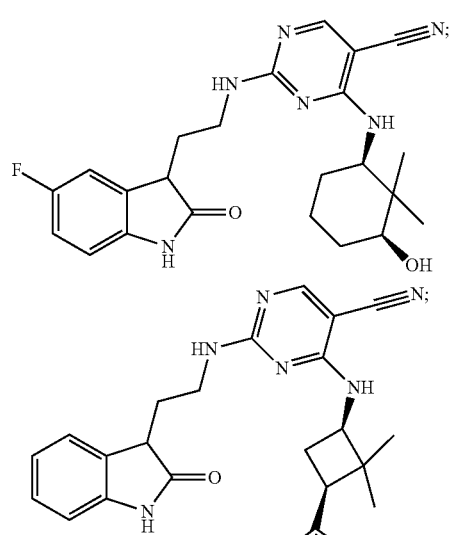
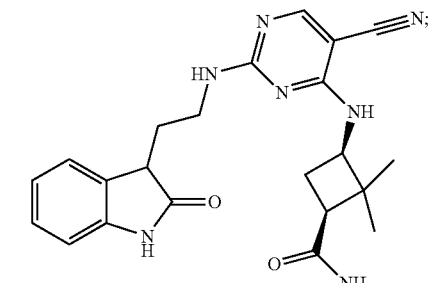
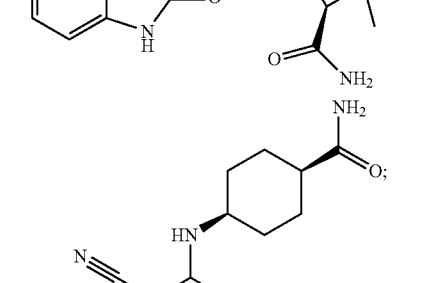
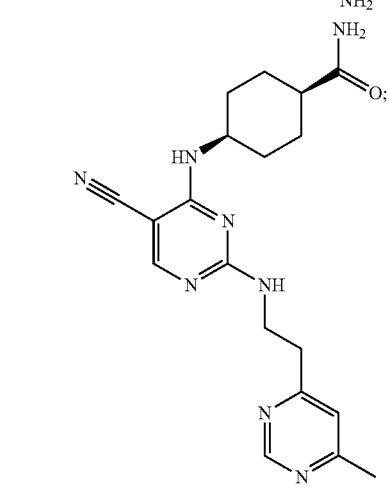
518
-continued
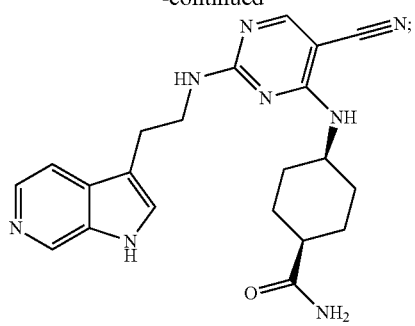
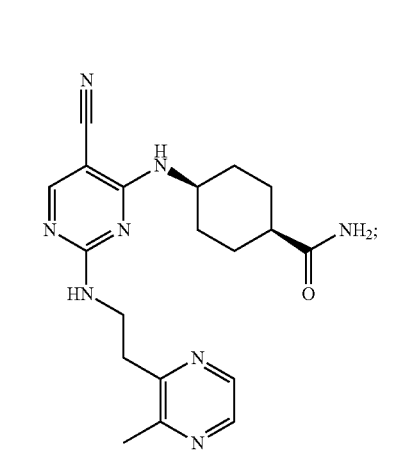
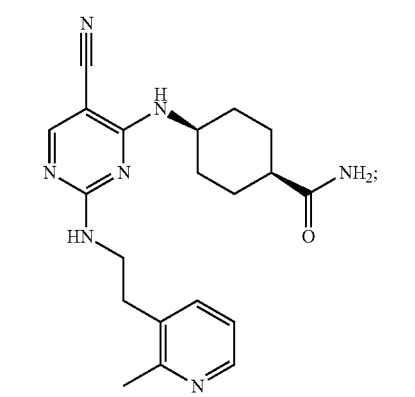
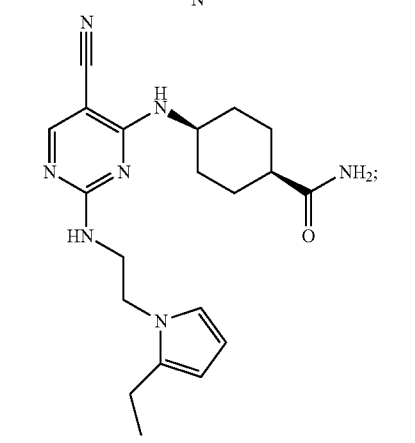

519
-continued
520
-continued
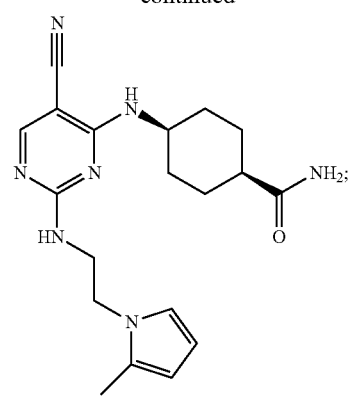
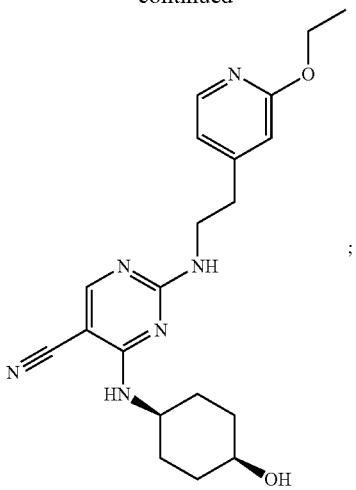
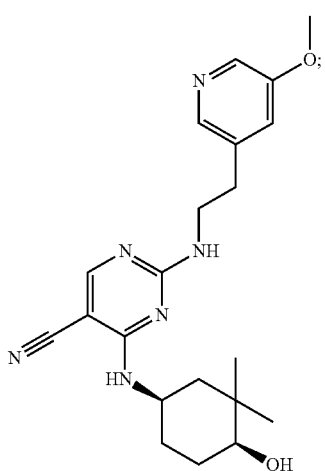
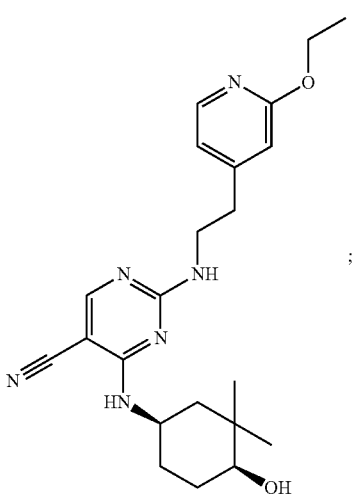

-continued
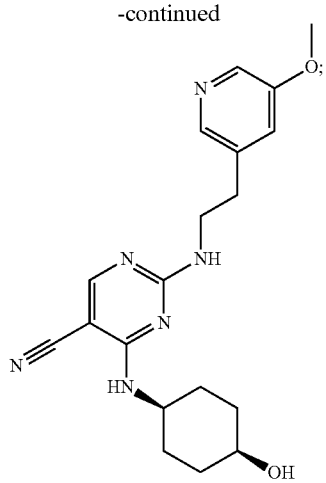
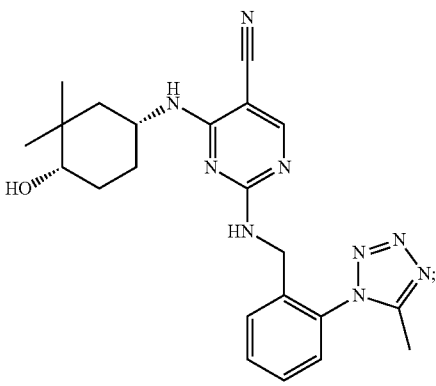
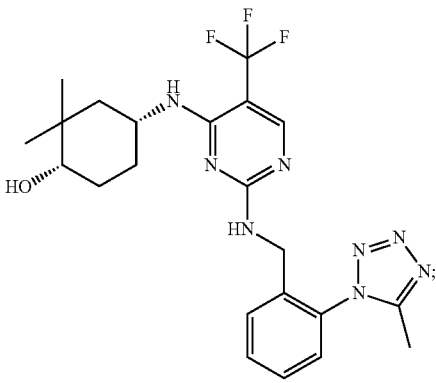
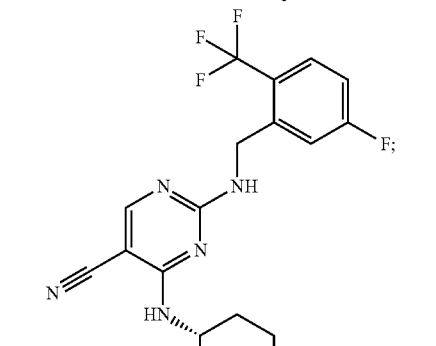
or a pharmaceutically acceptable salt, tautomer, or stereoisomer thereof.
25. A compound wherein the compound is
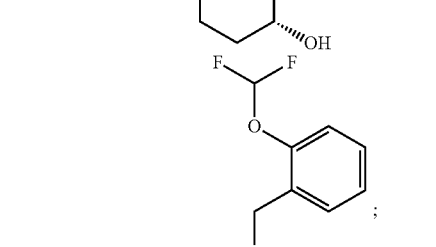
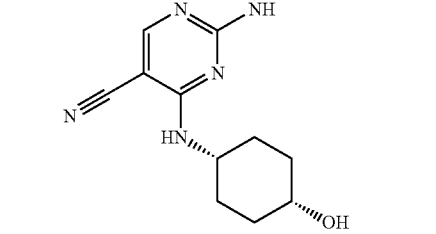

523
-continued
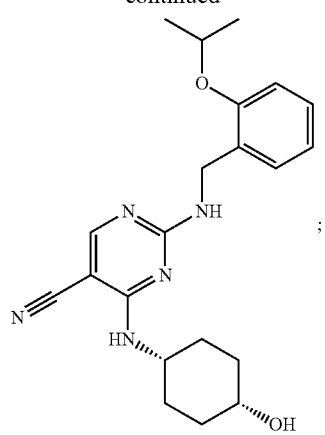
524
-continued
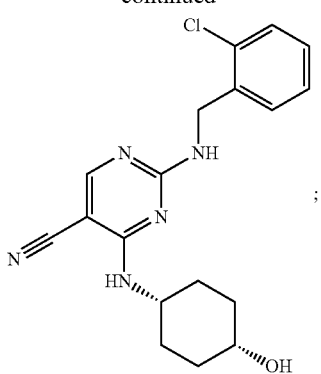
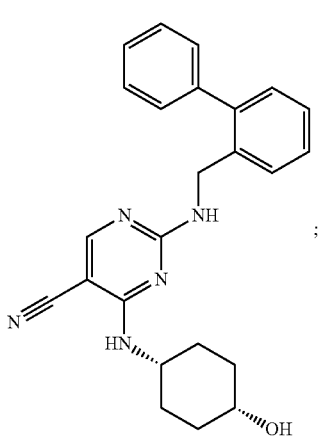
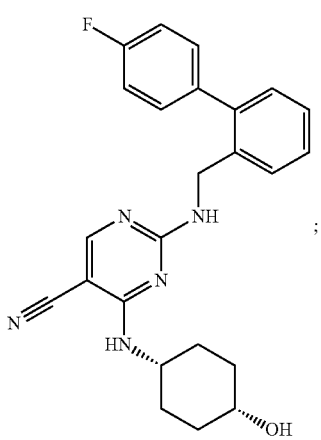

525 -continued
526 -continued
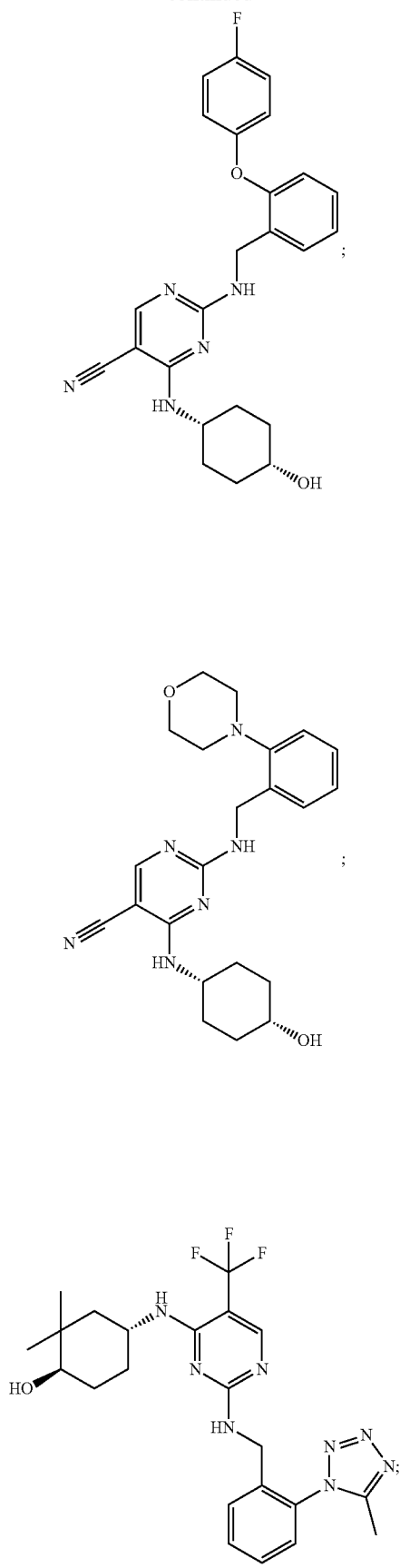

527
-continued
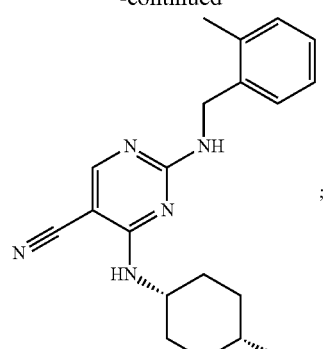
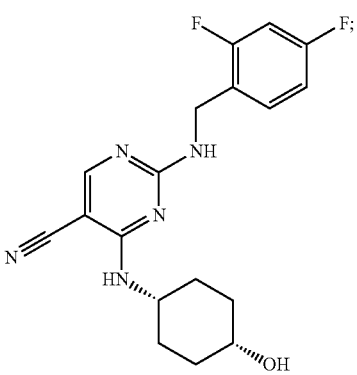
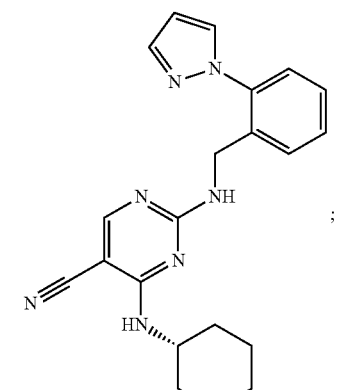
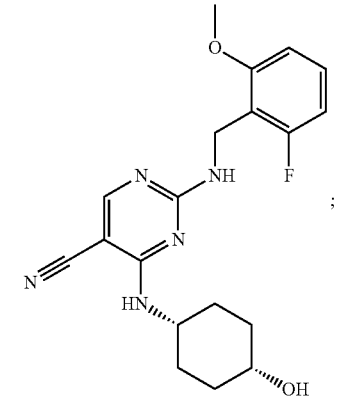
528
-continued
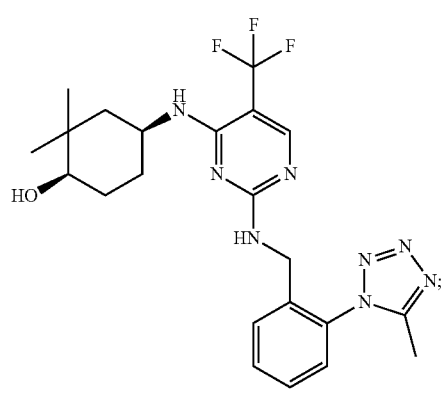
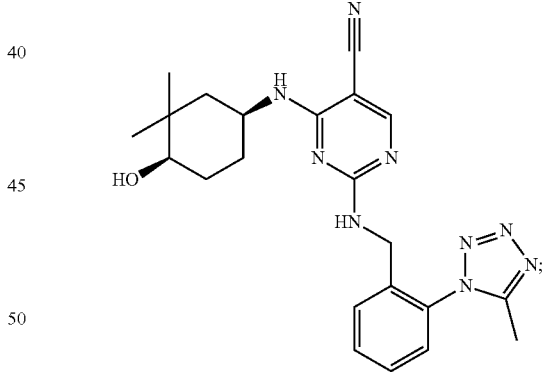
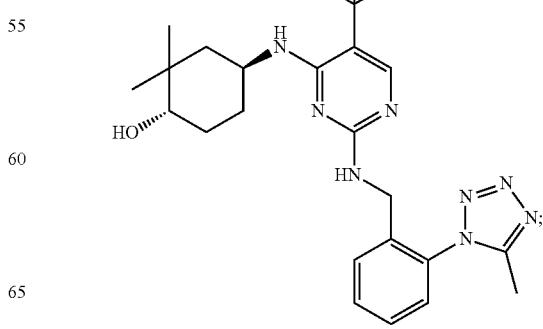

529
-continued
530
-continued
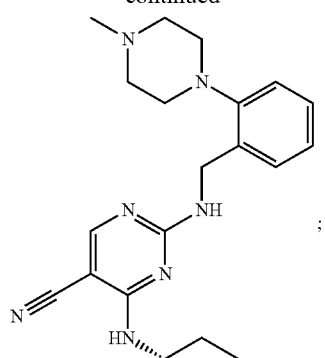
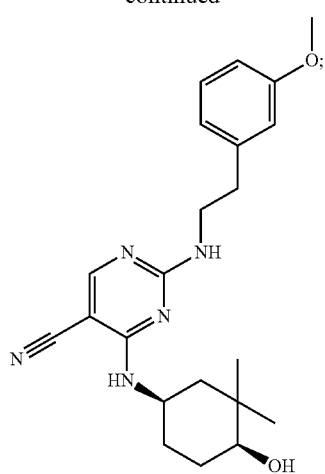

531
-continued
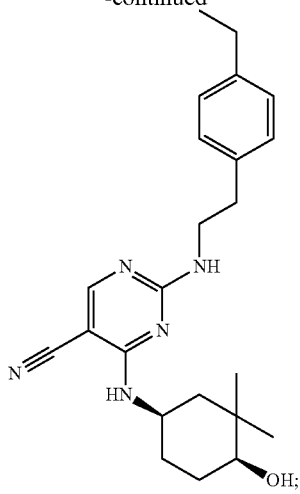
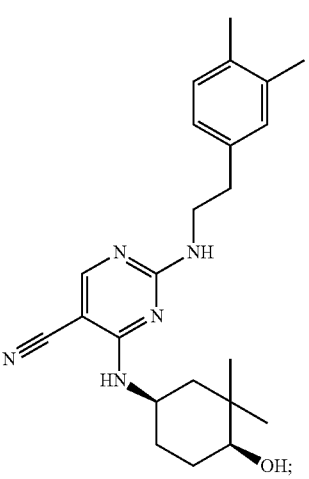
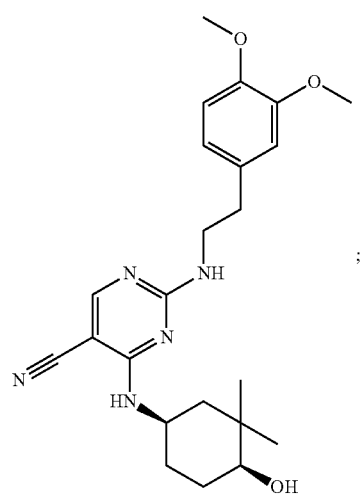
532
-continued
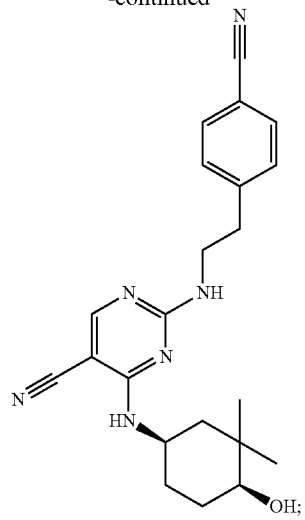
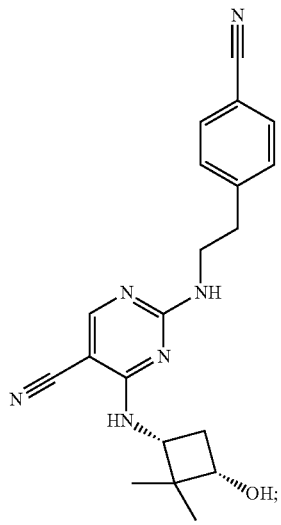
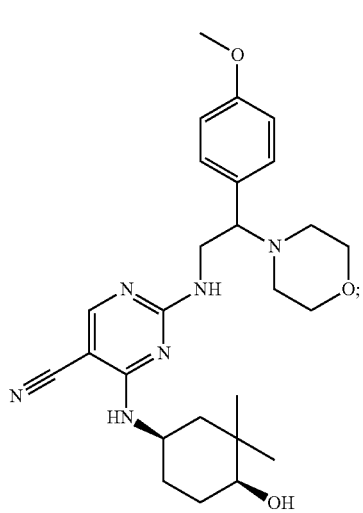

533
-continued
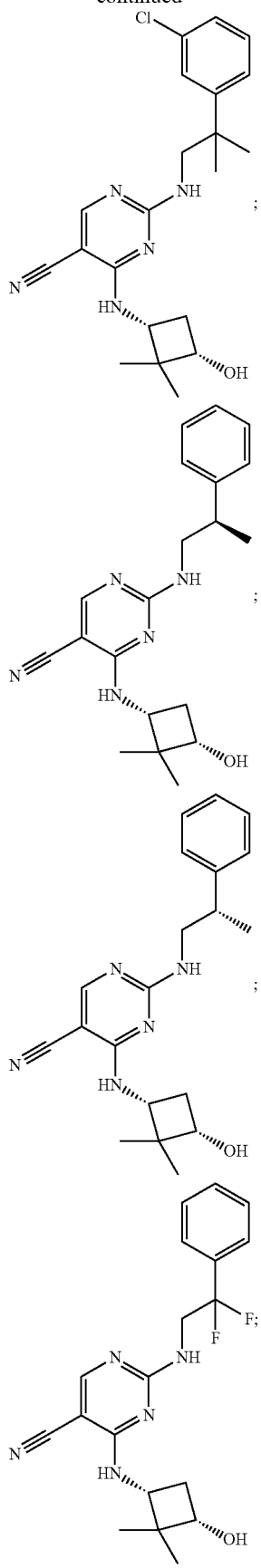
534
-continued
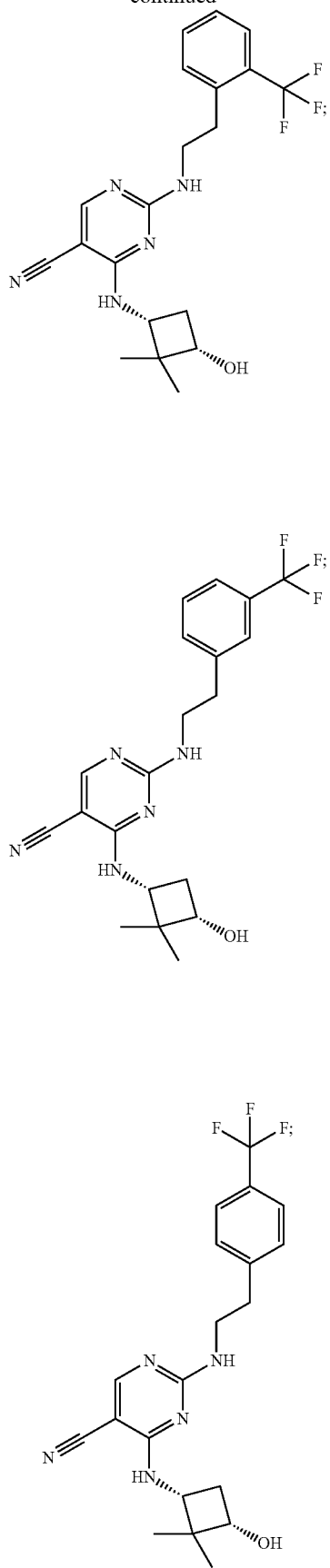

535
-continued
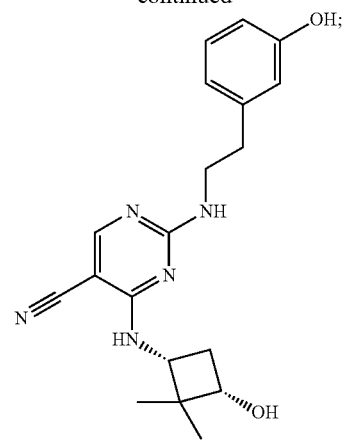
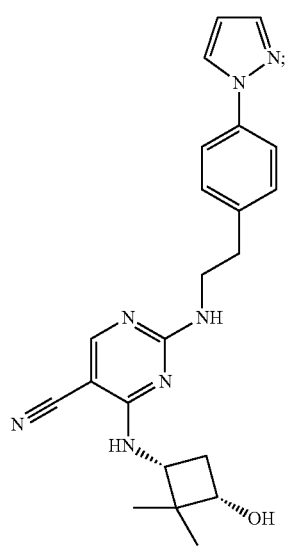
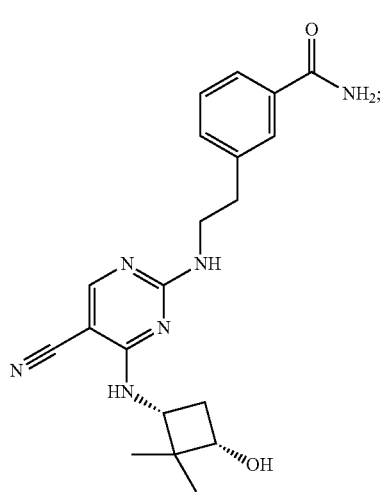
536
-continued
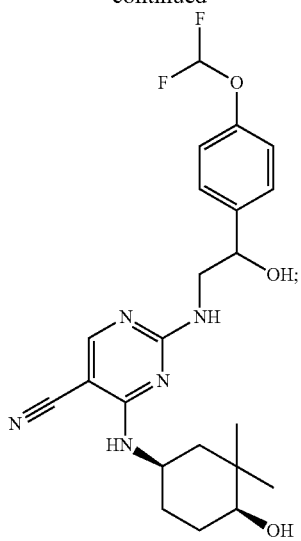
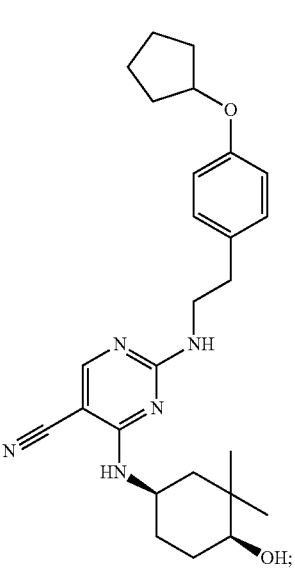
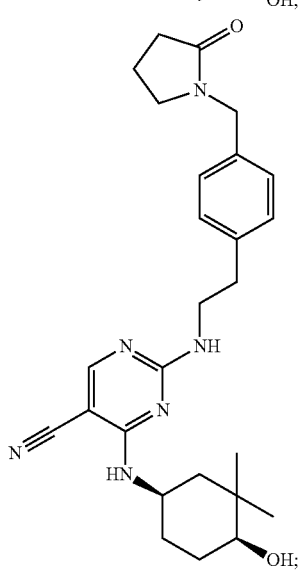

537
-continued
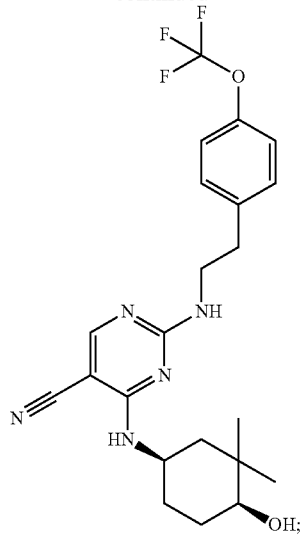
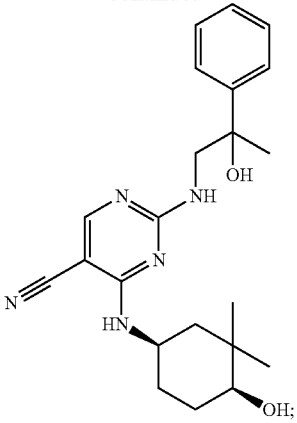
538
-continued
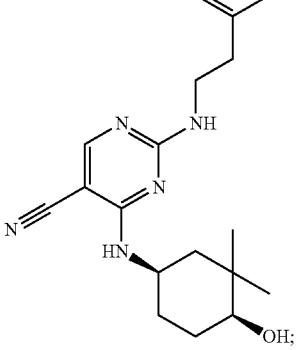
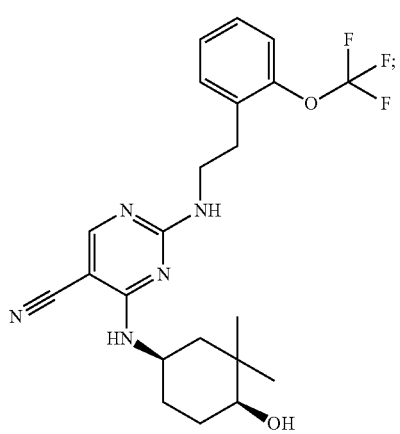
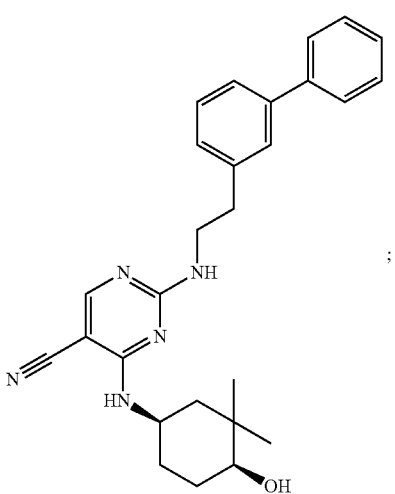

539
-continued
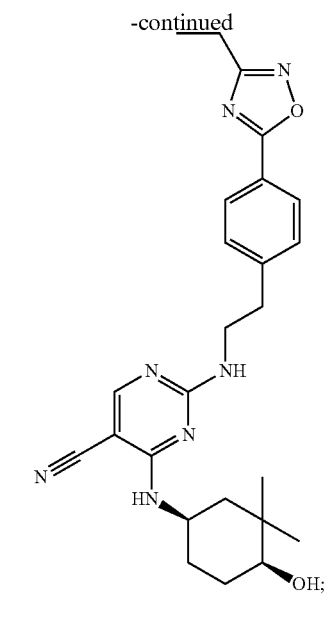
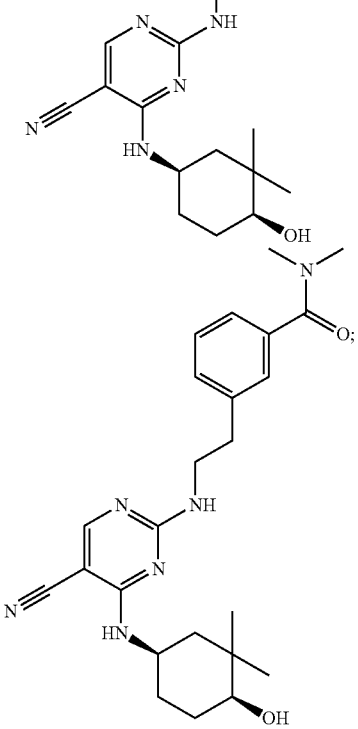
540
-continued
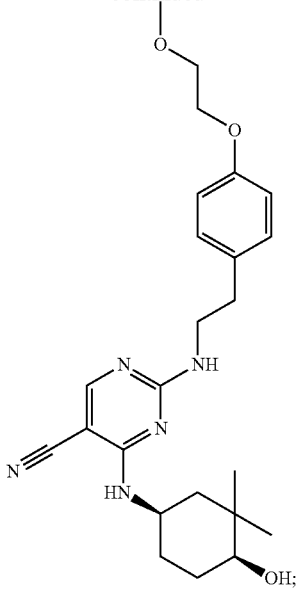
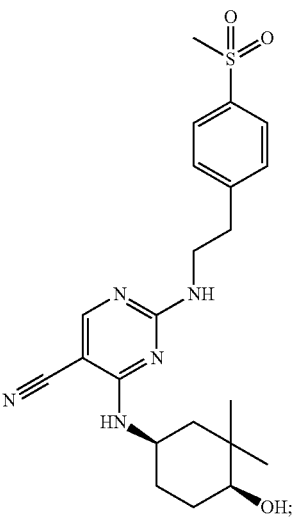
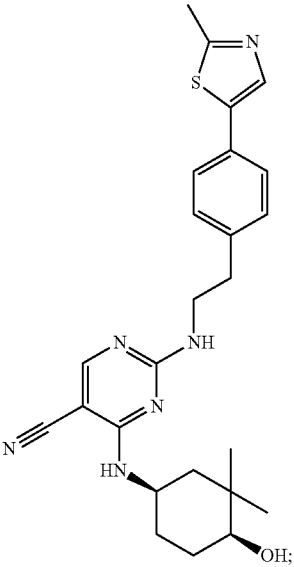

541
-continued
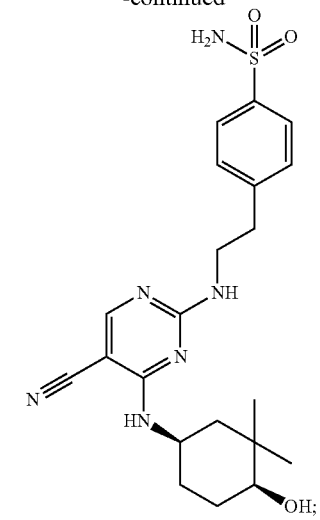
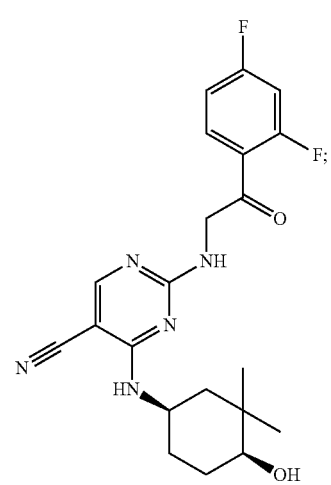
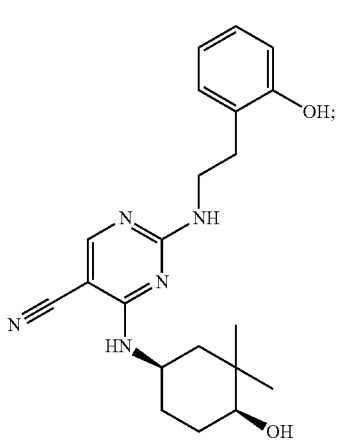
542
-continued
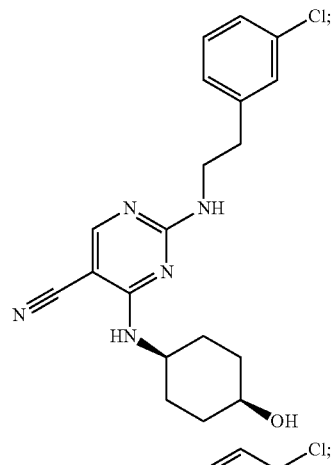
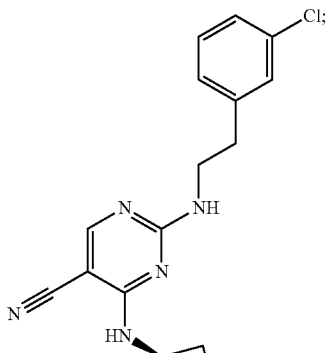
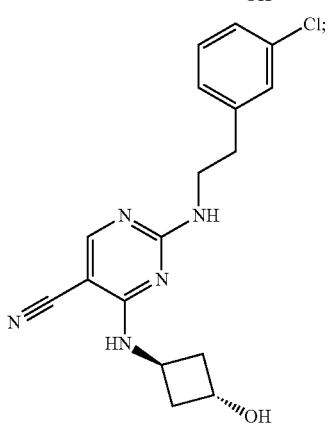

543
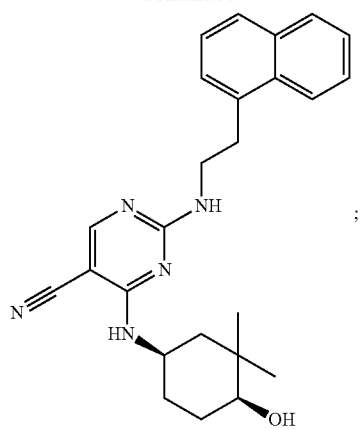
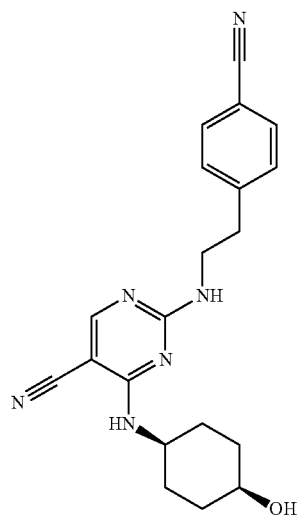
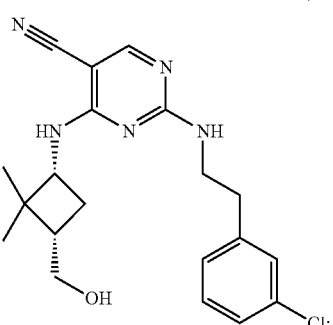
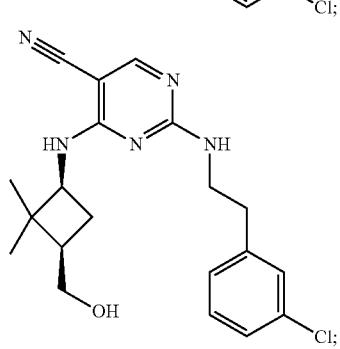
544
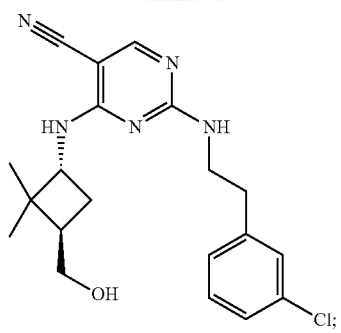
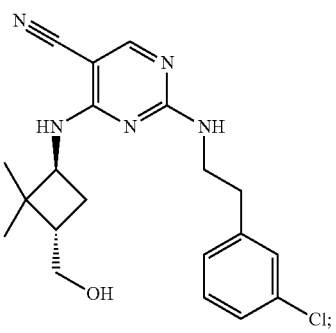
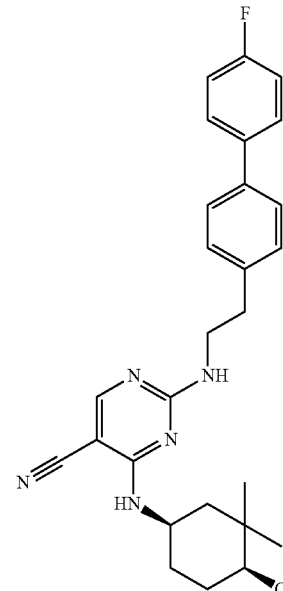

545
-continued
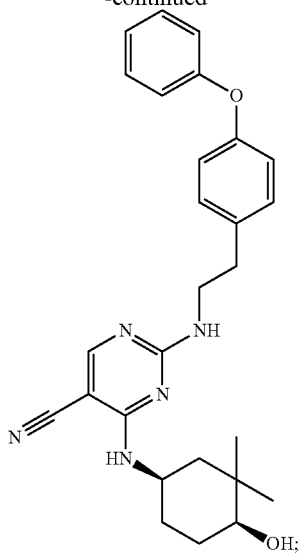
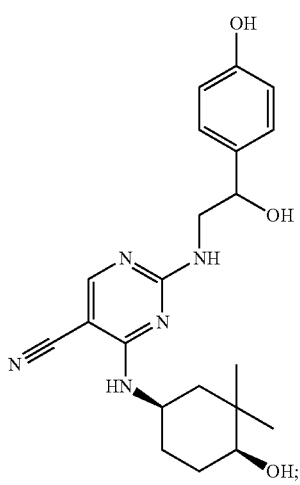
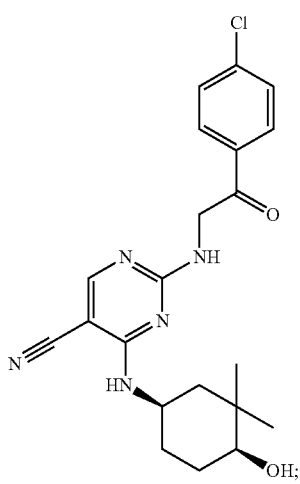
546
-continued
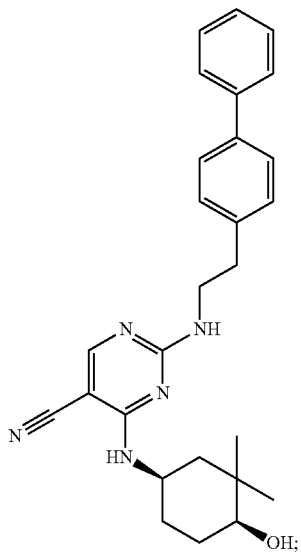
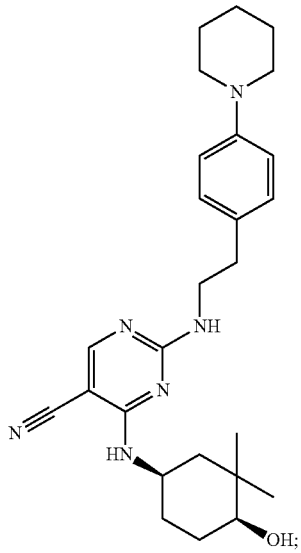
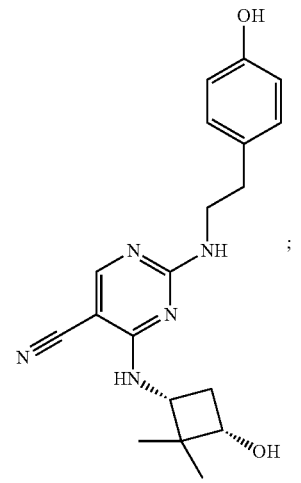

547
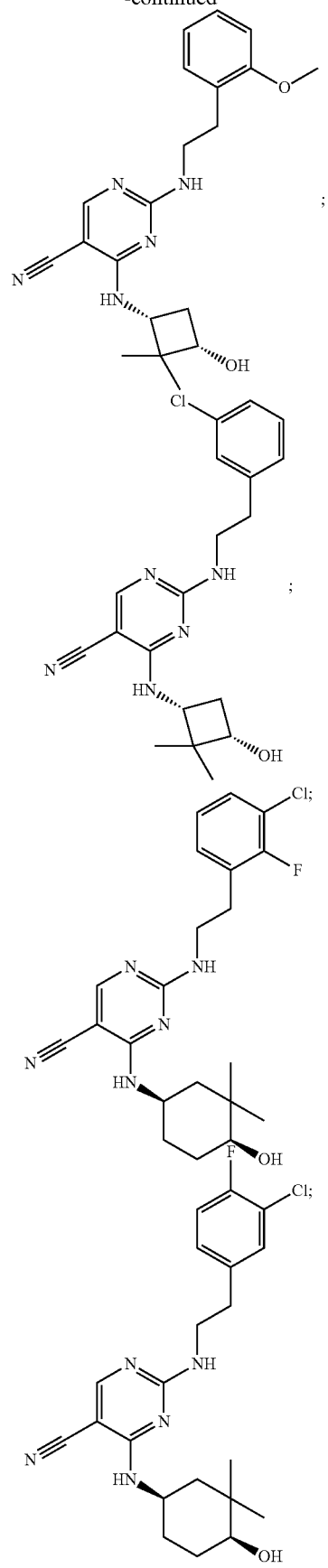
548
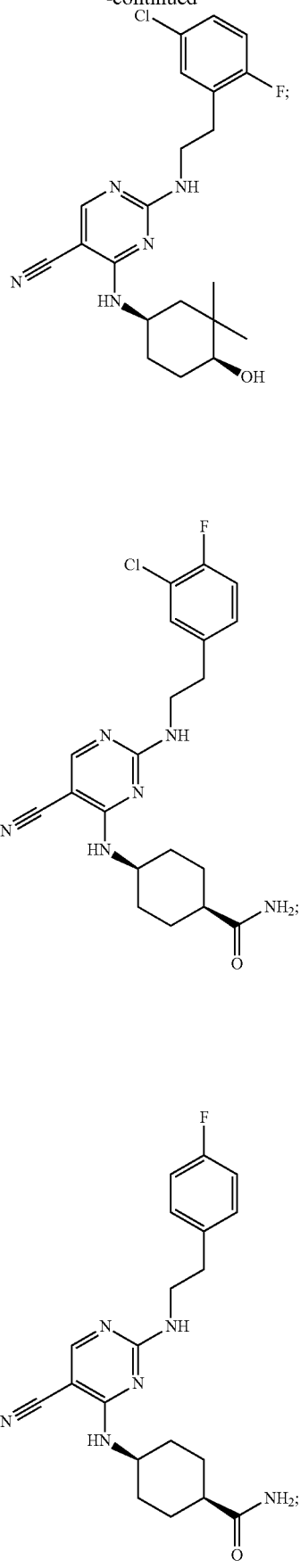

549
-continued
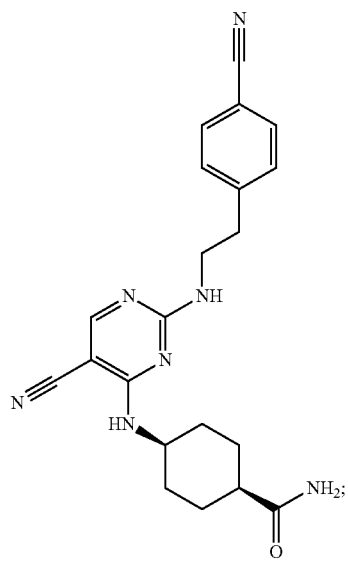
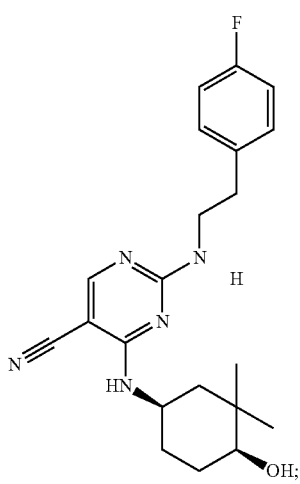
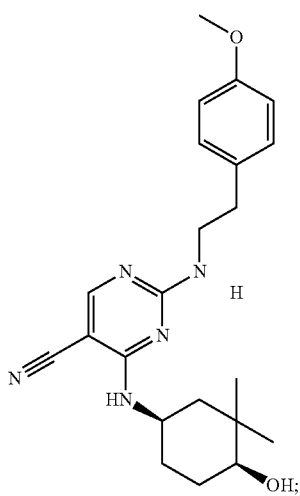
550
-continued
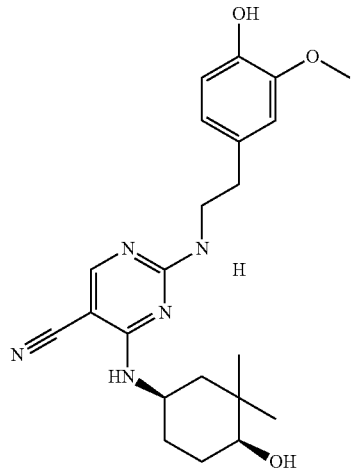
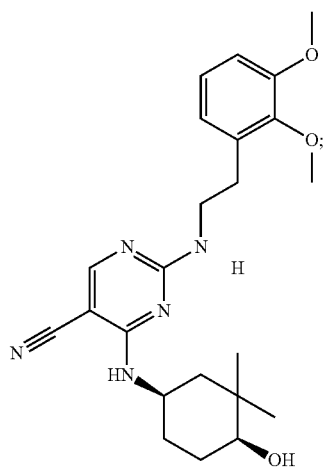
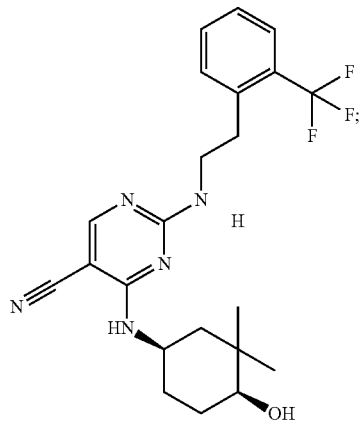

551
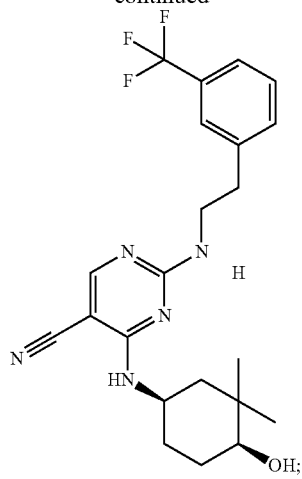
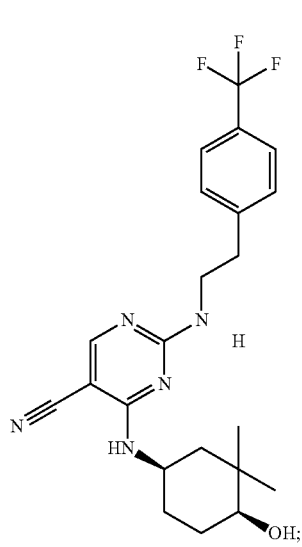
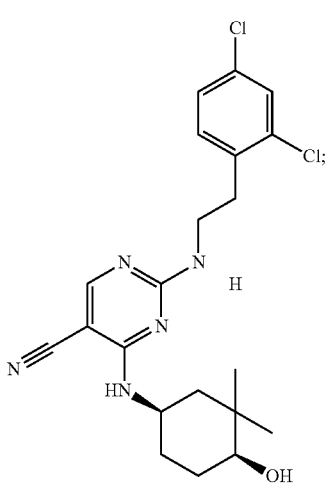
552
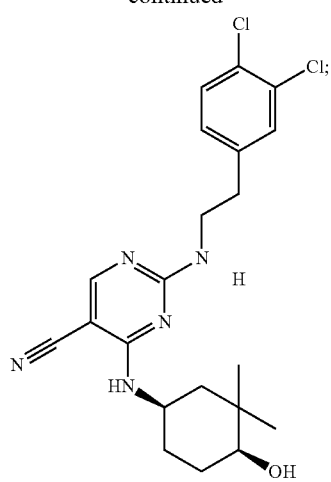
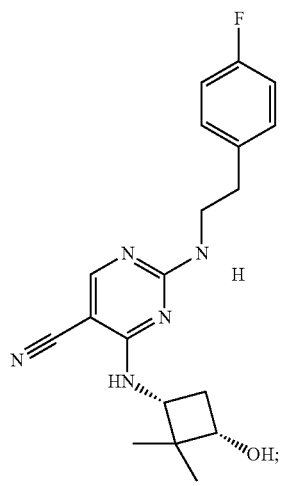
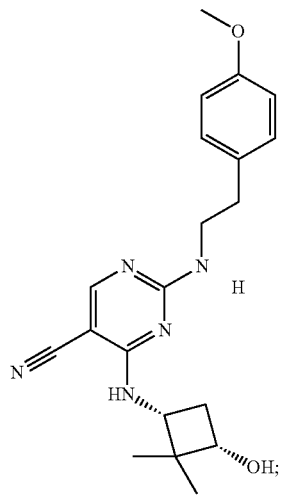

553
-continued
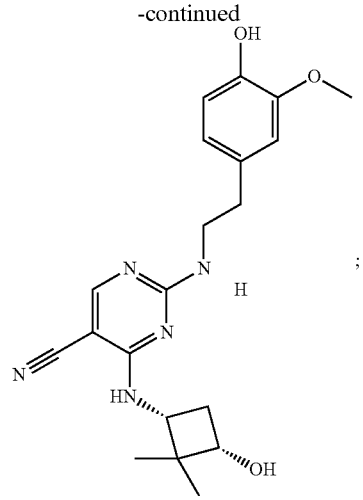
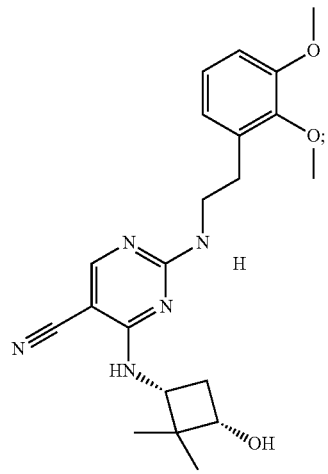
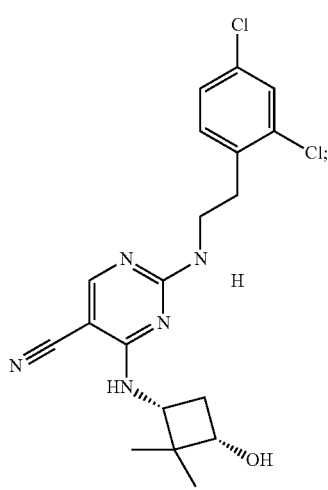
554
-continued
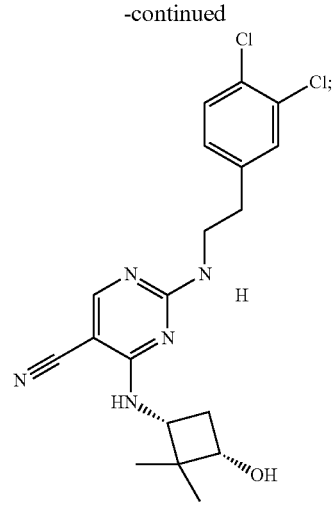
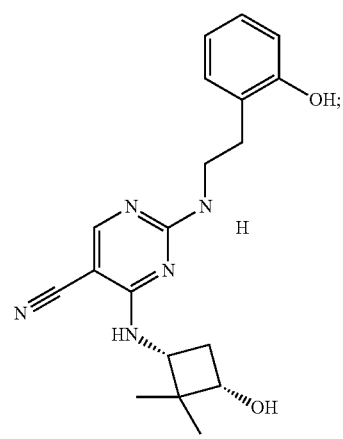
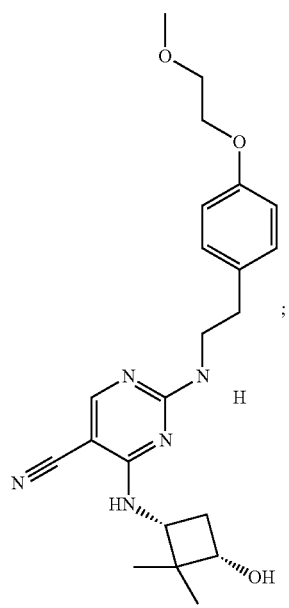

555
-continued
556
-continued
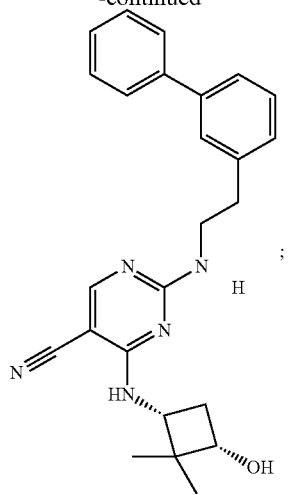
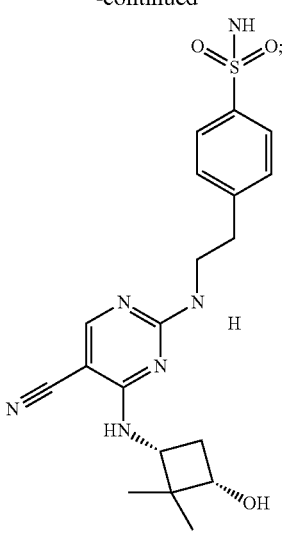

557
-continued
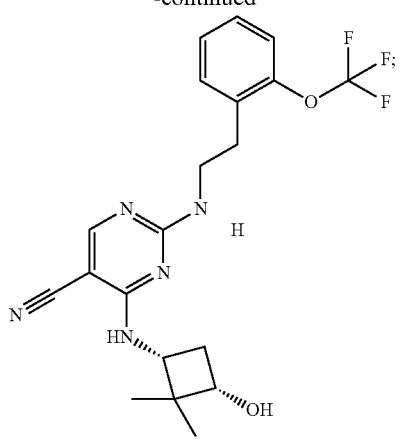
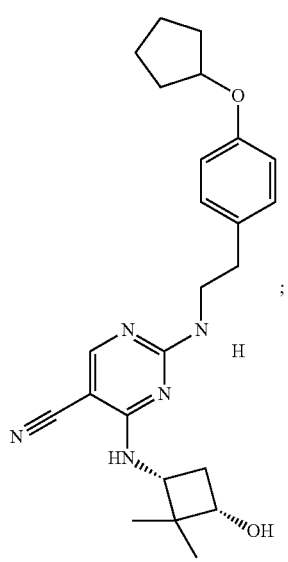
558
-continued
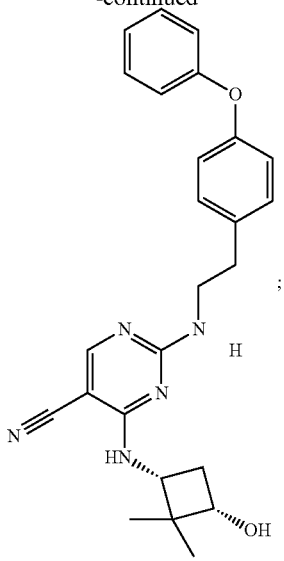
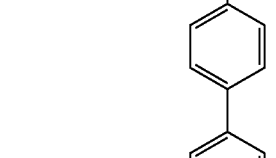
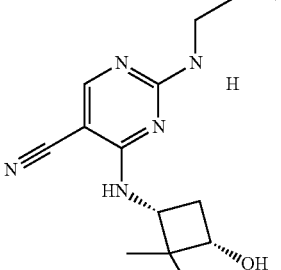
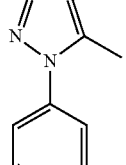

559
-continued
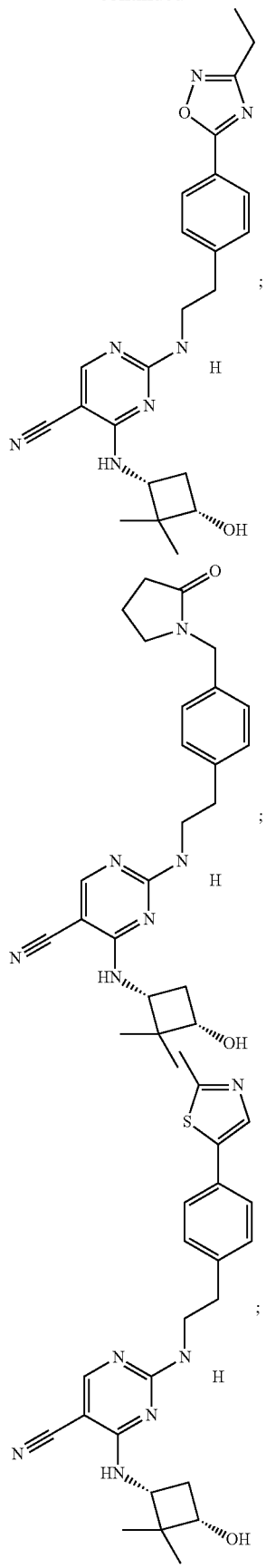
560
-continued
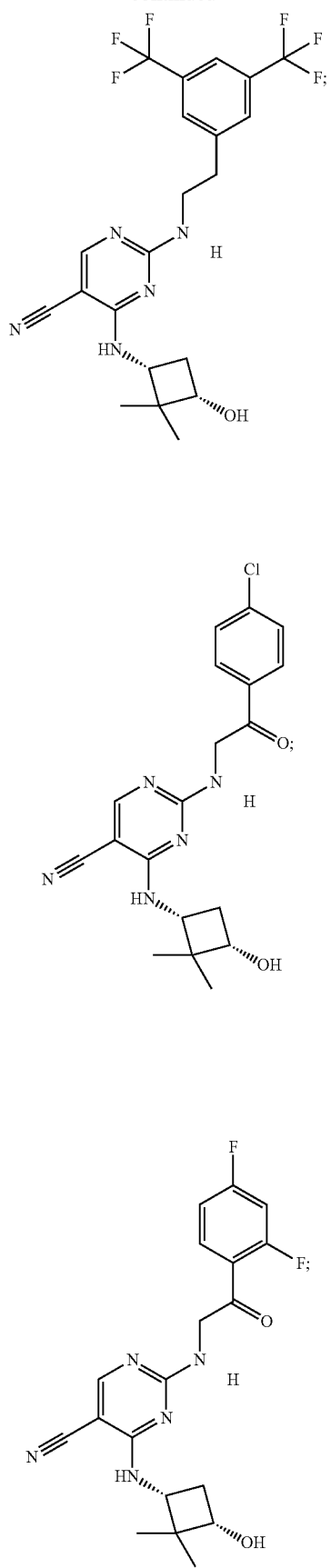

561
-continued
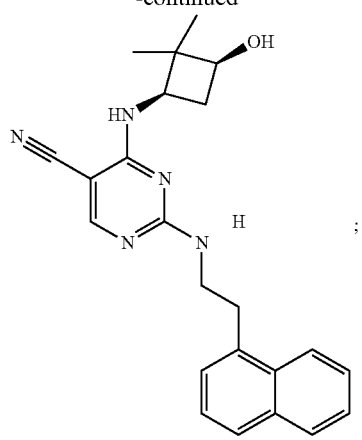
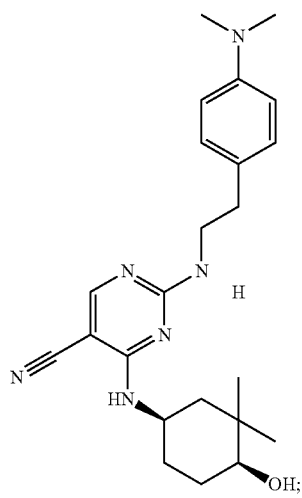
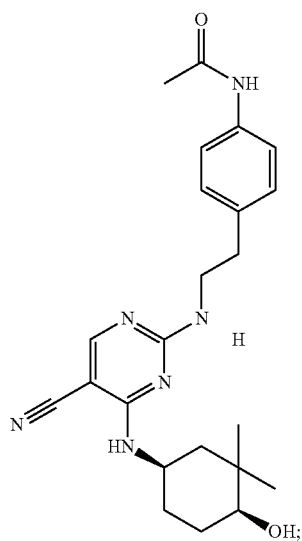
562
-continued
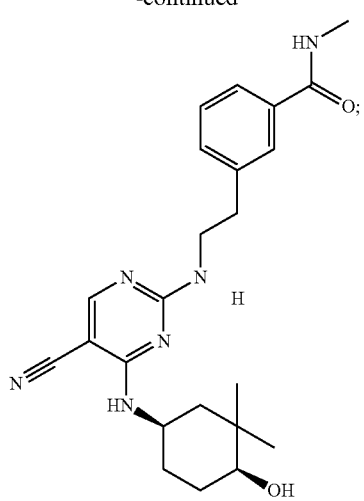
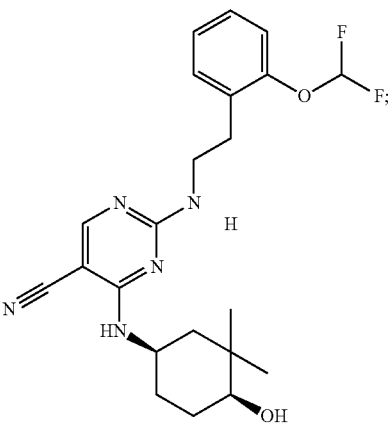
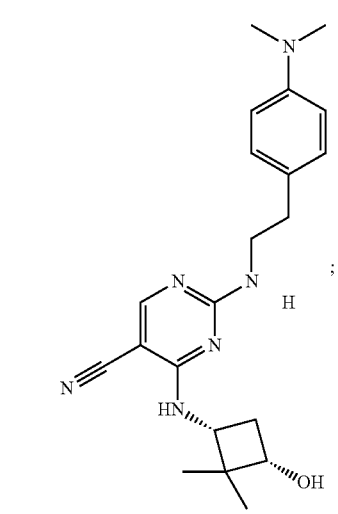

563
-continued
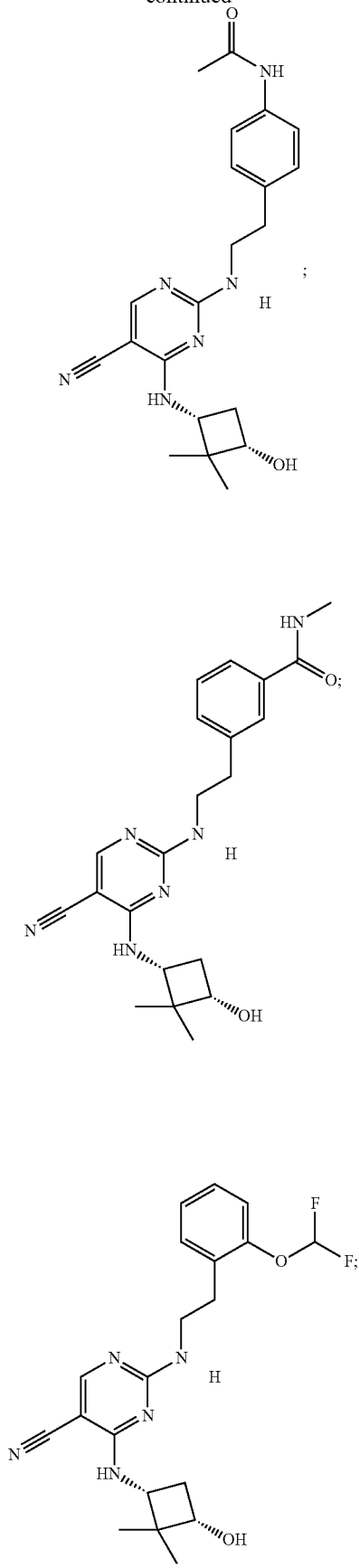
564
-continued
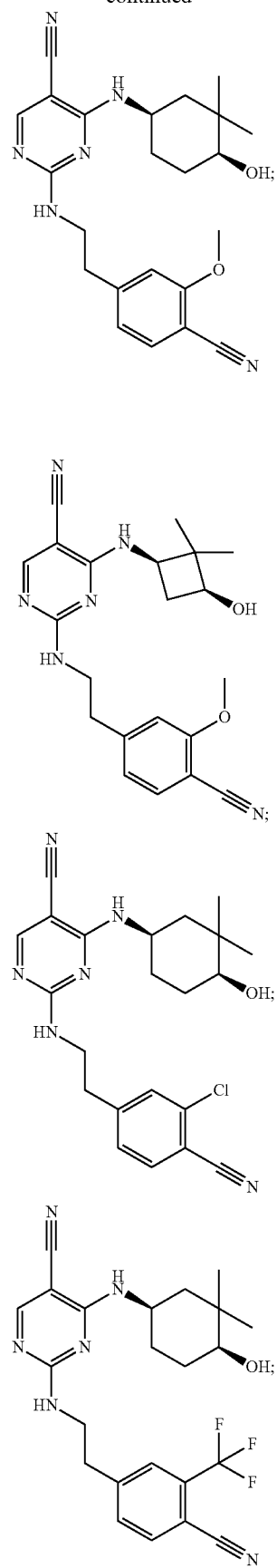

565
-continued
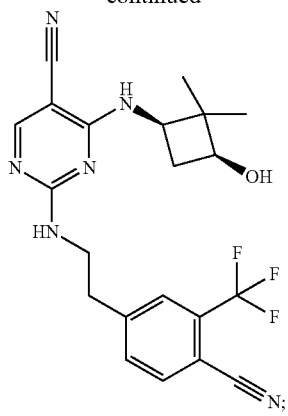
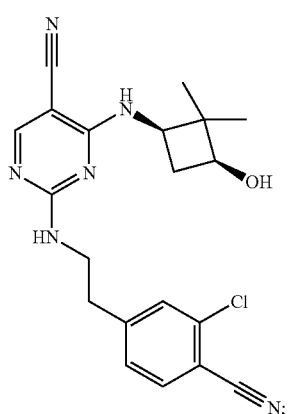
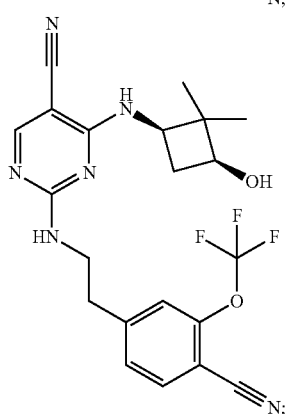
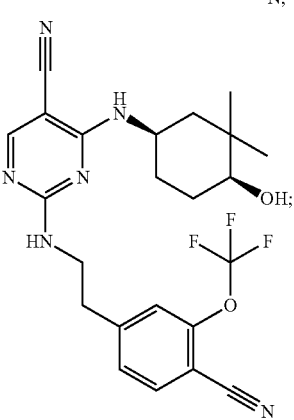
566
-continued
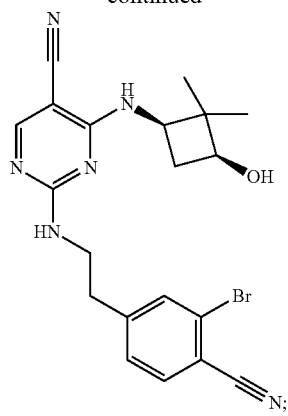
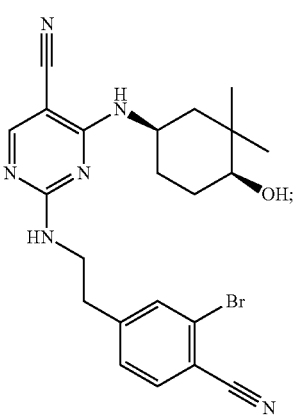
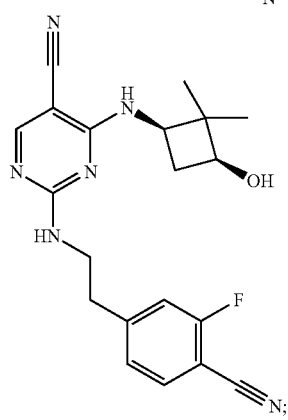
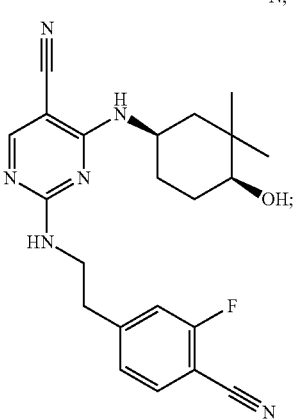

567
-continued
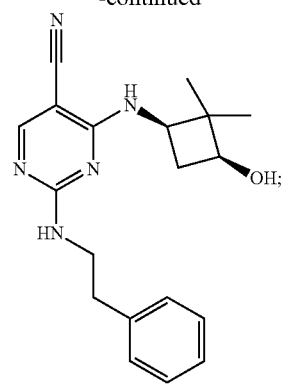
568
-continued
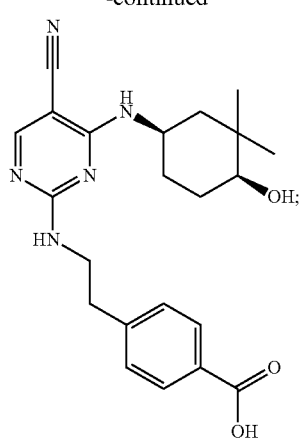
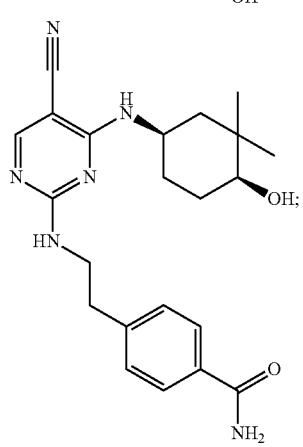
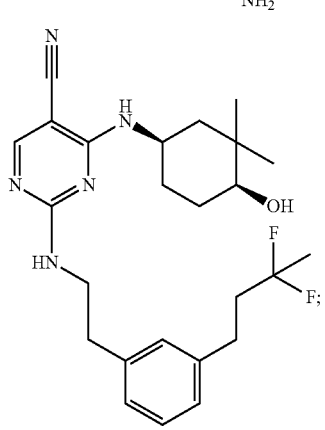
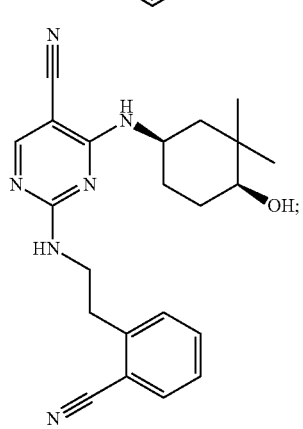

569
-continued
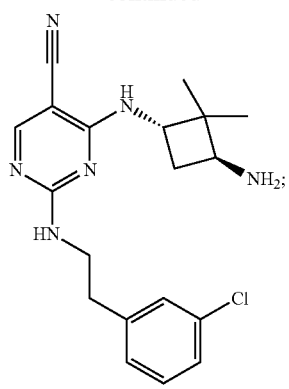
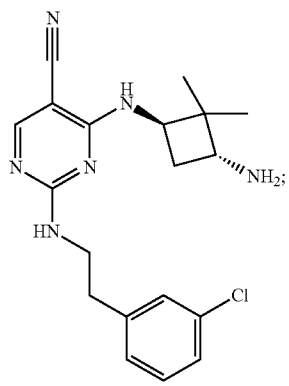
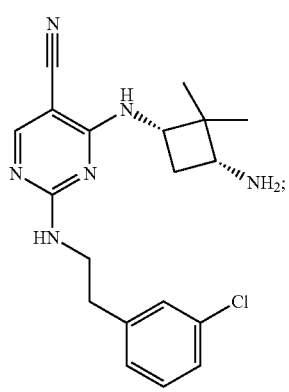
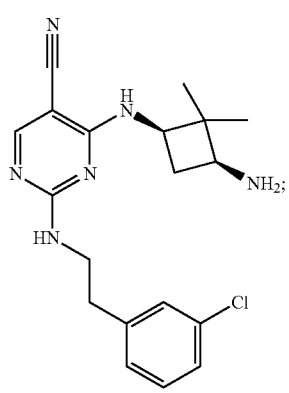
570
-continued
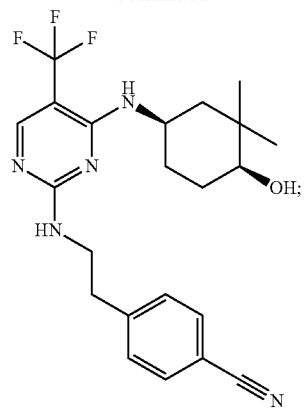
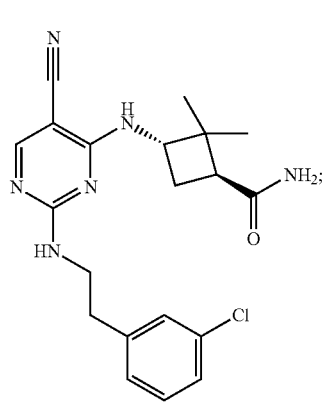
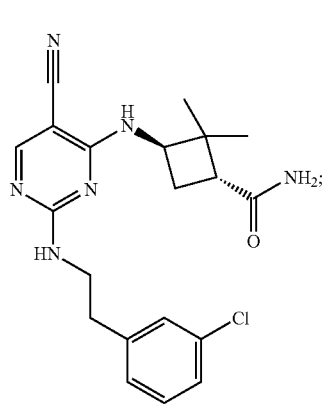
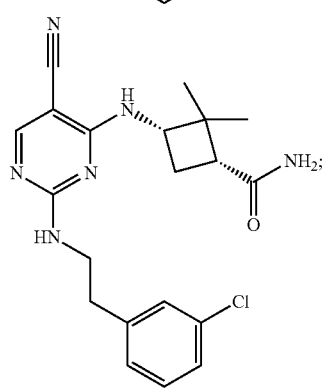

571
-continued
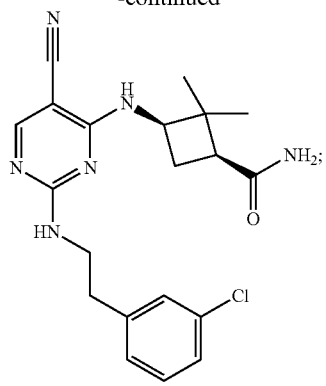
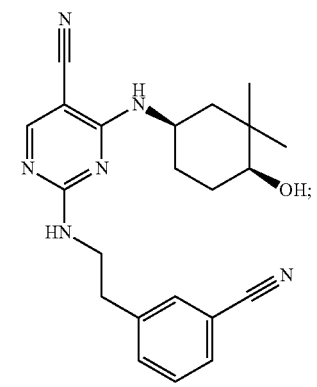
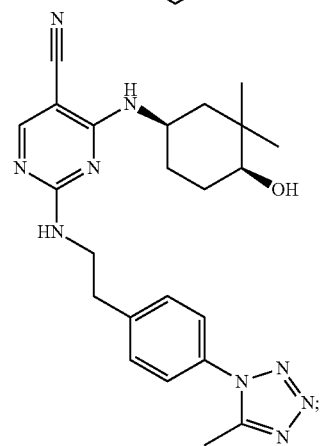
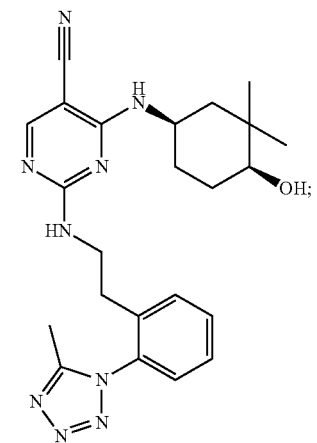
572
-continued
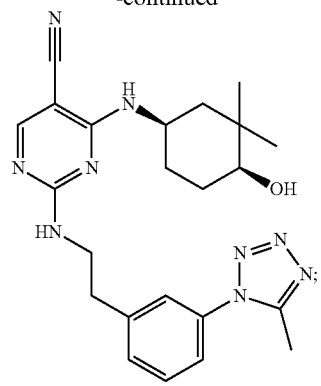
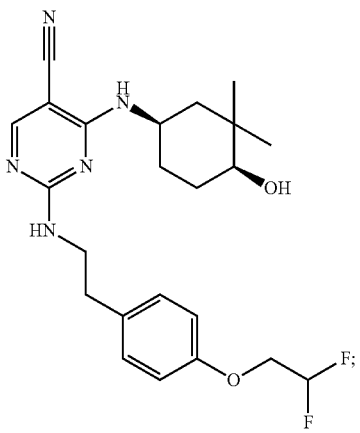
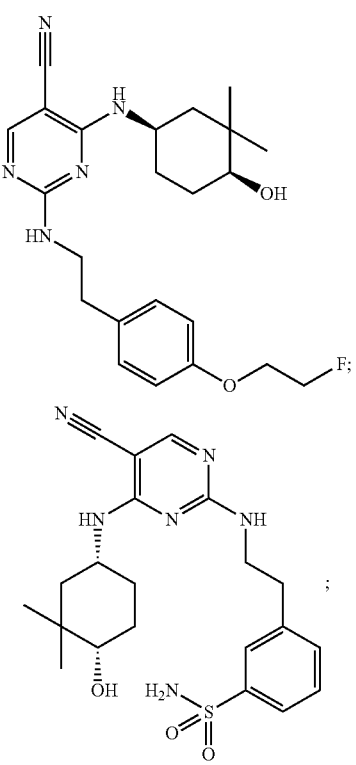

573
-continued
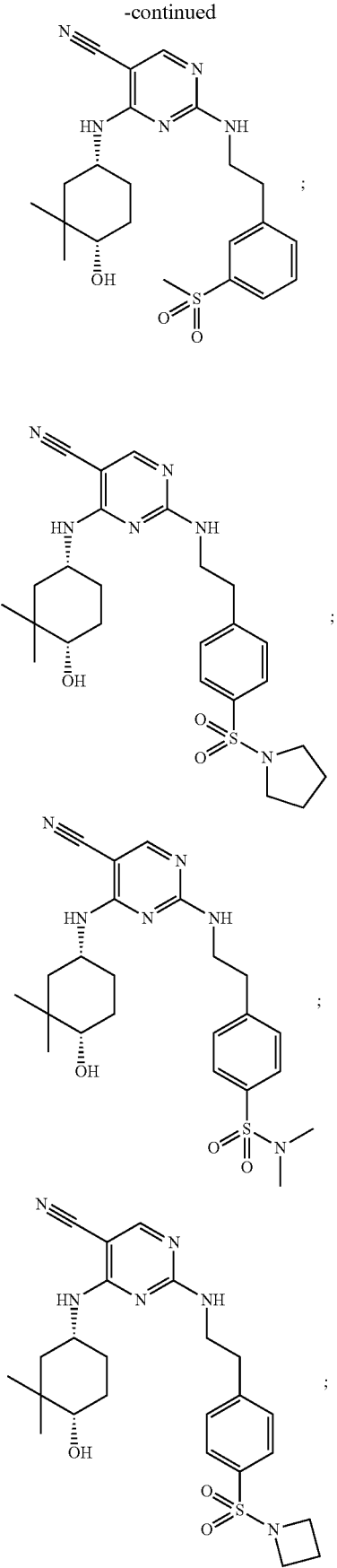
574
-continued
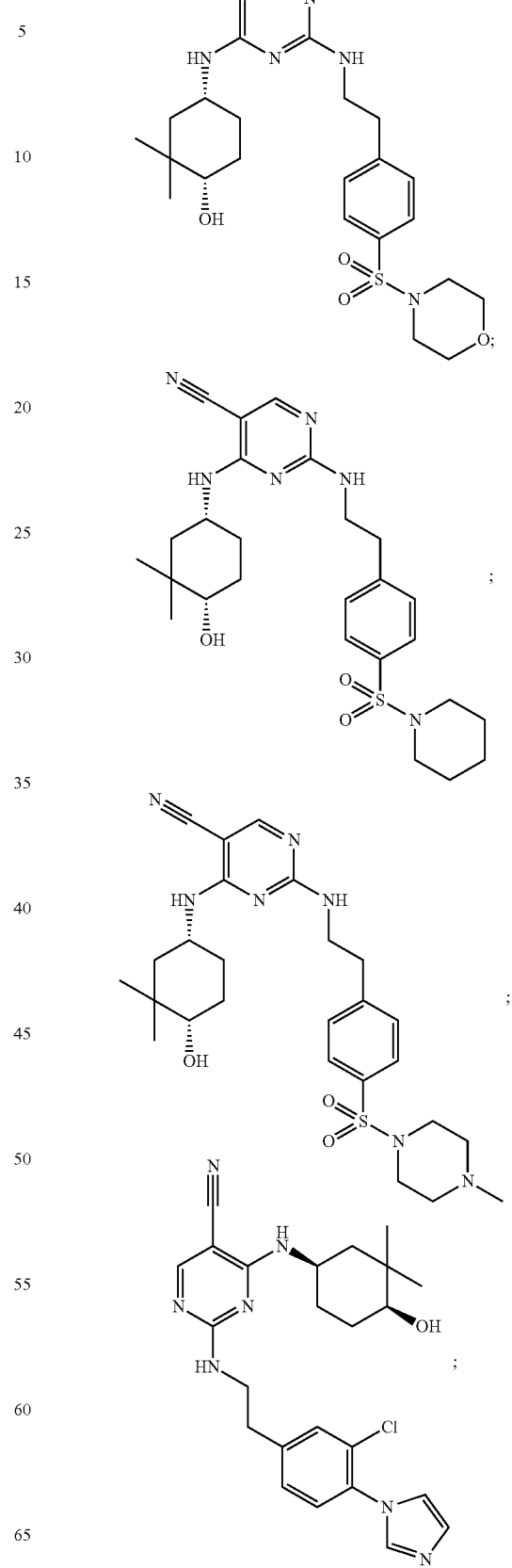

575
-continued
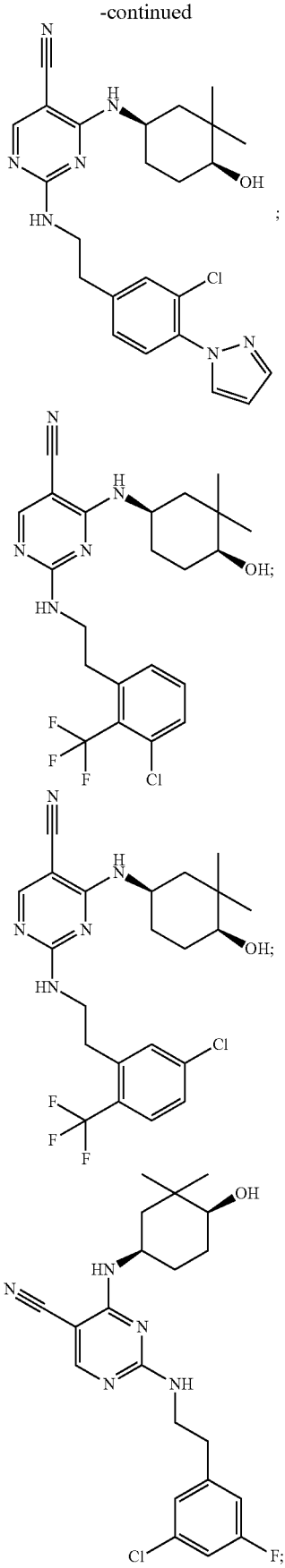
576
-continued
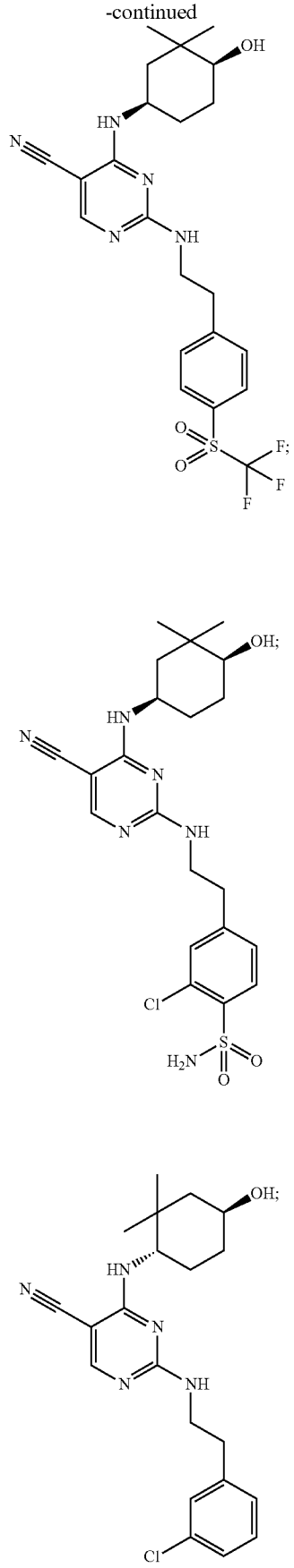

577
-continued
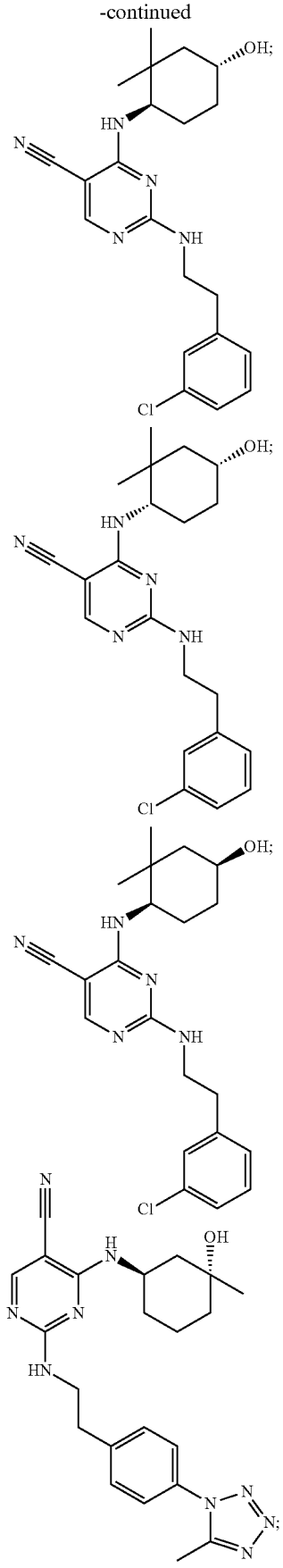
578
-continued
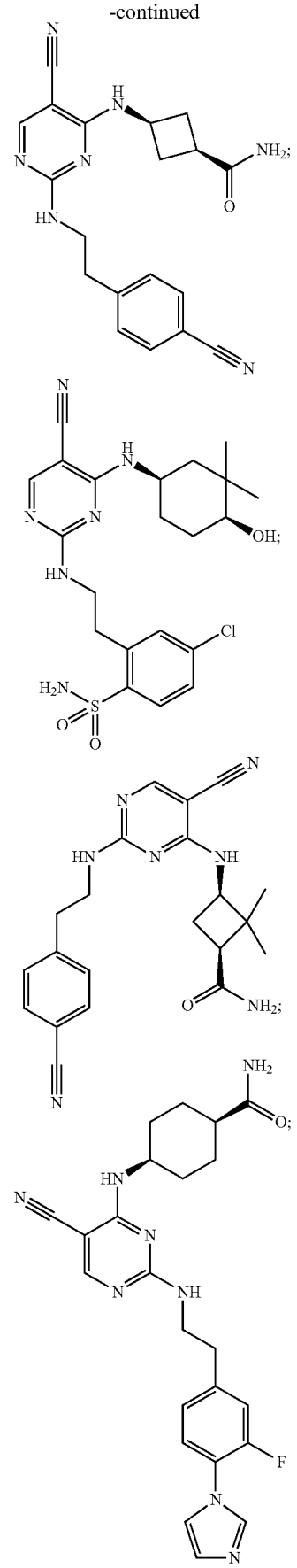

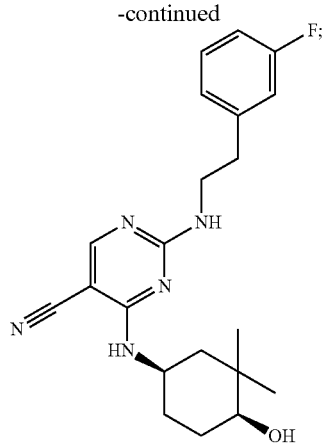
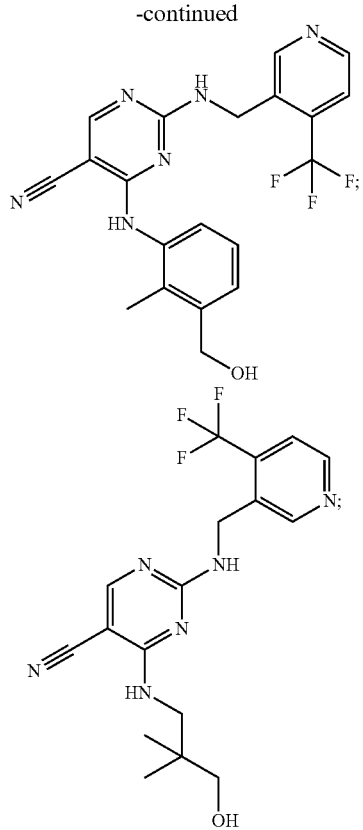

or a pharmaceutically acceptable salt, tautomer, or stereoisomer thereof.

26. A pharmaceutical composition comprising an effective amount of a compound of claim 1, 24, or 25, or a pharmaceutically acceptable salt, tautomer, or stereoisomer thereof, and a pharmaceutically acceptable carrier, excipient or vehicle.

27. A method of inhibiting PKC-theta in a cell expressing PKC-theta, comprising contacting said cell with an effective amount of a compound of claim 1, 24, or 25, or a pharmaceutically acceptable salt, tautomer, or stereoisomer thereof.

28. The method of claim 27, wherein the compound is selective for PKC-theta over PKC-delta.

29. The method of claim 27, wherein the compound is selective for PKC-theta over PKC-delta and PKC-eta.

30. The method of claim 28, wherein the compound is at least 5-fold selective for PKC-theta over PKC-delta.

31. The method of claim 28, wherein the compound is more than 100-fold selective for PKC-theta over PKC-delta.

32. A method for the treatment of PKC-theta mediated disorder, the methods comprising administering to a subject in need thereof an effective amount of a compound of claim 1, 24, or 25, or a pharmaceutically acceptable salt, tautomer, or stereoisomer thereof, wherein the PKC-theta mediated disorder is diabetes.

* * * * *